(12) United States Patent
Klinguer-Hamour et al.

(10) Patent No.: US 8,557,964 B2
(45) Date of Patent: Oct. 15, 2013

(54) ANTI CXCR4 ANTIBODIES AND THEIR USE FOR THE TREATMENT OF CANCER

(75) Inventors: Christine Klinguer-Hamour, Groisy (FR); Alexandra Jouhanneaud, Bonneville (FR); Véronique Grenier-Caussanel, Saint Martin du Fresne (FR)

(73) Assignee: Pierre Fabre Medicament, Boulogne Billancourt (FR)

( * ) Notice: Subject to any disclaimer, the term of this patent is extended or adjusted under 35 U.S.C. 154(b) by 291 days.

(21) Appl. No.: 12/749,891

(22) Filed: Mar. 30, 2010

(65) Prior Publication Data
US 2011/0020218 A1 Jan. 27, 2011

Related U.S. Application Data

(63) Continuation-in-part of application No. PCT/EP2009/062787, filed on Oct. 1, 2009.

(60) Provisional application No. 61/136,772, filed on Oct. 1, 2008, provisional application No. 61/173,743, filed on Apr. 29, 2009.

(30) Foreign Application Priority Data

Oct. 1, 2008 (EP) ..................................... 08305631

(51) Int. Cl.
*C07K 16/00* (2006.01)
*C12P 21/08* (2006.01)

(52) U.S. Cl.
USPC ................. 530/387.1; 530/387.3; 530/388.22

(58) Field of Classification Search
None
See application file for complete search history.

(56) References Cited

U.S. PATENT DOCUMENTS

| | | | |
|---|---|---|---|
| 4,424,200 A | 1/1984 | Crockford et al. | |
| 4,479,930 A | 10/1984 | Hnatowich | |
| 4,831,175 A | 5/1989 | Gansowe et al. | |
| 5,530,101 A | 6/1996 | Queen et al. | |
| 5,585,089 A | 12/1996 | Queen et al. | |
| 5,639,641 A | 6/1997 | Pedersen et al. | |
| 5,693,761 A | 12/1997 | Queen et al. | |
| 5,877,293 A | 3/1999 | Adair et al. | |
| 5,886,152 A | 3/1999 | Nakatani et al. | |
| 6,054,297 A | 4/2000 | Carter et al. | |
| 6,180,370 B1 | 1/2001 | Queen et al. | |
| 6,949,243 B1 * | 9/2005 | Mueller et al. | 424/130.1 |

FOREIGN PATENT DOCUMENTS

| | | |
|---|---|---|
| EP | 0 451 216 B1 | 10/1991 |
| EP | 0 682 040 B1 | 11/1995 |
| EP | 0939 127 A2 | 9/1999 |
| WO | WO 92/11018 A1 | 7/1992 |
| WO | WO 2004/059285 A2 | 7/2004 |

OTHER PUBLICATIONS

Paul, Fundamental Immunology, 3rd Edition, 1993, pp. 292-295.*
Rudikoff et al., Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*
MacCallum et al. J. Mol. Biol., 262, 732-745, 1996.*
Casset et al. Biochemical and Biophysical Research Communications, 307:198-205, 2003.*
Baribaud, F. et al., "Antigenically Distinct Conformations of CXCR4", *J. Virol.*, 75: 8957-8967, (2001).
International Search Report for PCT/EP2009/062787, dated Feb. 3, 2010.
Steward, J.M. et al., "Solid Phase Peptides Synthesis," Univ. of Mich. 71-95 (1984).
Allred, D. C. et al., "Prognostic and Predictive Factors in Breast Cancer by Immunohistochemical Analysis," *Mod. Pathol.*, 11:155-68 (1998).
Bachelder, R. et al., "Vascular Endothelial Growth Factor Promotes Breast Carcinoma Invasion in an Autocrine Manner by Regulating the Chemokine Receptor CXCR4," *Cancer Res.*, 62:7203-06 (2002).
Balkwill, F. "Cancer and the Chemokine Network," *Nature Rev. Cancer*, 4:540-50 (2004).
Barbero, S. et al., "Expression of the Chemokine Receptor CXCR4 and Its Ligand Stromal Cell-Derived Factor 1 in Human Brain Tumors and Their Involvement in Glia Proliferation in Vitro," *Ann. N.Y. Acad. Sci.*, 973:60-69 (2002).
Barbero, S. et al., "Stromal Cell-derived Factor 1α Stimulates Human Glioblastoma Cell Growth through the Activation of Both Extracellular Signal-regulated Kinases 1/2 and Akt," *Cancer Res.*, 63:1969-74 (2003).
Bebbington, C. et al., "High-Level of a Recombinant Antibody From Myeloma Cells Using a Glutamine Synthetase Gene as an Amplifiable Selectable Marker," *Biotech.*, 10:169-75 (1992).
Bès, C. et al., "PIN-bodies: A New Class of Antibody-like Proteins with CD4 Specificity Derived from the Protein Inhibitor of Neuronal Nitric Oxide Synthase," *Biochem. and Biophys. Res. Comm.*, 343:334-44 (2006).
Bès, C. et al., "Efficient CD4 Binding and Immunosuppressive Properties of the 13B8.2 Monoclonal Antibody are Displayed by its CDR-H1-Derived Peptide CB1," *FEBS Letters*, 508:67-74 (2001).
Bosier, B. et al., "Versatility of GPCR Recognition by Drugs: From Biological Implications to Therapeutic Relevance," *Trends in Pharma. Sci.*, 28:438-46 (2007).
Brechbiel, M. W. et al., "Backbone-Substituted DTPA Ligands for $^{90}$Y Radioimmunotherapy," *Bioconj. Chem.*, 2:187-94 (1991).
Carnec, X. et al., "Anti-CXCR4 Monoclonal Antibodies Recognizing Overlapping Epitopes Differ Significantly in Their Ability to Inhibit Entry of Human Immunodeficiency Virus Type 1," *J. Virol.*, 79:1930-33 (2005).

(Continued)

*Primary Examiner* — Hong Sang
(74) *Attorney, Agent, or Firm* — Finnegan

(57) ABSTRACT

The present invention relates to a novel isolated antibody, or the derived compounds or functional fragments of same, capable of binding to CXCR4 but also of inducing conformational changed of the CXCR4 homodimers and/or heterodimers. More particularly, the present invention relates to the 414H5 and 515H7 antibodies, specific to the CXCR4 protein, as well as their use for the treatment of cancer. Pharmaceutical compositions composed of such antibodies and a process for the selection of such antibodies are also covered.

43 Claims, 35 Drawing Sheets

(56) References Cited

OTHER PUBLICATIONS

De Falco, V. et al., "Biological Role and Potential Therapeutic Targeting of the Chemokine Receptor CXCR4 in Undifferentiated Thyroid Cancer," *Cancer Res.* 67:11821-28 (2007).
Galandrin, S. et al., "The Evasive Nature of Drug Efficacy: Implication for Drug Discovery," *Trends in Pharma. Sci.*, 28:423-30 (2007).
Gansow, O. et al., "Chelates and Antibodies: Current Methods and New Directions," in *Cancer Treatment and Research*, 153-71, Goldenberg, D.M. (ed.), Springer, NY (1990).
Gansow, O. "Newer Approaches to the Radiolabeling of Monoclonal Antibodies by Use of Metal Chelates," *Nucl. Med. Biol.* 18:369-81 (1991).
Glennie, M. et al., "Preparation and Performance of Bispecific F(ab'γ)$_2$ Antibody Containing Thioether-Linked Fab'γ Fragments," *J. Immunol.*, 39:2367-75 (1987).
Hereld, D. et al., "Slamming the DOR on Chemokine Receptor Signaling: Heterodimerization Silences Ligand-occupied CXCR4 and δ-opioid Receptors," *Eur. J. Immunol.*, 38:334-37 (2008).
Holliger, P. et al., "Engineering Antibodies for the Clinic," *Cancer and Met. Rev.* 18:411-19 (1999).
Hunter, W. et al., "Preparation of Iodine-131 Labelled Human Growth Hormone of High Specific Activity," *Nature*, 194:495-96 (1962).
Jones, P. et al., "Replacing the Complementarity-Determining Regions in a Human Antibody with those from a Mouse," *Nature*, 321:522-25 (1986).
Juarez, J. et al., "Chemokines and their Receptors as Therapeutic Targets: The Role of the SDF-1/CXCR4 Axis," *Curr. Pharma. Des.*, 10:1245-59 (2004).
Juarez, J. et al., "Effects of Inhibitors of the Chemokine Receptor CXCR4 on Acute Lymphoblastic Leukemia Cells in vitro," *Leukemia*, 17:1294-300 (2003).
Kaas, Q. et al., "IMGT Colliers de Perles: Standardized Sequence-Structure Representations of the IgSF and MheSF Superfamily Domains," *Curr. Bioinform.*, 2:21-30 (2007).
Kaas, Q. et al., "IMGT/3Dstructure-DB and IMGT/StructuralQuery, a Database and a Tool for Immunoglobulin, T Cell Receptor and MHC Structural Data," *Nucleic Acids Res. Database Issue*, 32:D208-10 (2004).
Kabat, E. et al., "Identical V Region Amino Acid Sequences and Segments of Sequences in Antibodies of Different Specificities," *J. Immunol.*, 47:1709-19 (1991).
Kato, M. et al., "Expression Pattern of CXC Chemokine Receptor-4 is Correlated with Lymph Node Metastasis in Human Invasive Ductal Carcinoma," *Breast Cancer Res.*, 5:144-50 (2003).
Kenakin, T., "Efficacy as a Vector: the Relative Prevalence and Paucity of Inverse Agonism," *Mol. Pharm.*, 65:2-11 (2004).
Kim, C.H., et al., "Codon Optimization for High-level Expression of Human Erythropoietin (EPO) in Mammalian Cells," *Gene*, 199:293-301 (1997).
Kohl, A., et al., "Designed to Be Stable: Crystal Structure of a Consensus Ankyrin Repeat Protein," *PNAS*, 100:1700-05 (2003).
Köhler, G. et al., "Continuous Cultures of Fused Cells Secreting Antibody of Predefined Specificity," *Nature*, 256:495-97 (1975).
Koshiba, T. et al., "Expression of Stromal Cell-derived Factor 1 and CXCR4 Ligand Receptor System in Pancreatic Cancer: A Possible Role for Tumor Progression," *Clin. Cancer Res.*, 6:3530-35 (2000).
Krejcarek, G. et al., "Covalent Attachment of Chelating Groups to Macromolecules," *Biochem. and Biophys. Res. Comm.*, 77:581-85 (1977).
Kucia, M. et al., "Trafficking of Normal Stem Cells and Metastasis of Cancer Stem Cells Involve Similar Mechanisms: Pivotal Role of the SDF-1-CXCR4 Axis," *Stem Cells*, 23:879-94 (2005).
Lefranc, M.-P., et al., "IMGT Unique Numbering for Immunoglobulin and T Cell Receptor Variable Domains and Ig Superfamily V-like Domains," *Devel. & Comp. Immunol.*, 27:55-77 (2003).
Lefranc, M.-P., "Unique Database Number System for Immunogenetic Analysis," *Immunol. Today*, 18 (1997).

Lefranc, M.-P., "The IMGT Unique Numbering for Immunoglobulins, T-Cell Receptors, and Ig-Like Domains," *The Immunologist*, 7:132-36 (1999).
Liang, Z. et al., "Silencing of CXCR4 Blocks Breast Cancer Metastasis," *Cancer Res.*, 65:967-71 (2005).
Mantovani, A. et al., "Chemokines in the Recruitment and Shaping of the Leukocyte Infiltrate of Tumors," *Sem. Canc. Bio.*, 14:155-60 (2004).
Meares, C.F. et al., "Conjugation of Antibodies with Bifunctional Chelating Agents: Isothiocyanate and Bromoacetamide Reagents, Methods of Analysis, and Subsequent Addition of Metal Ions," *Anal. Biochem.*, 142:68-78 (1984).
Merchant, A. et al., "An Efficient route to Human Bispecific IgG," *Nature Biotech.*, 16:677-81 (1998).
Mountain, A. et al., "Engineering Antibodies for Therapy," *Biotech. and Gen. Eng. Rev.*, 10:1-142 (1992).
Müller, A. et al., "Involvement of Chemokine Receptors in Breast Cancer Metastasis," *Nature*, 410:50-56 (2001).
Murphy, P., "Chemokines and the Molecular Basis of Cancer Metastasis," *N. Engl. J. Med.*, 345:833-5 (2001).
Needleman, S. B. et al., "A General Method Applicable to the Search for Similarities in the Amino Acid Sequence of Two Proteins," *J. Mol. Biol.*, 48:443-53 (1970).
Nicaise, M. et al., "Affinity Transfer by CDR Grafting on a Nonimmunoglobulin Scaffold," *Protein. Sci.*, 13:1882-91 (2004).
Ottaiano, A. et al., "Inhibitory Effects of Anti-CXCR4 Antibodies on Human Colon Cancer Cells," *Cancer Immunol. Immunother.*, 54:781-91 (2005).
Owen, J.D. et al., "Enhanced Tumor-Forming Capacity for Immortalized Melanocytes Expressing Melanoma Growth Stimulatory Activity/Growth-Regulated Cytokine β and γ Proteins," *Int. J. Cancer*, 73:94-103 (1997).
Pandini, G. et al., "Functional Responses and in vivo Anti-Tumor Activity of h7C10: A Humanised Monoclonal Antibody with Neutralising Activity Against the Insulin-like Growth Factor-1 (1GF-1) Receptor and Insulin/IGF-1 Hybrid Receptors," *Eur. J. of Cancer*, 43:1318-27 (2007).
Park, S.S. et al., "Generation and Characterization of a Novel Tetravalent Bispecific Antibody that Binds to Hepatitis B Virus Surface Antigens," *Mol. Immunol.*, 37:1123-30 (2000).
Pearson, W.R. et al., "Improved Tools for Biological Sequence Comparison," *PNAS*, 85:2444-48 (1988).
Percherancier, Y. et al., "Bioluminescence Resonance Energy Transfer Reveals Ligand-induced Conformational Changes in CXCR4 Homo- and Heterodimers," *J. Biol. Chem.*, 280:9895-903 (2005).
Phillips, R.J. et al., "The Stromal Derived Factor-1/CXCL12-CXC Chemokine Receptor 4 Biological Axis in Non-Small Cell Lung Cancer Metastases," *Am. J. Respir. Crit. Care Med.*, 167:1676-86 (2003).
"Monoclonal Anti-Human CXCR4 (fusin) Antibody," *R&D Systems, Inc.*, Product Sheet for Catalog # MAB173, 1-2, Nov. 13, 2007 version (2007).
Reeves, J. et al., "The Second Extracellular Loop of CXCR4 is Involved in CD4-independent Entry of Human Immunodeficiency Virus Type 2," *J. Gen. Virol.*, 79:1793-99 (1998).
Reichmann, L. et al., "Reshaping Human Antibodies for Therapy," *Nature*, 332:323-27 (1988).
Romagnani, P. et al, "CXC Chemokines: The Regulatory Link Between Inflammation and Angiogenesis," *Trends in Immunol.*, 25:201-9 (2004).
Rubin, J.B. et al., "A Small-molecule Antagonist of CXCR4 Inhibits Intracranial Growth of Primary Brain Tumors," *PNAS*, 100:13513-18 (2003).
Ruiz, M. et al., "IMGT Gene Identification and Colliers de Perles of Human Immunoglobulins with Known 3D Structures," *Immunogenet.*, 53:857-83 (2002).
Scotton, C.J. et al., "Multiple Actions of the Chemokine CXCL12 on Epithelial Tumor Cells in Human Ovarian Cancer," *Cancer Res.*, 62:5930-38 (2002).
Sierro, F. et al., "Disrupted Cardiac Development but Normal Hematopoiesis in Mice Deficient in the Second CXCL12/SDF-1 Receptor, CXCR7," *PNAS*, 104:14759-64 (2007).

(56) References Cited

OTHER PUBLICATIONS

Simpson, J.F. et al., "Prognostic Value of Histologic Grade and Proliferative Activity in Axillary Node-Positive Breast Cancer: Results From the Eastern Cooperative Oncology Group Companion Study, EST 4189," *J. Clin. Onc.*, 18:2059-69 (2000).

Singer, I., et al., "Optimal Humanization of 1B4, an Anti-CD18 Murine Monoclonal Antibody, is Achieved by Correct Choice of Human V-Region Framework Sequences," *J. Immunol.*, 150:2844-57 (1993).

Singh, R.K. et al., "Expression of Interleukin 7 Correlates with the Metastatic Potential of Human Melanoma Cells in Nude Mice," *Cancer Res.*, 54:3242-47 (1994).

Skerra, A. "Engineered Protein Scaffolds for Molecular Recognition," *J. Mol. Recognit.* 13:167-87 (2000).

Skerra, A. "'Anticalins': A New Class of Engineered Ligand-binding Proteins with Antibody-like Properties," *Rev. Mole. Biotech.*, 74:257-75 (2001).

Smith, T. et al., "Comparison of Biosequences," *Adv. Appl. Math.*, 2:482-89 (1981).

Staerz, U.D. et al., "Hybrid Hydridoma Producing a Bispecific Monoclonal Antibody that can Focus Effector T-cell Activity," *PNAS*, 83:1453-57(1986).

Strieter, R.M. et al., "CXC Chemokines in Angiogenesis of Cancer," *Sem. Canc. Bio.*, 14:195-200 (2004).

Sun, Y-X et al., "Expression of CXCR4 and CXCL12 (SDF-1) in Human Prostate Cancers (PCa) In Vivo," *J. Cell. Biochem.*, 89:462-73 (2003).

Suresh, M.R. et al. "Bispecific Monoclonal Antibodies from Hybrid Hybridomas," *Meth. in Enzymol.*, 121:210-228 (1986).

Tamamura, H. et al., "T140 Analogs as CXCR4 Antagonists Identified as Anti-metastatic Agents in the Treatment of Breast Cancer," *FEBS Ltrs.*, 550:79-83 (2003).

Tanaka, T. et al., "Chemokines in Tumor Progression and Metastasis," *Cancer Sci.*, 96:317-22 (2005).

Tatusova, T.A. et al., "Blast 2 Sequences, a New Tool for Comparing Protein and Nucleotide Sequences," *FEMS Microbiol. Ltrs.*, 174:247-50 (1999).

Verhoeyen, M. et al., "Engineering of Antibodies," *BioEssays*, 8:74-78 (1988).

Verhoeyen, M. et al., "Reshaping Human Antibodies: Grafting an Antilysozyme Activity," *Science*, 239:1534-36 (1988).

Wang, J. et al., "Dimerization of Chemokine Receptors in Living Cells: Key to Receptor Function and Novel Targets for Therapy," *Drug Discov. Today*, 13:625-32 (2008).

Wang, J. et al., "Dimerization of CXCR4 in Living Malignant Cells: Control of Cell Migration by a Synthetic Peptide that Reduces Homologous CXCR4 Interactions," *Mol. Canc. Ther.*, 5:2474-83 (2006).

Wurch, T. et al. "G-Protein Activation by Putative Antagonists at Mutant $Thr^{373}Lys$ $\alpha_{2A}$ Adrenergic Receptors," *Brit. J. Pharm.*, 126:939-48 (1999).

Zlotnik, A. et al., "Chemokines: A New Classification System and Their role in Immunity," *Immunity*, 12:121-27 (2000).

\* cited by examiner

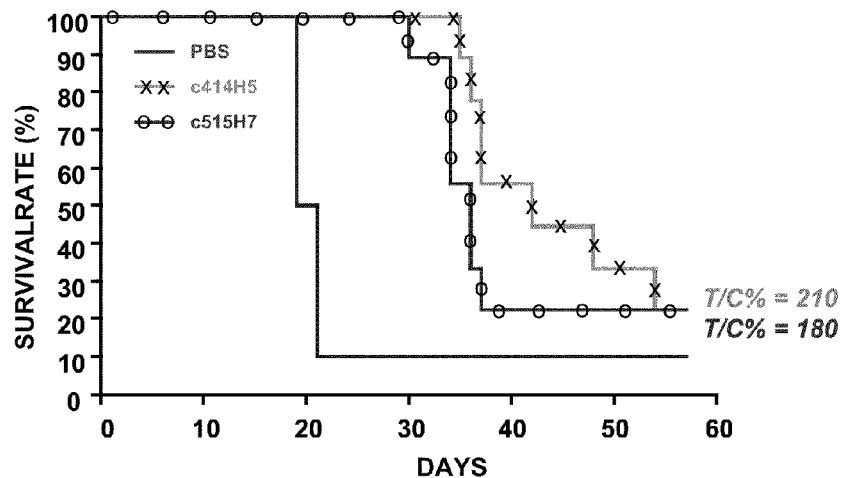

Figure 23

```
                       FR1-IMGT              CDR1-IMGT        FR2-IMGT            CDR2-IMGT
                       (1-26)                (27-38)          (39-55)             (56-65)

1        10        20           30             40        50          60
              ....|....|....|....|......   ...|........   .|........|.....    ....|.....
515H7 VH      EVNLVESGG.GLVQPGSSLRLSCATS   GFTF....TDNY   MSWVRQPPGKALEWLGF    IRNKANGYTT
IGHV3-49*04   EVQLVESGG.GLVQPGRSLRLSCTAS   GFTF....GDYA   MSWVRQAPGKGLEWVGF    IRSKAYGGTT
                N                G          AT               P    A  L
Priority        2                3          33               3    3  1

VH1           EVQLVESGG.GLVQPGRSLRLSCTAS   GFTF....TDNY   MSWVRQAPGKGLEWVGF    IRNKANGYTT
VH2           EVNLVESGG.GLVQPGRSLRLSCTAS   GFTF....TDNY   MSWVRQAPGKGLEWLGF    IRNKANGYTT

FR3-IMGT                           CDR3-IMGT    FR4-IMGT
                         (66-104)                           (105-115)    (116-125)

70         80         90        100
              ....|........|........|........|....
515H7 VH      DYSASVR.GRFTTSRDNSQSTLYLQMNALRAEDSATYYC   ARDVGSNYFDYW     GQGTTLTVSS
IGHV3-49*04   EYAASVK.GRFTTSRDDSKSTAYLQMNSLKTEDTAVYYC   TR
IGHJ4*01                                                YFDYW            GQGTLVTVSS
                D S   R         N Q   L       A RA  S T                   T
Priority        1 3   1         1 3   1       2 23  3 3                   3

VH1           EYAASVK.GRFTISRDDSKSIAYLQMNSLKTEDTAVYYC   ARDVGSNYFDYW     GQGTLVTVSS
VH2           DYAASVR.GRFTISRDNSKSTLYLQMNALRTEDTAVYYC   ARDVGSNYFDYW     GQGTLVTVSS
```

Figure 24

```
                        FR1-IMGT              CDR1-IMGT          FR2-IMGT           CDR2-IMGT
                         (1-26)                (27-38)           (39-55)             (56-65)

1        10        20          30              40        50            60
                  ....|....|....|....|....     ...|........      .|........|....      ....|....
515H7 VL          DIVMSQSPSSLAVSAGEKVIMSCKSS   QSLFNSRTRKNY      LAWYQQKPGQSPKLLIY    WA.......S
IGKV4-1*01        DIVMTQSPDSLAVSLGERATINCKSS   QSVLYSSNNKNY      LAWYQQKPGQPPKLLIY    WA.......S
                       S  S      A  KV MS                                  S
Priority               3  2      3  33 22                                  2

VL1               DIVMTQSPDSLAVSLGERATINCKSS   QSLFNSRTRKNY      LAWYQQKPGQPPKLLIY    WA.......S
VL3               DIVMTQSPDSLAVSLGERATINCKSS   QSLFNSRTRKNY      LAWYQQKPGQPPKLLIY    WA.......S
VL2               DIVMTQSPSSLAVSLGERATMSCKSS   QSLFNSRTRKNY      LAWYQQKPGQSPKLLIY    WA.......S

FR3-IMGT                         CDR3-IMGT   FR4-IMGT
                       (66-104)                         (106-113)   (114-123)

70        80        90        100
                  ....|....|....|....|....|....|....|....
515H7 VL          ARDSGVP.ARFTGSG..SETYFLTISRVQAEDLAVYYC   MQSFNLRT    FGGGTKLEK
IGKV4-1*01        TRESGVP.DRFSGSG..SGTDFTLTISSLQAEDVAVYYC  
IGKJ1*01                                                              WT FGQGTKVEIK
                   A D     A T       E Y      RV    L
Priority           1 1     2 1       1 1      22    2

VL1               TRESGVP.DRFSGSG..SGTDFTLTISSLQAEDVAVYYC  MQSFNLRT    FGQGTKVEIK
VL3               ARDSGVP.DRFTGSG..SETYFLT SSLQAEDVAVYYC   MQSFNLRT    FGQGTKVEIK
VL2               ARDSGVP.ARFTGSG..SETYFLTISRVQAEDLAVYYC   MQSFNLRT    FGQGTKVEIK
```

Figure 25

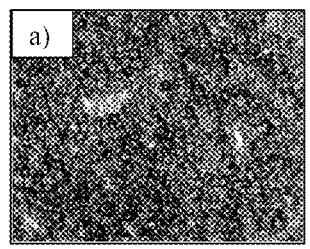
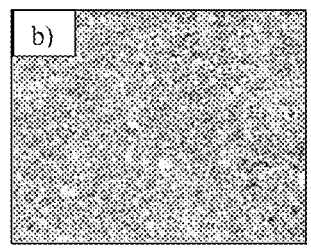
Figure 36A  Figure 36B
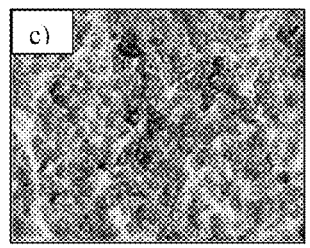
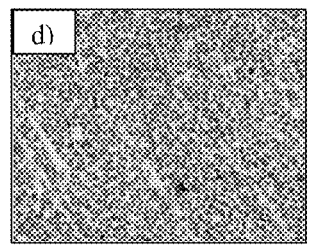
Figure 36C  Figure 36D
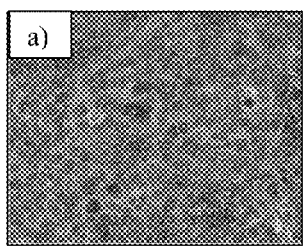
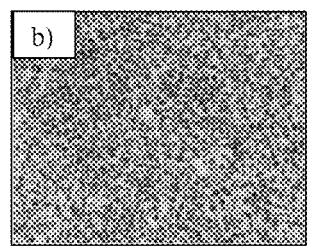
Figure 37A  Figure 37B
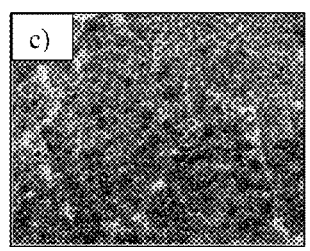
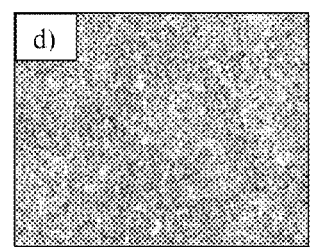
Figure 37C  Figure 37D

SEQUENCE LISTING

<160> NUMBER OF SEQ ID NOS: 124

<210> SEQ ID NO 1
<211> LENGTH: 12
<212> TYPE: PRT
<213> ORGANISM: mus musculus

-continued

```
<400> SEQUENCE: 1

Gln Ser Leu Tyr Asn Ser Arg Thr Arg Lys Asn Tyr
1               5                   10

<210> SEQ ID NO 2
<211> LENGTH: 3
<212> TYPE: PRT
<213> ORGANISM: mus musculus

<400> SEQUENCE: 2

Trp Ala Ser
1

<210> SEQ ID NO 3
<211> LENGTH: 8
<212> TYPE: PRT
<213> ORGANISM: mus musculus

<400> SEQUENCE: 3

Lys Gln Ser Tyr Asn Leu Arg Thr
1               5

<210> SEQ ID NO 4
<211> LENGTH: 4
<212> TYPE: PRT
<213> ORGANISM: mus musculus

<400> SEQUENCE: 4

Thr Asp Tyr Tyr
1

<210> SEQ ID NO 5
<211> LENGTH: 10
<212> TYPE: PRT
<213> ORGANISM: mus musculus

<400> SEQUENCE: 5

Ile Arg Asn Lys Ala Asn Gly Tyr Thr Thr
1               5                   10

<210> SEQ ID NO 6
<211> LENGTH: 7
<212> TYPE: PRT
<213> ORGANISM: mus musculus

<400> SEQUENCE: 6

Asp Ile Pro Gly Phe Ala Tyr
1               5

<210> SEQ ID NO 7
<211> LENGTH: 8
<212> TYPE: PRT
<213> ORGANISM: mus musculus

<400> SEQUENCE: 7

Gly Phe Thr Phe Thr Asp Tyr Tyr
1               5

<210> SEQ ID NO 8
<211> LENGTH: 9
<212> TYPE: PRT
<213> ORGANISM: mus musculus

<400> SEQUENCE: 8

Ala Arg Asp Ile Pro Gly Phe Ala Tyr
```

<210> SEQ ID NO 9
<211> LENGTH: 16
<212> TYPE: PRT
<213> ORGANISM: mus musculus

<400> SEQUENCE: 9

Lys Ser Ser Gln Ser Leu Tyr Asn Ser Arg Thr Arg Lys Asn Tyr Leu
1               5                   10                  15

<210> SEQ ID NO 10
<211> LENGTH: 7
<212> TYPE: PRT
<213> ORGANISM: mus musculus

<400> SEQUENCE: 10

Trp Ala Ser Thr Arg Glu Ser
1               5

<210> SEQ ID NO 11
<211> LENGTH: 6
<212> TYPE: PRT
<213> ORGANISM: mus musculus

<400> SEQUENCE: 11

Thr Asp Tyr Tyr Met Ser
1               5

<210> SEQ ID NO 12
<211> LENGTH: 19
<212> TYPE: PRT
<213> ORGANISM: mus musculus

<400> SEQUENCE: 12

Phe Ile Arg Asn Lys Ala Asn Gly Tyr Thr Thr Glu Tyr Ser Ala Ser
1               5                   10                  15

Val Lys Gly

<210> SEQ ID NO 13
<211> LENGTH: 112
<212> TYPE: PRT
<213> ORGANISM: mus musculus

<400> SEQUENCE: 13

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Tyr Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Thr Ser Val Gln Ala Glu Asp Leu Ala Val Phe Tyr Cys Lys Gln
                85                  90                  95

Ser Tyr Asn Leu Arg Thr Phe Gly Gly Gly Thr Lys Leu Glu Ile Lys
            100                 105                 110

<210> SEQ ID NO 14
<211> LENGTH: 118

```
<212> TYPE: PRT
<213> ORGANISM: mus musculus

<400> SEQUENCE: 14

Glu Val Lys Leu Val Glu Ser Gly Gly Gly Leu Val Gln Pro Gly Gly
1               5                   10                  15

Ser Leu Arg Leu Ser Cys Thr Thr Ser Gly Phe Thr Phe Thr Asp Tyr
            20                  25                  30

Tyr Met Ser Trp Val Arg Gln Ser Pro Gly Lys Ala Leu Glu Trp Leu
        35                  40                  45

Thr Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Ala Arg Asp Ile Pro Gly Phe Ala Tyr Trp Gly Gln Gly Thr
            100                 105                 110

Leu Val Thr Val Ser Ala
        115

<210> SEQ ID NO 15
<211> LENGTH: 36
<212> TYPE: DNA
<213> ORGANISM: mus musculus

<400> SEQUENCE: 15
cagagtctgt acaacagtag aacccgaaag aactac                              36

<210> SEQ ID NO 16
<211> LENGTH: 9
<212> TYPE: DNA
<213> ORGANISM: mus musculus

<400> SEQUENCE: 16 tgggcatcc                                                             9

<210> SEQ ID NO 17
<211> LENGTH: 24
<212> TYPE: DNA
<213> ORGANISM: mus musculus

<400> SEQUENCE: 17
aagcaatctt ataatcttcg gacg                                           24

<210> SEQ ID NO 18
<211> LENGTH: 12
<212> TYPE: DNA
<213> ORGANISM: mus musculus

<400> SEQUENCE: 18
actgattact ac                                                        12

<210> SEQ ID NO 19
<211> LENGTH: 30
<212> TYPE: DNA
<213> ORGANISM: mus musculus

<400> SEQUENCE: 19
attagaaaca agctaatgg ttacacaaca                                      30
```

```
<210> SEQ ID NO 20
<211> LENGTH: 21
<212> TYPE: DNA
<213> ORGANISM: mus musculus

<400> SEQUENCE: 20
gatatcccgg ggtttgctta c                                              21

<210> SEQ ID NO 21
<211> LENGTH: 24
<212> TYPE: DNA
<213> ORGANISM: mus musculus

<400> SEQUENCE: 21
gggttcacct tcactgatta ctac                                           24

<210> SEQ ID NO 22
<211> LENGTH: 27
<212> TYPE: DNA
<213> ORGANISM: mus musculus

<400> SEQUENCE: 22
gcaagagata tcccggggtt tgcttac                                        27

<210> SEQ ID NO 23
<211> LENGTH: 51
<212> TYPE: DNA
<213> ORGANISM: mus musculus

<400> SEQUENCE: 23
aaatccagtc agagtctgta caacagtaga acccgaaaga actacttggc t             51

<210> SEQ ID NO 24
<211> LENGTH: 21
<212> TYPE: DNA
<213> ORGANISM: mus musculus

<400> SEQUENCE: 24
tgggcatcca ctagggaatc t                                              21

<210> SEQ ID NO 25
<211> LENGTH: 18
<212> TYPE: DNA
<213> ORGANISM: mus musculus

<400> SEQUENCE: 25
actgattact acatgagc                                                  18

<210> SEQ ID NO 26
<211> LENGTH: 57
<212> TYPE: DNA
<213> ORGANISM: mus musculus

<400> SEQUENCE: 26
tttattagaa acaaagctaa tggttacaca acagagtaca gtgcatctgt gaagggt       57

<210> SEQ ID NO 27
<211> LENGTH: 336
<212> TYPE: DNA
<213> ORGANISM: mus musculus

<400> SEQUENCE: 27
gacattgtga tgtcacagtc tccatcctcc ctggctgtgt cagcaggaga gaaggtcact    60
atgagctgca aatccagtca gagtctgtac aacagtagaa cccgaaagaa ctacttggct   120
```

```
tggtaccagc agaaaccagg gcagtctcct aaactgctga tctactgggc atccactagg    180
gaatctgggg tccctgatcg cttcacaggc agtggatctg ggacagattt cactctcacc    240
atcaccagtg tgcaggctga ggacctggca gttttttact gcaagcaatc ttataatctt    300
cggacgttcg gtggaggcac caagctggaa atcaaa                              336
```

<210> SEQ ID NO 28
<211> LENGTH: 354
<212> TYPE: DNA
<213> ORGANISM: mus musculus

<400> SEQUENCE: 28

```
gaggtgaagc tggtggagtc tggaggaggc ttggtacagc ctgggggttc tctgagactc     60
tcctgtacaa cttctgggtt caccttcact gattactaca tgagctgggt ccgccagtct    120
ccaggaaagg cacttgagtg gttgactttt attagaaaca aagctaatgg ttacacaaca    180
gagtacagtg catctgtgaa gggtcggttc accatctcca gagataattc ccaaagcatc    240
ctctatcttc aaatgaacac cctgagagct gaggacagtg ccacttatta ctgtgcaaga    300
gatatcccgg ggtttgctta ctggggccaa gggactctgg tcactgtctc tgca           354
```

<210> SEQ ID NO 29
<211> LENGTH: 352
<212> TYPE: PRT
<213> ORGANISM: Mus musculus

<400> SEQUENCE: 29

```
Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
            20                  25                  30

Asn Ala Asn Phe Asn Lys Ile Phe Leu Pro Thr Ile Tyr Ser Ile Ile
        35                  40                  45

Phe Leu Thr Gly Ile Val Gly Asn Gly Leu Val Ile Leu Val Met Gly
    50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
            100                 105                 110

His Val Ile Tyr Thr Val Asn Leu Tyr Ser Ser Val Leu Ile Leu Ala
        115                 120                 125

Phe Ile Ser Leu Asp Arg Tyr Leu Ala Ile Val His Ala Thr Asn Ser
    130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
            180                 185                 190

Asp Leu Trp Val Val Phe Gln Phe Gln His Ile Met Val Gly Leu
        195                 200                 205

Ile Leu Pro Gly Ile Val Ile Leu Ser Cys Tyr Cys Ile Ile Ile Ser
    210                 215                 220

Lys Leu Ser His Ser Lys Gly His Gln Lys Arg Lys Ala Leu Lys Thr
```

```
            225                 230                 235                 240
Thr Val Ile Leu Ile Leu Ala Phe Phe Ala Cys Trp Leu Pro Tyr Tyr
                    245                 250                 255

Ile Gly Ile Ser Ile Asp Ser Phe Ile Leu Leu Glu Ile Ile Lys Gln
                    260                 265                 270

Gly Cys Glu Phe Glu Asn Thr Val His Lys Trp Ile Ser Ile Thr Glu
                    275                 280                 285

Ala Leu Ala Phe Phe His Cys Cys Leu Asn Pro Ile Leu Tyr Ala Phe
                    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                    325                 330                 335

His Ser Ser Val Ser Thr Glu Ser Glu Ser Ser Ser Phe His Ser Ser
                    340                 345                 350

<210> SEQ ID NO 30
<211> LENGTH: 356
<212> TYPE: PRT
<213> ORGANISM: Mus musculus

<400> SEQUENCE: 30

Met Ser Ile Pro Leu Pro Leu Leu Gln Ile Tyr Thr Ser Asp Asn Tyr
1               5                   10                  15

Thr Glu Glu Met Gly Ser Gly Asp Tyr Asp Ser Met Lys Glu Pro Cys
                    20                  25                  30

Phe Arg Glu Glu Asn Ala Asn Phe Asn Lys Ile Phe Leu Pro Thr Ile
                    35                  40                  45

Tyr Ser Ile Ile Phe Leu Thr Gly Ile Val Gly Asn Gly Leu Val Ile
                    50                  55                  60

Leu Val Met Gly Tyr Gln Lys Lys Leu Arg Ser Met Thr Asp Lys Tyr
65                  70                  75                  80

Arg Leu His Leu Ser Val Ala Asp Leu Leu Phe Val Ile Thr Leu Pro
                    85                  90                  95

Phe Trp Ala Val Asp Ala Val Ala Asn Trp Tyr Phe Gly Asn Phe Leu
                    100                 105                 110

Cys Lys Ala Val His Val Ile Tyr Thr Val Asn Leu Tyr Ser Ser Val
                    115                 120                 125

Leu Ile Leu Ala Phe Ile Ser Leu Asp Arg Tyr Leu Ala Ile Val His
                    130                 135                 140

Ala Thr Asn Ser Gln Arg Pro Arg Lys Leu Leu Ala Glu Lys Val Val
145                 150                 155                 160

Tyr Val Gly Val Trp Ile Pro Ala Leu Leu Leu Thr Ile Pro Asp Phe
                    165                 170                 175

Ile Phe Ala Asn Val Ser Glu Ala Asp Asp Arg Tyr Ile Cys Asp Arg
                    180                 185                 190

Phe Tyr Pro Asn Asp Leu Trp Val Val Val Phe Gln Phe Gln His Ile
                    195                 200                 205

Met Val Gly Leu Ile Leu Pro Gly Ile Val Ile Leu Ser Cys Tyr Cys
                    210                 215                 220

Ile Ile Ile Ser Lys Leu Ser His Ser Lys Gly His Gln Lys Arg Lys
225                 230                 235                 240

Ala Leu Lys Thr Thr Val Ile Leu Ile Leu Ala Phe Phe Ala Cys Trp
                    245                 250                 255

Leu Pro Tyr Tyr Ile Gly Ile Ser Ile Asp Ser Phe Ile Leu Leu Glu
```

```
                  260                 265                 270
Ile Ile Lys Gln Gly Cys Glu Phe Glu Asn Thr Val His Lys Trp Ile
            275                 280                 285
Ser Ile Thr Glu Ala Leu Ala Phe Phe His Cys Cys Leu Asn Pro Ile
        290                 295                 300
Leu Tyr Ala Phe Leu Gly Ala Lys Phe Lys Thr Ser Ala Gln His Ala
305                 310                 315                 320
Leu Thr Ser Val Ser Arg Gly Ser Ser Leu Lys Ile Leu Ser Lys Gly
            325                 330                 335
Lys Arg Gly Gly His Ser Ser Val Ser Thr Glu Ser Glu Ser Ser Ser
            340                 345                 350
Phe His Ser Ser
        355

<210> SEQ ID NO 31
<211> LENGTH: 360
<212> TYPE: PRT
<213> ORGANISM: Mus musculus

<400> SEQUENCE: 31

Met Glu Asp Phe Asn Met Glu Ser Asp Ser Phe Glu Asp Phe Trp Lys
1               5                   10                  15
Gly Glu Asp Leu Ser Asn Tyr Ser Tyr Ser Ser Thr Leu Pro Pro Phe
            20                  25                  30
Leu Leu Asp Ala Ala Pro Cys Glu Pro Glu Ser Leu Glu Ile Asn Lys
        35                  40                  45
Tyr Phe Val Val Ile Ile Tyr Ala Leu Val Phe Leu Leu Ser Leu Leu
    50                  55                  60
Gly Asn Ser Leu Val Met Leu Val Ile Leu Tyr Ser Arg Val Gly Arg
65                  70                  75                  80
Ser Val Thr Asp Val Tyr Leu Leu Asn Leu Ala Leu Ala Asp Leu Leu
                85                  90                  95
Phe Ala Leu Thr Leu Pro Ile Trp Ala Ala Ser Lys Val Asn Gly Trp
            100                 105                 110
Ile Phe Gly Thr Phe Leu Cys Lys Val Val Ser Leu Leu Lys Glu Val
        115                 120                 125
Asn Phe Tyr Ser Gly Ile Leu Leu Leu Ala Cys Ile Ser Val Asp Arg
    130                 135                 140
Tyr Leu Ala Ile Val His Ala Thr Arg Thr Leu Thr Gln Lys Arg Tyr
145                 150                 155                 160
Leu Val Lys Phe Ile Cys Leu Ser Ile Trp Gly Leu Ser Leu Leu Leu
                165                 170                 175
Ala Leu Pro Val Leu Leu Phe Arg Arg Thr Val Tyr Ser Ser Asn Val
            180                 185                 190
Ser Pro Ala Cys Tyr Glu Asp Met Gly Asn Asn Thr Ala Asn Trp Arg
        195                 200                 205
Met Leu Leu Arg Ile Leu Pro Gln Ser Phe Gly Phe Ile Val Pro Leu
    210                 215                 220
Leu Ile Met Leu Phe Cys Tyr Gly Phe Thr Leu Arg Thr Leu Phe Lys
225                 230                 235                 240
Ala His Met Gly Gln Lys His Arg Ala Met Arg Val Ile Phe Ala Val
                245                 250                 255
Val Leu Ile Phe Leu Leu Cys Trp Leu Pro Tyr Asn Leu Val Leu Leu
            260                 265                 270
Ala Asp Thr Leu Met Arg Thr Gln Val Ile Gln Glu Thr Cys Glu Arg
```

|  |  |  | 275 |  |  |  | 280 |  |  |  | 285 |  |

Arg Asn His Ile Asp Arg Ala Leu Asp Ala Thr Glu Ile Leu Gly Ile
290 295 300

Leu His Ser Cys Leu Asn Pro Leu Ile Tyr Ala Phe Ile Gly Gln Lys
305 310 315 320

Phe Arg His Gly Leu Leu Lys Ile Leu Ala Ile His Gly Leu Ile Ser
325 330 335

Lys Asp Ser Leu Pro Lys Asp Ser Arg Pro Ser Phe Val Gly Ser Ser
340 345 350

Ser Gly His Thr Ser Thr Thr Leu
355 360

<210> SEQ ID NO 32
<211> LENGTH: 24
<212> TYPE: DNA
<213> ORGANISM: Mus musculus

<400> SEQUENCE: 32
gaaactctgc attctcgctt cctg                                          24

<210> SEQ ID NO 33
<211> LENGTH: 22
<212> TYPE: DNA
<213> ORGANISM: Mus musculus

<400> SEQUENCE: 33
aggactcgtt tgtacccgtt ga                                            22

<210> SEQ ID NO 34
<211> LENGTH: 26
<212> TYPE: DNA
<213> ORGANISM: Mus musculus

<400> SEQUENCE: 34
tgcagattgg ctacccaact gttgca                                        26

<210> SEQ ID NO 35
<211> LENGTH: 22
<212> TYPE: DNA
<213> ORGANISM: Mus musculus

<400> SEQUENCE: 35
ctccttcatc ctcctggaaa tc                                            22

<210> SEQ ID NO 36
<211> LENGTH: 22
<212> TYPE: DNA
<213> ORGANISM: Mus musculus

<400> SEQUENCE: 36
ccaaggaaag catagaggat gg                                            22

<210> SEQ ID NO 37
<211> LENGTH: 22
<212> TYPE: DNA
<213> ORGANISM: Mus musculus

<400> SEQUENCE: 37
gtggtcatta tctatgccct gg                                            22

<210> SEQ ID NO 38
<211> LENGTH: 22

```
<212> TYPE: DNA
<213> ORGANISM: Mus musculus

<400> SEQUENCE: 38
cgaccctgct gtataagatg ac                                          22

<210> SEQ ID NO 39
<211> LENGTH: 25
<212> TYPE: DNA
<213> ORGANISM: Mus musculus

<400> SEQUENCE: 39
tattcctgct gagcctgctg ggaaa                                       25

<210> SEQ ID NO 40
<211> LENGTH: 12
<212> TYPE: PRT
<213> ORGANISM: Mus musculus

<400> SEQUENCE: 40

Gln Ser Leu Phe Asn Ser Arg Thr Arg Lys Asn Tyr
1               5                   10

<210> SEQ ID NO 41
<211> LENGTH: 8
<212> TYPE: PRT
<213> ORGANISM: Mus musculus

<400> SEQUENCE: 41

Met Gln Ser Phe Asn Leu Arg Thr
1               5

<210> SEQ ID NO 42
<211> LENGTH: 3
<212> TYPE: PRT
<213> ORGANISM: Mus musculus

<400> SEQUENCE: 42

Asp Asn Tyr
1

<210> SEQ ID NO 43
<211> LENGTH: 9
<212> TYPE: PRT
<213> ORGANISM: Mus musculus

<400> SEQUENCE: 43

Asp Val Gly Ser Asn Tyr Phe Asp Tyr
1               5

<210> SEQ ID NO 44
<211> LENGTH: 8
<212> TYPE: PRT
<213> ORGANISM: Mus musculus

<400> SEQUENCE: 44

Gly Phe Thr Phe Thr Asp Asn Tyr
1               5

<210> SEQ ID NO 45
<211> LENGTH: 11
<212> TYPE: PRT
<213> ORGANISM: Mus musculus

<400> SEQUENCE: 45
```

Ala Arg Asp Val Gly Ser Asn Tyr Phe Asp Tyr
1               5                   10

<210> SEQ ID NO 46
<211> LENGTH: 17
<212> TYPE: PRT
<213> ORGANISM: Mus musculus

<400> SEQUENCE: 46

Lys Ser Ser Gln Ser Leu Phe Asn Ser Arg Thr Arg Lys Asn Tyr Leu
1               5                   10                  15

Ala

<210> SEQ ID NO 47
<211> LENGTH: 7
<212> TYPE: PRT
<213> ORGANISM: Mus musculus

<400> SEQUENCE: 47

Trp Ala Ser Ala Arg Asp Ser
1               5

<210> SEQ ID NO 48
<211> LENGTH: 5
<212> TYPE: PRT
<213> ORGANISM: Mus musculus

<400> SEQUENCE: 48

Asp Asn Tyr Met Ser
1               5

<210> SEQ ID NO 49
<211> LENGTH: 19
<212> TYPE: PRT
<213> ORGANISM: Mus musculus

<400> SEQUENCE: 49

Phe Ile Arg Asn Lys Ala Asn Gly Tyr Thr Thr Asp Tyr Ser Ala Ser
1               5                   10                  15

Val Arg Gly

<210> SEQ ID NO 50
<211> LENGTH: 112
<212> TYPE: PRT
<213> ORGANISM: Mus musculus

<400> SEQUENCE: 50

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Phe Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Ala Arg Asp Ser Gly Val
        50                  55                  60

Pro Ala Arg Phe Thr Gly Ser Gly Ser Glu Tyr Phe Thr Leu Thr
65                  70                  75                  80

Ile Ser Arg Val Gln Ala Glu Asp Leu Ala Val Tyr Tyr Cys Met Gln
                85                  90                  95

Ser Phe Asn Leu Arg Thr Phe Gly Gly Gly Thr Lys Leu Glu Ile Lys
                100                 105                 110

-continued

```
<210> SEQ ID NO 51
<211> LENGTH: 142
<212> TYPE: PRT
<213> ORGANISM: Mus musculus

<400> SEQUENCE: 51
```

Glu Val Asn Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Asn
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Asp Tyr Ser Ala
    50                  55                  60

Ser Val Arg Gly Arg Phe Thr Ile Ser Arg Asp Asn Ser Gln Ser Ile
65                  70                  75                  80

Leu Tyr Leu Gln Met Asn Ala Leu Arg Ala Glu Asp Ser Ala Thr Tyr
                85                  90                  95

Tyr Cys Ala Arg Asp Val Gly Ser Asn Tyr Phe Asp Tyr Trp Gly Gln
            100                 105                 110

Gly Thr Thr Leu Thr Val Ser Ser Ala Lys Thr Thr Pro Pro Ser Val
        115                 120                 125

Tyr Pro Leu Ala Pro Gly Cys Gly Asp Thr Thr Gly Ser Ser
    130                 135                 140

```
<210> SEQ ID NO 52
<211> LENGTH: 36
<212> TYPE: DNA
<213> ORGANISM: Mus musculus

<400> SEQUENCE: 52
cagagtctgt tcaacagtcg aacccgaaag aactac                         36

<210> SEQ ID NO 53
<211> LENGTH: 24
<212> TYPE: DNA
<213> ORGANISM: Mus musculus

<400> SEQUENCE: 53
atgcaatctt ttaatcttcg gacg                                      24

<210> SEQ ID NO 54
<211> LENGTH: 9
<212> TYPE: DNA
<213> ORGANISM: Mus musculus

<400> SEQUENCE: 54 gataactac                                                        9

<210> SEQ ID NO 55
<211> LENGTH: 27
<212> TYPE: DNA
<213> ORGANISM: Mus musculus

<400> SEQUENCE: 55
gatgtcggtt ccaactactt tgactac                                   27

<210> SEQ ID NO 56
<211> LENGTH: 24
<212> TYPE: DNA
<213> ORGANISM: Mus musculus
```

<210> SEQ ID NO 57
<211> LENGTH: 33
<212> TYPE: DNA
<213> ORGANISM: Mus musculus

<400> SEQUENCE: 57
gcaagagatg tcggttccaa ctactttgac tac         33

<210> SEQ ID NO 58
<211> LENGTH: 51
<212> TYPE: DNA
<213> ORGANISM: Mus musculus

<400> SEQUENCE: 58
aaatccagtc agagtctgtt caacagtcga acccgaaaga actacttggc t      51

<210> SEQ ID NO 59
<211> LENGTH: 21
<212> TYPE: DNA
<213> ORGANISM: Mus musculus

<400> SEQUENCE: 59
tgggcatccg ctagggattc t         21

<210> SEQ ID NO 60
<211> LENGTH: 15
<212> TYPE: DNA
<213> ORGANISM: Mus musculus

<400> SEQUENCE: 60
gataactaca tgagt         15

<210> SEQ ID NO 61
<211> LENGTH: 57
<212> TYPE: DNA
<213> ORGANISM: Mus musculus

<400> SEQUENCE: 61
tttattagaa acaaagctaa tggttacaca acagactaca gtgcatctgt gagggt      57

<210> SEQ ID NO 62
<211> LENGTH: 336
<212> TYPE: DNA
<213> ORGANISM: Mus musculus

<400> SEQUENCE: 62
gacattgtga tgtcacagtc tccatcctcc ctggctgtgt cagcaggaga gaaggtcact      60
atgagctgca aatccagtca gagtctgttc aacagtcgaa cccgaaagaa ctacttggct     120
tggtaccagc agaagccagg gcagtctcct aaactgctga tctactgggc atccgctagg     180
gattctgggg tccctgctcg cttcacaggc agtggatctg agacatattt cactctcacc     240
atcagccgtg tgcaggctga agacctggca gtttattact gcatgcaatc ttttaatctt     300
cggacgttcg gtggaggcac caagctggaa atcaaa                              336

<210> SEQ ID NO 63
<211> LENGTH: 424
<212> TYPE: DNA
<213> ORGANISM: Mus musculus

<400> SEQUENCE: 56
gggttcacct tcactgataa ctac         24

<400> SEQUENCE: 63

```
gaggtgaacc tggtggagtc tggaggaggc ttggtacagc ctgggggttc tctgagactc    60
tcctgtgcaa cttctgggtt caccttcact gataactaca tgagttgggt ccgccagcct   120
ccaggaaagg cacttgagtg gttgggcttt attagaaaca aagctaatgg ttacacaaca   180
gactacagtg catctgtgag gggtcggttc accatctcaa gagataattc ccaaagcatc   240
ctctatcttc aaatgaacgc cctgagagcc gaagacagtg ccacttatta ctgtgcaaga   300
gatgtcggtt ccaactactt tgactactgg ccaaggcacc actctcacag tctcctcagc   360
caaaacaaca cccccatcag tctatccact ggcccctggg tgtggagata caactggttc   420
ctcc                                                                 424
```

<210> SEQ ID NO 64
<211> LENGTH: 239
<212> TYPE: PRT
<213> ORGANISM: mus musculus

<400> SEQUENCE: 64

```
Met Glu Ser Gln Ala Gln Val Leu Ile Leu Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Tyr Asn Ser Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Thr Ser Val Gln Ala Glu Asp Leu Ala Val Phe
            100                 105                 110

Tyr Cys Lys Gln Ser Tyr Asn Leu Arg Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 65
<211> LENGTH: 467
<212> TYPE: PRT
<213> ORGANISM: mus musculus

<400> SEQUENCE: 65

-continued

```
Met Lys Leu Trp Leu Asn Trp Val Phe Leu Val Thr Leu Asn Gly
 1               5                  10                  15

Phe Gln Cys Glu Val Lys Leu Val Glu Ser Gly Gly Gly Leu Val Gln
            20                  25                  30

Pro Gly Gly Ser Leu Arg Leu Ser Cys Thr Thr Ser Gly Phe Thr Phe
            35                  40                  45

Thr Asp Tyr Tyr Met Ser Trp Val Arg Gln Ser Pro Gly Lys Ala Leu
            50                  55                  60

Glu Trp Leu Thr Phe Ile Arg Asn Lys Ala Asn Gly Tyr Thr Thr Glu
 65                  70                  75                  80

Tyr Ser Ala Ser Val Lys Gly Arg Phe Thr Ile Ser Arg Asp Asn Ser
                 85                  90                  95

Gln Ser Ile Leu Tyr Leu Gln Met Asn Thr Leu Arg Ala Glu Asp Ser
            100                 105                 110

Ala Thr Tyr Tyr Cys Ala Arg Asp Ile Pro Gly Phe Ala Tyr Trp Gly
            115                 120                 125

Gln Gly Thr Leu Val Thr Val Ser Ala Ala Ser Thr Lys Gly Pro Ser
            130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
            290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Tyr Lys Thr Thr Pro Pro
                405                 410                 415

Val Leu Asp Ser Asp Gly Ser Phe Phe Leu Tyr Ser Lys Leu Thr Val
            420                 425                 430
```

Asp Lys Ser Arg Trp Gln Gln Gly Asn Val Phe Ser Cys Ser Val Met
          435                 440                 445

His Glu Ala Leu His Asn His Tyr Thr Gln Lys Ser Leu Ser Leu Ser
        450                 455                 460

Pro Gly Lys
465

<210> SEQ ID NO 66
<211> LENGTH: 239
<212> TYPE: PRT
<213> ORGANISM: mus musculus

<400> SEQUENCE: 66

Met Glu Ser Gln Thr Leu Val Phe Ile Ser Ile Leu Leu Trp Leu Tyr
1               5                   10                  15

Gly Thr Cys Gly Asp Ile Val Met Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Phe Asn Ser Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Ala Arg
65                  70                  75                  80

Asp Ser Gly Val Pro Ala Arg Phe Thr Gly Ser Gly Ser Glu Thr Tyr
                85                  90                  95

Phe Thr Leu Thr Ile Ser Arg Val Gln Ala Glu Asp Leu Ala Val Tyr
            100                 105                 110

Tyr Cys Met Gln Ser Phe Asn Leu Arg Thr Phe Gly Gly Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 67
<211> LENGTH: 469
<212> TYPE: PRT
<213> ORGANISM: mus musculus

<400> SEQUENCE: 67

Met Lys Met Trp Leu Asn Trp Val Phe Leu Val Thr Leu Leu Asn Gly
1               5                   10                  15

Ile Gln Cys Glu Val Asn Leu Val Glu Ser Gly Gly Gly Leu Val Gln
            20                  25                  30

Pro Gly Gly Ser Leu Arg Leu Ser Cys Ala Thr Ser Gly Phe Thr Phe
        35                  40                  45

```
Thr Asp Asn Tyr Met Ser Trp Val Arg Gln Pro Pro Gly Lys Ala Leu
    50                  55                  60

Glu Trp Leu Gly Phe Ile Arg Asn Lys Ala Asn Gly Tyr Thr Thr Asp
 65                  70                  75                  80

Tyr Ser Ala Ser Val Arg Gly Arg Phe Thr Ile Ser Arg Asp Asn Ser
                 85                  90                  95

Gln Ser Ile Leu Tyr Leu Gln Met Asn Ala Leu Arg Ala Glu Asp Ser
            100                 105                 110

Ala Thr Tyr Tyr Cys Ala Arg Asp Val Gly Ser Asn Tyr Phe Asp Tyr
            115                 120                 125

Trp Gly Gln Gly Thr Thr Leu Thr Val Ser Ser Ala Ser Thr Lys Gly
        130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465
```

<210> SEQ ID NO 68
<211> LENGTH: 720
<212> TYPE: DNA
<213> ORGANISM: mus musculus

<400> SEQUENCE: 68

```
atggagtcac aggcccaggt tcttatattg ctgctgctat gggtatctgg tacctgtggg      60
gacattgtga tgtcacagtc tccatcctcc ctggctgtgt cagcaggaga gaaggtcact     120
atgagctgca aatccagtca gagtctgtac aacagtagaa cccgaaagaa ctacttggct     180
tggtaccagc agaaaccagg gcagtctcct aaactgctga tctactgggc atccactagg     240
gaatctgggg tccctgatcg cttcacaggc agtggatctg gacagatttc cactctcacc     300
atcaccagtg tgcaggctga ggacctggca gttttttact gcaagcaatc ttataatctt     360
cggacgttcg gtggaggcac caagctggaa atcaaacgta cggtggccgc tcccagcgtg     420
ttcatcttcc ccccaagcga cgagcagctg aagagcggca ccgccagcgt ggtgtgtctg     480
ctgaacaact tctaccccag ggaggccaag gtgcagtgga aggtggacaa cgccctgcag     540
agcggcaaca gccaggagag cgtcaccgag caggacagca aggactccac ctacagcctg     600
agcagcaccc tgaccctgag caaggccgac tacgagaagc acaaggtgta cgcctgtgag     660
gtgacccacc agggcctgtc cagccccgtg accaagagct tcaacagggg cgagtgctga     720
```

<210> SEQ ID NO 69
<211> LENGTH: 1404
<212> TYPE: DNA
<213> ORGANISM: mus musculus

<400> SEQUENCE: 69

```
atgaagctgt ggctgaactg ggtgttcctg gtgaccctgc tgaacggctt ccagtgcgaa      60
gtgaaactgg tggagtctgg cggcggactg gtgcagccag cggcagcct gagactgagc     120
tgcaccacct ccggcttcac cttcaccgac tactacatga gctgggtgcg ccagagcccc     180
ggcaaggccc tggaatggct gaccttcatc cggaacaagg ccaacggcta caccaccgag     240
tacagcgcca gcgtgaaggg ccggttcacc atcagccggg acaacagcca gagcatcctg     300
tacctgcaga tgaacaccct gcgggccgag gactccgcca cctactactg cgccagagac     360
atccccggct tcgcctactg gggccagggc accctggtga ccgtgtccgc cgccagcacc     420
aagggcccaa gcgtgttccc gctagccccc agcagcaaga gcaccagcgg cggcacagcc     480
gccctgggct gcctggtgaa ggactacttc cccgagcccg tgaccgtgtc ctggaacagc     540
ggagccctga cctccggcgt gcacaccttc ccgccgtgc tgcagagcag cggcctgtac     600
agcctgagca gcgtggtgac cgtgcccagc agcagcctgg gcacccagac ctacatctgt     660
aacgtgaacc acaagcccag caacaccaag gtggacaaga gagtggagcc caagagctgt     720
gacaagaccc acacctgccc ccctgcccca gcccccgagc tgctgggcgg acccagcgtg     780
ttcctgttcc cccccaagcc caaggacacc ctgatgatca gcagaacccc cgaggtgacc     840
tgtgtggtgg tggacgtgtc ccacgaggac ccagaggtga agttcaactg gtacgtggac     900
ggcgtggagg tgcacaacgc caagaccaag cccagagagg agcagtacaa cagcacctac     960
agggtggtgt ccgtgctgac cgtgctgcac caggactggc tgaacggcaa ggagtacaag    1020
tgtaaggtgt ccaacaaggc cctgccagcc ccaatcgaaa agaccatcag caaggccaag    1080
ggccagccaa gagagcccca ggtgtacacc ctgccaccca gcaggagga gatgaccaag    1140
aaccaggtgt ccctgacctg tctggtgaag ggcttctacc caagcgacat cgccgtggag    1200
```

```
tgggagagca acggccagcc cgagaacaac tacaagacca ccccccagt gctggacagc    1260 gacggcagct tcttcctgta cagcaagctg accgtggaca agagcagatg gcagcagggc    1320
aacgtgttca gctgctccgt gatgcacgag gccctgcaca accactacac ccagaagagc    1380
ctgagcctgt ccccaggcaa gtga                                            1404

<210> SEQ ID NO 70
<211> LENGTH: 720
<212> TYPE: DNA
<213> ORGANISM: mus musculus

<400> SEQUENCE: 70
atggagtcac agactctggt cttcatatcc atactgctct ggttatatgg tacctgtggg     60
gacattgtga tgtcacagtc tccatcctcc ctggctgtgt cagcaggaga gaaggtcact    120
atgagctgca aatccagtca gagtctgttc aacagtcgaa cccgaaagaa ctacttggct    180
tggtaccagc agaagccagg gcagtctcct aaactgctga tctactgggc atccgctagg    240
gattctgggg tccctgctcg cttcacaggc agtggatctg agacatattt cactctcacc    300
atcagccgtg tgcaggctga agacctggca gtttattact gcatgcaatc ttttaatctt    360
cggacgttcg gtggaggcac caagctggaa atcaaacgta cggtggccgc tcccagcgtg    420
ttcatcttcc ccccaagcga cgagcagctg aagagcggca ccgccagcgt ggtgtgtctg    480
ctgaacaact tctaccccag ggaggccaag gtgcagtgga aggtggacaa cgccctgcag    540
agcggcaaca gccaggagag cgtcaccgag caggacagca aggactccac ctacagcctg    600
agcagcaccc tgaccctgag caaggccgac tacgagaagc acaaggtgta cgcctgtgag    660
gtgacccacc agggcctgtc cagccccgtg accaagagct caacagggg cgagtgctga    720

<210> SEQ ID NO 71
<211> LENGTH: 1410
<212> TYPE: DNA
<213> ORGANISM: mus musculus

<400> SEQUENCE: 71
atgaagatgt ggctgaactg ggtgttcctg gtgaccctgc tgaacggcat ccagtgcgaa     60
gtgaacctgg tggagtctgg cggcggactg gtgcagcctg ggggcagcct gagactgagc    120
tgcgccacct ccggcttcac cttcaccgac aactacatga gctgggtgcg ccagccccct    180
ggcaaggccc tggaatggct gggcttcatc cggaacaagg ccaacggcta caccaccgac    240
tacagcgcca gcgtgcgggg cagattcacc atcagccggg acaacagcca gagcatcctg    300
tacctgcaga tgaacgccct gcgggccgag gacagcgcca cctactactg tgcccgggac    360
gtgggcagca actacttcga ctactgggggc cagggcacca cactgaccgt gtccagcgcc    420
agcaccaagg gcccctccgt gttcccgcta gccccccagca gcaagagcac cagcggcggc    480
acagccgccc tgggctgcct ggtgaaggac tacttccccg agcccgtgac cgtgtcctgg    540
aacagcggag ccctgacctc cggcgtgcac accttccccg ccgtgctgca gagcagcggc    600
ctgtacagcc tgagcagcgt ggtgaccgtg cccagcagca gcctgggcac ccagacctac    660
atctgtaacg tgaaccacaa gcccagcaac accaaggtgg acaagagagt ggagcccaag    720
agctgtgaca gacccacac ctgccccccc tgcccagccc ccgagctgct gggcggaccc    780
agcgtgttcc tgttcccccc caagcccaag gacaccctga tgatcagcag aacccccgag    840
gtgacctgtg tggtggtgga cgtgtcccac gaggacccag aggtgaagtt caactggtac    900
gtggacggcg tggaggtgca caacgccaag accaagccca gagaggagca gtacaacagc    960
```

```
acctacaggg tggtgtccgt gctgaccgtg ctgcaccagg actggctgaa cggcaaggag    1020
tacaagtgta aggtgtccaa caaggccctg ccagccccaa tcgaaaagac catcagcaag    1080
gccaagggcc agccaagaga gccccaggtg tacaccctgc cacccagcag ggaggagatg    1140
accaagaacc aggtgtccct gacctgtctg gtgaagggct tctacccaag cgacatcgcc    1200
gtggagtggg agagcaacgg ccagcccgag aacaactaca agaccacccc cccagtgctg    1260
gacagcgacg gcagcttctt cctgtacagc aagctgaccg tggacaagag cagatggcag    1320
cagggcaacg tgttcagctg ctccgtgatg cacgaggccc tgcacaacca ctacacccag    1380
aagagcctga gcctgtcccc aggcaagtga                                     1410
```

<210> SEQ ID NO 72
<211> LENGTH: 120
<212> TYPE: PRT
<213> ORGANISM: artificial sequence
<220> FEATURE:
<223> OTHER INFORMATION: humanized VH

<400> SEQUENCE: 72

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Asp Asn
            20                  25                  30

Tyr Met Ser Trp Val Arg Gln Ala Pro Gly Lys Gly Leu Glu Trp Val
        35                  40                  45

Gly Phe Ile Arg Asn Lys Ala Asn Gly Tyr Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Arg Asp Val Gly Ser Asn Tyr Phe Asp Tyr Trp Gly Gln
            100                 105                 110

Gly Thr Leu Val Thr Val Ser Ser
        115                 120
```

<210> SEQ ID NO 73
<211> LENGTH: 120
<212> TYPE: PRT
<213> ORGANISM: artificial sequence
<220> FEATURE:
<223> OTHER INFORMATION: humanized VH

<400> SEQUENCE: 73

```
Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Asp Asn
            20                  25                  30

Tyr Met Ser Trp Val Arg Gln Ala Pro Gly Lys Gly Leu Glu Trp Val
        35                  40                  45

Gly Phe Ile Arg Asn Lys Ala Asn Gly Tyr Thr Thr Glu Tyr Ala Ala
    50                  55                  60

Ser Val Lys Gly Arg Phe Thr Ile Ser Arg Asp Asn Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Arg Asp Val Gly Ser Asn Tyr Phe Asp Tyr Trp Gly Gln
```

-continued

```
                100                 105                 110
Gly Thr Leu Val Thr Val Ser Ser
        115                 120

<210> SEQ ID NO 74
<211> LENGTH: 120
<212> TYPE: PRT
<213> ORGANISM: artificial sequence
<220> FEATURE:
<223> OTHER INFORMATION: humanized VH

<400> SEQUENCE: 74

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Asp Asn
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ala Ala
    50                  55                  60

Ser Val Lys Gly Arg Phe Thr Ile Ser Arg Asp Asn Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Arg Asp Val Gly Ser Asn Tyr Phe Asp Tyr Trp Gly Gln
            100                 105                 110

Gly Thr Leu Val Thr Val Ser Ser
        115                 120

<210> SEQ ID NO 75
<211> LENGTH: 120
<212> TYPE: PRT
<213> ORGANISM: artificial sequence
<220> FEATURE:
<223> OTHER INFORMATION: humanized VH

<400> SEQUENCE: 75

Glu Val Asn Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Asp Asn
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Asp Tyr Ala Ala
    50                  55                  60

Ser Val Arg Gly Arg Phe Thr Ile Ser Arg Asp Asn Ser Lys Ser Ile
65                  70                  75                  80

Leu Tyr Leu Gln Met Asn Ala Leu Arg Thr Glu Asp Thr Ala Val Tyr
                85                  90                  95

Tyr Cys Ala Arg Asp Val Gly Ser Asn Tyr Phe Asp Tyr Trp Gly Gln
            100                 105                 110

Gly Thr Leu Val Thr Val Ser Ser
        115                 120

<210> SEQ ID NO 76
<211> LENGTH: 112
<212> TYPE: PRT
<213> ORGANISM: artificial sequence
<220> FEATURE:
<223> OTHER INFORMATION: humanized VL
```

<400> SEQUENCE: 76

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Met Gln
                85                  90                  95

Ser Phe Asn Leu Arg Thr Phe Gly Gln Gly Thr Lys Val Glu Ile Lys
            100                 105                 110

<210> SEQ ID NO 77
<211> LENGTH: 112
<212> TYPE: PRT
<213> ORGANISM: artificial sequence
<220> FEATURE:
<223> OTHER INFORMATION: humanized VL

<400> SEQUENCE: 77

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Ala Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Met Gln
                85                  90                  95

Ser Phe Asn Leu Arg Thr Phe Gly Gln Gly Thr Lys Val Glu Ile Lys
            100                 105                 110

<210> SEQ ID NO 78
<211> LENGTH: 112
<212> TYPE: PRT
<213> ORGANISM: artificial sequence
<220> FEATURE:
<223> OTHER INFORMATION: humanized VL

<400> SEQUENCE: 78

Asp Ile Val Met Thr Gln Ser Pro Ser Ser Leu Ala Val Ser Leu Gly
1               5                   10                  15

Glu Arg Ala Thr Met Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Ala Arg Asp Ser Gly Val
    50                  55                  60

Pro Ala Arg Phe Thr Gly Ser Gly Ser Glu Thr Tyr Phe Thr Leu Thr
65                  70                  75                  80

```
Ile Ser Arg Val Gln Ala Glu Asp Leu Ala Val Tyr Tyr Cys Met Gln
            85                  90                  95

Ser Phe Asn Leu Arg Thr Phe Gly Gln Gly Thr Lys Val Glu Ile Lys
            100                 105                 110
```

<210> SEQ ID NO 79
<211> LENGTH: 112
<212> TYPE: PRT
<213> ORGANISM: artificial sequence
<220> FEATURE:
<223> OTHER INFORMATION: humanized VL

<400> SEQUENCE: 79

```
Asp Ile Val Met Thr Gln Ser Pro Asp Ser Leu Ala Val Ser Leu Gly
1               5                   10                  15

Glu Arg Ala Thr Met Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
            35                  40                  45

Pro Pro Lys Leu Leu Ile Tyr Trp Ala Ser Ala Arg Asp Ser Gly Val
        50                  55                  60

Pro Asp Arg Phe Ser Gly Ser Gly Ser Glu Thr Tyr Phe Thr Leu Thr
65                  70                  75                  80

Ile Ser Arg Val Gln Ala Glu Asp Leu Ala Val Tyr Tyr Cys Met Gln
            85                  90                  95

Ser Phe Asn Leu Arg Thr Phe Gly Gln Gly Thr Lys Val Glu Ile Lys
            100                 105                 110
```

<210> SEQ ID NO 80
<211> LENGTH: 112
<212> TYPE: PRT
<213> ORGANISM: artificial sequence
<220> FEATURE:
<223> OTHER INFORMATION: humanized VL

<400> SEQUENCE: 80

```
Asp Ile Val Met Thr Gln Ser Pro Asp Ser Leu Ala Val Ser Leu Gly
1               5                   10                  15

Glu Arg Ala Thr Met Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
            35                  40                  45

Pro Pro Lys Leu Leu Ile Tyr Trp Ala Ser Ala Arg Asp Ser Gly Val
        50                  55                  60

Pro Asp Arg Phe Thr Gly Ser Gly Ser Glu Thr Tyr Phe Thr Leu Thr
65                  70                  75                  80

Ile Ser Arg Val Gln Ala Glu Asp Val Ala Val Tyr Tyr Cys Met Gln
            85                  90                  95

Ser Phe Asn Leu Arg Thr Phe Gly Gln Gly Thr Lys Val Glu Ile Lys
            100                 105                 110
```

<210> SEQ ID NO 81
<211> LENGTH: 112
<212> TYPE: PRT
<213> ORGANISM: artificial sequence
<220> FEATURE:
<223> OTHER INFORMATION: humanized VL

<400> SEQUENCE: 81

```
Asp Ile Val Met Thr Gln Ser Pro Asp Ser Leu Ala Val Ser Leu Gly
1               5                   10                  15
```

Glu Arg Ala Thr Met Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Ala Arg Asp Ser Gly Val
50                  55                  60

Pro Asp Arg Phe Thr Gly Ser Gly Ser Glu Thr Tyr Phe Thr Leu Thr
65                  70                  75                  80

Ile Ser Ser Leu Gln Ala Glu Asp Leu Ala Val Tyr Tyr Cys Met Gln
                85                  90                  95

Ser Phe Asn Leu Arg Thr Phe Gly Gln Gly Thr Lys Val Glu Ile Lys
            100                 105                 110

<210> SEQ ID NO 82
<211> LENGTH: 112
<212> TYPE: PRT
<213> ORGANISM: artificial sequence
<220> FEATURE:
<223> OTHER INFORMATION: humanized VL

<400> SEQUENCE: 82

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Ala Arg Asp Ser Gly Val
50                  55                  60

Pro Asp Arg Phe Thr Gly Ser Gly Ser Glu Thr Tyr Phe Thr Leu Thr
65                  70                  75                  80

Ile Ser Ser Leu Gln Ala Glu Asp Val Ala Val Tyr Tyr Cys Met Gln
                85                  90                  95

Ser Phe Asn Leu Arg Thr Phe Gly Gln Gly Thr Lys Val Glu Ile Lys
            100                 105                 110

<210> SEQ ID NO 83
<211> LENGTH: 450
<212> TYPE: PRT
<213> ORGANISM: artificial sequence
<220> FEATURE:
<223> OTHER INFORMATION: humanized VH

<400> SEQUENCE: 83

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Asp Asn
            20                  25                  30

Tyr Met Ser Trp Val Arg Gln Ala Pro Gly Lys Gly Leu Glu Trp Val
        35                  40                  45

Gly Phe Ile Arg Asn Lys Ala Asn Gly Tyr Thr Thr Glu Tyr Ala Ala
50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Arg Asp Val Gly Ser Asn Tyr Phe Asp Tyr Trp Gly Gln
            100                 105                 110

```
Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
450

<210> SEQ ID NO 84
<211> LENGTH: 450
<212> TYPE: PRT
<213> ORGANISM: artificial sequence
<220> FEATURE:
<223> OTHER INFORMATION: humanized VH

<400> SEQUENCE: 84

Glu Val Gln Leu Val Glu Ser Gly Gly Gly Leu Val Gln Pro Gly Arg
1               5                   10                  15
```

-continued

```
Ser Leu Arg Leu Ser Cys Thr Ala Ser Gly Phe Thr Phe Thr Asp Asn
         20              25                  30

Tyr Met Ser Trp Val Arg Gln Ala Pro Gly Lys Gly Leu Glu Trp Val
         35                  40                  45

Gly Phe Ile Arg Asn Lys Ala Asn Gly Tyr Thr Thr Glu Tyr Ala Ala
 50                      55                  60

Ser Val Lys Gly Arg Phe Thr Ile Ser Arg Asp Asn Ser Lys Ser Ile
 65                  70                  75                  80

Ala Tyr Leu Gln Met Asn Ser Leu Lys Thr Glu Asp Thr Ala Val Tyr
                 85                  90                  95

Tyr Cys Ala Arg Asp Val Gly Ser Asn Tyr Phe Asp Tyr Trp Gly Gln
                100                 105                 110

Gly Thr Leu Val Thr Val Ser Ser Ala Ser Thr Lys Gly Pro Ser Val
             115                 120                 125

Phe Pro Leu Ala Pro Ser Ser Lys Ser Thr Ser Gly Gly Thr Ala Ala
         130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Gln Thr Tyr Ile Cys Asn Val Asn His Lys
         195                 200                 205

Pro Ser Asn Thr Lys Val Asp Lys Arg Val Glu Pro Lys Ser Cys Asp
 210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                 245                 250                 255

Ser Arg Thr Pro Glu Val Thr Cys Val Val Val Asp Val Ser His Glu
             260                 265                 270

Asp Pro Glu Val Lys Phe Asn Trp Tyr Val Asp Gly Val Glu Val His
         275                 280                 285

Asn Ala Lys Thr Lys Pro Arg Glu Glu Gln Tyr Asn Ser Thr Tyr Arg
 290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Arg Glu Glu Met Thr Lys Asn Gln Val Ser Leu
         355                 360                 365

Thr Cys Leu Val Lys Gly Phe Tyr Pro Ser Asp Ile Ala Val Glu Trp
 370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                 405                 410                 415

Lys Ser Arg Trp Gln Gln Gly Asn Val Phe Ser Cys Ser Val Met His
             420                 425                 430

Glu Ala Leu His Asn His Tyr Thr Gln Lys Ser Leu Ser Leu Ser Pro
         435                 440                 445
```

Gly Lys
    450

<210> SEQ ID NO 85
<211> LENGTH: 450
<212> TYPE: PRT
<213> ORGANISM: artificial sequence
<220> FEATURE:
<223> OTHER INFORMATION: humanized VH

<400> SEQUENCE: 85

Glu Val Gln Leu Val Glu Ser Gly Gly Leu Val Gln Pro Gly Arg
1               5                   10                  15

Ser Leu Arg Leu Ser Cys Thr Ala Ser Gly Phe Thr Phe Thr Asp Asn
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ala Ala
    50                  55                  60

Ser Val Lys Gly Arg Phe Thr Ile Ser Arg Asp Asn Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Arg Asp Val Gly Ser Asn Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

```
Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly Lys
    450

<210> SEQ ID NO 86
<211> LENGTH: 450
<212> TYPE: PRT
<213> ORGANISM: artificial sequence
<220> FEATURE:
<223> OTHER INFORMATION: humanized VH

<400> SEQUENCE: 86

Glu Val Asn Leu Val Glu Ser Gly Gly Gly Leu Val Gln Pro Gly Arg
1               5                   10                  15

Ser Leu Arg Leu Ser Cys Thr Ala Ser Gly Phe Thr Phe Thr Asp Asn
                20                  25                  30

Tyr Met Ser Trp Val Arg Gln Ala Pro Gly Lys Gly Leu Glu Trp Leu
            35                  40                  45

Gly Phe Ile Arg Asn Lys Ala Asn Gly Tyr Thr Thr Asp Tyr Ala Ala
        50                  55                  60

Ser Val Arg Gly Arg Phe Thr Ile Ser Arg Asp Asn Ser Lys Ser Ile
65                  70                  75                  80

Leu Tyr Leu Gln Met Asn Ala Leu Arg Thr Glu Asp Thr Ala Val Tyr
                85                  90                  95

Tyr Cys Ala Arg Asp Val Gly Ser Asn Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
```

-continued

```
                260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
        340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
        420                 425                 430
Glu Ala Leu His Asn His Tyr Thr Gln Lys Ser Leu Ser Leu Ser Pro
            435                 440                 445
Gly Lys
    450

<210> SEQ ID NO 87
<211> LENGTH: 219
<212> TYPE: PRT
<213> ORGANISM: artificial sequence
<220> FEATURE:
<223> OTHER INFORMATION: humanized VL

<400> SEQUENCE: 87

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Leu Phe Asn Ser
            20                  25                  30
Arg Thr Arg Lys Asn Tyr Leu Ala Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Met Gln
                85                  90                  95
Ser Phe Asn Leu Arg Thr Phe Gly Gln Gly Thr Lys Val Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
```

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 88
<211> LENGTH: 219
<212> TYPE: PRT
<213> ORGANISM: artificial sequence
<220> FEATURE:
<223> OTHER INFORMATION: humanized VL

<400> SEQUENCE: 88

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Ala Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Met Gln
                85                  90                  95

Ser Phe Asn Leu Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 89
<211> LENGTH: 219
<212> TYPE: PRT
<213> ORGANISM: artificial sequence
<220> FEATURE:
<223> OTHER INFORMATION: humanised VL

<400> SEQUENCE: 89

Asp Ile Val Met Thr Gln Ser Pro Ser Ser Leu Ala Val Ser Leu Gly
1               5                   10                  15

Glu Arg Ala Thr Met Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45
```

Ser Pro Lys Leu Leu Ile Tyr Trp Ala Ser Ala Arg Asp Ser Gly Val
    50                  55                  60

Pro Ala Arg Phe Thr Gly Ser Gly Ser Glu Thr Tyr Phe Thr Leu Thr
65                  70                  75                  80

Ile Ser Arg Val Gln Ala Glu Asp Leu Ala Val Tyr Tyr Cys Met Gln
                85                  90                  95

Ser Phe Asn Leu Arg Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 90
<211> LENGTH: 219
<212> TYPE: PRT
<213> ORGANISM: artificial sequence
<220> FEATURE:
<223> OTHER INFORMATION: humanized VL

<400> SEQUENCE: 90

Asp Ile Val Met Thr Gln Ser Pro Asp Ser Leu Ala Val Ser Leu Gly
1               5                   10                  15

Glu Arg Ala Thr Met Ser Cys Lys Ser Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Ala Arg Asp Ser Gly Val
    50                  55                  60

Pro Asp Arg Phe Ser Gly Ser Gly Ser Glu Thr Tyr Phe Thr Leu Thr
65                  70                  75                  80

Ile Ser Arg Val Gln Ala Glu Asp Leu Ala Val Tyr Tyr Cys Met Gln
                85                  90                  95

Ser Phe Asn Leu Arg Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 91
<211> LENGTH: 219
<212> TYPE: PRT
<213> ORGANISM: artificial sequence
<220> FEATURE:
<223> OTHER INFORMATION: humanized VL

<400> SEQUENCE: 91

Asp Ile Val Met Thr Gln Ser Pro Asp Ser Leu Ala Val Ser Leu Gly
1               5                   10                  15

Glu Arg Ala Thr Met Ser Cys Lys Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Ala Arg Asp Ser Gly Val
    50                  55                  60

Pro Asp Arg Phe Thr Gly Ser Gly Ser Glu Thr Tyr Phe Thr Leu Thr
65                  70                  75                  80

Ile Ser Arg Val Gln Ala Glu Asp Val Ala Val Tyr Tyr Cys Met Gln
                85                  90                  95

Ser Phe Asn Leu Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 92
<211> LENGTH: 219
<212> TYPE: PRT
<213> ORGANISM: artificial sequence
<220> FEATURE:
<223> OTHER INFORMATION: humanized VL

<400> SEQUENCE: 92

Asp Ile Val Met Thr Gln Ser Pro Asp Ser Leu Ala Val Ser Leu Gly
1               5                   10                  15

Glu Arg Ala Thr Met Ser Cys Lys Ser Gln Ser Leu Phe Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Ala Arg Asp Ser Gly Val
    50                  55                  60

```
Pro Asp Arg Phe Thr Gly Ser Gly Ser Glu Thr Tyr Phe Thr Leu Thr
 65                  70                  75                  80

Ile Ser Ser Leu Gln Ala Glu Asp Leu Ala Val Tyr Tyr Cys Met Gln
                 85                  90                  95

Ser Phe Asn Leu Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 93
<211> LENGTH: 219
<212> TYPE: PRT
<213> ORGANISM: artificial sequence
<220> FEATURE:
<223> OTHER INFORMATION: humanized VL

<400> SEQUENCE: 93

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Phe Asn Ser
             20                  25                  30

Arg Thr Arg Lys Asn Tyr Leu Ala Trp Tyr Gln Gln Lys Pro Gly Gln
         35                  40                  45

Pro Pro Lys Leu Leu Ile Tyr Trp Ala Ser Ala Arg Asp Ser Gly Val
     50                  55                  60

Pro Asp Arg Phe Thr Gly Ser Gly Ser Glu Thr Tyr Phe Thr Leu Thr
 65                  70                  75                  80

Ile Ser Ser Leu Gln Ala Glu Asp Val Ala Val Tyr Tyr Cys Met Gln
                 85                  90                  95

Ser Phe Asn Leu Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
```

<210> SEQ ID NO 94
<211> LENGTH: 360
<212> TYPE: DNA
<213> ORGANISM: artificial sequence
<220> FEATURE:
<223> OTHER INFORMATION: humanized VH

<400> SEQUENCE: 94

```
gaggtgcagc tggtggagtc tggcggagga ctggtgcagc ccggcagaag cctgagactg    60
agctgcaccg ccagcggctt caccttcacc gacaactaca tgtcctgggt gcgccaggcc   120
cctggaaagg gcctggaatg ggtgggcttc atccggaaca aggccaacgg ctacaccaca   180
gagtacgccg ccagcgtgaa gggccggttc accatcagcc gggacgacag caagagcatt   240
gcctacctgc agatgaacag cctgaaaacc gaggacaccg ccgtgtacta ctgcgccagg   300
gacgtgggca gcaactactt cgactactgg ggccagggca cactggtgac cgtgtctagc   360
```

<210> SEQ ID NO 95
<211> LENGTH: 360
<212> TYPE: DNA
<213> ORGANISM: artificial sequence
<220> FEATURE:
<223> OTHER INFORMATION: humanized VH

<400> SEQUENCE: 95

```
gaggtgcagc tggtggagtc tggcggagga ctggtgcagc ccggcagaag cctgagactg    60
agctgcaccg ccagcggctt caccttcacc gacaactaca tgtcctgggt gcgccaggcc   120
cctggaaagg gcctggaatg ggtgggcttc atccggaaca aggccaacgg ctacaccaca   180
gagtacgccg ccagcgtgaa gggccggttc accatcagcc gggacaacag caagagcatt   240
gcctacctgc agatgaacag cctgaaaacc gaggacaccg ccgtgtacta ctgcgccagg   300
gacgtgggca gcaactactt cgactactgg ggccagggca cactggtgac cgtgtctagc   360
```

<210> SEQ ID NO 96
<211> LENGTH: 360
<212> TYPE: DNA
<213> ORGANISM: artificial sequence
<220> FEATURE:
<223> OTHER INFORMATION: humanized VH

<400> SEQUENCE: 96

```
gaggtgcagc tggtggagtc tggcggagga ctggtgcagc ccggcagaag cctgagactg    60
agctgcaccg ccagcggctt caccttcacc gacaactaca tgtcctgggt gcgccaggcc   120
cctggaaagg gcctggaatg gctgggcttc atccggaaca aggccaacgg ctacaccaca   180
gagtacgccg ccagcgtgaa gggccggttc accatcagcc gggacaacag caagagcatt   240
gcctacctgc agatgaacag cctgaaaacc gaggacaccg ccgtgtacta ctgcgccagg   300
gacgtgggca gcaactactt cgactactgg ggccagggca cactggtgac cgtgtctagc   360
```

<210> SEQ ID NO 97
<211> LENGTH: 360
<212> TYPE: DNA
<213> ORGANISM: artificial sequence
<220> FEATURE:
<223> OTHER INFORMATION: humanized VH

<400> SEQUENCE: 97

```
gaggtgaacc tggtggagtc tggcggagga ctggtgcagc ccggcagaag cctgagactg    60
```

| agctgcaccg | ccagcggctt | caccttcacc | gacaactaca | tgtcctgggt | gcgccaggcc | 120 |
| cctggaaagg | gcctggaatg | gctgggcttc | atccggaaca | aggccaacgg | ctacaccaca | 180 |
| gactacgccg | ccagcgtgag | aggccggttc | accatcagcc | gggacaacag | caagagcatt | 240 |
| ctgtacctgc | agatgaacgc | cctgcggacc | gaggacaccg | ccgtgtacta | ctgcgccagg | 300 |
| gacgtgggca | gcaactactt | cgactactgg | ggccagggca | cactggtgac | cgtgtctagc | 360 |

<210> SEQ ID NO 98
<211> LENGTH: 336
<212> TYPE: DNA
<213> ORGANISM: artificial sequence
<220> FEATURE:
<223> OTHER INFORMATION: humanized VL

<400> SEQUENCE: 98

| gacatcgtga | tgacccagag | ccccgatagc | ctggccgtgt | ctctgggcga | gcgggccacc | 60 |
| atcaactgca | agagcagcca | gagcctgttc | aacagccgga | cccggaagaa | ctacctggcc | 120 |
| tggtatcagc | agaagcccgg | ccagcccccc | aagctgctga | tctactgggc | cagcacaaga | 180 |
| gaaagcggcg | tgcccgaccg | ctttagctggc | agcggcagcg | gcaccgactt | caccctgacc | 240 |
| atcagctccc | tgcaggccga | ggacgtggcc | gtgtactact | gcatgcagag | cttcaacctg | 300 |
| cggaccttcg | gccagggcac | caaggtggag | atcaag | | | 336 |

<210> SEQ ID NO 99
<211> LENGTH: 336
<212> TYPE: DNA
<213> ORGANISM: artificial sequence
<220> FEATURE:
<223> OTHER INFORMATION: humanized VL

<400> SEQUENCE: 99

| gacatcgtga | tgacccagag | ccccgatagc | ctggccgtgt | ctctgggcga | gcgggccacc | 60 |
| atcaactgca | agagcagcca | gagcctgttc | aacagccgga | cccggaagaa | ctacctggcc | 120 |
| tggtatcagc | agaagcccgg | ccagcccccc | aagctgctga | tctactgggc | cagcgccaga | 180 |
| gacagcggcg | tgcccgaccg | ctttagctggc | agcggcagcg | gcaccgactt | caccctgacc | 240 |
| atcagctccc | tgcaggccga | ggacgtggcc | gtgtactact | gcatgcagag | cttcaacctg | 300 |
| cggaccttcg | gccagggcac | caaggtggag | atcaag | | | 336 |

<210> SEQ ID NO 100
<211> LENGTH: 336
<212> TYPE: DNA
<213> ORGANISM: artificial sequence
<220> FEATURE:
<223> OTHER INFORMATION: humanized VL

<400> SEQUENCE: 100

| gacatcgtga | tgacccagag | ccccagcagc | ctggccgtgt | ctctgggcga | gcgggccacc | 60 |
| atgagctgca | agagcagcca | gagcctgttc | aacagccgga | cccggaagaa | ctacctggcc | 120 |
| tggtatcagc | agaagcccgg | ccagtccccc | aagctgctga | tctactgggc | cagcgccaga | 180 |
| gatagcggcg | tgcccgctcg | ctttaccggc | agcggcagcg | agacctactt | caccctgacc | 240 |
| atcagccggg | tgcaggccga | ggacctcgcc | gtgtactact | gcatgcagag | cttcaacctg | 300 |
| cggaccttcg | gccagggcac | caaggtggag | atcaag | | | 336 |

<210> SEQ ID NO 101
<211> LENGTH: 336
<212> TYPE: DNA

```
<213> ORGANISM: artificial sequence
<220> FEATURE:
<223> OTHER INFORMATION: humanized VL

<400> SEQUENCE: 101
gacatcgtga tgacccagtc ccccgactcc ctggccgtgt ctctgggcga gcgggccacc      60
atgtcctgca gtcctccca gtccctgttc aactcccgga cccggaagaa ctacctggcc     120
tggtatcagc agaagcccgg ccagcccccc aagctgctga tctactgggc ctctgctaga    180
gactctggcg tgcccgacag attctccggc tccggcagcg agacatactt caccctgacc    240
atctcccggg tgcaggccga ggatctggcc gtgtactact gcatgcagtc cttcaacctg    300
cggaccttcg gccagggcac caaggtggaa atcaag                              336

<210> SEQ ID NO 102
<211> LENGTH: 336
<212> TYPE: DNA
<213> ORGANISM: artificial sequence
<220> FEATURE:
<223> OTHER INFORMATION: humanized VL

<400> SEQUENCE: 102
gacatcgtga tgacccagtc ccccgactcc ctggccgtgt ctctgggcga gcgggccacc      60
atgtcctgca gtcctccca gtccctgttc aactcccgga cccggaagaa ctacctggcc     120
tggtatcagc agaagcccgg ccagcccccc aagctgctga tctactgggc ctctgctaga    180
gactctggcg tgcccgacag attcaccggc tccggcagcg agacatactt caccctgacc    240
atctcccggg tgcaggccga ggatgtggcc gtgtactact gcatgcagtc cttcaacctg    300
cggaccttcg gccagggcac caaggtggaa atcaag                              336

<210> SEQ ID NO 103
<211> LENGTH: 336
<212> TYPE: DNA
<213> ORGANISM: artificial sequence
<220> FEATURE:
<223> OTHER INFORMATION: humanized VL

<400> SEQUENCE: 103
gacatcgtga tgacccagtc ccccgactcc ctggccgtgt ctctgggcga gcgggccacc      60
atgtcctgca gtcctccca gtccctgttc aactcccgga cccggaagaa ctacctggcc     120
tggtatcagc agaagcccgg ccagcccccc aagctgctga tctactgggc ctctgctaga    180
gactctggcg tgcccgacag attcaccggc tccggcagcg agacatactt caccctgacc    240
atctccagcc tgcaggccga ggatctggcc gtgtactact gcatgcagtc cttcaacctg    300
cggaccttcg gccagggcac caaggtggaa atcaag                              336

<210> SEQ ID NO 104
<211> LENGTH: 336
<212> TYPE: DNA
<213> ORGANISM: artificial sequence
<220> FEATURE:
<223> OTHER INFORMATION: humanized VL

<400> SEQUENCE: 104
gacatcgtga tgacccagag ccccgatagc ctggccgtgt ctctgggcga gcgggccacc      60
atcaactgca agagcagcca gagcctgttc aacagccgga cccggaagaa ctacctggcc     120
tggtatcagc agaagcccgg ccagcccccc aagctgctga tctactgggc cagcgccaga    180
gatagcggcg tgcccgaccg ctttaccggc agcggcagcg agacctactt caccctgacc    240
```

| | |
|---|---|
| atcagctccc tgcaggccga ggacgtggcc gtgtactact gcatgcagag cttcaacctg | 300 |
| cggaccttcg gccagggcac caaggtggag atcaag | 336 |

<210> SEQ ID NO 105
<211> LENGTH: 1350
<212> TYPE: DNA
<213> ORGANISM: artificial sequence
<220> FEATURE:
<223> OTHER INFORMATION: humanized VH

<400> SEQUENCE: 105

| | |
|---|---|
| gaggtgcagc tggtggagtc tggcggagga ctggtgcagc ccggcagaag cctgagactg | 60 |
| agctgcaccg ccagcggctt caccttcacc gacaactaca tgtcctgggt gcgccaggcc | 120 |
| cctggaaagg gcctggaatg ggtgggcttc atccggaaca aggccaacgg ctacaccaca | 180 |
| gagtacgccg ccagcgtgaa gggccggttc accatcagcc gggacgacag caagagcatt | 240 |
| gcctacctgc agatgaacag cctgaaaacc gaggacaccg ccgtgtacta ctgcgccagg | 300 |
| gacgtgggca gcaactactt cgactactgg ggccagggca cactggtgac cgtgtctagc | 360 |
| gccagcacaa agggcccaag cgtgttcccg ctagccccca gcagcaagag caccagcggc | 420 |
| ggcacagccg ccctgggctg cctggtgaag gactacttcc ccgagcccgt gaccgtgtcc | 480 |
| tggaacagcg gagccctgac ctccggcgtg cacaccttcc ccgccgtgct gcagagcagc | 540 |
| ggcctgtaca gcctgagcag cgtggtgacc gtgcccagca gcagcctggg cacccagacc | 600 |
| tacatctgta acgtgaacca caagcccagc aacaccaagg tggacaagag agtggagccc | 660 |
| aagagctgtg acaagaccca cacctgcccc ccctgcccag cccccgagct gctgggcgga | 720 |
| cccagcgtgt tcctgttccc ccccaagccc aaggacaccc tgatgatcag cagaaccccc | 780 |
| gaggtgacct gtgtggtggt ggacgtgtcc cacgaggacc cagaggtgaa gttcaactgg | 840 |
| tacgtggacg gcgtggaggt gcacaacgcc aagaccaagc ccagagagga gcagtacaac | 900 |
| agcacctaca gggtggtgtc cgtgctgacc gtgctgcacc aggactggct gaacggcaag | 960 |
| gagtacaagt gtaaggtgtc caacaaggcc ctgccagccc caatcgaaaa gaccatcagc | 1020 |
| aaggccaagg gccagccaag agagcccag gtgtacaccc tgccacccag cagggaggag | 1080 |
| atgaccaaga accaggtgtc cctgacctgt ctggtgaagg gcttctaccc aagcgacatc | 1140 |
| gccgtggagt gggagagcaa cggccagccc gagaacaact acaagaccac ccccccagtg | 1200 |
| ctggacagcg acggcagctt cttcctgtac agcaagctga ccgtggacaa gagcagatgg | 1260 |
| cagcagggca cgtgttcag ctgctccgtg atgcacgagg ccctgcacaa ccactacacc | 1320 |
| cagaagagcc tgagcctgtc cccaggcaag | 1350 |

<210> SEQ ID NO 106
<211> LENGTH: 1350
<212> TYPE: DNA
<213> ORGANISM: artificial sequence
<220> FEATURE:
<223> OTHER INFORMATION: humanized VH

<400> SEQUENCE: 106

| | |
|---|---|
| gaggtgcagc tggtggagtc tggcggagga ctggtgcagc ccggcagaag cctgagactg | 60 |
| agctgcaccg ccagcggctt caccttcacc gacaactaca tgtcctgggt gcgccaggcc | 120 |
| cctggaaagg gcctggaatg ggtgggcttc atccggaaca aggccaacgg ctacaccaca | 180 |
| gagtacgccg ccagcgtgaa gggccggttc accatcagcc gggacaacag caagagcatt | 240 |
| gcctacctgc agatgaacag cctgaaaacc gaggacaccg ccgtgtacta ctgcgccagg | 300 |

```
gacgtgggca gcaactactt cgactactgg ggccagggca cactggtgac cgtgtctagc    360
gccagcacaa agggcccaag cgtgttcccg ctagccccca gcagcaagag caccagcggc    420
ggcacagccg ccctgggctg cctggtgaag gactacttcc ccgagcccgt gaccgtgtcc    480
tggaacagcg gagccctgac ctccggcgtg cacaccttcc ccgccgtgct gcagagcagc    540
ggcctgtaca gcctgagcag cgtggtgacc gtgcccagca gcagcctggg cacccagacc    600
tacatctgta acgtgaacca caagcccagc aacaccaagg tggacaagag agtggagccc    660
aagagctgtg acaagaccca cacctgcccc cctgcccag cccccgagct gctgggcgga    720
cccagcgtgt tcctgttccc ccccaagccc aaggacaccc tgatgatcag cagaaccccc    780
gaggtgacct gtgtggtggt ggacgtgtcc cacgaggacc cagaggtgaa gttcaactgg    840
tacgtggacg gcgtggaggt gcacaacgcc aagaccaagc cagagagga gcagtacaac    900 agcacctaca gggtggtgtc cgtgctgacc gtgctgcacc aggactggct gaacggcaag    960
gagtacaagt gtaaggtgtc caacaaggcc ctgccagccc caatcgaaaa gaccatcagc   1020
aaggccaagg gccagccaag agagcccag gtgtacaccc tgccacccag cagggaggag   1080
atgaccaaga accaggtgtc cctgacctgt ctggtgaagg gcttctaccc aagcgacatc   1140
gccgtggagt gggagagcaa cggccagccc gagaacaact acaagaccac cccccagtg   1200 ctggacagcg acggcagctt cttcctgtac agcaagctga ccgtggacaa gagcagatgg   1260
cagcagggca acgtgttcag ctgctccgtg atgcacgagg ccctgcacaa ccactacacc   1320
cagaagagcc tgagcctgtc cccaggcaag                                    1350
```

<210> SEQ ID NO 107
<211> LENGTH: 1350
<212> TYPE: DNA
<213> ORGANISM: artificial sequence
<220> FEATURE:
<223> OTHER INFORMATION: humanized VH

<400> SEQUENCE: 107

```
gaggtgcagc tggtggagtc tggcggagga ctggtgcagc ccggcagaag cctgagactg     60
agctgcaccg ccagcggctt caccttcacc gacaactaca tgtcctgggt gcgccaggcc    120
cctggaaagg gcctggaatg gctgggcttc atccggaaca aggccaacgg ctacaccaca    180
gagtacgccg ccagcgtgaa gggccggttc accatcagcc gggacaacag caagagcatt    240
gcctacctgc agatgaacag cctgaaaacc gaggacaccg ccgtgtacta ctgcgccagg    300
gacgtgggca gcaactactt cgactactgg ggccagggca cactggtgac cgtgtctagc    360
gccagcacaa agggcccaag cgtgttcccg ctagccccca gcagcaagag caccagcggc    420
ggcacagccg ccctgggctg cctggtgaag gactacttcc ccgagcccgt gaccgtgtcc    480
tggaacagcg gagccctgac ctccggcgtg cacaccttcc ccgccgtgct gcagagcagc    540
ggcctgtaca gcctgagcag cgtggtgacc gtgcccagca gcagcctggg cacccagacc    600
tacatctgta acgtgaacca caagcccagc aacaccaagg tggacaagag agtggagccc    660
aagagctgtg acaagaccca cacctgcccc cctgcccag cccccgagct gctgggcgga    720
cccagcgtgt tcctgttccc ccccaagccc aaggacaccc tgatgatcag cagaaccccc    780
gaggtgacct gtgtggtggt ggacgtgtcc cacgaggacc cagaggtgaa gttcaactgg    840
tacgtggacg gcgtggaggt gcacaacgcc aagaccaagc cagagagga gcagtacaac    900 agcacctaca gggtggtgtc cgtgctgacc gtgctgcacc aggactggct gaacggcaag    960
gagtacaagt gtaaggtgtc caacaaggcc ctgccagccc caatcgaaaa gaccatcagc   1020
```

| aaggccaagg gccagccaag agagcccag gtgtacaccc tgccacccag cagggaggag | 1080 |
| atgaccaaga accaggtgtc cctgacctgt ctggtgaagg gcttctaccc aagcgacatc | 1140 |
| gccgtggagt gggagagcaa cggccagccc gagaacaact acaagaccac ccccccagtg | 1200 |
| ctggacagcg acggcagctt cttcctgtac agcaagctga ccgtggacaa gagcagatgg | 1260 |
| cagcagggca acgtgttcag ctgctccgtg atgcacgagg ccctgcacaa ccactacacc | 1320 |
| cagaagagcc tgagcctgtc cccaggcaag | 1350 |

<210> SEQ ID NO 108
<211> LENGTH: 1350
<212> TYPE: DNA
<213> ORGANISM: artificial sequence
<220> FEATURE:
<223> OTHER INFORMATION: humanized VH

<400> SEQUENCE: 108

| gaggtgaacc tggtggagtc tggcggagga ctggtgcagc ccggcagaag cctgagactg | 60 |
| agctgcaccg ccagcggctt caccttcacc gacaactaca tgtcctgggt gcgccaggcc | 120 |
| cctggaaagg gcctggaatg gctgggcttc atccggaaca aggccaacgg ctacaccaca | 180 |
| gactacgccg ccagcgtgag aggccggttc accatcagcc gggacaacag caagagcatt | 240 |
| ctgtacctgc agatgaacgc cctgcggacc gaggacaccg ccgtgtacta ctgcgccagg | 300 |
| gacgtgggca gcaactactt cgactactgg ggccagggca cactggtgac cgtgtctagc | 360 |
| gccagcacaa agggcccaag cgtgttcccg ctagccccca gcagcaagag caccagcggc | 420 |
| ggcacagccg ccctgggctg cctggtgaag gactacttcc ccgagcccgt gaccgtgtcc | 480 |
| tggaacagcg gagccctgac ctccggcgtg cacaccttcc ccgccgtgct gcagagcagc | 540 |
| ggcctgtaca gcctgagcag cgtggtgacc gtgcccagca gcagcctggg cacccagacc | 600 |
| tacatctgta acgtgaacca caagcccagc aacaccaagg tggacaagag agtggagccc | 660 |
| aagagctgtg acaagaccca cacctgcccc cctgcccag ccccgagct gctgggcgga | 720 |
| cccagcgtgt tcctgttccc ccccaagccc aaggacaccc tgatgatcag cagaaccccc | 780 |
| gaggtgacct gtgtggtggt ggacgtgtcc cacgaggacc cagaggtgaa gttcaactgg | 840 |
| tacgtggacg gcgtggaggt gcacaacgcc aagaccaagc cagagagga gcagtacaac | 900 |
| agcacctaca gggtggtgtc cgtgctgacc gtgctgcacc aggactggct gaacggcaag | 960 |
| gagtacaagt gtaaggtgtc caacaaggcc ctgccagccc caatcgaaaa gaccatcagc | 1020 |
| aaggccaagg gccagccaag agagcccag gtgtacaccc tgccacccag cagggaggag | 1080 |
| atgaccaaga accaggtgtc cctgacctgt ctggtgaagg gcttctaccc aagcgacatc | 1140 |
| gccgtggagt gggagagcaa cggccagccc gagaacaact acaagaccac ccccccagtg | 1200 |
| ctggacagcg acggcagctt cttcctgtac agcaagctga ccgtggacaa gagcagatgg | 1260 |
| cagcagggca acgtgttcag ctgctccgtg atgcacgagg ccctgcacaa ccactacacc | 1320 |
| cagaagagcc tgagcctgtc cccaggcaag | 1350 |

<210> SEQ ID NO 109
<211> LENGTH: 657
<212> TYPE: DNA
<213> ORGANISM: artificial sequence
<220> FEATURE:
<223> OTHER INFORMATION: humanized VL

<400> SEQUENCE: 109

| gacatcgtga tgacccagag ccccgatagc ctggccgtgt ctctgggcga gcgggccacc | 60 |

| | | |
|---|---|---|
| atcaactgca agagcagcca gagcctgttc aacagccgga cccggaagaa ctacctggcc | 120 |
| tggtatcagc agaagcccgg ccagcccccc aagctgctga tctactgggc agcacaaga | 180 |
| gaaagcggcg tgcccgaccg ctttctggc agcggcagcg gcaccgactt caccctgacc | 240 |
| atcagctccc tgcaggccga ggacgtggcc gtgtactact gcatgcagag cttcaacctg | 300 |
| cggaccttcg gccagggcac caaggtggag atcaagcgta cggtggccgc tcccagcgtg | 360 |
| ttcatcttcc ccccaagcga cgagcagctg aagagcggca ccgccagcgt ggtgtgtctg | 420 |
| ctgaacaact tctaccccag ggaggccaag gtgcagtgga aggtggacaa cgccctgcag | 480 |
| agcggcaaca gccaggagag cgtcaccgag caggacagca aggactccac ctacagcctg | 540 |
| agcagcaccc tgaccctgag caaggccgac tacgagaagc acaaggtgta cgcctgtgag | 600 |
| gtgacccacc agggcctgtc cagccccgtg accaagagct caacagggg cgagtgc | 657 |

<210> SEQ ID NO 110
<211> LENGTH: 657
<212> TYPE: DNA
<213> ORGANISM: artificial sequence
<220> FEATURE:
<223> OTHER INFORMATION: humanized VL

<400> SEQUENCE: 110

| | | |
|---|---|---|
| gacatcgtga tgacccagag ccccgatagc ctggccgtgt ctctgggcga gcgggccacc | 60 |
| atcaactgca agagcagcca gagcctgttc aacagccgga cccggaagaa ctacctggcc | 120 |
| tggtatcagc agaagcccgg ccagcccccc aagctgctga tctactgggc agcgccaga | 180 |
| gacagcggcg tgcccgaccg ctttctggc agcggcagcg gcaccgactt caccctgacc | 240 |
| atcagctccc tgcaggccga ggacgtggcc gtgtactact gcatgcagag cttcaacctg | 300 |
| cggaccttcg gccagggcac caaggtggag atcaagcgta cggtggccgc tcccagcgtg | 360 |
| ttcatcttcc ccccaagcga cgagcagctg aagagcggca ccgccagcgt ggtgtgtctg | 420 |
| ctgaacaact tctaccccag ggaggccaag gtgcagtgga aggtggacaa cgccctgcag | 480 |
| agcggcaaca gccaggagag cgtcaccgag caggacagca aggactccac ctacagcctg | 540 |
| agcagcaccc tgaccctgag caaggccgac tacgagaagc acaaggtgta cgcctgtgag | 600 |
| gtgacccacc agggcctgtc cagccccgtg accaagagct caacagggg cgagtgc | 657 |

<210> SEQ ID NO 111
<211> LENGTH: 657
<212> TYPE: DNA
<213> ORGANISM: artificial sequence
<220> FEATURE:
<223> OTHER INFORMATION: humanized VL

<400> SEQUENCE: 111

| | | |
|---|---|---|
| gacatcgtga tgacccagag ccccagcagc ctggccgtgt ctctgggcga gcgggccacc | 60 |
| atgagctgca agagcagcca gagcctgttc aacagccgga cccggaagaa ctacctggcc | 120 |
| tggtatcagc agaagcccgg ccagtccccc aagctgctga tctactgggc agcgccaga | 180 |
| gatagcggcg tgcccgctcg ctttaccggc agcggcagcg agacctactt caccctgacc | 240 |
| atcagccggg tgcaggccga ggacctcgcc gtgtactact gcatgcagag cttcaacctg | 300 |
| cggaccttcg gccagggcac caaggtggag atcaagcgta cggtggccgc tcccagcgtg | 360 |
| ttcatcttcc ccccaagcga cgagcagctg aagagcggca ccgccagcgt ggtgtgtctg | 420 |
| ctgaacaact tctaccccag ggaggccaag gtgcagtgga aggtggacaa cgccctgcag | 480 |
| agcggcaaca gccaggagag cgtcaccgag caggacagca aggactccac ctacagcctg | 540 |

```
agcagcaccc tgaccctgag caaggccgac tacgagaagc acaaggtgta cgcctgtgag      600
gtgacccacc agggcctgtc cagccccgtg accaagagct caacagggg cgagtgc          657

<210> SEQ ID NO 112
<211> LENGTH: 657
<212> TYPE: DNA
<213> ORGANISM: artificial sequence
<220> FEATURE:
<223> OTHER INFORMATION: humanized VL

<400> SEQUENCE: 112
gacatcgtga tgacccagtc ccccgactcc ctggccgtgt ctctgggcga gcgggccacc      60
atgtcctgca gtcctcccca gtccctgttc aactcccgga cccggaagaa ctacctggcc     120
tggtatcagc agaagcccgg ccagcccccc aagctgctga tctactgggc ctctgctaga     180
gactctggcg tgcccgacag attctccggc tccggcagcg agacatactt caccctgacc     240
atctcccggg tgcaggccga ggatctggcc gtgtactact gcatgcagtc cttcaacctg     300
cggaccttcg gccagggcac caaggtggaa atcaagcgta cggtggccgc tcccagcgtg     360
ttcatcttcc ccccaagcga cgagcagctg aagagcggca ccgccagcgt ggtgtgtctg     420
ctgaacaact ctaccccag ggaggccaag gtgcagtgga aggtggacaa cgccctgcag      480
agcggcaaca gccaggagag cgtcaccgag caggacagca aggactccac ctacagcctg     540
agcagcaccc tgaccctgag caaggccgac tacgagaagc acaaggtgta cgcctgtgag     600
gtgacccacc agggcctgtc cagccccgtg accaagagct caacagggg cgagtgc          657

<210> SEQ ID NO 113
<211> LENGTH: 657
<212> TYPE: DNA
<213> ORGANISM: artificial sequence
<220> FEATURE:
<223> OTHER INFORMATION: humanized VL

<400> SEQUENCE: 113
gacatcgtga tgacccagtc ccccgactcc ctggccgtgt ctctgggcga gcgggccacc      60
atgtcctgca gtcctcccca gtccctgttc aactcccgga cccggaagaa ctacctggcc     120
tggtatcagc agaagcccgg ccagcccccc aagctgctga tctactgggc ctctgctaga     180
gactctggcg tgcccgacag attcaccggc tccggcagcg agacatactt caccctgacc     240
atctcccggg tgcaggccga ggatgtggcc gtgtactact gcatgcagtc cttcaacctg     300
cggaccttcg gccagggcac caaggtggaa atcaagcgta cggtggccgc tcccagcgtg     360
ttcatcttcc ccccaagcga cgagcagctg aagagcggca ccgccagcgt ggtgtgtctg     420
ctgaacaact ctaccccag ggaggccaag gtgcagtgga aggtggacaa cgccctgcag      480
agcggcaaca gccaggagag cgtcaccgag caggacagca aggactccac ctacagcctg     540
agcagcaccc tgaccctgag caaggccgac tacgagaagc acaaggtgta cgcctgtgag     600
gtgacccacc agggcctgtc cagccccgtg accaagagct caacagggg cgagtgc          657

<210> SEQ ID NO 114
<211> LENGTH: 657
<212> TYPE: DNA
<213> ORGANISM: artificial sequence
<220> FEATURE:
<223> OTHER INFORMATION: humanized VL

<400> SEQUENCE: 114
gacatcgtga tgacccagtc ccccgactcc ctggccgtgt ctctgggcga gcgggccacc      60
```

```
atgtcctgca agtcctccca gtccctgttc aactcccgga cccggaagaa ctacctggcc    120
tggtatcagc agaagcccgg ccagcccccc aagctgctga tctactgggc ctctgctaga    180
gactctggcg tgcccgacag attcaccggc tccggcagcg agacatactt caccctgacc    240
atctccagcc tgcaggccga ggatctggcc gtgtactact gcatgcagtc cttcaacctg    300
cggaccttcg gccagggcac caaggtggaa atcaagcgta cggtggccgc tcccagcgtg    360
ttcatcttcc ccccaagcga cgagcagctg aagagcggca ccgccagcgt ggtgtgtctg    420
ctgaacaact tctaccccag ggaggccaag gtgcagtgga aggtggacaa cgccctgcag    480
agcggcaaca gccaggagag cgtcaccgag caggacagca aggactccac ctacagcctg    540
agcagcaccc tgaccctgag caaggccgac tacgagaagc acaaggtgta cgcctgtgag    600
gtgacccacc agggcctgtc cagccccgtg accaagagct caacagggg cgagtgc       657
```

```
<210> SEQ ID NO 115
<211> LENGTH: 657
<212> TYPE: DNA
<213> ORGANISM: artificial sequence
<220> FEATURE:
<223> OTHER INFORMATION: humanized VL

<400> SEQUENCE: 115
```

```
gacatcgtga tgacccagag ccccgatagc ctggccgtgt ctctgggcga gcgggccacc     60
atcaactgca gagcagcca gagcctgttc aacagccgga cccggaagaa ctacctggcc    120
tggtatcagc agaagcccgg ccagcccccc aagctgctga tctactgggc cagcgccaga    180
gatagcggcg tgcccgaccg ctttaccggc agcggcagcg agacctactt caccctgacc    240
atcagctccc tgcaggccga ggacgtggcc gtgtactact gcatgcagag cttcaacctg    300
cggaccttcg gccagggcac caaggtggag atcaagcgta cggtggccgc tcccagcgtg    360
ttcatcttcc ccccaagcga cgagcagctg aagagcggca ccgccagcgt ggtgtgtctg    420
ctgaacaact tctaccccag ggaggccaag gtgcagtgga aggtggacaa cgccctgcag    480
agcggcaaca gccaggagag cgtcaccgag caggacagca aggactccac ctacagcctg    540
agcagcaccc tgaccctgag caaggccgac tacgagaagc acaaggtgta cgcctgtgag    600
gtgacccacc agggcctgtc cagccccgtg accaagagct caacagggg cgagtgc       657
```

```
<210> SEQ ID NO 116
<211> LENGTH: 24
<212> TYPE: DNA
<213> ORGANISM: artificial sequence
<220> FEATURE:
<223> OTHER INFORMATION: optimized CDR

<400> SEQUENCE: 116
ggcttcacct tcaccgacaa ctac                                            24
```

```
<210> SEQ ID NO 117
<211> LENGTH: 30
<212> TYPE: DNA
<213> ORGANISM: artificial sequence
<220> FEATURE:
<223> OTHER INFORMATION: optimized CDR

<400> SEQUENCE: 117
atccggaaca aggccaacgg ctacaccaca                                      30
```

```
<210> SEQ ID NO 118
<211> LENGTH: 33
<212> TYPE: DNA
```

```
<213> ORGANISM: artificial sequence
<220> FEATURE:
<223> OTHER INFORMATION: optimized CDR

<400> SEQUENCE: 118
gccagggacg tgggcagcaa ctacttcgac tac                              33

<210> SEQ ID NO 119
<211> LENGTH: 36
<212> TYPE: DNA
<213> ORGANISM: artificial sequence
<220> FEATURE:
<223> OTHER INFORMATION: optimized CDR

<400> SEQUENCE: 119
cagagcctgt tcaacagccg gacccggaag aactac                           36

<210> SEQ ID NO 120
<211> LENGTH: 36
<212> TYPE: DNA
<213> ORGANISM: artificial sequence
<220> FEATURE:
<223> OTHER INFORMATION: optimized CDR

<400> SEQUENCE: 120
cagtccctgt tcaactcccg gacccggaag aactac                           36

<210> SEQ ID NO 121
<211> LENGTH: 9
<212> TYPE: DNA
<213> ORGANISM: artificial sequence
<220> FEATURE:
<223> OTHER INFORMATION: optimized CDR

<400> SEQUENCE: 121 tgggccagc                                                          9

<210> SEQ ID NO 122
<211> LENGTH: 9
<212> TYPE: DNA
<213> ORGANISM: artificial sequence
<220> FEATURE:
<223> OTHER INFORMATION: optimized CDR

<400> SEQUENCE: 122 tgggcctct                                                          9

<210> SEQ ID NO 123
<211> LENGTH: 24
<212> TYPE: DNA
<213> ORGANISM: artificial sequence
<220> FEATURE:
<223> OTHER INFORMATION: optimized CDR

<400> SEQUENCE: 123
atgcagagct tcaacctgcg gacc                                        24

<210> SEQ ID NO 124
<211> LENGTH: 24
<212> TYPE: DNA
<213> ORGANISM: artificial sequence
<220> FEATURE:
<223> OTHER INFORMATION: optimized CDR

<400> SEQUENCE: 124
atgcagtcct tcaacctgcg gacc                                        24
```

ANTI CXCR4 ANTIBODIES AND THEIR USE FOR THE TREATMENT OF CANCER

CROSS REFERENCE TO RELATED APPLICATIONS

This application is a continuation-in-part of International Application No. PCT/EP2009/062787, filed Oct. 1, 2009, and claims the benefit of priority of EP application No. 08305631.7, filed Oct. 1, 2008, as well as of U.S. provisional patent application Nos. 61/136,772, filed Oct. 1, 2008, and 61/173,743, filed Apr. 29, 2009, the entire content of all of which is relied upon and incorporated herein by reference.

The present invention relates to novel antibodies, in particular murine monoclonal antibodies, chimeric and humanized, able to bind specifically to chemokine receptors (CXCR) as well as the amino and nucleic acid sequences coding for such antibodies. From one aspect, the invention relates to novel antibodies, derived compounds or functional fragments, able to bind specifically to the CXCR4 and having strong anti-tumor activities. The invention also comprises the use of such antibodies as a drug for the preventive and/or therapeutic treatment of cancer, as well as in the procedures or kits related to cancer diagnosis. Finally, the invention comprises compositions comprising such antibodies in combination or conjugation with other anti-cancer compounds, such as antibodies, toxins, cytotoxic/cytostatic, and the use of same for the prevention and/or treatment of certain cancers.

Chemokines are small, secreted peptides that control the migration of leukocytes along a chemical gradient of ligand, known as chemokine gradient, especially during immune reactions (Zlotnick A. et al., 2000). They are divided into two major subfamilies, CC and CXC, based on the position of their $NH_2$-terminal cysteine residues, and bind to G protein coupled receptors, whose two major sub families are designated CCR and CXCR. More than 50 human chemokines and 18 chemokine receptors have been discovered so far.

Many cancers have a complex chemokine network that influences the immune-cell infiltration of tumor, as well as tumor cell growth, survival, migration and angiogenesis. Immune cells, endothelial cells and tumor cells themselves express chemokine receptors and can respond to chemokine gradients. Studies of human cancer biopsy samples and mouse cancer models show that cancer cell chemokine-receptor expression is associated with increase metastatic capacity. Malignant cells from different cancer types have different profiles of chemokine-receptor expression, but Chemokine receptor 4 (CXCR4) is most commonly found. Cells from at least 23 different types of human cancers of epithelial, mesenchymal and haematopoietic origin express CXCR4 receptor (Balkwill F. et al., 2004).

Chemokine receptor 4 (also known as fusin, CD184, LESTR or HUMSTR) exists as two isoforms comprising 352 or 360 amino acids. Residue Asn11 is glycosylated, residue Tyr21 is modified by the addition of a sulfate group and Cys 109 and 186 are bond with a disulfide bridge on the extracellular part of the receptor (Juarez J. et al., 2004).

This receptor is expressed by different kind of normal tissues, naïve, non-memory T-cells, regulatory T cells, B-cells, neutrophils, endothelial cells, primary monocytes, dendritic cells, Natural Killer cells, CD34+ hematopoietic stem cells and at a low level in heart, colon, liver, kidneys and brain. CXCR4 plays a key role in leukocytes trafficking, B cell lymphopoiesis and myelopoiesis.

CXCR4 receptor is over-expressed in a large number of cancers including but not limited to colon (Ottaiano A. et al., 2004), breast (Kato M. et al., 2003), prostate (Sun Y. X. et al., 2003), lung [small-cell- and non-small-cell-carcinoma (Phillips R. J. et al., 2003)], ovary (Scotton C. J. et al., 2002), pancreas (Koshiba T. et al., 2000), kidneys, brain (Barbero S et al., 2002), glioblastoma and lymphomas.

The unique ligand of CXCR4 receptor described so far is the Stromal-cell-Derived Factor-1 (SDF-1) or CXCL12. SDF-1 is secreted in large amount in lymph node, bone marrow, liver, lung and to a less extent by kidneys, brain and skin. CXCR4 is also recognized by an antagonistic chemokine, the viral macrophage inflammatory protein II (vMIP-II) encoded by human herpesvirus type III.

CXCR4/SDF-1 axis plays a key role in cancer and is implicated directly in migration, invasion leading to metastases. Indeed, cancer cells express CXCR4 receptor, they migrate and enter the systemic circulation. Then cancer cells are arrested in vascular beds in organs that produce high levels of SDF-1 where they proliferate, induce angiogenesis and form metastatic tumors (Murphy P M., 2001). This axis is also involved in cell proliferation via activation of Extracellular-signal-Regulated Kinase (ERK) pathway (Barbero S. et al., 2003) and angiogenesis (Romagnani P., 2004). Indeed, CXCR4 receptor and its ligand SDF-1 clearly promote angiogenesis by stimulating VEGF-A expression which in turns increases expression of CXCR4/SDF-1 (Bachelder R. E. et al., 2002). It is also known that tumor associated macrophages (TAM) accumulated in hypoxic areas of tumors and are stimulated to co-operate with tumor cells and promote angiogenesis. It was observed that hypoxia up-regulated selectively expression of CXCR4 in various cell types including TAM (Mantovani A. et al., 2004). It has been recently demonstrated that CXCR4/SDF-1 axis regulates the trafficking/homing of CXCR4+ hematopoietic stem/progenitor cells (HSC) and could play a role in neovascularization. Evidence indicates that besides HSC, functional CXCR4 is also expressed on stem cells from other tissues (tissue-committed stem cells=TCSCs) so SDF-1 may play a pivotal role in chemottracting CXCR4+ TCSCs necessary for organ/tissue regeneration but these TCSC may also be a cellular origin of cancer development (cancer stem cells theory). A stem cell origin of cancer was demonstrated for human leukemia and recently for several solid tumors such as brain and breast. There are several examples of CXCR4+ tumors that may derive from the normal CXCR4+ tissue/organ-specific stem cells such as leukemias, brain tumors, small cell lung cancer, breast cancer, hepatoblastoma, ovarian and cervical cancers (Kucia M. et al., 2005).

Targeting cancer metastases by interfering with CXCR4 receptor was demonstrated in vivo using a monoclonal antibody directed against CXCR4 receptor (Muller A. et al., 2001). Briefly, it was shown that a monoclonal antibody directed against CXCR4 receptor (Mab 173 R&D Systems) decreased significantly the number of lymph node metastases in an orthotopic breast cancer model (MDA-MB231) in SCID mice. Another study (Phillips R. J et al., 2003) also showed the critical role of SDF-1/CXCR4 axis in metastases in an orthotopic lung carcinoma model (A549) using polyclonal antibodies against SDF-1 but in this study there was no effect neither on tumor growth nor on angiogenesis. Several other studies described also the inhibition of either metastasis in vivo using siRNAs duplexes of CXCR4 (Liang Z. et al., 2005) biostable CXCR4 peptide antagonists (Tamamura H. et al., 2003) or tumor growth in vivo using small molecule antagonist of CXCR4 like AMD 3100 (Rubin J. B. et al., 2003; De Falco V. et al., 2007) or Mab (patent WO2004/059285 A2). Thus, CXCR4 is a validated therapeutic target for cancers.

Chemokine receptor 2 (CXCR2), another chemokine receptor is also described as an interesting target in oncology.

Indeed, CXCR2 transmits an autocrine cell growth signal in several tumor cell types and can also affect tumor growth indirectly by promoting angiogenesis (Tanaka T. et al. 2005).

CXCR2 chemokine receptor encompasses 360 amino acids. It is expressed mainly in endothelial cells and specially during neovascularization. Several chemokines bind CXCR2 receptor: CXCL5, -6, -7, IL-8, GRO-α, -β and γ which belong to ERL+pro-angiogenic chemokines The CXCR2 receptor share sequence homologies with CXCR4 receptor: 37% sequence identity and 48% sequence homology. The CXCR2/ligands axis is involved in several tumor growth mechanisms such as metastasis (Singh R. K. et al., 1994) cell proliferation (Owen J. D. et al., 1997) and in ERL+chemokines-mediated angiogenesis (Strider R. M. et al., 2004; Romagnani et al., 2004). Finally, tumor-associated macrophages and neutrophils are key elements of inflammatory-induced tumor growth and chemokines such as CXCL5, IL-8 and GRO-α initiate neutrophils recruitment.

Dimerization has emerged as a common mechanism for regulating the function of G-protein-coupled receptors, among these are chemokine receptors (Wang J. and Norcross M., 2008). Homo- and heterodimerization in response to chemokine binding has been shown to be required for the initiation and the alteration of signaling by a number of chemokine receptors. Growing evidence supports the concept that receptor dimers or oligomers are probably the basic functional unit of chemokine receptors. Chemokine receptor dimers are found in the absence of ligands and chemokines induce conformational changes of receptor dimers. CXCR4 is known to form homodimers but also heterodimers, for examples with the δ-opioid receptor (DOR) (Hereld D., 2008) or CCR2 (Percherancier Y. et al., 2005). In the latter example, peptides derived from the transmembrane domains of CXCR4 inhibited activation by blocking the ligand-induced conformational transitions of the dimer (Percherancier Y. et al., 2005). Another study showed that CXCR4-TM4 peptide, a synthetic peptide of the transmembrane region of CXCR4, decreases energy transfer between protomers of CXCR4 homodimers and inhibits SDF-1-induced migration and actin polymerization in malignant cells (Wang J. et al., 2006). More recently, it was also described that CXCR7 formed functional heterodimers with CXCR4 and enhanced SDF-1-induced signaling (Sierro F. et al., 2007). Other examples of constitutive heterodimers include studies showing CXCR1 and CXCR2 interact as well as forming respective homodimers. No interactions were noted for either of them with another GPCR (alpha(1A)-adrenoreceptor), indicating the specificity of CXCR1 and CXCR2 interaction (Wilson S. et al., 2005).

As previously mentioned, CXCR4 and CXCR2 receptors are interesting tumor targets. Interfering with those receptors should inhibit tumor growth and metastases in a very efficient way, by decreasing tumor cell proliferation, angiogenesis, tumor cell migration and invasion, neutrophils and macrophages recruitment by tumors and by inhibiting CXCR4 cancer stem cells.

One of the inventive aspects of the present invention is to generate a mouse monoclonal antibody inducing CXCR4 dimers conformational changes. The invention encompasses a CXCR4 Mab 414H5 (or fragments thereof) able to bind and to induce conformational changes of both CXCR4 homodimers and CXCR4/CXCR2 heterodimers, and having strong anti-tumor activities both in mice xenograft and survival models. The invention also encompasses a CXCR4 Mab 515H7 (or fragments thereof) able to bind and to induce conformational changes of both CXCR4 homodimers and CXCR4/CXCR2 heterodimers, and having strong anti-tumor activities. Anti-CXCR4 414H5 Mab inhibits tumor growth in MDA-MB-231 xenograft model and increases mice survival in U937 model. They induce conformational changes on CXCR4 homodimers but also on CXCR4/CXCR2 heterodimers. This new property should be of interest for cancer therapy application given the important roles of these two chemokine receptors in cancer.

Targeting both homo- and hetero-dimers of receptors has already been found to increase Mab therapeutic effect. Indeed, it has been demonstrated for example, that a Mab (h7C10) targeting both IGF-1R and insulin/IGF-1 hybrid receptors was more potent to inhibit tumor growth in vivo than a Mab targeting solely IGF-1R (Pandini G., 2007).

Moreover the anti-CXCR4 Mabs 414H5 and 515H7 are silent antagonists for CXCR4, they do not change basal signal in in vitro assays but inhibit signaling induced by SDF-1 in different assays (GTPγS binding, cAMP release) and are also able to inhibit SDF-1 induced tumor cells proliferation and migration in vitro.

Molecules acting as either partial agonists or inverse agonists exhibit intrinsic activity in the absence of ligands. These types of molecules stabilize, respectively a high-affinity or a low-affinity GPCR state, even in the absence of ligand, thereby activating or inhibiting downstream signaling cascades (Galandin et al., 2007; Kenakin, 2004).

In case of 414H5 and 515H7 Mabs, these molecules behaved as silent antagonists, without any intrinsic activity at CXCR4 receptor in the absence of SDF-1. This pharmacological feature is likely to be associated with less adverse side-effects as compared to partial or inverse agonists, as already observed for opioid receptor ligands (Bosier and Hermans, 2007). Indeed, the functional activity of both 414H5 and 515H7 Mabs is totally dependent on the presence of SDF-1 and no modulation of CXCR4 receptor activity will be observed in tissues and organs where SDF-1 ligand is not expressed, secreted or provided by the blood flow. Thus, 414H5 and 515H7 Mabs are likely to be less toxic as compared to other CXCR4 receptor ligands with positive or negative efficacy. In addition, silent antagonists are the minority species in the pharmacological space (Wurch et al., 1999, Kenakin, 2004).

Surprisingly, for the first time, inventors have managed to generate antibodies capable of binding to CXCR4 but also capable of inducing conformational changes of the CXCR4 homodimers and/or heterodimers. More particularly, the antibodies of the invention are capable of inducing conformational changes of the CXCR4 homodimers but also of the CXCR4/CXCR2 heterodimers.

In the following specification, the plural expression "CXCR4 dimers" must be understood as encompassing the CXCR4 homodimers and also the CXCR4/CXCR2 heterodimers.

It must be mentioned at this stage that such antibodies have never been described in the prior art. Moreover, it must be mentioned that the existence of CXCR4/CXCR2 heterodimers was never described.

A part of the invention is the discovery of the existence of a heterodimer formed by CXCR4 and CXCR2.

So, in a particular aspect, the present invention is directed to an isolated complex comprising or consisting of the CXCR4/CXCR2 heterodimer.

Preferably, CXCR4 compound part of said CXCR4/CXCR2 heterodimer complex is one of the two human CXCR4 isoforms selected from the group consisting of:
the chemokine (C-X-C motif) receptor 4 isoform b [*Homo sapiens*] having the sequence as depicted under the Genbank accession number NP_003458 SEQ ID No. 29:

MEGISIYTSDNYTEEMGSGDYDSMKEPCFREENANFNKIFLPTIYSIIFL

TGIVGNGLVILVMGYQKKLRSMTDKYRLHLSVADLLFVITLPFWAVDAVA

NWYFGNFLCKAVHVIYTVNLYSSVLILAFISLDRYLAIVHATNSQRPRKL

LAEKVVYVGVWIPALLLTIPDFIFANVSEADDRYICDRFYPNDLWVVVFQ

FQHIMVGLILPGIVILSCYCIIISKLSHSKGHQKRKALKTTVILILAFFA

CWLPYYIGISIDSFILLEIIKQGCEFENTVHKWISITEALAFFHCCLNPI

LYAFLGAKFKTSAQHALTSVSRGSSLKILSKGKRGGHSSVSTESESSSFH

SS;

the chemokine (C-X-C motif) receptor 4 isoform a [*Homo sapiens*] having the sequence as depicted under the Genbank accession number NP_001008540 SEQ ID No. 30:

MSIPLPLLQIYTSDNYTEEMGSGDYDSMKEPCFREENANFNKIFLPTIYS

IIFLTGIVGNGLVILVMGYQKKLRSMTDKYRLHLSVADLLFVITLPFWAV

DAVANWYFGNFLCKAVHVIYTVNLYSSVLILAFISLDRYLAIVHATNSQR

PRKLLAEKVVYVGVWIPALLLTIPDFIFANVSEADDRYICDRFYPNDLWV

VVFQFQHIMVGLILPGIVILSCYCIIISKLSHSKGHQKRKALKTTVILIL

AFFACWLPYYIGISIDSFILLEIIKQGCEFENTVHKWISITEALAFFHCC

LNPILYAFLGAKFKTSAQHALTSVSRGSSLKILSKGKRGGHSSVSTESES

SSFHSS;

an alternate transcriptional splice variant or a natural variant thereof having at least 95% identity with one of these b or a isoforms having the SEQ ID No. 29 or 30; and a fragment thereof capable of being specifically recognizing by its natural ligand stromal cell-derived factor-1 (SDF-1) and having preferably at least 100, 150 and 200 amino acid length.

Preferably, CXCR2 compound part of said CXCR4/CXCR2 heterodimer complex is selected from the group consisting of:

the interleukin 8 receptor beta [*Homo sapiens*] having the sequence as depicted under the Genbank accession number NP_001548 SEQ ID No. 31:

MEDFNMESDSFEDFWKGEDLSNYSYSSTLPPFLLDAAPCEPESLEINKYF

VVIIYALVFLLSLLGNSLVMLVILYSRVGRSVTDVYLLNLALADLLFALT

LPIWAASKVNGWIFGTFLCKVVSLLKEVNFYSGILLLACISVDRYLAIVH

ATRTLTQKRYLVKFICLSIWGLSLLLALPVLLFRRTVYSSNVSPACYEDM

GNNTANWRMLLRILPQSFGFIVPLLIMLFCYGFTLRTLFKAHMGQKHRAM

RVIFAVVLIFLLCWLPYNLVLLADTLMRTQVIQETCERRNHIDRALDATE

ILGILHSCLNPLIYAFIGQKFRHGLLKILAIHGLISKDSLPKDSRPSFVG

SSSGHTSTTL;

an alternate transcriptional splice variant or a natural variant thereof having at least 95% identity with this interleukin 8 receptor beta having the SEQ ID No. 31; and a fragment thereof capable of being specifically recognizing by IL-8 and having preferably at least 100, 150 and 200 amino acid length.

In this particular aspect, the present invention also comprises an isolated RNA or DNA encoding for a polypeptide comprising said CXCR4/CXCR2 heterodimer complex.

This invention further comprises a nucleic construct, preferably an expression vector, such as a plasmid, encoding said CXCR4/CXCR2 heterodimer complex.

The invention further comprises a composition comprising at least one nucleic construct, preferably an expression vector, such as a plasmid, encoding the part CXCR4 of said CXCR4/CXCR2 heterodimer complex, and a second construct, preferably an expression vector, such as a plasmid, encoding the part CXCR2 of said CXCR4/CXCR2 heterodimer complex.

In this aspect, the invention further comprises a method for the preparation of a recombinant host cell which expresses said CXCR4/CXCR2 heterodimer complex, wherein this method comprises a step of transforming said host cell:

a) with a nucleic construct, preferably an expression vector, such as a plasmid, encoding said CXCR4/CXCR2 heterodimer complex; or b) with at least one nucleic construct, preferably an expression vector, such as a plasmid, encoding the part CXCR4 of said CXCR4/CXCR2 heterodimer complex, and a second construct, preferably an expression vector, such as a plasmid, encoding the part CXCR2 of said CXCR4/CXCR2 heterodimer complex.

In a preferred embodiment, said host cell is an eukaryotic cell, such as a mammalian cell.

In a preferred embodiment, the nucleic construct(s) encoding said CXCR4/CXCR2 heterodimer complex encode also for a first marker which is associated (particularly by covalent coupling) with the CXCR4 sequence, such as the luc marker, and for a second marker which is associated (particularly by covalent coupling) with the CXCR2 sequence, such as the GFP marker (i.e. for BRET analysis).

The invention also comprises a method for selecting a compound having an anti-cancer activity or which can be used for the preparation of a composition for the treatment of cancer, characterized in that said method comprises the step of:

a) contacting a recombinant host cell of the present invention which expresses said CXCR4/CXCR2 heterodimer complex, with the compound to be tested; and b) determining whether this compound is capable of modulating, preferably inhibiting, the activity of this CXCR4/CXCR2 heterodimer complex in the recombinant host cell.

In a first aspect, a subject of the present invention is a process for the generation and the selection of antibodies according to the invention.

More particularly, the invention concerns a process for the selection of an anti CXCR4 antibody, or one of its functional fragments or derivatives, capable to inhibit both ligand-dependent and ligand-independent activation of CXCR4, said process comprising the following steps:

i) screening the generated antibodies and selecting antibodies capable to bind specifically to CXCR4 and also to modulate CXCR4 activation;

ii) testing the selected antibodies of step i) and selecting antibodies capable to induce CXCR4 homodimers conformational change, and then iii) testing the selected antibodies of step ii) and selecting antibodies capable to induce CXCR4/CXCR2 heterodimers conformational change.

By the expression "to modulate", it must be understood an increase or an inhibition. Preferably, the selected antibodies of the invention must inhibit the CXCR4 activation.

As it was explained before, the induction of CXCR4 dimers conformational changes is a capital aspect of the invention as such antibodies will present a real interest for a larger population of patients.

The generation of the antibody can be realized by any method known by the man skilled in the art, such as for example, fusion of a myeloma cell with spleen cells from immunized mice or other species compatible with the selected myeloma cells [Kohler & Milstein, 1975, Nature, 256:495-497]. The immunized animals could include transgenic mice with human immunoglobulin loci which then directly produce human antibodies. Another possible embodiment could consist in using phage display technologies to screen libraries.

The screening step i) can be realized by any method or process known by the man skilled in the art. As non limitative examples, can be mentioned ELISA, BIAcore, immunohistochemistry, FACS analysis and functional screens. A preferred process consists in a screen by FACS analysis on CXCR4 transfectant and on at least a tumoral cell line to be sure that the produced antibodies will be able to also recognize the native receptor on tumor cells. This process will be described more precisely in the following examples.

By the expression "to modulate CXCR4 activation" it is intended to modulate at leas one of the activity depicted in the examples 4, 5, 7 and 13 below:
Preferably to modulate:
The specific binding at cellular membranes of the ligand SDF-1 on the receptor CXCR4 (see example 4), particularly by competition on eukaryotic transformed cell membrane, such as CHO-K1 membranes, stably expressing human wild type CXCR4 receptor;
The specific binding at cellular membranes of the GTPγS on the receptor CXCR4 (see example 5), particularly on eukaryotic transformed cells membrane, such as NIH-3T3 cells, stably and constitutively expressing wild-type CXCR4 receptor membranes;
The CXCR4-mediated inhibition of cAMP production (see Example 7); and
The CXCR4 receptor-mediated mobilization of intracellular calcium stores (see Example 13).

More preferably, this modulation of at least one of these activities is an inhibition of the activity.

In a preferred embodiment of the steps ii) and iii) of selection of the process of the invention, said steps ii) and iii) consist in evaluating antibodies by BRET analysis on cells expressing CXCR4-RLuc/CXCR4-YFP and CXCR4-Rluc/CXCR2-YFP, respectively, and selecting antibodies capable to inhibit at least 40%, preferably 45%, 50%, 55% and most preferably 60% of the BRET signal.

The technology BRET is a technology known as being representative of the protein dimerization [Angers et al., PNAS, 2000, 97:3684-89].

The technology BRET, used in the steps ii) and iii) of the process, is well known by the man skilled in the art and will be detailed in the following examples. More particularly, BRET (Bioluminescence Resonance Energy Transfer) is a non-radiative energy transfer occurring between a bioluminescent donor (*Renilla* Luciferase (Rluc)) and a fluorescent acceptor, a mutant of GFP (Green Fluorescent Protein) or YFP (Yellow fluorescent protein). In the present case EYFP (Enhanced Yellow Fluorescent Protein) was used. The efficacy of transfer depends on the orientation and the distance between the donor and the acceptor. Then, the energy transfer can occur only if the two molecules are in close proximity (1-10 nm). This property is used to generate protein-protein interaction assays. Indeed, in order to study the interaction between two partners, the first one is genetically fused to the *Renilla* Luciferase and the second one to the yellow mutant of the GFP. Fusion proteins are generally, but not obligatory, expressed in mammalian cells. In presence of its membrane permeable substrate (coelenterazine), Rluc emits blue light. If the GFP mutant is closer than 10 nm from the Rluc, an energy transfer can occur and an additional yellow signal can be detected. The BRET signal is measured as the ratio between the light emitted by the acceptor and the light emitted by the donor. So the BRET signal will increase as the two fusion proteins are brought into proximity or if a conformational change brings Rluc and GFP mutant closer.

If the BRET analysis consists in a preferred embodiment, any method known by the man skilled in the art can be used to measure CXCR4 dimers conformational changes. Without limitation, the following technologies can be mentioned: FRET (Fluorescence Resonance Energy Transfer), HTRF (Homogenous Time resolved Fluorescence), FLIM (Fluorescence Lifetime Imaging Microscopy) or SW-FCCS single wavelength fluorescence cross-correlation spectroscopy).

Other classical technologies could also be used, such as Co-immunoprecipitation, Alpha screen, Chemical cross-linking, Double-Hybrid, Affinity Chromatography, ELISA or Far western blot.

In a particular aspect of the process according to the invention, step ii) consists in evaluating antibodies by BRET analysis on cells expressing both CXCR4-RLuc/CXCR4-YFP and selecting antibodies capable to inhibit at least 40%, of the BRET signal.

In another particular aspect of the process according to the invention, step iii) consists in evaluating antibodies by BRET analysis on cells expressing both CXCR4-RLuc/CXCR2-YFP and selecting antibodies capable to inhibit at least 40%, of the BRET signal.

In a second aspect, a subject of the invention is an isolated antibody, or one of its functional fragments or derivatives, being obtained by said process. Said antibody or one of its said fragments or derivatives, is capable of binding specifically to the human CXCR4 and, if necessary, preferably moreover capable of inhibiting the natural attachment of its ligand, said antibody being also capable to induce CXCR4 dimers conformational changes.

The expressions "functional fragments and derivatives" will be defined in details later in the present specification.

It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described further on.

More particularly, according to another aspect of the invention, it is claimed an antibody, or one of its functional fragments or derivatives, said antibody being characterized in that it comprises at least one complementary determining region CDR chosen from CDRs comprising the amino acid sequence SEQ ID Nos. 1 to 12.

More particularly, according to another aspect of the invention, it is claimed an antibody, or one of its functional fragments or derivatives, said antibody being characterized in that it comprises at least one complementary determining region CDR chosen from CDRs comprising the amino acid sequence SEQ ID Nos. 2, 5 or 40 to 49.

According to a first aspect, the invention relates to an isolated antibody, or a derived compound or functional fragment of same, comprising at least one CDR chosen among the CDRs of sequences SEQ ID Nos. 1, 2, 3, 4, 5 or 6 or at least one CDR whose sequence has at least 80%, preferably 85%, 90%, 95% and 98% identity after optimal alignment with sequences SEQ ID No. 1, 2, 3, 4, 5 or 6.

According to a another aspect, the invention relates to an isolated antibody, or a derived compound or functional fragment of same, comprising at least one CDR chosen among the CDRs of sequences SEQ ID Nos. 40, 2, 41, 42, 5 or 43 or at least one CDR whose sequence has at least 80%, preferably 85%, 90%, 95% and 98% identity after optimal alignment with sequences SEQ ID Nos. 40, 2, 41, 42, 5 or 43.

A "functional fragment" of an antibody means in particular an antibody fragment, such as fragments Fv, scFv (sc=single chain), Fab, F(ab')$_2$, Fab', scFv-Fc or diabodies, or any fragment whose half-life has been increased. Such functional fragments will be described in detail later in the present description.

A "derived compound" or "derivative" of an antibody means in particular a binding protein composed of a peptide scaffold and at least one of the CDRs of the original antibody in order to preserve its ability to recognize CXCR4. Such derived compounds, well-known to a person skilled in the art, will be described in more detail later in the present description.

More preferably, the invention comprises the antibodies, their derived compounds or their functional fragments, according to the present invention, notably chimeric or humanized, obtained by genetic recombination or chemical synthesis.

According to a preferred embodiment, the antibody according to the invention, or its derived compounds or functional fragments, is characterized in that it consists of a monoclonal antibody.

"Monoclonal antibody" is understood to mean an antibody arising from a nearly homogeneous antibody population. More particularly, the individual antibodies of a population are identical except for a few possible naturally-occurring mutations which can be found in minimal proportions. In other words, a monoclonal antibody consists of a homogeneous antibody arising from the growth of a single cell clone (for example a hybridoma, a eukaryotic host cell transfected with a DNA molecule coding for the homogeneous antibody, a prokaryotic host cell transfected with a DNA molecule coding for the homogeneous antibody, etc.) and is generally characterized by heavy chains of one and only one class and subclass, and light chains of only one type. Monoclonal antibodies are highly specific and are directed against a single antigen. In addition, in contrast with preparations of polyclonal antibodies which typically include various antibodies directed against various determinants, or epitopes, each monoclonal antibody is directed against a single epitope of the antigen.

It must be understood here that the invention does not relate to antibodies in natural form, i.e., they are not taken from their natural environment but are isolated or obtained by purification from natural sources or obtained by genetic recombination or chemical synthesis and thus they can carry unnatural amino acids as will be described below.

More particularly, according to a preferred embodiment of the invention, the antibody, or its derived compounds or functional fragments, is characterized in that it comprises a light chain comprising at least one CDR chosen among the CDRs of amino acid sequences SEQ ID No. 1, 2 or 3, or at least one CDR whose sequence has at least 80%, preferably 85%, 90%, 95% and 98% identity after optimal alignment with sequences SEQ ID No. 1, 2 or 3; or it comprises a heavy chain comprising at least one CDR chosen among the CDRs of amino acid sequences SEQ ID Nos. 4, 5 or 6, or at least one CDR whose sequence has at least 80%, preferably 85%, 90%, 95% and 98% identity after optimal alignment with sequences SEQ ID Nos. 4, 5 or 6.

According to another embodiment, the antibodies of the invention, or one of their derived compounds or functional fragments, are characterized in that they comprise a light chain comprising at least one of the three CDRs of the sequences SEQ ID No. 1, 2 or 3, or at least one sequence with at least 80%, preferably 85%, 90%, 95% and 98% identity after optimal alignment with sequences SEQ ID Nos. 1, 2 or 3.

In a preferred manner, the antibodies of the invention, or one of their derived compounds or functional fragments, are characterized in that they comprise a light chain comprising the following three CDRs, respectively CDR-L1, CDR-L2 and CDR-L3, wherein:

CDR-L1 comprises the sequence SEQ ID No. 1 or 9, or a sequence with at least 80% identity after optimal alignment with sequence SEQ ID No. 1 or 9;

CDR-L2 comprises the sequences SEQ ID No. 2 or 10, or a sequence with at least 80% identity after optimal alignment with sequence SEQ ID No. 2 or 10; and CDR-L3 comprises the sequence SEQ ID No. 3, or a sequence with at least 80% identity after optimal alignment with sequence SEQ ID No. 3.

According to a particular embodiment, antibodies, or one of their derived compounds or functional fragments, are characterized in that they comprise a light chain comprising the CDR-L1 of the sequence SEQ ID No. 1, the CDR-L2 of the sequence SEQ ID No. 2 and the CDR-L3 of the sequence SEQ ID No. 3.

According to another particular embodiment, antibodies, or one of their derived compounds or functional fragments, are characterized in that they comprise a light chain comprising the CDR-L1 of the sequence SEQ ID No. 9, the CDR-L2 of the sequence SEQ ID No. 10 and the CDR-L3 of the sequence SEQ ID No. 3.

More particularly, the antibodies of the invention, or one of their derived compounds or functional fragments, are characterized in that they comprise a heavy chain comprising at least one of the three CDRs of the sequences SEQ ID Nos. 4, 5 or 6, or at least one sequence with at least 80%, preferably 85%, 90%, 95% and 98% identity after optimal alignment with sequences SEQ ID Nos. 4, 5 or 6.

Even more preferably, the antibodies of the invention, or one of their derived compounds or functional fragments, are characterized in that they comprise a heavy chain comprising the following three CDRs, respectively CDR-H1, CDR-H2 and CDR-H3, wherein:

CDR-H1 comprises the sequence SEQ ID Nos. 4, 7 or 11, or a sequence with at least 80% identity after optimal alignment with sequence SEQ ID Nos. 4, 7 or 11;

CDR-H2 comprises the sequences SEQ ID Nos. 5 or 12, or a sequence with at least 80% identity after optimal alignment with sequence SEQ ID No. 5 or 12; and CDR-H3 comprises the sequences SEQ ID No. 6 or 8, or a sequence with at least 80% identity after optimal alignment with sequence SEQ ID No. 6 or 8.

According to a particular embodiment, antibodies, or one of their derived compounds or functional fragments, are characterized in that they comprise a heavy chain comprising the CDR-H1 of the sequence SEQ ID No. 7, the CDR-H2 of the sequence SEQ ID No. 5 and the CDR-H3 of the sequence SEQ ID No. 8.

According to another particular embodiment, antibodies, or one of their derived compounds or functional fragments, are characterized in that they comprise a heavy chain comprising the CDR-H1 of the sequence SEQ ID No. 11, the CDR-H2 of the sequence SEQ ID No. 12 and the CDR-H3 of the sequence SEQ ID No. 6.

More particularly, according to a preferred embodiment of the invention, the antibody, or its derived compounds or functional fragments, is characterized in that it comprises a light chain comprising at least one CDR chosen among the CDRs of amino acid sequences SEQ ID Nos. 40, 2 or 41 or at least one CDR whose sequence has at least 80%, preferably 85%, 90%, 95% and 98% identity after optimal alignment with sequences SEQ ID No. 40, 2 or 41; or it comprises a heavy chain comprising at least one CDR chosen among the CDRs of amino acid sequences SEQ ID Nos. 42, 5 or 43, or at least one CDR whose sequence has at least 80%, preferably 85%, 90%, 95% and 98% identity after optimal alignment with sequences SEQ ID Nos. 42, 5 or 43.

According to another embodiment, the antibodies of the invention, or one of their derived compounds or functional fragments, are characterized in that they comprise a light chain comprising at least one of the three CDRs of the sequences SEQ ID Nos. 40, 2 or 41, or at least one sequence with at least 80%, preferably 85%, 90%, 95% and 98% identity after optimal alignment with sequences SEQ ID Nos. 40, 2 or 41.

In a preferred manner, the antibodies of the invention, or one of their derived compounds or functional fragments, are characterized in that they comprise a light chain comprising the following three CDRs, respectively CDR-L1, CDR-L2 and CDR-L3, wherein:

CDR-L1 comprises the sequence SEQ ID No. 40 or 46, or a sequence with at least 80% identity after optimal alignment with sequence SEQ ID No. 40 or 46;

CDR-L2 comprises the sequences SEQ ID No. 2 or 47, or a sequence with at least 80% identity after optimal alignment with sequence SEQ ID No. 2 or 47; and CDR-L3 comprises the sequence SEQ ID No. 41, or a sequence with at least 80% identity after optimal alignment with sequence SEQ ID No 41.

According to a particular embodiment, antibodies, or one of their derived compounds or functional fragments, are characterized in that they comprise a light chain comprising the CDR-L1 of the sequence SEQ ID No. 40, the CDR-L2 of the sequence SEQ ID No. 2 and the CDR-L3 of the sequence SEQ ID No. 41.

According to another particular embodiment, antibodies, or one of their derived compounds or functional fragments, are characterized in that they comprise a light chain comprising the CDR-L1 of the sequence SEQ ID No. 46, the CDR-L2 of the sequence SEQ ID No. 47 and the CDR-L3 of the sequence SEQ ID No. 41.

More particularly, the antibodies of the invention, or one of their derived compounds or functional fragments, are characterized in that they comprise a heavy chain comprising at least one of the three CDRs of the sequences SEQ ID Nos. 42, 5 or 43, or at least one sequence with at least 80%, preferably 85%, 90%, 95% and 98% identity after optimal alignment with sequences SEQ ID Nos. 42, 5 or 43.

Even more preferably, the antibodies of the invention, or one of their derived compounds or functional fragments, are characterized in that they comprise a heavy chain comprising the following three CDRs, respectively CDR-H1, CDR-H2 and CDR-H3, wherein:

CDR-H1 comprises the sequence SEQ ID Nos. 42, 44 or 48, or a sequence with at least 80% identity after optimal alignment with sequence SEQ ID Nos. 42, 44 or 48;

CDR-H2 comprises the sequences SEQ ID No. 5 or 49, or a sequence with at least 80% identity after optimal alignment with sequence SEQ ID No. 5 or 49; and CDR-H3 comprises the sequences SEQ ID No. 45 or 43, or a sequence with at least 80% identity after optimal alignment with sequence SEQ ID No. 45 or 43.

According to a particular embodiment, antibodies, or one of their derived compounds or functional fragments, are characterized in that they comprise a heavy chain comprising the CDR-H1 of the sequence SEQ ID No. 44, the CDR-H2 of the sequence SEQ ID No. 5 and the CDR-H3 of the sequence SEQ ID No. 45.

According to another particular embodiment, antibodies, or one of their derived compounds or functional fragments, are characterized in that they comprise a heavy chain comprising the CDR-H1 of the sequence SEQ ID No. 48, the CDR-H2 of the sequence SEQ ID No. 49 and the CDR-H3 of the sequence SEQ ID No. 43.

In the present description, the terms "polypeptides", "polypeptide sequences", "peptides" and "proteins attached to antibody compounds or to their sequences" are interchangeable.

It must be understood here that the invention does not relate to antibodies in natural form, i.e., they are not taken from their natural environment but are isolated or obtained by purification from natural sources or obtained by genetic recombination or chemical synthesis and thus they can carry unnatural amino acids as will be described below.

In a first embodiment, complementarity-determining region, or CDR, means the hypervariable regions of the heavy and light chains of immunoglobulins as defined by Kabat et al. (Kabat et al., Sequences of proteins of immunological interest, 5$^{th}$ Ed., U.S. Department of Health and Human Services, NIH, 1991, and later editions). There are three heavy-chain CDRs and three light-chain CDRs. Here, the terms "CDR" and "CDRs" are used to indicate, depending on the case, one or more, or even all, of the regions containing the majority of the amino acid residues responsible for the antibody's binding affinity for the antigen or epitope it recognizes.

In a second embodiment, by CDR regions or CDR(s), it is intended to indicate the hypervariable regions of the heavy and light chains of the immunoglobulins as defined by IMGT.

The IMGT unique numbering has been defined to compare the variable domains whatever the antigen receptor, the chain type, or the species [Lefranc M.-P., Immunology Today 18, 509 (1997)/Lefranc M.-P., The Immunologist, 7, 132-136 (1999)/Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003)]. In the IMGT unique numbering, the conserved amino acids always have the same position, for instance cystein 23 (1st-CYS), tryptophan 41 (CONSERVED-TRP), hydrophobic amino acid 89, cystein 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become crucial information. The IMGT unique numbering is used in 2D graphical representations, designated as IMGT Colliers de Perles [Ruiz, M. and Lefranc, M.-P., Immunogenetics, 53, 857-883 (2002)/Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., T cell receptor and MHC structural data. Nucl. Acids. Res., 32, D208-D210 (2004)].

Three heavy chain CDRs and 3 light chain CDRs exist. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

For more clarity, it must be understood that in the following description, and more particularly in tables 2 and 3, the CDRs will be defined by IMGT numbering, Kabat numbering and by common numbering.

Common numbering regroups the residues part of each CDR which are common to the CDRs as defined by the IMGT and the Kabat numbering systems.

IMGT numbering system defines the CDRs according to the IMGT system as above defined whereas Kabat numbering system defines the CDRs according to the Kabat system as above defined.

More particularly, CDR-L1 consists of SEQ ID No. 1 (QSLYNSRTRKNY) in the common and IMGT numbering systems and of SEQ ID No. 9 (KSSQSLYNSRTRKNYLA) in the Kabat numbering system.

Concerning the CDR-L2, it consists of SEQ ID No. 2 (WAS) in the common and IMGT numbering systems and of SEQ ID No. 10 (WASTRES) in the Kabat numbering system.

The CDR-L3 consists of SEQ ID No. 3 (KQSYNLRT) for each of the three numbering systems.

For the heavy chain, the CDR-H1 consists of the SEQ ID No. 4 (TDYY) in the common numbering system, of SEQ ID No. 7 (GFTFTDYY) in the IMGT numbering system and of SEQ ID No. 11 (TDYYMS) in the kabat numbering system.

The CDR-H2 consists of SEQ ID No. 5 (IRNKANGYTT) in the common and IMGT numbering systems and of SEQ ID No. 12 (FIRNKANGYTTEYSASVKG) in the kabat numbering system.

At last, the CDR-H3 consists in the SEQ ID No. 6 (DIPGFAY) in the common and kabat numbering systems whereas it consists of SEQ ID No. 8 (ARDIPGFAY) in the IMGT numbering system.

More particularly, CDR-L1 consists of SEQ ID No. 40 (QSLFNSRTRKNY) in the common and IMGT numbering systems and of SEQ ID No. 46 (KSSQSLFNSRTRKNYLA) in the Kabat numbering system.

Concerning the CDR-L2, it consists of SEQ ID No. 2 (WAS) in the common and IMGT numbering systems and of SEQ ID No. 47 (WASARDS) in the Kabat numbering system.

The CDR-L3 consists of SEQ ID No. 41 (MQSFNLRT) for each of the three numbering systems.

For the heavy chain, the CDR-H1 consists of the SEQ ID No. 42 (DNY) in the common numbering system, of SEQ ID No. 44 (GFTFTDNY) in the IMGT numbering system and of SEQ ID No. 48 (DNYMS) in the kabat numbering system.

The CDR-H2 consists of SEQ ID No. 5 (IRNKANGYTT) in the common and IMGT numbering systems and of SEQ ID No. 49 (FIRNKANGYTTDYSASVRG) in the kabat numbering system.

At last, the CDR-H3 consists in the SEQ ID No. 43 (DVGSNYFDY) in the common and kabat numbering systems whereas it consists of SEQ ID No. 45 (ARDVGSNYFDY) in the IMGT numbering system.

In the sense of the present invention, the "percentage identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444] or by means of computer software using these algorithms (GAP, BESTFIT, FASTA and TFASTA in the Wisconsin Genetics Software Package, Genetics Computer Group, 575 Science Dr., Madison, Wis., or by the comparison software BLAST NR or BLAST P).

The percentage identity between two nucleic acid or amino acid sequences is determined by comparing the two optimally-aligned sequences in which the nucleic acid or amino acid sequence to compare can have additions or deletions compared to the reference sequence for optimal alignment between the two sequences. Percentage identity is calculated by determining the number of positions at which the amino acid nucleotide or residue is identical between the two sequences, preferably between the two complete sequences, dividing the number of identical positions by the total number of positions in the alignment window and multiplying the result by 100 to obtain the percentage identity between the two sequences.

For example, the BLAST program, "BLAST 2 sequences" (Tatusova et al., "Blast 2 sequences—a new tool for comparing protein and nucleotide sequences", FEMS Microbiol., 1999, Lett. 174:247-250), can be used with the default parameters (notably for the parameters "open gap penalty": 5, and "extension gap penalty": 2; the selected matrix being for example the "BLOSUM 62" matrix proposed by the program); the percentage identity between the two sequences to compare is calculated directly by the program.

For the amino acid sequence exhibiting at least 80%, preferably 85%, 90%, 95% and 98% identity with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below.

Equivalent amino acids can be determined either on their structural homology with the amino acids for which they are substituted or on the results of comparative tests of biological activity between the various antibodies likely to be generated.

As a non-limiting example, table 1 below recalls the substitution possibilities likely to be carried out without resulting in a significant modification of the biological activity of the corresponding modified antibody; inverse substitutions are naturally possible under the same conditions.

TABLE 1

| Original residue | Substitution(s) |
|---|---|
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (E) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

It is known by those skilled in the art that in the current state of the art the greatest variability (length and composition) between the six CDRs is found at the three heavy-chain CDRs and, more particularly, at CDR-H3 of this heavy chain. Consequently, it will be evident that the preferred characteristic CDRs of the antibodies of the invention, or of one of their derived compounds or functional fragments, will be the three CDRs of the heavy chain, i.e., for the 414H5 the CDRs coded by sequences SEQ ID Nos. 7, 5, 8 and 11, 12, 6, respectively defined according to IMGT and Kabat and, for the 515H7, the CDRs coded by sequences SEQ ID Nos. 44, 5, 45 and 48, 49, 43, respectively defined according to IMGT and Kabat. Even more preferentially, the CDR corresponding to the CDR-H3 coded by sequence SEQ ID No. 8 or 6 for the 414H5 and 45 or 43 for the 515H7.

In a specific embodiment, the present invention relates to a murine antibody, or derived compounds or functional fragments of same.

Another embodiment of the invention discloses an antibody, or its derived compounds or functional fragments, comprising a light chain comprising the following three CDRs:

CDR-L1 of the sequence SEQ ID No. 1 or of a sequence with at least 80%, preferably 85%, 90%, 95% and 98% identity after optimal alignment with sequence SEQ ID No. 1;

CDR-L2 of the sequence SEQ ID No. 2 or of a sequence with at least 80%, preferably 85%, 90%, 95% and 98% identity after optimal alignment with sequence SEQ ID No. 2; and CDR-L3 of the sequence SEQ ID No. 3 or of a sequence with at least 80%, preferably 85%, 90%, 95% and 98% identity after optimal alignment with sequence SEQ ID No. 3, and a heavy chain comprising the following three CDRs:

CDR-H1 of the sequence SEQ ID No. 4 or of a sequence with at least 80%, preferably 85%, 90%, 95% and 98% identity after optimal alignment with sequence SEQ ID No. 4;

CDR-H2 of the sequence SEQ ID No. 5 or of a sequence with at least 80%, preferably 85%, 90%, 95% and 98% identity after optimal alignment with sequence SEQ ID No. 5; and CDR-H3 of the sequence SEQ ID No. 6 or of a sequence with at least 80%, preferably 85%, 90%, 95% and 98% identity after optimal alignment with sequence SEQ ID No. 6.

Still another embodiment of the invention discloses an antibody, or a derived compound or functional fragment of same, comprising a light chain comprising the following three CDRs:

CDR-L1 of the sequence SEQ ID No. 1 or of a sequence with at least 80% identity after optimal alignment with sequence SEQ ID No. 1;

CDR-L2 of the sequence SEQ ID No. 2 or of a sequence with at least 80% identity after optimal alignment with sequence SEQ ID No. 2; and CDR-L3 of the sequence SEQ ID No. 3 or of a sequence with at least 80% identity after optimal alignment with sequence SEQ ID No. 3, and a heavy chain comprising the following three CDRs:

CDR-H1 of the sequence SEQ ID No. 7 or of a sequence with at least 80% identity after optimal alignment with sequence SEQ ID No. 7;

CDR-H2 of the sequence SEQ ID No. 5 or of a sequence with at least 80% identity after optimal alignment with sequence SEQ ID No. 5; and CDR-H3 of the sequence SEQ ID No. 8 or of a sequence with at least 80% identity after optimal alignment with sequence SEQ ID No. 8.

Still another embodiment of the invention discloses an antibody, or a derived compound or functional fragment of same, comprising a light chain comprising the following three CDRs:

CDR-L1 of the sequence SEQ ID No. 9 or of a sequence with at least 80% identity after optimal alignment with sequence SEQ ID No. 9;

CDR-L2 of the sequence SEQ ID No. 10 or of a sequence with at least 80% identity after optimal alignment with sequence SEQ ID No. 10; and CDR-L3 of the sequence SEQ ID No. 3 or of a sequence with at least 80% identity after optimal alignment with sequence SEQ ID No. 3, and a heavy chain comprising the following three CDRs:

CDR-H1 of the sequence SEQ ID No. 11 or of a sequence with at least 80% identity after optimal alignment with sequence SEQ ID No. 11;

CDR-H2 of the sequence SEQ ID No. 12 or of a sequence with at least 80% identity after optimal alignment with sequence SEQ ID No. 12; and CDR-H3 of the sequence SEQ ID No. 6 or of a sequence with at least 80% identity after optimal alignment with sequence SEQ ID No. 6.

An antibody, or a derived compound or functional fragment of same, according to the invention is characterized in that it comprises:

a light chain comprising the CDR-L1 of the sequence SEQ ID No. 1, the CDR-L2 of the sequence SEQ ID No. 2 and the CDR-L3 of the sequence SEQ ID No. 3; and a heavy chain comprising the CDR-H1 of the sequence SEQ ID No. 7, the CDR-H2 of the sequence SEQ ID No. 5 and the CDR-H3 of the sequence SEQ ID No. 8.

In another embodiment, an antibody, or a derived compound or functional fragment of same, according to the invention is characterized in that it comprises:

a light chain comprising the CDR-L1 of the sequence SEQ ID No. 9, the CDR-L2 of the sequence SEQ ID No. 10 and the CDR-L3 of the sequence SEQ ID No. 3; and a heavy chain comprising the CDR-H1 of the sequence SEQ ID No. 11, the CDR-H2 of the sequence SEQ ID No. 12 and the CDR-H3 of the sequence SEQ ID No. 6.

According to still another embodiment, the antibody of the invention, or its derived compounds or functional fragments, is characterized in that it comprises a light-chain sequence comprising the amino acid sequence SEQ ID No. 13 or a sequence with at least 80%, preferably 85%, 90%, 95% and 98% identity after optimal alignment with sequence SEQ ID No. 13; and in that it comprises a heavy-chain sequence comprising the amino acid sequence SEQ ID No. 14 or a sequence with at least 80%, preferably 85%, 90%, 95% and 98% identity after optimal alignment with sequence SEQ ID No. 14.

Another embodiment of the invention discloses an antibody, or its derived compounds or functional fragments, comprising a light chain comprising the following three CDRs:
- CDR-L1 of the sequence SEQ ID No. 40 or of a sequence with at least 80%, preferably 85%, 90%, 95% and 98% identity after optimal alignment with sequence SEQ ID No. 40;
- CDR-L2 of the sequence SEQ ID No. 2 or of a sequence with at least 80%, preferably 85%, 90%, 95% and 98% identity after optimal alignment with sequence SEQ ID No. 2; and
- CDR-L3 of the sequence SEQ ID No. 41 or of a sequence with at least 80%, preferably 85%, 90%, 95% and 98% identity after optimal alignment with sequence SEQ ID No. 41, and a heavy chain comprising the following three CDRs:
- CDR-H1 of the sequence SEQ ID No. 42 or of a sequence with at least 80%, preferably 85%, 90%, 95% and 98% identity after optimal alignment with sequence SEQ ID No. 42;
- CDR-H2 of the sequence SEQ ID No. 5 or of a sequence with at least 80%, preferably 85%, 90%, 95% and 98% identity after optimal alignment with sequence SEQ ID No. 5; and
- CDR-H3 of the sequence SEQ ID No. 43 or of a sequence with at least 80%, preferably 85%, 90%, 95% and 98% identity after optimal alignment with sequence SEQ ID No. 43.

Still another embodiment of the invention discloses an antibody, or a derived compound or functional fragment of same, comprising a light chain comprising the following three CDRs:
- CDR-L1 of the sequence SEQ ID No. 40 or of a sequence with at least 80% identity after optimal alignment with sequence SEQ ID No. 40;
- CDR-L2 of the sequence SEQ ID No. 2 or of a sequence with at least 80% identity after optimal alignment with sequence SEQ ID No. 2; and
- CDR-L3 of the sequence SEQ ID No. 41 or of a sequence with at least 80% identity after optimal alignment with sequence SEQ ID No. 41, and a heavy chain comprising the following three CDRs:
- CDR-H1 of the sequence SEQ ID No. 44 or of a sequence with at least 80% identity after optimal alignment with sequence SEQ ID No. 44;
- CDR-H2 of the sequence SEQ ID No. 5 or of a sequence with at least 80% identity after optimal alignment with sequence SEQ ID No. 5; and
- CDR-H3 of the sequence SEQ ID No. 45 or of a sequence with at least 80% identity after optimal alignment with sequence SEQ ID No. 45.

Still another embodiment of the invention discloses an antibody, or a derived compound or functional fragment of same, comprising a light chain comprising the following three CDRs:
- CDR-L1 of the sequence SEQ ID No. 46 or of a sequence with at least 80% identity after optimal alignment with sequence SEQ ID No. 46;
- CDR-L2 of the sequence SEQ ID No. 47 or of a sequence with at least 80% identity after optimal alignment with sequence SEQ ID No. 47; and
- CDR-L3 of the sequence SEQ ID No. 41 or of a sequence with at least 80% identity after optimal alignment with sequence SEQ ID No. 41, and a heavy chain comprising the following three CDRs:
- CDR-H1 of the sequence SEQ ID No. 48 or of a sequence with at least 80% identity after optimal alignment with sequence SEQ ID No. 48;
- CDR-H2 of the sequence SEQ ID No. 49 or of a sequence with at least 80% identity after optimal alignment with sequence SEQ ID No. 49; and
- CDR-H3 of the sequence SEQ ID No. 43 or of a sequence with at least 80% identity after optimal alignment with sequence SEQ ID No. 43.

An antibody, or a derived compound or functional fragment of same, according to the invention is characterized in that it comprises:
- a light chain comprising the CDR-L1 of the sequence SEQ ID No. 40, the CDR-L2 of the sequence SEQ ID No. 2 and the CDR-L3 of the sequence SEQ ID No. 41; and
- a heavy chain comprising the CDR-H1 of the sequence SEQ ID No. 44, the CDR-H2 of the sequence SEQ ID No. 5 and the CDR-H3 of the sequence SEQ ID No. 45.

In another embodiment, an antibody, or a derived compound or functional fragment of same, according to the invention is characterized in that it comprises:
- a light chain comprising the CDR-L1 of the sequence SEQ ID No. 46, the CDR-L2 of the sequence SEQ ID No. 47 and the CDR-L3 of the sequence SEQ ID No. 41; and
- a heavy chain comprising the CDR-H1 of the sequence SEQ ID No. 48, the CDR-H2 of the sequence SEQ ID No. 49 and the CDR-H3 of the sequence SEQ ID No. 43.

According to still another embodiment, the antibody of the invention, or its derived compounds or functional fragments, is characterized in that it comprises a light-chain sequence comprising the amino acid sequence SEQ ID No. 50 or a sequence with at least 80%, preferably 85%, 90%, 95% and 98% identity after optimal alignment with sequence SEQ ID No. 50; and in that it comprises a heavy-chain sequence comprising the amino acid sequence SEQ ID No. 51 or a sequence with at least 80%, preferably 85%, 90%, 95% and 98% identity after optimal alignment with sequence SEQ ID No. 51.

As seen above, the invention also relates to any compound derived from an antibody as described in the invention.

More particularly, the antibody of the invention, or its derived compounds or functional fragments, is characterized in that said derived compound consists of a binding protein comprising a peptide scaffold on which is grafted at least one CDR in such a way as to preserve all or part of the paratope recognition properties of the initial antibody.

One or more sequences among the six CDR sequences described in the present invention can also be present on the various immunoglobulin protein scaffolding. In this case, the protein sequence makes it possible to recreate a peptide skeleton favorable to the folding of the grafted CDRs, enabling them to preserve their paratope antigen-recognition properties.

Generally, a person skilled in the art knows how to determine the type of protein scaffold on which to graft at least one of the CDRs arising from the original antibody. More particularly, it is known that to be selected such scaffolds must meet the greatest number of criteria as follows (Skerra A., J. Mol. Recogn., 2000, 13:167-187):
- good phylogenetic conservation;
- known three-dimensional structure (as, for example, by crystallography, NMR spectroscopy or any other technique known to a person skilled in the art);

small size;

few or no post-transcriptional modifications; and/or easy to produce, express and purify.

The origin of such protein scaffolds can be, but is not limited to, the structures selected among: fibronectin and preferentially fibronectin type III domain 10, lipocalin, anticalin (Skerra A., J. Biotechnol., 2001, 74(4):257-75), protein Z arising from domain B of protein A of *Staphylococcus aureus*, thioredoxin A or proteins with a repeated motif such as the "ankyrin repeat" (Kohl et al., PNAS, 2003, vol. 100, No. 4, 1700-1705), the "armadillo repeat", the "leucine-rich repeat" and the "tetratricopeptide repeat".

Scaffolds derived from toxins such as, for example, toxins from scorpions, insects, plants, mollusks, etc., and the protein inhibitors of neuronal NO synthase (PIN) should also be mentioned.

An example, in no way limiting, of such hybrid constructions, is the insertion of the CDR-H1 (heavy chain) of an antiCD4 antibody, namely 13B8.2, in one of the loops in the PIN, the new binding protein thus obtained preserving the same binding properties as the original antibody (Bes et al., Biochem. Biophys. Res. Commun., 2006, 343(1), 334-344). On a purely illustrative basis, grafting the CDR-H3 (heavy chain) of an anti-lysozyme VHH antibody on one of the loops of neocarzinostatin (Nicaise et al., Protein Science, 2004, 13(7):1882-1891) can also be mentioned.

Lastly, as described above, such peptide scaffolds can comprise from one to six CDRs arising from the original antibody. Preferably, but not being a requirement, a person skilled in the art will select at least one CDR from the heavy chain, the latter being known to be primarily responsible for the specificity of the antibody. The selection of one or more relevant CDRs is obvious to a person skilled in the art, who will then choose suitable known techniques (Bes et al., FEBS letters 508, 2001, 67-74).

A specific aspect of the present invention relates to a method for selecting a compound derived from an antibody according to the invention, said derived compound being capable of inhibiting in vitro and/or in vivo the growth of tumor cells and said derived compound comprising a peptide scaffold on which is grafted at least one antibody CDR, characterized in that it comprises the following steps:

a) the placing in contact in vitro of a compound composed of a peptide scaffold on which is grafted at least one antibody CDR with a biological sample containing tumor cells able to grow and under conditions allowing these cells to grow; and b) selection of said compound if said compound is capable of inhibiting the growth of these tumor cells, and characterized in that said at least one grafted CDR is selected among the following CDRs:

the CDR of sequence SEQ ID No. 1, 9, 40, 46 or a sequence with at least 80%, preferably 85%, 90%, 95% and 98% identity after optimal alignment with sequence SEQ ID No. 1, 9, 40, 46;

the CDR of sequence SEQ ID No. 2, 10, 47 or a sequence with at least 80%, preferably 85%, 90%, 95% and 98% identity after optimal alignment with sequence SEQ ID No. 2, 10, 47;

the CDR of sequence SEQ ID No. 3, 41 or a sequence with at least 80%, preferably 85%, 90%, 95% and 98% identity after optimal alignment with sequence SEQ ID No. 3, 41;

the CDR of sequence SEQ ID No. 4, 7, 11, 42, 44, 48 or a sequence with at least 80%, preferably 85%, 90%, 95% and 98% identity after optimal alignment with sequence SEQ ID No. 4, 7, 11, 42, 44, 48;

the CDR of sequence SEQ ID No. 5, 12, 49 or a sequence with at least 80%, preferably 85%, 90%, 95% and 98% identity after optimal alignment with sequence SEQ ID No. 5, 12, 49; and the CDR of sequence SEQ ID No. 6, 8, 43, 45 or a sequence with at least 80%, preferably 85%, 90%, 95% and 98% identity after optimal alignment with sequence SEQ ID No. 6, 8, 43, 45.

According to a preferred mode, the method can include in step a) the placing in contact in vitro of a compound comprising a peptide scaffold on which is grafted at least two or three antibody CDRs.

According to an even more preferred mode of this method, the peptide scaffold is selected among the scaffolds or binding proteins whose structures were mentioned above.

Obviously, these examples are in no way limiting, and any other structure known or obvious to a person skilled in the art should be considered as being covered by the protection conferred by the present patent application.

The present invention thus relates to an antibody, or its derived compounds or functional fragments, characterized in that the peptide scaffold is selected among proteins that are a) phylogenetically well preserved, b) of robust architecture, c) with a well-known 3-D molecular organization, d) of small size and/or e) comprising regions that can be modified by deletion and/or insertion without modifying stability properties.

According to a preferred embodiment, the antibody of the invention, or its derived compounds or functional fragments, is characterized in that said peptide scaffold is selected among i) scaffolds arising from fibronectin, preferentially fibronectin type 3 domain 10, lipocalin, anticalin, protein Z arising from domain B of protein A of *Staphylococcus aureus*, thioredoxin A or proteins with a repeated motif such as the "ankyrin repeat" (Kohl et al., PNAS, 2003, vol. 100, No. 4, 1700-1705), the "armadillo repeat", the "leucine-rich repeat" and the "tetratricopeptide repeat" or iii) protein inhibiters of neuronal NO synthase (PIN).

Another aspect of the invention relates to the functional fragments of the antibody described above.

More particularly, the invention targets an antibody, or its derived compounds or functional fragments, characterized in that said functional fragment is selected among the fragments Fv, Fab, (Fab')$_2$, Fab', scFv, scFv-Fc and diabodies, or any fragment whose half-life has been increased such as PEGylated fragments.

Such functional fragments of the antibody according to the invention consist, for example, of the fragments Fv, scFv (sc=simple chain), Fab, F(ab')$_2$, Fab', scFv-Fc or diabodies, or any fragment whose half-life has been increased by chemical modification, such as the addition of polyalkylene glycol such as polyethylene glycol (PEGylation) (PEGylated fragments are referred to as Fv-PEG, scFv-PEG, Fab-PEG, F(ab')$_2$-PEG and Fab'-PEG), or by incorporation in a liposome, microspheres or PLGA, said fragments possessing at least one of the characteristic CDRs of the invention which is notably capable of exerting in a general manner activity, even partial, of the antibody from which it arises.

Preferably, said functional fragments will comprise or include a partial sequence of the variable heavy or light chain of the antibody from which they are derived, said partial sequence being sufficient to retain the same binding specificity as the antibody from which it arises and sufficient affinity, preferably at least equal to 1/100, more preferably at least 1/10 of that of the antibody from which it arises.

Such a functional fragment will contain at least five amino acids, preferably 6, 7, 8, 10, 15, 25, 50 or 100 consecutive amino acids of the sequence of the antibody from which it arises.

Preferably, these functional fragments will be of the types Fv, scFv, Fab, F(ab')$_2$, F(ab'), scFv-Fc or diabodies, which generally have the same binding specificity as the antibody from which they result. According to the present invention, fragments of the antibody of the invention can be obtained from the antibodies described above by methods such as enzyme digestion, including pepsin or papain, and/or by cleavage of the disulfide bridges by chemical reduction. The antibody fragments can be also obtained by recombinant genetics techniques also known to a person skilled in the art or by peptide synthesis by means, for example, of automatic peptide synthesizers such as those sold by Applied BioSystems, etc.

For more clarity, table 2 below summarizes the various amino acid sequences corresponding to the antibody of the invention.

TABLE 2

| Antibody | CDR numbering | Heavy chain | Light chain | SEQ ID NO. |
|---|---|---|---|---|
| 414H5 | Common | | CDR-L1 | 1 |
| | | | CDR-L2 | 2 |
| | | | CDR-L3 | 3 |
| | | CDR-H1 | | 4 |
| | | CDR-H2 | | 5 |
| | | CDR-H3 | | 6 |
| | IMGT | | CDR-L1 | 1 |
| | | | CDR-L2 | 2 |
| | | | CDR-L3 | 3 |
| | | CDR-H1 | | 7 |
| | | CDR-H2 | | 5 |
| | | CDR-H3 | | 8 |
| | Kabat | | CDR-L1 | 9 |
| | | | CDR-L2 | 10 |
| | | | CDR-L3 | 3 |
| | | CDR-H1 | | 11 |
| | | CDR-H2 | | 12 |
| | | CDR-H3 | | 6 |
| | | | Mu. variable domain | 13 |
| | | Mu. variable domain | | 14 |
| | | | Ch. variable domain | 64 |
| | | Ch. variable domain | | 65 |
| 515H7 | Common | | CDR-L1 | 40 |
| | | | CDR-L2 | 2 |
| | | | CDR-L3 | 41 |
| | | CDR-H1 | | 42 |
| | | CDR-H2 | | 5 |
| | | CDR-H3 | | 43 |
| | IMGT | | CDR-L1 | 40 |
| | | | CDR-L2 | 2 |
| | | | CDR-L3 | 41 |
| | | CDR-H1 | | 44 |
| | | CDR-H2 | | 5 |
| | | CDR-H3 | | 45 |
| | Kabat | | CDR-L1 | 46 |
| | | | CDR-L2 | 47 |
| | | | CDR-L3 | 41 |
| | | CDR-H1 | | 48 |
| | | CDR-H2 | | 49 |
| | | CDR-H3 | | 43 |
| | | | Mu. variable domain | 50 |
| | | Mu. variable domain | | 51 |
| | | | Ch. variable domain | 66 |
| | | Ch. variable domain | | 67 |

(wherein Mu. = murine and Ch. = chimeric)

Another specific aspect of the present invention relates to a chimeric antibody, or its derived compounds or functional fragments, characterized in that said antibody also comprises light-chain and heavy-chain constant regions derived from an antibody of a species heterologous with the mouse, notably man.

Yet another specific aspect of the present invention relates to a humanized antibody, or its derived compounds or functional fragments, characterized in that the constant regions of the light-chain and the heavy-chain derived from human antibody are, respectively, the lambda or kappa region and the gamma-1, gamma-2 or gamma-4 region.

According to another aspect, the invention relates to a murine hybridoma capable of secreting a monoclonal antibody according to the invention, notably the hybridoma of murine origin filed with the French collection for microorganism cultures (CNCM, Institut Pasteur, Paris, France) on Oct. 22, 2007, under number I-3860. Said hybridoma was obtained by the fusion of Balb/C immunized mice splenocytes and cells of the myeloma Sp 2/O—Ag 14 lines.

The monoclonal antibody, here referred to as 414H5, or its derived compounds or functional fragments, characterized in that said antibody is secreted by the hybridoma filed with the CNCM on Oct. 22, 2007, under number 1-3860 obviously forms part of the present invention.

According to another aspect, the invention relates to a murine hybridoma capable of secreting a monoclonal antibody according to the invention, notably the hybridoma of murine origin filed with the French collection for microorganism cultures (CNCM, Institut Pasteur, Paris, France) on Jun. 25, 2008, under number I-4019. Said hybridoma was obtained by the fusion of Balb/C immunized mice splenocytes and cells of the myeloma Sp 2/O—Ag 14 lines.

The monoclonal antibody, here referred to as 515H7, or its derived compounds or functional fragments, characterized in that said antibody is secreted by the hybridoma filed with the Collection Nationale de Cultures de Microorganismes (CNCM) (Institut Pasteur, 28, rue du Dr. Roux, 75724, Paris, Cédex 15, France, on Jun. 25, 2008, under number I-4019 obviously forms part of the present invention.

The antibody of the invention also comprises chimeric or humanized antibodies.

A chimeric antibody is one containing a natural variable region (light chain and heavy chain) derived from an antibody of a given species in combination with constant regions of the light chain and the heavy chain of an antibody of a species heterologous to said given species.

The antibodies, or chimeric fragments of same, can be prepared by using the techniques of recombinant genetics. For example, the chimeric antibody could be produced by cloning recombinant DNA containing a promoter and a sequence coding for the variable region of a nonhuman monoclonal antibody of the invention, notably murine, and a sequence coding for the human antibody constant region. A chimeric antibody according to the invention coded by one such recombinant gene could be, for example, a mouse-human chimera, the specificity of this antibody being determined by the variable region derived from the murine DNA and its isotype determined by the constant region derived from human DNA. Refer to Verhoeyn et al. (BioEssays, 8:74, 1988) for methods for preparing chimeric antibodies.

In another aspect, the invention describes an antibody, or a derived compound or functional fragment of same, which consists in a chimeric antibody.

In a particular preferred embodiment, the chimeric antibody, or a derived compound or functional fragment of same, of the invention comprises a light chain sequence comprising the amino acid sequence SEQ ID No. 64, and in that it comprises a heavy chain sequence comprising the amino acid sequence SEQ ID No. 65.

In another preferred embodiment, the chimeric antibody, or a derived compound or functional fragment of same, of the invention comprises a light chain sequence comprising the amino acid sequence SEQ ID No. 66, and in that it comprises a heavy chain sequence comprising the amino acid sequence SEQ ID No. 67.

"Humanized antibodies" means an antibody that contains CDR regions derived from an antibody of nonhuman origin, the other parts of the antibody molecule being derived from one (or several) human antibodies. In addition, some of the skeleton segment residues (called FR) can be modified to preserve binding affinity (Jones et al., Nature, 321:522-525, 1986; Verhoeyen et al., Science, 239:1534-1536, 1988; Riechmann et al., Nature, 332:323-327, 1988). In the following specification, the expression hz, HZ, Hz or hz Mab are similar and referred to the humanized form of the antibody.

The humanized antibodies of the invention or fragments of same can be prepared by techniques known to a person skilled in the art (such as, for example, those described in the documents Singer et al., J. Immun., 150:2844-2857, 1992; Mountain et al., Biotechnol. Genet. Eng. Rev., 10:1-142, 1992; and Bebbington et al., Bio/Technology, 10:169-175, 1992). Such humanized antibodies are preferred for their use in methods involving in vitro diagnoses or preventive and/or therapeutic treatment in vivo. Other humanization techniques, also known to a person skilled in the art, such as, for example, the "CDR grafting" technique described by PDL in patents EP 0 451 261, EP 0 682 040, EP 0 939 127, EP 0 566 647 or U.S. Pat. No. 5,530,101, U.S. Pat. No. 6,180,370, U.S. Pat. No. 5,585,089 and U.S. Pat. No. 5,693,761. U.S. Pat. Nos. 5,639, 641 or 6,054,297, 5,886,152 and 5,877,293 can also be cited.

In addition, the invention also relates to humanized antibodies arising from the murine antibodies described above.

In a preferred manner, constant regions of the light-chain and the heavy-chain derived from human antibody are, respectively, the lambda or kappa and the gamma-1, gamma-2 or gamma-4 region.

In the embodiment corresponding to IgG1 isotype IgG1, an additional characteristic of the antibody is to exhibit effector functions, such as antibody-dependant cellular cytotoxicity (ADCC) and/or complement-dependant cytotoxicity (CDC).

More particularly, the invention relates to a humanized antibody heavy chain characterized in that it comprises i) a framework region homologous to corresponding framework region of a human antibody heavy chain, and ii) CDRs homologous to corresponding CDRs of an antibody derived from a different mammalian species, wherein said CDRs consist of CDR-H1, CDR-H2 and CDR-H3 comprising respectively the sequences SEQ ID Nos. 44, 5 and 45.

In another embodiment, the invention relates to a humanized antibody heavy chain comprising a variable region of sequence selected from the group consisting of SEQ ID Nos. 72, 73, 74 or 75.

In still another embodiment, the invention relates to a humanized antibody heavy chain comprising the complete sequence selected from the group consisting of SEQ ID Nos. 83, 84, 85 or 86.

More particularly, the invention relates to a humanized antibody light chain characterized in that it comprises i) a framework region homologous to corresponding framework region of a human antibody light chain, and ii) CDRs homologous to corresponding CDRs of an antibody derived from a different mammalian species, wherein said CDRs consist of CDR-L1, CDR-L2 and CDR-L3 comprising respectively the sequences SEQ ID Nos. 40, 2 and 41.

In another embodiment, the invention relates to a humanized antibody light chain comprising a variable region of sequence selected from the group consisting of SEQ ID Nos. 76, 77, 78, 79, 80, 81 or 82.

In still another embodiment, the invention relates to a humanized antibody light chain comprising the complete sequence selected from the group consisting of SEQ ID Nos. 87, 88, 89, 90, 91, 92 or 93.

More particularly, the invention relates to a humanized antibody, or a derived compound or functional fragment of same, characterized in that it comprises heavy and light chains each having i) framework regions homologous to corresponding framework regions of a human antibody, and ii) CDRs homologous to corresponding CDRs of an antibody derived from a different mammalian species, wherein said CDRs consist of CDR-H1, CDR-H2 and CDR-H3 of the heavy chain comprising respectively the sequences SEQ ID Nos. 44, 5 and 45, and CDR-L1, CDR-L2 and CDR-L3 of the light chain comprising respectively the sequences SEQ ID Nos. 40, 2 and 41.

In another embodiment, the invention relates to a humanized antibody, or a derived compound or functional fragment of same, comprising a heavy chain variable region of sequence selected from the group consisting of SEQ ID Nos. 72, 73, 74 or 75, and a light chain variable region of sequence selected from the group consisting of SEQ ID Nos. 76, 77, 78, 79, 80, 81 or 82.

In still another embodiment, the invention relates to a humanized antibody, or a derived compound or functional fragment of same, comprising a heavy chain of sequence selected from the group consisting of SEQ ID Nos. 83, 84, 85 or 86, and a light chain of sequence selected from the group consisting of SEQ ID Nos. 87, 88, 89, 90, 91, 92 or 93.

In a preferred embodiment, the humanized antibody Hz515H7 VH1 D76N VL2, or a derived compound or functional fragment of same, according to the invention comprises a heavy chain variable region of sequence SEQ ID No. 73, and a light chain variable region of sequence SEQ ID No. 78.

In another preferred embodiment, the humanized antibody Hz515H7 VH1 D76N VL2, or a derived compound or functional fragment of same, according to the invention comprises a heavy chain of sequence SEQ ID No. 84, and a light chain of sequence SEQ ID No. 89.

In another preferred embodiment, the humanized antibody Hz515H7 VH1 D76N VL2.1, or a derived compound or functional fragment of same, according to the invention comprises a heavy chain variable region of sequence SEQ ID No. 73, and a light chain variable region of sequence SEQ ID No. 79.

In another preferred embodiment, the humanized antibody Hz515H7 VH1 D76N VL2.1, or a derived compound or functional fragment of same, according to the invention comprises a heavy chain of sequence SEQ ID No. 84, and a light chain of sequence SEQ ID No. 90.

In another preferred embodiment, the humanized antibody Hz515H7 VH1 D76N VL2.2, or a derived compound or functional fragment of same, according to the invention comprises a heavy chain variable region of sequence SEQ ID No. 73, and a light chain variable region of sequence SEQ ID No. 80.

In another preferred embodiment, the humanized antibody Hz515H7 VH1 D76N VL2.2, or a derived compound or functional fragment of same, according to the invention comprises a heavy chain of sequence SEQ ID No. 84, and a light chain of sequence SEQ ID No. 91.

In another preferred embodiment, the humanized antibody Hz515H7 VH1 D76N VL2.3, or a derived compound or functional fragment of same, according to the invention comprises a heavy chain variable region of sequence SEQ ID No. 73, and a light chain variable region of sequence SEQ ID No. 81.

In another preferred embodiment, the humanized antibody Hz515H7 VH1 D76N VL2.3, or a derived compound or functional fragment of same, according to the invention comprises a heavy chain of sequence SEQ ID No. 84, and a light chain of sequence SEQ ID No. 92.

In another preferred embodiment, the humanized antibody Hz515H7 VH1 V48L D76N VL1, or a derived compound or functional fragment of same, according to the invention, comprises a heavy chain variable region of sequence SEQ ID No. 74, and a light chain variable region of sequence SEQ ID No. 76.

In another preferred embodiment, the humanized antibody Hz515H7 VH1 V48L D76N VL1, or a derived compound or functional fragment of same, according to the invention comprises a heavy chain of sequence SEQ ID No. 85, and a light chain of sequence SEQ ID No. 87.

In another preferred embodiment, the humanized antibody Hz515H7 VH1 V48L D76N VL1 T59A E61D, or a derived compound or functional fragment of same, according to the invention comprises a heavy chain variable region of sequence SEQ ID No. 74, and a light chain variable region of sequence SEQ ID No. 77.

In another preferred embodiment, the humanized antibody Hz515H7 VH1 V48L D76N VL1 T59A E61D, or a derived compound or functional fragment of same, according to the invention comprises a heavy chain of sequence SEQ ID No. 85, and a light chain of sequence SEQ ID No. 88.

In another preferred embodiment, the humanized antibody Hz515H7 VH1 VL1, or a derived compound or functional fragment of same, according to the invention comprises a heavy chain variable region of sequence SEQ ID No. 72, and a light chain variable region of sequence SEQ ID No. 76.

In another preferred embodiment, the humanized antibody Hz515H7 VH1 VL1, or a derived compound or functional fragment of same, according to the invention comprises a heavy chain of sequence SEQ ID No. 83, and a light chain of sequence SEQ ID No. 87.

The table 3 herein-under summarizes the amino acids sequences of the various heavy and light chains variable domains and full length (or complete), respectively, of the humanized antibody according to the invention.

TABLE 3

| Antibody Hz515H7 | Heavy chain | Light chain | SEQ ID NO. |
|---|---|---|---|
| Variable Domains | VH1 | — | 72 |
| | VH1 D76N | — | 73 |
| | VH1 V48L D76N | — | 74 |
| | VH2 | — | 75 |
| | — | VL1 | 76 |
| | — | VL1 T59A E61D | 77 |
| | — | VL2 | 78 |
| | — | VL2.1 | 79 |
| | — | VL2.2 | 80 |
| | — | VL2.3 | 81 |
| | — | VL3 | 82 |
| Complete Sequences (without signal peptide) | VH1 | — | 83 |
| | VH1 D76N | — | 84 |
| | VH1 V48L D76N | — | 85 |
| | VH2 | — | 86 |
| | — | VL1 | 87 |
| | — | VL1 T59A E61D | 88 |
| | — | VL2 | 89 |
| | — | VL2.1 | 90 |
| | — | VL2.2 | 91 |

TABLE 3-continued

| Antibody Hz515H7 | Heavy chain | Light chain | SEQ ID NO. |
|---|---|---|---|
| | — | VL2.3 | 92 |
| | — | VL3 | 93 |

As an example, for the avoidance of doubt, the expression "VH1" is similar to the expressions "VH Variant 1", "VH variant 1", "VH Var 1" or "VH var 1".

It must be understood that the above exemplified VH/VL combinations are not limitative. The man skilled in the art could of course, without undue burden and without applying inventive skill, rearrange all the VH and VL disclosed in the present specification.

A novel aspect of the present invention relates to an isolated nucleic acid characterized in that it is selected among the following nucleic acids (including any degenerate genetic code):

a nucleic acid, DNA or RNA, coding for an antibody, or for a derived compound or functional fragment of same, according to the invention;

a nucleic acid complementary to a nucleic acid as defined in a);

a nucleic acid of at least 18 nucleotides capable of hybridizing under highly stringent conditions with at least one of the CDRs of nucleic acid sequences SEQ ID Nos. 15 to 26 or SEQ ID Nos. 52 to 61 or a sequence with at least 80%, preferably 85%, 90%, 95% and 98% identity after optimal alignment with sequences SEQ ID Nos. 15 to 26 or SEQ ID Nos. 52 to 61; and a nucleic acid of at least 18 nucleotides capable of hybridizing under highly stringent conditions with at least the light chain of nucleic acid sequence SEQ ID No. 27 or SEQ ID No. 62 or SEQ ID No. 68 or 70 and/or the heavy chain of nucleic acid sequence SEQ ID No. 28 or SEQ ID No. 63 or SEQ ID No. 69 or 71 or a sequence with at least 80%, preferably 85%, 90%, 95% and 98% identity after optimal alignment with sequences SEQ ID Nos. 27 and/or 28 or SEQ ID Nos. 62 and/or 63 or SEQ ID Nos. 68 and/or 69 or SEQ ID Nos. 70 and/or 71, preferably with at least one of the CDRs therefrom according to the IMGT or to the Kabat CDR numbering.

Table 4 below summarizes the various nucleotide sequences concerning the antibody of the invention.

TABLE 4

| Antibody | CDR numbering | Heavy chain | Light chain | SEQ ID NO. |
|---|---|---|---|---|
| 414H5 | Common | | CDR-L1 | 15 |
| | | | CDR-L2 | 16 |
| | | | CDR-L3 | 17 |
| | | CDR-H1 | | 18 |
| | | CDR-H2 | | 19 |
| | | CDR-H3 | | 20 |
| | IMGT | | CDR-L1 | 15 |
| | | | CDR-L2 | 16 |
| | | | CDR-L3 | 17 |
| | | CDR-H1 | | 21 |
| | | CDR-H2 | | 19 |
| | | CDR-H3 | | 22 |
| | Kabat | | CDR-L1 | 23 |
| | | | CDR-L2 | 24 |
| | | | CDR-L3 | 17 |
| | | CDR-H1 | | 25 |
| | | CDR-H2 | | 26 |
| | | CDR-H3 | | 20 |
| | | | Mu. variable domain | 27 |

TABLE 4-continued

| Antibody | CDR numbering | Heavy chain | Light chain | SEQ ID NO. |
|---|---|---|---|---|
| | | Mu. variable domain | | 28 |
| | | | Ch. variable domain | 68 |
| | | Ch. variable domain | | 69 |
| 515H7 | Common | | CDR-L1 | 52 |
| | | | CDR-L2 | 16 |
| | | | CDR-L3 | 53 |
| | | CDR-H1 | | 54 |
| | | CDR-H2 | | 19 |
| | | CDR-H3 | | 55 |
| | IMGT | | CDR-L1 | 52 |
| | | | CDR-L2 | 16 |
| | | | CDR-L3 | 53 |
| | | CDR-H1 | | 56 |
| | | CDR-H2 | | 19 |
| | | CDR-H3 | | 57 |
| | Kabat | | CDR-L1 | 58 |
| | | | CDR-L2 | 59 |
| | | | CDR-L3 | 53 |
| | | CDR-H1 | | 60 |
| | | CDR-H2 | | 61 |
| | | CDR-H3 | | 55 |
| | | | Mu. variable domain | 62 |
| | | Mu. variable domain | | 63 |
| | | | Ch. variable domain | 70 |
| | | Ch. variable domain | | 71 |

(wherein Mu = murine and Ch = chimeric)

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, defining a fragment or a region of a nucleic acid, containing unnatural nucleotides or not, and being either a double-strand DNA, a single-strand DNA or transcription products of said DNAs.

It should also be included here that the present invention does not relate to nucleotide sequences in their natural chromosomal environment, i.e., in a natural state. The sequences of the present invention have been isolated and/or purified, i.e., they were sampled directly or indirectly, for example by a copy, their environment having been at least partially modified. Isolated nucleic acids obtained by recombinant genetics, by means, for example, of host cells, or obtained by chemical synthesis should also be mentioned here.

"Nucleic sequences exhibiting a percentage identity of at least 80%, preferably 85%, 90%, 95% and 98%, after optimal alignment with a preferred sequence" means nucleic sequences exhibiting, with respect to the reference nucleic sequence, certain modifications such as, in particular, a deletion, a truncation, an extension, a chimeric fusion and/or a substitution, notably punctual. Preferably, these are sequences which code for the same amino acid sequences as the reference sequence, this being related to the degeneration of the genetic code, or complementarity sequences that are likely to hybridize specifically with the reference sequences, preferably under highly stringent conditions, notably those defined below.

Hybridization under highly stringent conditions means that conditions related to temperature and ionic strength are selected in such a way that they allow hybridization to be maintained between two complementarity DNA fragments. On a purely illustrative basis, the highly stringent conditions of the hybridization step for the purpose of defining the polynucleotide fragments described above are advantageously as follows.

DNA-DNA or DNA-RNA hybridization is carried out in two steps: (1) prehybridization at 42° C. for three hours in phosphate buffer (20 mM, pH 7.5) containing 5×SSC (1×SSC corresponds to a solution of 0.15 M NaCl+0.015 M sodium citrate), 50% formamide, 7% sodium dodecyl sulfate (SDS), 10×Denhardt's, 5% dextran sulfate and 1% salmon sperm DNA; (2) primary hybridization for 20 hours at a temperature depending on the length of the probe (i.e.: 42° C. for a probe>100 nucleotides in length) followed by two 20-minute washings at 20° C. in 2×SSC+2% SDS, one 20-minute washing at 20° C. in 0.1×SSC+0.1% SDS. The last washing is carried out in 0.1×SSC+0.1% SDS for 30 minutes at 60° C. for a probe>100 nucleotides in length. The highly stringent hybridization conditions described above for a polynucleotide of defined size can be adapted by a person skilled in the art for longer or shorter oligonucleotides, according to the procedures described in Sambrook, et al. (Molecular cloning: a laboratory manual, Cold Spring Harbor Laboratory; 3rd edition, 2001).

The invention also encompasses an isolated nucleic acid molecule characterized in that it is selected among the following nucleic acids:

a) a nucleic acid, DNA or RNA, coding for a humanized antibody heavy chain, or for a derived compound or functional fragment of same, according to the invention;

b) a nucleic acid, DNA or RNA, coding for a humanized antibody light chain, or for a derived compound or functional fragment of same, according to the invention;

c) a nucleic acid, DNA or RNA, coding for a humanized antibody, or for a derived compound or functional fragment of same, according to the invention;

d) a nucleic acid complementary to a nucleic acid as defined in a), b) or c);

e) a nucleic acid of at least 18 nucleotides capable of hybridizing under highly stringent conditions with at least a heavy chain comprising the nucleic acid sequences SEQ ID Nos. 94 to 97 or 105 to 108, preferably with at least one of the 3 CDRs therefrom according to the IMGT or to the Kabat CDR numbering;

f) a nucleic acid of at least 18 nucleotides capable of hybridizing under highly stringent conditions with at least a light chain comprising the nucleic acid sequences SEQ ID Nos. 98 to 104 or 109 to 115, preferably with at least one of the 3 CDRs therefrom according to the IMGT or to the Kabat CDR numbering.

The invention also relates to an isolated nucleic acid molecule comprising a nucleic acid sequence encoding a heavy chain variable region of a humanized antibody, said heavy chain variable region nucleotide sequence comprising a CDR-H1 nucleotide sequence of SEQ ID No. 56 or 116; a CDR-H2 nucleotide sequence of SEQ ID No. 19 or 117; and a CDR-H3 nucleotide sequence of SEQ ID No. 57 or 118.

The invention also relates to an isolated nucleic acid molecule comprising a nucleic acid sequence encoding a light chain variable region of a humanized antibody, said light chain variable region nucleotide sequence comprising a CDR-L1 nucleotide sequence of SEQ ID No. 52, 119 or 120; a CDR-L2 nucleotide sequence of SEQ ID No. 16, 121 or 122; and a CDR-L3 nucleotide sequence of SEQ ID No. 53, 123 or 124.

The invention also relates to an isolated nucleic acid molecule comprising a nucleic acid sequence encoding a heavy chain variable region and a light chain variable region of a humanized antibody, said heavy chain variable region nucleotide sequence comprising a CDR-H1 nucleotide sequence of SEQ ID No. 56 or 116; a CDR-H2 nucleotide sequence of SEQ ID No. 19 or 117; and a CDR-H3 nucleotide sequence of SEQ ID No. 57 or 118;

said light chain variable region nucleotide sequence comprising a CDR-L1 nucleotide sequence of SEQ ID No. 52, 119 or 120; a CDR-L2 nucleotide sequence of SEQ ID No. 16, 121 or 122; and a CDR-L3 nucleotide sequence of SEQ ID No. 53, 123 or 124.

The table 5 thereafter summarizes the nucleotide sequences of the various heavy and light chains variable domains and full length (or complete), respectively, of the humanized antibody according to the invention.

TABLE 5

| Antibody Hz515H7 | | Heavy chain | Light chain | SEQ ID NO. |
|---|---|---|---|---|
| Variable Domains | | VH1 | — | 94 |
| | | VH1 D76N | — | 95 |
| | | VH1 V48L D76N | — | 96 |
| | | VH2 | — | 97 |
| | | — | VL1 | 98 |
| | | — | VL1 T59A E61D | 99 |
| | | — | VL2 | 100 |
| | | — | VL2.1 | 101 |
| | | — | VL2.2 | 102 |
| | | — | VL2.3 | 103 |
| | | — | VL3 | 104 |
| Complete Sequences (without signal peptide) | | VH1 | — | 105 |
| | | VH1 D76N | — | 106 |
| | | VH1 V48L D76N | — | 107 |
| | | VH2 | — | 108 |
| | | — | VL1 | 109 |
| | | — | VL1 T59A E61D | 110 |
| | | — | VL2 | 111 |
| | | — | VL2.1 | 112 |
| | | — | VL2.2 | 113 |
| | | — | VL2.3 | 114 |
| | | — | VL3 | 115 |

The expression "optimized sequence" means that the codons encoding the amino acids constitutive of the protein of interest (herein the antibody variable domains) have been optimized for a better recognition by the translation machinery in a dedicated cell type, herewith mammalian cells. With this respect, the amino acid sequence of the given protein encoded by the optimized sequence is identical to that of the non-optimized sequence, but the nucleotide sequence is different. Optimization also include G/C content adaptation and prevention of stable RNA secondary structure (see as example Kim et al., 1997 Gene199(1-2):293-301).

For example, the nucleotide sequence of the murine CDR-H1 (SEQ ID No. 56) has been optimized and corresponds to the nucleotide sequence of the humanized CDR-H1 (SEQ ID No. 116) wherein the codons ggg, act and gat (coding for the residues Gly, Thr and Asp, respectively) have been replaced by the codons ggc, acc and gac, respectively (also coding for the residue Gly, Thr and Asp, respectively).

It is the same for the CDRs of the light chain with two humanized forms corresponding to the VL1, VL2 and VL3 (CDR-L1, L2 and L3) and to the VL2.1, VL2.2 and VL2.3 (CDR-L1bis, L2bis and L3bis).

Such mutations in the nucleotide sequences are common and are obvious for the man skilled in the art.

The following table 6 summarizes the different optimized nucleotide sequences corresponding to the CDRs of the Hz515H7.

TABLE 6

| Antibody | IMGT numbering | Heavy chain | Light chain | SEQ ID NO. |
|---|---|---|---|---|
| Hz515H7 | Optimized sequences | CDR-H1 | — | 116 |
| | | CDR-H2 | — | 117 |
| | | CDR-H3 | — | 118 |
| | | — | CDR-L1 | 119 |
| | | — | CDR-L1 (bis) | 120 |
| | | — | CDR-L2 | 121 |
| | | — | CDR-L2 (bis) | 122 |
| | | — | CDR-L3 | 123 |
| | | — | CDR-L3 (bis) | 124 |

The invention also relates to a vector comprising a nucleic acid as described in the invention.

The invention notably targets cloning and/or expression vectors that contain such a nucleotide sequence.

The vectors of the invention preferably contain elements which allow the expression and/or the secretion of nucleotide sequences in a given host cell. The vector thus must contain a promoter, translation initiation and termination signals, as well as suitable transcription regulation regions. It must be able to be maintained in a stable manner in the host cell and may optionally have specific signals which specify secretion of the translated protein. These various elements are selected and optimized by a person skilled in the art according to the host cell used. For this purpose, the nucleotide sequences can be inserted in self-replicating vectors within the chosen host or be integrative vectors of the chosen host.

Such vectors are prepared by methods typically used by a person skilled in the art and the resulting clones can be introduced into a suitable host by standard methods such as lipofection, electroporation, heat shock or chemical methods.

The vectors are, for example, vectors of plasmid or viral origin. They are used to transform host cells in order to clone or express the nucleotide sequences of the invention.

The invention also comprises host cells transformed by or comprising a vector as described in the present invention.

The host cell can be selected among prokaryotic or eukaryotic systems such as bacterial cells, for example, but also yeast cells or animal cells, notably mammal cells. Insect or plant cells can also be used.

The invention also relates to animals, other than man, that have a transformed cell according to the invention.

Another aspect of the invention relates to a method for the production of an antibody according to the invention, or one of its functional fragments, characterized in that said method comprises the following steps:

a) the culture in a medium of and the suitable culture conditions for a host cell according to the invention; and b) the recovery of said antibody, or one of its functional fragments, thus produced from the culture medium or from said cultured cells.

The transformed cells according to the invention are of use in methods for the preparation of recombinant polypeptides according to the invention. Methods for the preparation of polypeptide according to the invention in recombinant form, characterized in that said methods use a vector and/or a cell transformed by a vector according to the invention, are also comprised in the present invention. Preferably, a cell transformed by a vector according to the invention is cultured under conditions that allow the expression of the aforesaid polypeptide and recovery of said recombinant peptide.

As already mentioned, the host cell can be selected among prokaryotic or eukaryotic systems. In particular, it is possible to identify the nucleotide sequences of the invention that facilitate secretion in such a prokaryotic or eukaryotic system. A vector according to the invention carrying such a sequence can thus be used advantageously for the production of recombinant proteins to be secreted. Indeed, the purification of these recombinant proteins of interest will be facilitated by the fact that they are present in the supernatant of the cellular culture rather than inside host cells.

The polypeptides of the invention can also be prepared by chemical synthesis. One such method of preparation is also an object of the invention. A person skilled in the art knows methods for chemical synthesis, such as solid-phase techniques (see notably Steward et al., 1984, Solid phase peptides synthesis, Pierce Chem. Company, Rockford, 111, 2nd ed.) or partial solid-phase techniques, by condensation of fragments or by conventional synthesis in solution. Polypeptides obtained by chemical synthesis and capable of containing corresponding unnatural amino acids are also comprised in the invention.

The antibodies, or the derived compounds or functional fragments of same, likely to be obtained by the method of the invention are also comprised in the present invention.

According to still another aspect, the present invention relates to an antibody as described above, characterized in that it is, in addition, capable of specifically binding to a human chemokine family receptor and/or capable of specifically inhibiting the signaling of such a receptor.

According to a novel embodiment, the invention relates to an antibody, or its derived compounds or functional fragments, consisting of an antibody that is bispecific in the sense that it comprises a second motif capable of interacting with any receptor implicated in the development of tumors, such as, for example, VEGFR, VEGF, EGFR, IGF-1R, HER2neu, HGF, cMET, FGF, tetraspanins, integrins, CXCR4 (other than the antibody of the present invention, i.e. targeting another epitope), CXCR7 or CXCR2.

The bispecific or bifunctional antibodies constitute a second generation of monoclonal antibodies in which two different variable regions are combined in the same molecule (Hollinger and Bohlen, 1999, Cancer and metastasis, rev. 18:411-419). Their utility was demonstrated in both diagnostic and therapeutic domains relative to their capacity to recruit new effector functions or to target several molecules on the surface of tumor cells; such antibodies can be obtained by chemical methods (Glennie M J et al., 1987, J. Immunol. 139, 2367-2375; Repp R. et al., 1995, J. Hemat., 377-382) or somatic methods (Staerz U. D. and Bevan M. J., 1986, PNAS 83, 1453-1457; Suresh M. R. et al., 1986, Method Enzymol., 121:210-228) but also, preferentially, by genetic engineering techniques that make it possible to force heterodimerization and thus facilitate the purification of the antibody sought (Merchand et al., 1998, Nature Biotech., 16:677-681).

These bispecific antibodies can be constructed as whole IgG, bispecific Fab'2, Fab'PEG, diabodies or bispecific scFv, but also as a tetravalent bispecific antibody in which two binding sites are present for each antigen targeted (Park et al., 2000, Mol. Immunol., 37(18):1123-30) or the fragments of same as described above.

In addition to an economic advantage given that the production and administration of a bispecific antibody are cheaper than the production of two specific antibodies, the use of such bispecific antibodies has the advantage of reducing the treatment's toxicity. Indeed, the use of a bispecific antibody makes it possible to decrease the overall quantity of circulating antibodies and, consequently, possible toxicity.

In a preferred embodiment of the invention, the bispecific antibody is a bivalent or tetravalent antibody.

Lastly, the present invention relates to the antibody described above, or its derived compounds or functional fragments, for use as a drug.

The invention also relates to a pharmaceutical composition comprising as an active ingredient a compound consisting of an antibody of the invention, or one of its derived compounds or functional fragments. Preferably, said antibody is supplemented by an excipient and/or a pharmaceutically acceptable carrier.

The invention also relates to a composition characterized in that it comprises, in addition, as a combination product for use in a simultaneous, separated or extended fashion, an antitumor antibody other that an antibody directed against CXCR4.

According to still another embodiment, the present invention also relates to a pharmaceutical composition as described above that comprises at least a second antitumor compound selected among the compounds capable of specifically inhibiting the tyrosine kinase activity of receptors such as IGF-IR, EGFR, HER2/neu, cMET, VEGFR or VEGF, or any other antitumor compound known to a person skilled in the art.

In a second preferred aspect of the invention, said second compound can be selected among the antibodies antiEGFR, antiIGF-IR, antiHER2/neu, anticMET, VEGFR, VEGF, etc., isolated, or their functional fragments and derived compounds, capable of inhibiting the proliferative and/or anti-apoptotic and/or angiogenic and/or inductive activity of metastatic dissemination promoted by said receptors.

Also suitable for mention are antiCD20 antibodies such as a rituximab, ibritumomab or tositumomab; antiCD33 antibodies such as gemtuzumab or lintuzumab; antiCD22 antibodies such as epratuzumab; antiCD52 antibodies such as alemtuzumab; antiEpCAM antibodies such as edrecolomab, Ch 17-1A or IGN-101; antiCTP21 or 16 antibodies such as Xactin; antiDNA-Ag antibodies such as $^{131}$I-Cotara TNT-1; antiMUC1 antibodies such as pemtumomab or R1150; anti-MUC18 antibodies such as ABX-MA1; antiGD3 antibodies such as mitumomab; antiECA antibodies such as CeaVac or labetuzumab; antiCA125 antibodies such as OvaRex; antiHLA-DR antibodies such as apolizumab; antiCTLA4 antibodies such as MDX-010; antiPSMA antibodies such as MDX-070, $^{111}$In & $^{90}$Y-4591, $^{177}$Lu J591, J591-DM1; anti-Lewis Y antibodies such as IGN311; antiangiogenesis antibodies such as AS1405 and 90YmuBC1; antiTrail-R1 antibodies such as TRAIL R1mAb or TRAIL R2 mAb.

Another embodiment complementary to the invention consists of a composition as described above comprised of, in addition, as a combination or conjugaison product for simultaneous, separated or extended use, a cytotoxic/cytostatic agent.

"Simultaneous use" means the administration of both compounds of the composition comprised in a single dosage form.

"Separated use" means administration, at the same time, of both compounds of the composition, comprised in distinct dosage forms.

"Extended use" means the successive administration of both compounds of the composition, each comprised in a distinct dosage form.

Generally, the composition according to the invention considerably increases cancer treatment effectiveness. In other words, the therapeutic effect of the antibody of the invention is enhanced in an unexpected way by the administration of a cytotoxic agent. Another major subsequent advantage produced by a composition of the invention relates to the possibility of using lower effective doses of the active ingredient, thus making it possible to avoid or reduce the risks of the appearance of side effects, in particular the effect of the cytotoxic agent. Moreover, this composition makes it possible to achieve the expected therapeutic effect more quickly.

"Therapeutic anticancer agent" or "cytotoxic agent" means a substance which, when it is administered to a patient, treats or prevents the development of cancer in the patient. Non-limiting examples of such agents include "alkylating" agents, antimetabolites, antitumor antibiotics, mitotic inhibitors, inhibitors of chromatin functioning, antiangiogenics, antiestrogens, antiandrogens and immunomodulators.

Such agents, for example, are cited in VIDAL, on the page devoted to compounds related to oncology and hematology under the heading "Cytotoxic"; the cytotoxic compounds cited by reference to this document are cited herein as preferred cytotoxic agents.

"Alkylating agent" refers to any substance that can bind covalently with or can alkylate any molecule, preferentially a nucleic acid (e.g., DNA), within a cell. Examples of such alkylating agents include nitrogen mustards such as mechlorethamine, chlorambucil, melphalan, chlorhydrate, pipobroman, prednimustine, disodium phosphate or estramustine; oxazaphosphorines such as cyclophosphamide, altretamine, trofosfamide, sulfofosfamide or ifosfamide; aziridines or ethylene-imines such as thiotepa, triethyleneamine or altetramine; nitrosoureas such as carmustine, streptozocine, fotemustine or lomustine; alkyl sulfonates such as busulfan, treosulfan or improsulfan; triazenes such as dacarbazine; or platinum complexes such as cisplatine, oxaliplatine or carboplatine.

"Antimetabolite" refers to a substance that blocks growth and/or cellular metabolism by interfering with certain activities, generally DNA synthesis. Examples of antimetabolites include methotrexate, 5-fluorouracile, floxuridine, 5-fluorodeoxyuridine, capecitabine, cytarabine, fludarabine, cytosine arabinoside, 6-mercaptopurine (6-MP), 6-thioguanine (6-TG), chlorodesoxyadenosine, 5-azacytidine, gemcitabine, cladribine, deoxycoformycin and pentostatin.

"Antitumor antibiotic" refers to a compound that can prevent or inhibit the synthesis of DNA, RNA and/or proteins. Examples of such antitumor antibiotics include doxorubicin, daunorubicin, idarubicin valrubicin, mitoxantrone, dactinomycin, mithramycin, plicamycin, mitomycin C, bleomycin and procarbazine.

"Mitotic inhibiters" prevent the normal progression of the cell cycle and mitosis. In general, microtubule inhibitors or "taxoids" such as paclitaxel and docetaxel are capable of inhibiting mitosis. The vinca alkaloids, such as vinblastine, vincristine, vindesine and vinorelbine, are also capable of inhibiting mitosis.

"Chromatin inhibiters" or "topoisomerase inhibiters" are substances that inhibit the normal functioning of proteins that shape chromatin, such as topoisomerases I and II. Examples of such inhibiters include, for topoisomerase I, camptothecine and its derivatives, such as irinotecan or topotecan; for topoisomerase II, etoposide, etiposide phosphate and teniposide.

An "antiangiogenic" is any drug, compound, substance or agent that inhibits the growth of the blood vessels. Examples of antiangiogenics include, without being limiting, razoxin, marimastat, batimastat, prinomastat, tanomastat, ilomastat, CGS-27023A, halofuginone, COL-3, neovastat, BMS-275291, thalidomide, CDC 501, DMXAA, L-651582, squalamine, endostatine, SU5416, SU6668, interferon-alpha, EMD121974, interleukin-12, IM862, angiostatin and vitaxin.

"Antiestrogen" or "estrogen antagonist" refers to any substance that decreases, antagonizes or inhibits estrogen action. Examples of such agents are tamoxifene, toremifene, raloxifene, droloxifene, iodoxyfene, anastrozole, letrozole and exemestane.

"Antiandrogen" or "androgen antagonist" refers to any substance that reduces, antagonizes or inhibits androgen action. Examples of antiandrogens include flutamide, nilutamide, bicalutamide, sprironolactone, cyproterone acetate, finasteride and cimitidine.

Immunomodulators are substances that stimulate the immune system. Examples of immunomodulators include interferon, interleukins such as aldesleukin, OCT-43, denileukin diftitox or interleukine-2, tumor necrosis factors such as tasonermine, or other types of immunomodulators such as lentinan, sizofuran, roquinimex, pidotimod, pegademase, thymopentine, poly I:C or levamisole in combination with 5-fluorouracil.

For further details, a person skilled in the art can refer to the manual published by the French Association of Therapeutic Chemistry Teachers titled "Therapeutic chemistry, vol. 6, Antitumor drugs and perspectives in the treatment of cancer, TEC and DOC edition, 2003 [ in French]".

In a particularly preferred embodiment, said composition of the invention as a combination product is characterized in that said cytotoxic agent is bound chemically to said antibody for use simultaneously.

In a particularly preferred embodiment, said composition is characterized in that said cytotoxic/cytostatic agent is selected among the spindle inhibitors or stabilizers, preferably vinorelbine and/or vinflunine and/or vincristine.

In order to facilitate binding between said cytotoxic agent and the antibody according to the invention, spacer molecules can be introduced between the two compounds to bind, such as the poly(alkylene)glycol polyethyleneglycol or the amino acids; or, in another embodiment, said cytotoxic agents' active derivatives, into which have been introduced functions capable of reacting with said antibody, can be used. These binding techniques are well-known to a person skilled in the art and will not be discussed in more detail in the present description.

Other EGFR inhibiters include, without being limiting, monoclonal antibodies C225 and antiEGFR 22Mab (ImClone Systems Incorporated), ABX-EGF (Abgenix/Cell Genesys), EMD-7200 (Merck KgaA) or compounds ZD-1834, ZD-1838 and ZD-1839 (AstraZenec a), PKI-166 (Novartis), PKI-166/CGP-75166 (Novartis), PTK 787 (Novartis), CP 701 (Cephalon), flunomide (Pharmacia/Sugen), CI-1033 (Warner Lambert Parke Davis), CI-1033/PD 183, 805 (Warner Lambert Parke Davis), CL-387, 785 (Wyeth-Ayerst), BBR-1611 (Boehringer Mannheim GMBH/Roche), Naamidine A (Bristol-board Myers Squibb), RC-3940-II (Pharmacia), BIBX-1382 (Boehringer Ingelheim), OLX-103 (Merck & Co), VRCTC-310 (Ventech Research), EGF fusion toxin (Seragen Inc.), DAB-389 (Seragen/Lilgand), ZM-252808 (Imperial Cancer Research Fund), RG-50864 (INSERM), LFM-A12 (Parker Hughes Center Cancer), WHI-P97 (Parker Hughes Center Cancer), GW-282974 (Glaxo), KT-8391 (Kyowa Hakko) or the "EGFR vaccine" (York Medical/Centro of Immunologia Molecular).

Another aspect of the invention relates to a composition characterized in that at least one of said antibodies, or of the derived compounds or functional fragments of same, is combined or conjugated with a cellular toxin and/or a radioisotope.

Preferably, said toxin or said radioisotope is capable of preventing the growth or proliferation of the tumor cell, notably of completely inactivating said tumor cell.

Also preferably, said toxin is an enterobacteria toxin, notably *Pseudomonas* exotoxin A.

The radioisotopes preferentially combined with therapeutic antibodies are radioisotopes that emit gamma rays, preferentially iodine$^{131}$, yttrium$^{90}$, gold$^{199}$, palladium$^{100}$, copper$^{67}$, bismuth$^{217}$ and antimony$^{211}$. Radioisotopes that emit alpha and beta rays can also be used in therapy.

"Toxin or radioisotope combined with at least one antibody of the invention, or a functional fragment of same" refers to any means that makes it possible to bind said toxin or said radioisotope to that at least one antibody, notably by covalent binding between the two compounds, with or without the introduction of the binding molecule.

Examples of agents that allow chemical (covalent), electrostatic, or non-covalent bonding of all or part of the conjugate's elements include, in particular, benzoquinone, carbodiimide and more particularly EDC (1-ethyl-3-[3-dimethyl-aminopropyl]-carbodiimide-hydrochloride), dimaleimide, dithiobis-nitrobenzoic (DTNB) acid, N-succinimidyl S-acetyl thio-acetate (SATA), bridging agents with one or more groups, with one or more phenylaside groups, reacting with ultraviolet (UV) rays, most preferentially N-[-4 (azidosalicylamino)butyl]-3'-(2'-pyridyldithio)-propionamide (APDP), N-succinimid-yl 3(2-pyridyldithio) propionate (SPDP) and 6-hydrazino-nicotinamide (HYNIC).

Another form of binding, notably for radioisotopes, can consist of the use of bifunctional ion chelating agents.

Examples of such chelators include the chelators derived from EDTA (ethylenediaminetetraacetic acid) or DTPA (diethylenetriaminepentaacetic acid) which were developed to bind metals, particularly radioactive metals, with immunoglobulins. Thus, DTPA and its derivatives can be substituted on the carbon chain by various groups in such a way as to increase the stability and the rigidity of the ligand-metal complex (Krejcarek et al., 1977; Brechbiel et al., 1991; Gansow, 1991; U.S. Pat. No. 4,831,175).

For example, DTPA (diethylenetriaminepentaacetic acid) and its derivatives, which long have been widely used in drug and biology either in its free form or in a complex with a metal ion, exhibit the remarkable characteristic of forming stable chelates with metal ions which can be coupled with proteins of therapeutic or diagnostic interest, such as antibodies, for the development of radio-immuno conjugates for cancer therapy (Meases et al., 1984; Gansow et al., 1990).

Also preferably, said at least one antibody of the invention forming said conjugate is selected among its functional fragments, notably fragments that have lost their Fc component, such as scFv fragments.

The present invention also comprises the use of the composition for the preparation of a drug intended for the prevention or the treatment of cancer.

The present invention also relates to the use of an antibody, or a derived compound or functional fragment of same, preferably humanized, and/or of a composition according to the invention for the preparation of a drug for inhibiting the growth of tumor cells. Generally, the present invention relates to the use of an antibody, or a derived compound or functional fragment of same, preferably humanized, and/or of a composition, for the preparation of a drug for cancer prevention or treatment.

Preferred cancers that can be prevented and/or treated include prostate cancer, osteosarcoma, lung cancer, breast cancer, endometrial cancer, colon cancer, multiple myeloma, ovarian cancer, pancreatic cancer or any other cancer.

The invention also concerns the use of an antibody, or a derived compound or functional fragment of same, and/or of a composition as above described for the preparation of a drug for modulating CXCR4 activity in a cell.

Another aspect of the present invention relates to the use of the antibody as described in a diagnostic method, preferably in vitro, of diseases related to CXCR4 expression level. Preferably, said CXCR4 protein related diseases in said diagnostic method will be cancers.

Thus, the antibodies of the invention, or the derived compounds or functional fragments of same, can be employed in a method for the detection and/or quantification of CXCR4 protein in a biological sample in vitro, notably for the diagnosis of diseases associated with an abnormal expression with this protein, such as cancers, wherein said method comprises the following steps:

a) placing the biological sample in contact with an antibody according to the invention, or a derived compound or functional fragment of same;

b) demonstrating the antigen-antibody complex possibly formed.

Thus, the present invention also comprises the kits or accessories for the implementation of a method as described, comprising the following elements:

a) a polyclonal or monoclonal antibody of the invention;

b) optionally, reagents for constituting the medium favorable to immunological reactions;

c) optionally, reagents that reveal the antigen-antibodies complexes produced by the immunological reaction.

Advantageously, the antibodies or functional fragments of same can be immobilized on a support, notably a protein chip. One such protein chip is an object of the invention.

Advantageously, the protein chips can be used in the kits or accessories required for detecting and/or quantifying CXCR4 protein in a biological sample.

It must be stated that the term "biological sample" relates herein to samples taken from a living organism (notably blood, tissue, organ or other samples taken from a mammal, notably man) or any sample likely to contain one such CXCR4 protein (such as a sample of cells, transformed if needed).

Said antibody, or a functional fragment of same, can be in the form of an immunoconjugate or of a labeled antibody in order to obtain a detectable and/or quantifiable signal.

The labeled antibodies of the invention, or the functional or fragments of same, include, for example, antibody conjugates (immunoconjugates), which can be combined, for example, with enzymes such as peroxidase, alkaline phosphatase, α-D-galactosidase, glucose oxidase, glucose amylase, carbonic anhydrase, acetyl-cholinesterase, lysozyme, malate dehydrogenase or glucose-6 phosphate dehydrogenase or by a molecule such as biotin, digoxigenin or 5-bromo-desoxyuridine. Fluorescent labels can be also combined with the antibodies of the invention or functional fragments of same, including notably fluorescein and its derivatives, fluorochrome, rhodamine and its derivatives, green fluorescent protein (GFP), dansyl, umbelliferone, etc. In such conjugates, the antibodies of the invention or functional fragments of same can be prepared by methods known to a person skilled in the art. They can be bound with enzymes or fluorescent labels directly; via a spacer group or a linkage group such as polyaldehyde, glutaraldehyde, ethylenediaminetetraacetic acid (EDTA) or diethylenetriaminepentaacetic acid (DPTA); or in the presence of binding agents such as those mentioned above for therapeutic conjugates. Conjugates carrying fluorescein labels can be prepared by reaction with an isothiocyanate.

Others conjugates can also include chemiluminescent labels such as luminol and dioxetane, bioluminescent labels such as luciferase and luciferin, or radioactive labels such as iodine$^{123}$, iodine$^{125}$, iodine$^{126}$, iodine$^{133}$, bromine$^{77}$, technetium$^{99m}$, indium$^{111}$, indium$^{113m}$, gallium$^{67}$, gallium$^{68}$, ruthenium$^{95}$, ruthenium$^{97}$, ruthenium$^{103}$, ruthenium$^{105}$, mercury$^{107}$, mercury$^{203}$, rhenium$^{99m}$, rhenium$^{101}$, rhenium$^{105}$, scandium$^{47}$, tellurium$^{121m}$, tellurium$^{122m}$, tellurium$^{125m}$, thulium$^{165}$, thulium$^{167}$, thulium$^{168}$, fluorine$^{18}$, yttrium$^{199}$ and iodine$^{131}$. Existing methods known to a person skilled in the art for binding radioisotopes with antibodies, either directly or via a chelating agent such as the EDTA or DTPA mentioned above, can be used for as diagnostic radioisotopes. Thus should be mentioned labeling with [I$^{125}$]Na by the chloramine-T technique [Hunter W. M. and Greenwood F. C. (1962) Nature 194:495]; labeling with technetium$^{99m}$ as described by Crockford et al. (U.S. Pat. No. 4,424,200) or bound via DTPA as described by Hnatowich (U.S. Pat. No. 4,479,930).

The use of the antibody of the invention as biomarker is also disclosed. The methods may be used for detecting or diagnosing various hyperproliferative oncogenic disorders associated with expression of CXCR4 exemplified by, but not limited to breast cancer, ovarian cancer, prostate cancer, pancreatic cancer, skin cancers, oesophageal cancer, lung cancer, head and neck cancer, bladder cancer, colorectal cancer, osteosarcomas, neuroblastoma, acute lymphoblastic leukemia, Acute myeloid leukemia, chronic myeloid leukemia, chronic lymphocytic leukemia, multiple myeloma, lymphomas, renal cancer, glioblastoma, thyroid cancer, rhabdomyosarcoma, or any other cancer associated with expression of CXCR4. As would be recognized by one of ordinary skill in this art, the level of antibody expression associated with a particular disorder will vary depending on the nature and/or the severity of the pre-existing condition.

Administration of the antibodies of the present invention in any of the conventional ways known to one skilled in the art (e.g., topical, parenteral, intramuscular, etc.), will provide an extremely useful method of detecting dysplastic cells in a sample as well as allowing a clinician to monitor the therapeutic regiment of a patient undergoing treatment for a hyperproliferative disorder associated with or mediated by expression of CXCR4.

In another embodiment, the invention relates to a pharmaceutical composition for in vivo imaging of an oncogenic disorder associated with expression of CXCR4 comprising the above monoclonal antibody or fragment thereof which is labeled and which binds CXCR4 in vivo; and a pharmaceutically acceptable carrier.

The antibody of the invention, or a functional fragment or derivative thereof, will find use in various medical or research purposes, including the detection, diagnosis, and staging of various pathologies associated with expression of CXCR4.

Stage determination has potential prognostic value and provides criteria for designing optimal therapy [Simpson et al. J. Clin. Oncology 18:2059 (2000)]. Generally, pathological staging of breast cancer for example, is preferable to clinical staging because the former gives a more accurate prognosis. However, clinical staging would be preferred if it were as accurate as pathological staging because it does not depend on an invasive procedure to obtain tissue for pathological evaluation.

When used with suitable labels or other appropriate detectable biomolecule or chemicals, the antibody of the invention is particularly useful for in vitro and in vivo diagnostic and prognostic applications.

Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA). Various types of labels and methods of conjugating the labels to the antibodies of the invention are well known to those skilled in the art, such as the ones set forth below.

As used herein, the term "an oncogenic disorder associated with expression of CXCR4" is intended to include diseases and other disorders in which the presence of high levels or abnormally low levels of CXCR4 (aberrant) in a subject suffering from the disorder has been shown to be or is suspected of being either responsible for the pathophysiology of the disorder or a factor that contributes to a worsening of the disorder. Alternatively, such disorders may be evidenced, for example, by an increase in the levels of CXCR4 on the cell surface in the affected cells or tissues of a subject suffering from the disorder. The increase in CXCR4 levels may be detected, for example, using the antibody 515H7 of the invention. More, it refers to cells which exhibit relatively autonomous growth, so that they exhibit an aberrant growth phenotype characterized by a significant loss of control of cell proliferation. Alternatively, the cells may express normal levels of CXCR4 but are marked by abnormal proliferation.

In certain embodiments, "increased expression" as it relates to CXCR4 refers to protein or gene expression levels that demonstrate a statistically significant increase in expression (as measured by RNA expression or protein expression) relative to a control.

More particularly, it is considered the use of an antibody, or a functional fragment or derivative thereof, according to the invention as described, for diagnosing in vitro an oncogenic disorder associated with expression of CXCR4 or determining in vitro the prognosis for developing an oncogenic disorder associated with expression of CXCR4, for example a cancer associated with expression of CXCR4.

Another broad aspect in accordance with the invention concerns a method of diagnosing pathological hyperproliferative oncogenic disorder or a susceptibility to a pathological condition associated with expression of CXCR4 in a subject comprising determining the presence or absence of CXCR4 bearing cells in a sample, and diagnosing a pathological condition or susceptibility to a pathological condition based on the presence or absence of said CXCR4 bearing cells. The diagnostic uses of the antibody of the invention comprise primary tumors, cancers metastases, cancer stem cells. The antibody can be present in the form of an immunoconjugate or of a labeled antibody as to obtain a detectable and/or quantifiable signal.

More particularly, an preferred subject in accordance with the invention is a process of detecting in vitro the presence and/or the location of a CXCR4 expressing tumor in a subject, wherein said process comprises the steps of (a) contacting a sample from the subject with an antibody, or a functional fragment or derivative thereof, according to the invention, and (b) detecting the binding of said antibody with the sample. Another aspect of the subject is the follow-up of CXCR4 expression as a response to a CXCR4 targeted therapy during clinical trials, and more particularly when the downregulation and or degradation of the CXCR4 receptor is one of the component of the mechanism of action of the tested compound.

As will be apparent to the skilled artisan, the detection of the binding of the antibody of the invention may be revealed by various assays. Although any means for carrying out the assays is compatible with the invention, it can be mentioned, as examples, FACS, ELISA or IHC.

As used herein, the term "sample" is intended to mean any biological fluid, cell, tissue, organ or portion thereof, that includes or potentially includes a neoplastic cell, such as a cell from the colon, gastric, rectum, breast, ovary, prostate, kidney, lung, blood, brain, skin, thyroid, lymph node, bone marrow or other organ or tissue that contains or is suspected to contain a neoplastic cell. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid molecule or protein preparation.

Clinical sample is intended to encompass a variety of sample types obtained from a subject and useful in the procedure of the invention, such as for example, a diagnostic or monitoring test of determining or detecting CXCR4 expression levels. The definition encompasses solid tissue samples obtained by surgical removal, a pathology specimen, an archived sample, or a biopsy specimen, tissue cultures or cells derived therefrom and the progeny thereof, and sections or smears prepared from any of these sources. Non-limiting examples are samples obtained from colon, gastric, rectum, breast, ovary, prostate, kidney, lung, blood, brain, skin, thyroid, lymph node, bone marrow etc. The definition also encompasses liquid samples of biologic origin, and may refer to either the cells or cell fragments suspended therein, or to the liquid medium and its solutes.

Another aspect in accordance with the invention relates to a process of determining in vitro the expression level of CXCR4 in a CXCR4 expressing tumor from a subject, wherein said process comprises the steps of (a') contacting a sample from the subject with an antibody, or a functional fragment or derivative thereof, according to the invention, and (b') quantifying the level of antibody binding to CXCR4 in said sample.

As will be apparent to the skilled artisan, the level of antibody binding to CXCR4 may be quantified in a number of ways such as by various assays. Although any means for carrying out the assays is compatible with the invention, a preferred method brings into play immunoenzymatic processes according to the ELISA technique, by immunofluorescence, by immunohistochemistry or radio-immunoassay (RIA) technique or equivalent.

Preferably, the biological sample is formed by a biological fluid, such as serum, whole blood, cells, a tissue sample or biopsies of human origin. The sample, may for example include, biopsied tissue, which can be conveniently assayed for the presence of a pathological hyperproliferative oncogenic disorder associated with expression of CXCR4.

Once a determination is made of the amount of CXCR4 present in the test sample, the results can be compared with those of control samples, which are obtained in a manner similar to the test samples but from individuals that do not have or present with a hyperproliferative oncogenic disorder associated with expression of CXCR4. If the level of the CXCR4 is significantly elevated in the test sample, it may be concluded that there is an increased likelihood of the subject from which it was derived has or will develop said disorder.

The invention relates, more particularly, to a process of diagnosing in vitro a CXCR4 expressing tumor or determining in vitro the prognosis for developing a CXCR4 expressing tumor in a subject, wherein said process comprises the steps of (i) determining the expression level of CXCR4 as above described, and (ii) comparing the expression level of step (i) with a reference expression level of CXCR4 from normal tissue or a non expressing CXCR4 tissue.

"Diagnosing" a disease as used in the application is intended to include, for example, diagnosing or detecting the presence of a pathological hyperproliferative oncogenic disorder associated with or mediated by expression of CXCR4, monitoring the progression of the disease, and identifying or detecting cells or samples that are indicative of a disorder associated with the expression of CXCR4.

"Prognosis" as used in this application means the likelihood of recovery from a disease or the prediction of the probable development or outcome of a disease. For example, if a sample from a subject is positive for staining with the antibody of the invention, then the "prognosis" for that subject is better than if the sample was negative for CXCR4 staining Samples may be scored for CXCR4 expression levels on an appropriate scale as it will be more detailed hereinafter.

However another aspect of the invention is also related to the monitoring of CXCR4 expression for therapeutic compounds that induce a degradation of CXCR4 as one of their mechanisms of action. In that case following CXCR4 expression on cell membrane could be a critical tool to evaluate the efficacy of the treatment during clinical trials and "personalized" therapies.

The expression level of CXCR4 is advantageously compared or measured in relation to levels in a control cell or sample also referred to as a "reference level" or "reference expression level". "Reference level", "reference expression level", "control level" and "control" are used interchangeably in the specification. Broadly speaking, a "control level" means a separate baseline level measured in a comparable control cell, which is generally disease or cancer free. It may be from the same individual or from another individual who is normal or does not present with the same disease from which the diseased or test sample is obtained. Within the context of the present invention, the term "reference level" refers to a "control level" of expression of CXCR4 used to evaluate a test level of expression of CXCR4 in a cancer cell-containing sample of a patient. For example, when the level of CXCR4 in the biological sample of a patient is higher than the reference level of CXCR4, the cells will be considered to have a high level of expression, or overexpression, of CXCR4. The reference level can be determined by a plurality of methods. Expression levels may thus define CXCR4 bearing cells or alternatively the level of expression of CXCR4 independent of the number of cells expressing CXCR4. Thus the reference level for each patient can be proscribed by a reference ratio of CXCR4, wherein the reference ratio can be determined by any of the methods for determining the reference levels described herein.

For example, the control may be a predetermined value, which can take a variety of forms. It can be a single cut-off value, such as a median or mean. The "reference level" can be a single number, equally applicable to every patient individually, or the reference level can vary, according to specific subpopulations of patients. Thus, for example, older men might have a different reference level than younger men for the same cancer, and women might have a different reference level than men for the same cancer. Alternatively, the "reference level" can be determined by measuring the level of expression of CXCR4 in non-oncogenic cancer cells from the same tissue as the tissue of the neoplastic cells to be tested. As well, the "reference level" might be a certain ratio of CXCR4 in the neoplastic cells of a patient relative to the CXCR4 levels in non-tumor cells within the same patient. The "reference level" can also be a level of CXCR4 of in vitro cultured cells, which can be manipulated to simulate tumor cells, or can be manipulated in any other manner which yields expression levels which accurately determine the reference level. On the other hand, the "reference level" can be established based upon comparative groups, such as in groups not having elevated CXCR4 levels and groups having elevated CXCR4 levels. Another example of comparative groups would be groups having a particular disease, condition or symptoms and groups without the disease. The predetermined value can be arranged, for example, where a tested population is divided equally (or unequally) into groups, such as a low-risk group, a medium-risk group and a high-risk group or into quandrants or quintiles, the lowest quandrant or quintile being individuals with the lowest risk or highest amount of CXCR4 and the highest quandrant or quintile being individuals with the highest risk or lowest amount of CXCR4.

The reference level can also be determined by comparison of the level of CXCR4 in populations of patients having the same cancer. This can be accomplished, for example, by histogram analysis, in which an entire cohort of patients are graphically presented, wherein a first axis represents the level of CXCR4, and a second axis represents the number of patients in the cohort whose tumor cells express CXCR4 at a given level. Two or more separate groups of patients can be determined by identification of subsets populations of the cohort which have the same or similar levels of CXCR4. Determination of the reference level can then be made based on a level which best distinguishes these separate groups. A reference level also can represent the levels of two or more markers, one of which is CXCR4. Two or more markers can be represented, for example, by a ratio of values for levels of each marker.

Likewise, an apparently healthy population will have a different 'normal' range than will have a population which is known to have a condition associated with expression of CXCR4. Accordingly, the predetermined value selected may take into account the category in which an individual falls. Appropriate ranges and categories can be selected with no more than routine experimentation by those of ordinary skill in the art. By "elevated" "increased" it is meant high relative to a selected control. Typically the control will be based on apparently healthy normal individuals in an appropriate age bracket.

It will also be understood that the controls according to the invention may be, in addition to predetermined values, samples of materials tested in parallel with the experimental materials. Examples include tissue or cells obtained at the same time from the same subject, for example, parts of a single biopsy, or parts of a single cell sample from the subject.

In the clinical diagnosis or monitoring of patients with a CXCR4 mediated diseases, the detection of CXCR4 expressing cells or an increase in the levels of CXCR4, in comparison to the levels in a corresponding biological sample from a normal subject or non-cancerous tissue is generally indicative of a patient with or suspected of presenting with a CXCR4 mediated disorder.

In accordance with the above, the invention provides for a method for predicting susceptibility to cancer comprising detecting the expression level of CXCR4 in a tissue sample, its presence indicating susceptibility to cancer, wherein the degree of CXCR4 expression correlates to the degree of susceptibility. Thus, in specific embodiments, the expression of CXCR4 in, for example, breast tissue ovarian tissue, prostate tissue, pancreatic tissue, skin tissue, oesophageal tissue, lung tissue, head and neck tissue, bladder tissue, colorectal tissue, osteosarcoma tissue, neuroblastoma tissue, acute lymphoblastic leukemia cells, acute myeloid leukemia cells, chronic myeloid leukemia cells, chronic lymphocytic leukemia cells, multiple myeloma cells, lymphoma cells, renal tissue, glioblastoma tissue, thyroid tissue, rhabdomyosarcoma tissue, or any other tissue suspected of cells expressing CXCR4 is examined, with the presence of CXCR4 in the sample providing an indication of cancer susceptibility or the emergence or existence of a tissue specific tumor.

A method for evaluating tumor aggressiveness is also provided. In one embodiment, a method for observing the progression of a malignancy in an individual over time comprises determining the level of CXCR4 expressed by cells in a sample of the tumor, comparing the level so determined to the level of CXCR4 expressed in an equivalent tissue sample taken from the same individual at a different time, wherein the degree of CXCR4 expression in the tumor sample over time provides information on the progression of the cancer.

In yet another embodiment, the application provides methods for determining the appropriate therapeutic protocol for a subject.

The presence or absence or a change in the level of CXCR4 in accordance with the invention may be indicative that the subject is likely to have a relapse or a progressive, or a persistent cancer associated with CXCR4. Thus, by measuring an increase in the number of cells expressing CXCR4 or changes in the concentration of CXCR4 present in various tissues or cells, it is possible to determine whether a particular therapeutic regimen aimed at ameliorating a malignancy associated with CXCR4 is effective.

Another subject of the invention is an in vivo method of imaging an oncogenic disorder associated with expression of CXCR4. For example, such a method can be used on a patient presenting symptoms of an oncogenic disorder. If the patient has, for example increased expression levels of CXCR4, then the patient is likely suffering from a cancerous disorder. As well, the method can be useful for monitoring progression and/or response to treatment in patients who have been previously diagnosed with a CXCR4 mediated cancer. In accordance with the above objective, the invention provides an in vivo imaging reagent comprising an antibody according to the invention, or a functional fragment or derivative thereof, preferably labeled, especially radiolabeled, and its use in medical imaging. Thus, a general method in accordance with the invention works by administering to a patient an imaging-effective amount of an imaging reagent such as the above described monoclonal antibody which is labeled and a pharmaceutically effective carrier and then detecting the agent after it has bound to CXCR4 present in the sample. In certain embodiments, the method works by administering an imaging-effective amount of an imaging agent comprising a targeting moiety and an active moiety. The imaging agent is administered in an amount effective for diagnostic use in a mammal such as a human and the localization and accumulation of the imaging agent is then detected. The localization and accumulation of the imaging agent may be detected by radionucleide imaging, radioscintigraphy, nuclear magnetic resonance imaging, computed tomography, positron emission tomography, computerized axial tomography, X-ray or magnetic resonance imaging method, fluorescence detection, and chemiluminescent detection.

In regards to the development of targeted antitumor therapy, the diagnosis with immunohistological technics gives in situ information on the receptor expression level and thus enable to select patients susceptible to be treated following the expression level of receptors needed for such a treatment.

For immunotherapy using monoclonal antibodies, the response to the treatment depending of the receptor targeted expression level as treatment with trastuzumab where determination of Her2 overexpression in breast carcinoma is now of major clinical importance with the advent of the humanised anti-Her2 monoclonal antibody trastuzumab. Demonstration of Her2 overexpression is a prerequisite for treatment with trastuzumab as it acts by specifically targeting Her2 overexpressing carcinoma cells. Accurate testing for Her2 aims to ensure that costly and potentially toxic trastuzumab treatment is not given to patients with non-overexpessing tumours and that every patient who might benefit from trastuzumab receives appropriate treatment.

The teaching with trastuzumab concerning the patient selection that overexpressed Her2 showed the benefit to determine the expression level of receptor when using a therapy with a monoclonal antibody and to develop, in the same time than a therapeutic monoclonal antibody, a monoclonal antibody which can be used for the patient selection.

As a consequence, the invention relates to a process of determining in vitro the CXCR4 status of a tumor of a subject, wherein said process comprises the steps of (1) determining the expression level of CXCR4 as above described, (2) scoring said tumor for CXCR4 expression level, and (3) comparing said scoring to that obtained from a control sample.

"CXCR4 status" within the meaning of the invention, relates to the classification of tumor to a CXCR4 positive [CXCR4 (+)] CXCR4 negative [CXCR4 (−)] class based on the determination of the expression level of the CXCR4 gene as measured by any methods such as immunohistochemistry (IHC), fluorescence in situ hybridization (FISH), chromosome in situ hybridization (CISH), gene chip or other methods known by the man skilled in the art.

In a preferred embodiment, the antibody for diagnostic has to be to able to bind the targeted receptor when tissue samples are, formalin fixed or Glyco-fixx fixed, and paraffin embedded.

More particularly, the CXCR4 expression level is measured by immunohistochemistry (IHC).

As an example, samples may be scored for CXCR4 expression levels on a scale from $0-3^+$ for levels of antibody staining, where 0 is negative and $1^+-3^+$ represents positive staining at four semiquantitative steps of increasing intensity. Scores $1^+-3^+$ can be recoded as positive because each positive score may be associated with significantly reduced risk for relapse and fatal disease when compared to score 0 (negative), but increasing intensity among the positive scores may provide additional risk reduction. Any conventional hazard analysis method may be used to estimate the prognostic value of CXCR4. Representative analysis methods include Cox regression analysis, which is a semiparametric method for modeling survival or time-to-event data in the presence of censored cases (Hosmer and Lemeshow, 1999; Cox, 1972). In contrast to other survival analyses, e.g. Life Tables or Kaplan-Meyer, Cox allows the inclusion of predictor variables (covariates) in the models. Using a convention analysis method, e.g., Cox one may be able to test hypotheses regarding the correlation of CXCR4 expression status of in a primary tumor to time-to-onset of either disease relapse (disease-free survival time, or time to metastatic disease), or time to death from the disease (overall survival time). Cox regression analysis is also known as Cox proportional hazard analysis. This method is standard for testing the prognostic value of a tumor marker on patient survival time. When used in multivariate mode, the effect of several covariates are tested in parallel so that individual covariates that have independent prognostic value can be identified, i.e. the most useful markers. The term positive or negative "CXCR4 status" [also referred as CXCR4 (+) or CXCR4 (−)] of tumors refers to scores 0 or scores $1^+-3^+$, respectively.

A sample may be "scored" during the diagnosis or monitoring of breast cancer. In its simplest form, scoring may be categorical negative or positive as judged by visual examination of samples by immunohistochemistry. More quantitative scoring involves judging the two parameters intensity of staining and the proportion of stained ("positive") cells that are sampled. Based on these two parameters numbers may be assigned that reflect increasing levels of positive staining Allred et al (Allred, Harvey et al. 1998) have described one way of achieving this, which involved scoring both parameters on a scale from 0 (negative) to $3^+$, and summarizing the scores of the individual parameters to an overall score. This results in a scale with possible scores of 0, 2, 3, 4, 5, 6, 7 or 8. (Note that a score of 11s not possible on Allred's scale). A somewhat simpler scoring method integrates the intensity of nuclear staining and the proportion of cells that display stained nuclei into a combined scale from 0 to $3^+$. Either scoring method may be applied to scoring intensity and proportion of staining of activated Stat5 in the cell nuclei. The terms positive or negative "CXCR4 status" of tumors used in the present description refers to levels of expression of CXCR4 that correspond to scores 0 or $1^+-3^+$ on the simplified scale, respectively.

Generally, the results of a test or assay according to the invention can be presented in any of a variety of formats. The results can be presented in a qualitative fashion. For example, the test report may indicate only whether or not a particular polypeptide was detected, perhaps also with an indication of the limits of detection. The results may be presented in a semi-quantitative fashion. For example, various ranges may be defined, and the ranges may be assigned a score (e.g., $1^+$ to $3^+$) that provides a certain degree of quantitative information. Such a score may reflect various factors, e.g., the number of cells in which CXCR4 is detected, the intensity of the signal (which may indicate the level of expression of CXCR4 or CXCR4 bearing cells), etc. The results may be presented in a quantitative fashion, e.g., as a percentage of cells in which the polypeptide (CXCR4) is detected, as a protein concentration, etc. As will be appreciated by one of ordinary skill in the art, the type of output provided by a test will vary depending upon the technical limitations of the test and the biological significance associated with detection of the polypeptide. For example, in the case of certain polypeptides a purely qualitative output (e.g., whether or not the polypeptide is detected at a certain detection level) provides significant information. In other cases a more quantitative output (e.g., a ratio of the level of expression of the polypeptide in the sample being tested versus the normal level) is necessary.

In a more preferred embodiment, scoring of CXCR4 expression level is graded from 0 to $3^+$, based on an assessment of the intensity of the reaction product and the percentage of positive cells. For more clarity, table 4 hereinafter summarizes these parameters. Only complete circumferential membranous reactivity of the invasive tumor should be considered and often resembled a "chicken wire" appearance. Under current guidelines, samples scored as borderline (score of $2^+$ or more) for CXCR4 IHC must be considered as CXCR4 (+) and are required to undergo further assessment. The IHC analysis should be rejected, and either repeated or tested by FISCH or any other method if, as non limitative example, controls are not as expected, artifacts involve most of the sample and the sample has strong membranous positivity of normal breast ducts (internal controls) suggesting excessive antigen retrieval.

TABLE 7

| CXCR4 status | IHC description |
|---|---|
| 0 | No reactivity or membranous reactivity in less than 10% of tumour cells |

TABLE 7-continued

| CXCR4 status | IHC description |
|---|---|
| 1+ | Faint/barely perceptible membranous reactivity is detected in more than 10% of tumour cells. The cells are immunoreactive only in part of the membrane |
| 2+ | Weak to moderate complete membranous reactivity is seen in more than 10% of tumour cells |
| 3+ | Strong complete reactivity is seen in more than 10% of tumour cells |

In a more preferred embodiment of the process according to the invention, said scoring comprises using an appropriate scale based on two parameters which are the intensity of the staining and the percentage of positive cells.

In a preferred embodiment, the process according to the invention, refers to an appropriate scale is a scale of 0 to 3+ wherein no membranous reactivity of tumor cells is scored 0, and strong complete reactivity in more than 10% of tumor cells is scored 3+.

In more details, as above described, said appropriate scale is a scale of 0 to 3 wherein no membranous reactivity of tumor cells is scored 0; faint perceptible membranous reactivity in more than 10% of tumor cells is scored 1+; weak to moderate complete membranous reactivity in more than 10% of tumor cells is scored 2+; and strong complete reactivity in more than 10% of tumor cells is scored 3+.

In a particular aspect of the invention, a tumor is CXCR4 (+) with a score of 2+.

In a particular aspect of the invention, a tumor is CXCR4 (+) with a score of 3+.

In another particular aspect of the invention, a tumor is CXCR4 (+) with a score of 2+ or 3+.

According to the invention, it is also described a process of determining whether an oncogenic disorder is susceptible to treatment with a anti-CXCR4 antibody, or a fragment or derivative thereof, wherein said process comprises the steps of (a) determining in vitro the CXCR4 status of a tumor of a subject as above described, and (b) determining that, if the status is CXCR4 (+), the oncogenic disorder is susceptible to treatment with an anti-CXCR4 antibody, or a fragment or derivative thereof.

In another aspect of the invention, it is considered a kit useful for such diagnosing or prognosing process, said kit comprising the antibody of the invention.

As a matter of convenience, a packaged combination of reagents in predetermined amounts with instructions for performing the diagnostic assay, e.g. kits are also within the scope of the invention. The kit contains the antibodies for detection and quantitation of CXCR4 in vitro, e.g. in an ELISA or a Western blot. The antibody of the present invention can be provided in a kit for detection and quantitation of CXCR4 in vitro, e.g. in an ELISA or a Western blot. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. Such a kit may comprise a receptacle being compartmentalized to receive one or more containers such as vials, tubes and the like, such containers holding separate elements of the invention. For example, one container may contain a first antibody bound to an insoluble or partly soluble carrier. A second container may contain soluble, detectably-labeled second antibody, in lyophilized form or in solution. The receptacle may also contain a third container holding a detectably labeled third antibody in lyophilized form or in solution. A kit of this nature can be used in the sandwich assay of the invention. The label or package insert may provide a description of the composition as well as instructions for the intended in vitro or diagnostic use.

The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

In yet a further aspect of the invention, monoclonal antibodies or binding fragments thereof as detailed herein are provided labeled with a detectable moiety, such that they may be packaged and used, for example, in kits, to diagnose or identify cells having the aforementioned antigen. Non-limiting examples of such labels include fluorophores such as fluorescein isothiocyanate; chromophores, radionuclides, or enzymes. Such labeled antibodies or binding fragments may be used for the histological localization of the antigen, ELISA, cell sorting, as well as other immunological techniques for detecting or quantifying CXCR4, and cells bearing this antigen, for example.

Kits are also provided that are useful as a positive control for apoptosis assays, for purification or immunoprecipitation of CXCR4 from cells. For isolation and purification of CXCR4, the kit can contain the antibodies described herein or antigen binding fragments thereof coupled to beads (e.g., sepharose beads). Kits can be provided which contain the antibodies for detection and quantitation of CXCR4 in vitro, e.g. in an ELISA or a Western blot. As with the article of manufacture, the kit comprises a container and a label or package insert on or associated with the container. The container holds a composition comprising at least one anti-CXCR4 antibody or binding fragment thereof of the invention. Additional containers may be included that contain, e.g., diluents and buffers, control antibodies. The label or package insert may provide a description of the composition as well as instructions for the intended in vitro or diagnostic use.

More particularly, the invention concerns a kit for the determination of the CXCR4 status of a tumor by any method known by the man skilled in the art. In a preferred embodiment, as it will be described in the example, the invention relates to a kit for the determination of the CXCR4 status of a tumor by IHC methods.

In a particular embodiment, the invention consists in a kit comprising at least an anti-CXCR4 antibody, or a functional fragment or derivative thereof, as above describes, said antibody being preferably labeled.

It must be understood that any labeling method can be used by the man skilled in the art such as, for example, the use of labels above mentioned.

In a preferred embodiment, the kit according to the invention, useful for detecting in vitro the presence and/or the location of a CXCR4 expressing tumor in a subject, further comprises a reagent useful for detecting the extent of binding between the said anti-CXCR4 antibody and CXCR4.

In another preferred embodiment, the kit of the invention useful for determining in vitro the expression level of CXCR4 in a CXCR4 expressing tumor, further comprises a reagent useful for quantifying the level of binding between the said labeled antibody and CXCR4.

In still another embodiment, the kit according to the invention useful for determining in vitro the CXCR4 status of a tumor, further comprises:

i) a reagent useful for detecting the extent of binding between the said labeled antibody and CXCR4; and ii) positive and negative control samples useful for the scoring the CXCR4 expression level.

Said kit for determining in vitro the CXCR4 status of a tumor can further comprise a polyclonal antibody specific to murine antibodies, preferably said polyclonal antibody specific to murine antibodies is labeled.

The invention also relates to the use of an antibody according to the invention for the preparation of a drug for the specific targeting of a compound that is biologically active toward cells expressing or overexpressing CXCR4.

In the sense of the present description, a "biologically active compound" is any compound capable of modulating, notably inhibiting, cellular activity, notably growth, proliferation, transcription and gene translation.

The invention also relates to an in vivo diagnostic reagent composed of an antibody according to the invention, or a functional fragment of same, preferably labeled, notably radiolabeled, and its use in medical imaging, notably for the detection of cancer related to the cellular expression or overexpression of CXCR4.

The invention also relates to a composition as a combination product or to an anti-CXCR4/toxin conjugate or radio-isotope, according to the invention, used as drug.

Preferably, said composition as a combination product or said conjugate will be supplemented by an excipient and/or a pharmaceutical vehicle.

In the present description, "pharmaceutical vehicle" means a compound, or a combination of compounds, entering a pharmaceutical composition that does not cause secondary reactions and that, for example, facilitates administration of the active compounds, increases its lifespan and/or effectiveness in the organism, increases its solubility in solution or improves its storage. Such pharmaceutical carriers are well-known and will be adapted by a person skilled in the art according to the nature and the administration route of the active compounds selected.

Preferably, such compounds will be administered by systemic route, notably by intravenous, intramuscular, intradermal, intraperitoneal, subcutaneous or oral route. More preferably, the composition composed of the antibody according to the invention will be administered in several doses spaced equally over time.

Their administration routes, dosing schedules and optimal galenic forms can be determined according to the criteria generally taken into account when establishing a treatment suited to a patient such as, for example, the patient's age or body weight, the seriousness of his general state, his tolerance for the treatment and the side effects experienced.

Thus, the invention relates to the use of an antibody, or one of its functional fragments, for the preparation of a drug for the specific targeting of a compound that is biologically active toward cells expressing or overexpressing CXCR4.

As previously demonstrated, CXCR4 Mabs according to the invention have strong activities in the field of cancer treatment, so such antibodies could be used in screening assays for identification of CXCR4 antagonist anti-tumoral agents to treat cancer. In the first step of these assays, cells expressing CXCR4 are incubated with the antibodies of the invention and then molecules can be evaluated for their potential to inhibit antibodies binding. Cells used in this type of assays can be transfected cell lines such as CHO-CXCR4, NIH3T3-CXCR4 or CXCR4 transfected human cell lines such as U373-MAGI-CXCR4, human cell lines expressing CXCR4 such as NALM6 or primary cells such as PBMC. The method used to screen antagonists of CXCR4 inhibiting antibodies binding on CXCR4 expressing cells can be cell-based competitive enzyme-linked immunosorbent Assay (ELISA) as described by Zhao Q. et al. (AIDS Research And Human Retroviruses, 2003, 19, pp 947-955) or protocols using Fluorescence-Activated cell Sorting (FACS) such as described by Juarez J. et al. (Leukemia 2003, 17, pp 1294-1300).

Thus, in a particular aspect of the invention, it is considered a process for the screening and/or the identification of molecules as CXCR4 antagonist anti-tumoral agents comprising the steps of:

a) selecting cells expressing CXCR4, b) incubating said cells with an antibody, or one of its functional fragments or derivatives, of the invention, and c) evaluating the tested molecules for their potential inhibition of the binding between the antibody, or one of its functional fragments or derivatives, to CXCR4, and d) selecting molecules capable of said inhibition.

Other characteristics and advantages of the invention appear further in the description with the examples and figures whose legends are presented below.

FIGURE LEGENDS

(FIGS. 6A and 6B: CXCR4:CXCR4 homo-dimerization; FIGS. 6C and 6D: CXCR2:CXCR4 hetero-dimerization and FIGS. 6E and 6F: CXCR4-mediated recruitment of β-arrestin).

(FIG. 20A: CXCR4:CXCR4 homo-dimerization; FIG. 20B: CXCR2:CXCR4 hetero-dimerization and FIG. 20C: CXCR4-mediated recruitment of β-arrestin).

FIG. 23 shows the anti-CXCR4 chimeric Mabs c414H5 and c515H7 activity in U937 Nod/Scid mice survival model.

FIG. 24 shows the amino acid sequences alignment of 515H7 heavy chain variable domain residues 1-120 of SEQ ID NO. 51 with the human germline IGHV3-49*04 and IGHJ4*01. The 515H7 VH amino acid sequence (residues 1-120 of SEQ ID NO. 51) is aligned with the selected human acceptor framework sequences. VH 1 (SEQ ID NO. 72) and VH2 (SEQ ID NO. 75) (VH3 is not represented) sequences correspond to implemented humanized variants of the 515H7 VH domain, with back mutated residues in bold. Variant 1 VH1 (SEQ ID NO. 72) carries no back mutated residue and represents a fully human variant. Variant VH2 VH2 (SEQ ID NO. 75) has 8 back mutations and is the most murine variant. Variant VH3 carry 5 back mutations (not represented).

FIG. 25 shows the amino acid sequences alignment of 515H7 light chain (SEQ ID NO. 50) with the human germline IGKV4-1*01 and IGKJ1*01. The 515H7 VL amino acid sequence is aligned with the selected human acceptor framework sequences. VL1 to VL3 sequences correspond to implemented humanized variants of the 515H7 VL domain, with back mutated residues in bold. Variant VL1 (SEQ ID NO. 76) carries no back mutated residue and represents the most human variant. Variant VL2 (SEQ ID NO. 78) has 13 back mutations and is the most murine variant. Variant VL3 (SEQ ID NO. 82) carry 5 back mutations.

Figure 26B:
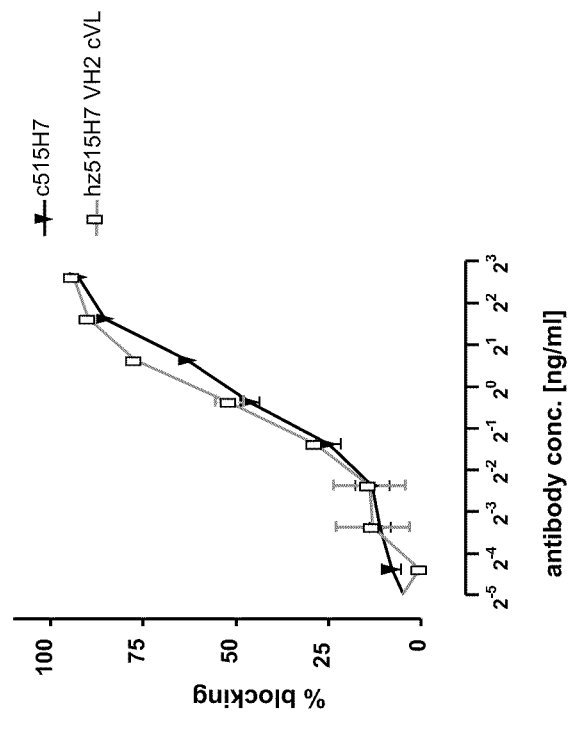
Figure 26A:
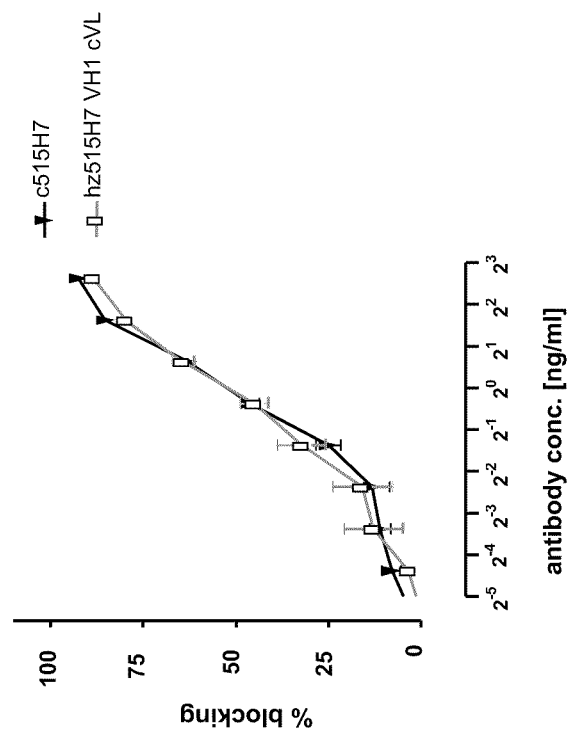
Figure 26D:
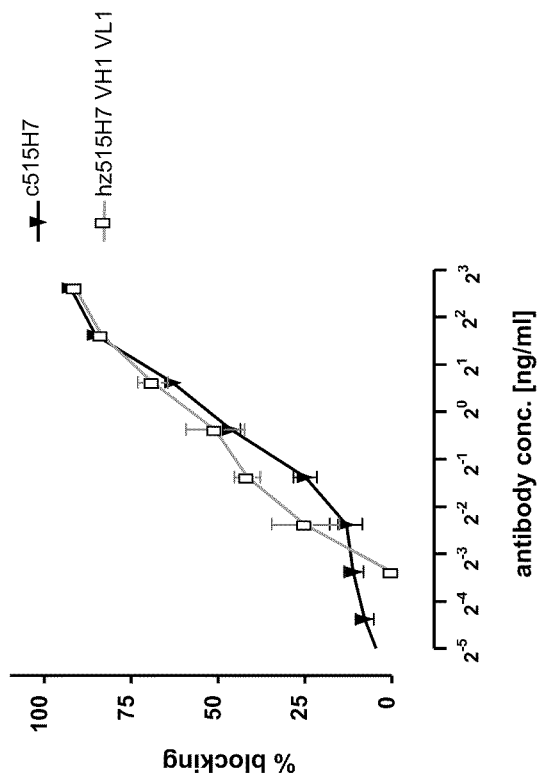
Figure 26C:
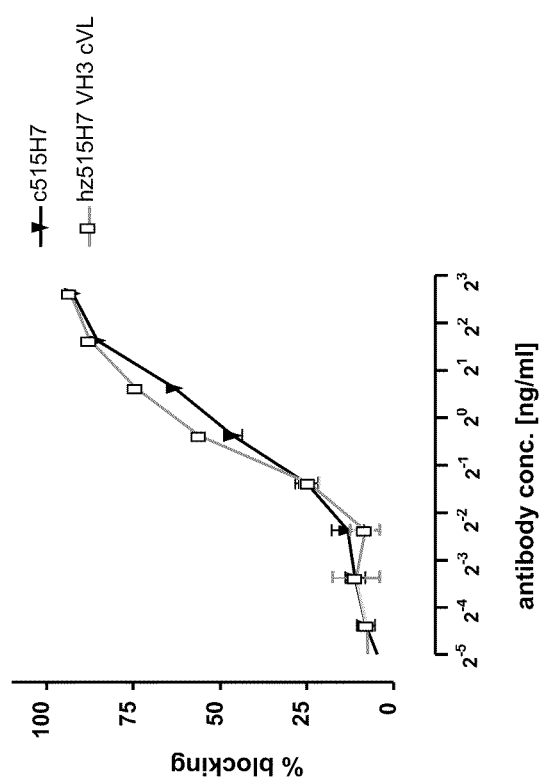
Figure 26F:
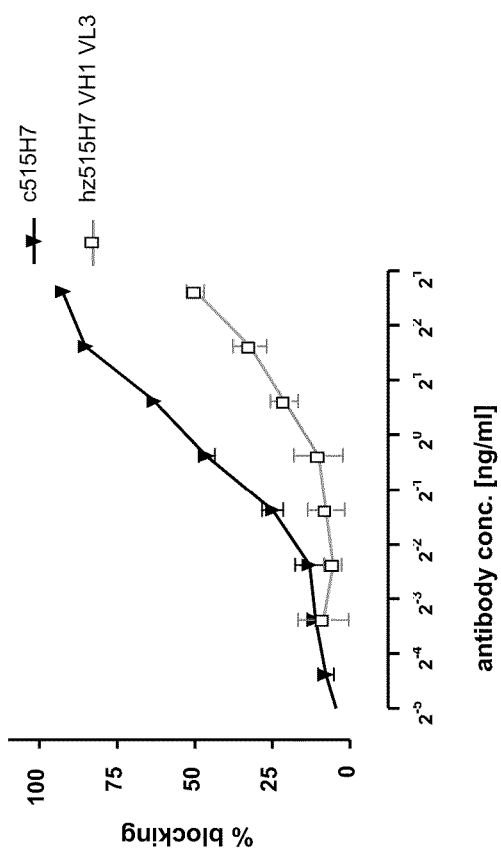
Figure 26E:
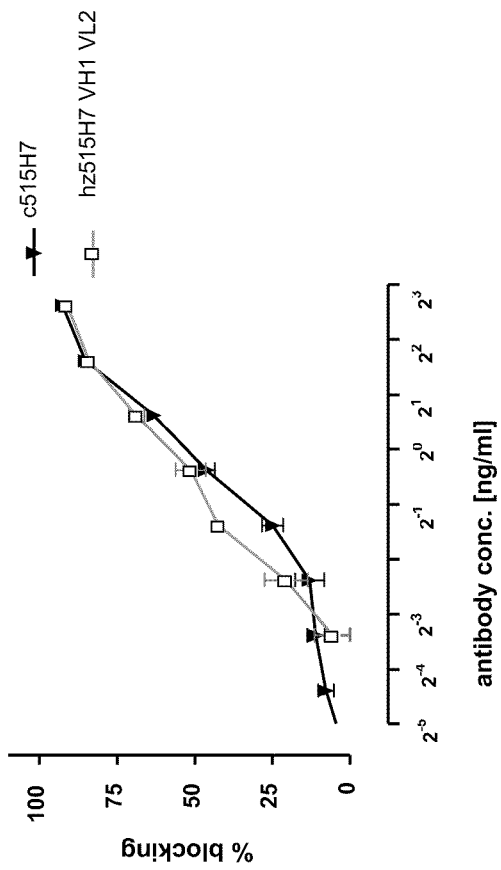

FIGS. 26A-26F show cross blocking of the biotinylated murine antibody 515H7 by the chimeric 515H7 and different variants of the humanized 515H7. The activity of the humanized variants of 515H7 (hz515H7) to cross block the parental murine antibody 515H7 was evaluated by flow cytometry using CXCR4 transfected NIH3T3 cells. The activity of the humanized variants was compared to the chimeric 515H7. The cross blocking activity of the three different variants of VH (VH1-VH3) combined with the chimeric VL (cVL) were very similar (FIGS. 26A-26C). No reduction in the activity of VH variant 1 (VH1, the variant with no back mutations) was determined when combined with variant 1 and 2 of VL (FIGS. 26D, 26E). A significant reduction of the activity was detected for the construct hz515H7 VH1 VL3 (FIG. F).

Figure 27:
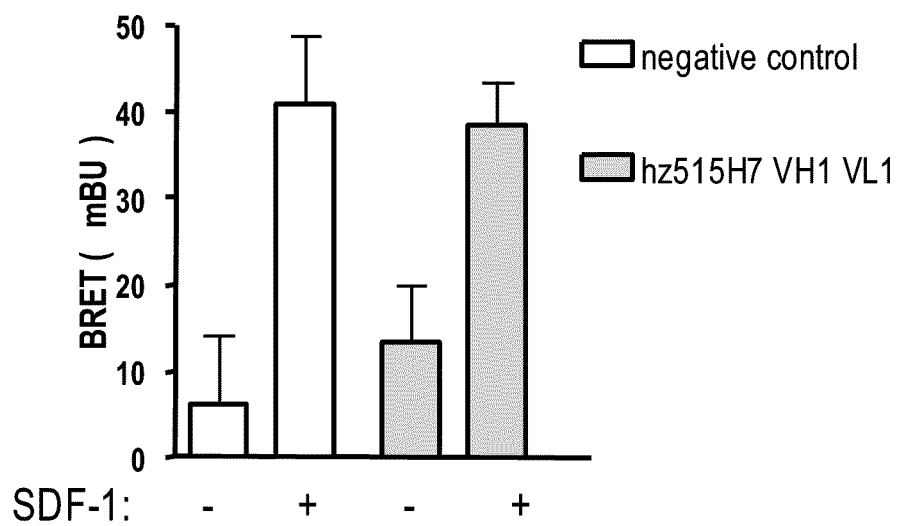

FIG. 27 shows the BRET assay for testing the activity of the humanized antibody 515H7 variant VH1 VL1. The activity of the humanized variant 515H7 VH variant 1 VL variant 1 (hz515H7 VH1 VL1) was evaluated by its capacity to inhibit SDF-1 mediated signal transduction. This variant showed only a minor inhibition of the SDF-1 mediated signal transduction as determined by BRET. SDF-1 was used at a concentration of 100 nM.

FIGS. 28A-28D show comparison of different mutants of the VH1 with single or double back mutations and combinations of different VL variants with hz515H7 VH1 D76N. Single and double back mutations were made in the VH1 and combined with the VL1. These constructs were evaluated in BRET assays (A-C). Of these single back mutants only the construct with the back mutation D76N showed an increased inhibition of the SDF-1 mediated signal transduction. None of the double back mutant in VH had strong inhibitory activity (C). The single back mutant D76N of the VH1 was combined with different variants of VL(D). The SDF-1 concentration was 100 nM.

Figure 29:
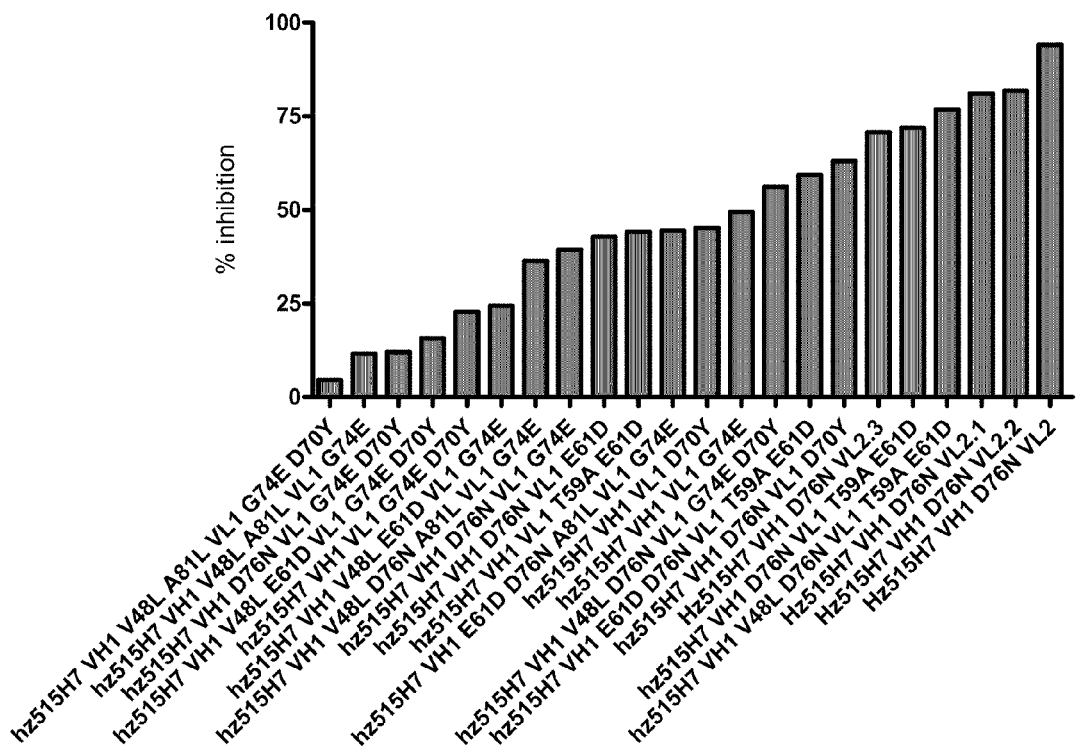

FIG. 29 shows ranking of different mutants of the VH variants 1 and VL variant 1 with single or double back mutations in comparison to the construct VH1 D76N VL2. Single and double back mutations were made in the VH1 and combined with the VL1. All constructs were evaluated in BRET assays and their percent inhibition calculated. The SDF-1 concentration was 100 nM.

Figures 30A, 30B:
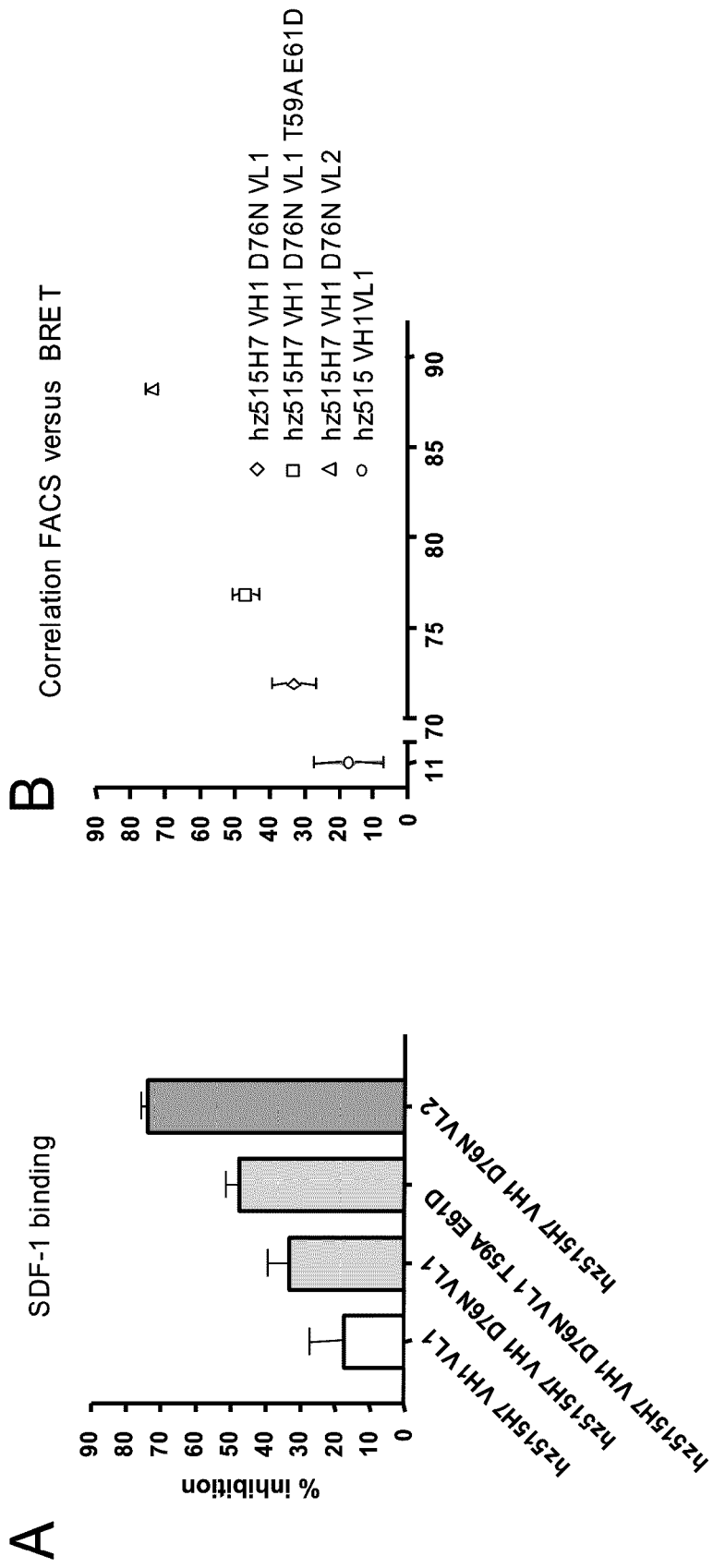

FIGS. 30A and 30B show inhibition of SDF-1 binding by different constructs of the humanized 515H7 and correlation between result obtained by FACS and BRET. The different variants of the humanized antibody 515H7 with a strong activity in blocking the recruitment of β-arrestin were tested in their capacity to inhibit the binding of biotinylated SDF-1 in flow cytometry (FACS) (A). These were compared with the variant 1 of VH and VL. Results from the FACS-based assay are correlated with the results obtained by BRET (B).

Figures 31, 32A:
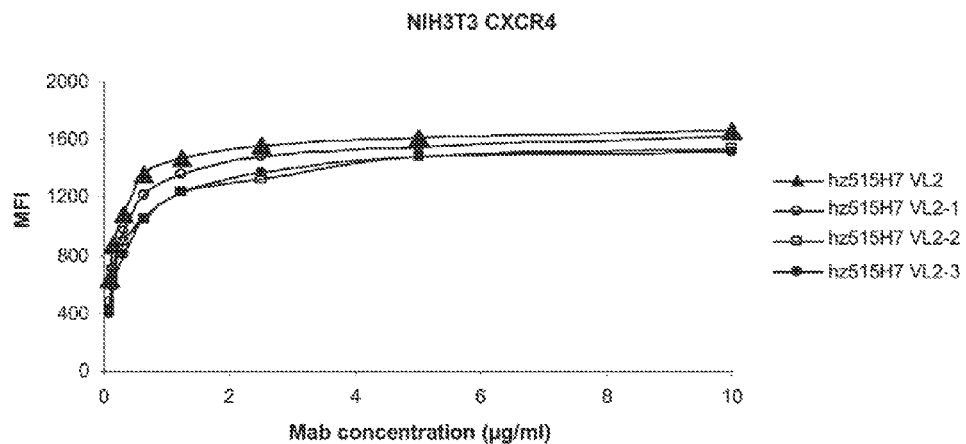

FIG. 31 shows the amino acid sequences alignment of humanized 515H7 VL2 and further humanized versions 515H7 VL2.1, 515H7 VL2.2 and 515H7 VL2.3. The 515H7 VL amino acid sequence (SEQ ID NO. 50) is aligned with the selected human acceptor framework sequences. VL2.1, VL2.2 and VL2.3 sequences correspond to implemented humanized variants of the humanized 515H7 VL2 (SEQ ID NO. 78), with mutated residues in bold. VL2.1 (SEQ ID NO. 79) and VL2.2 (SEQ ID NO. 80) carry 4 more humanized residues whereas VL2.3 (SEQ ID NO. 81) contains 5 more human residues.

Figure 32B:
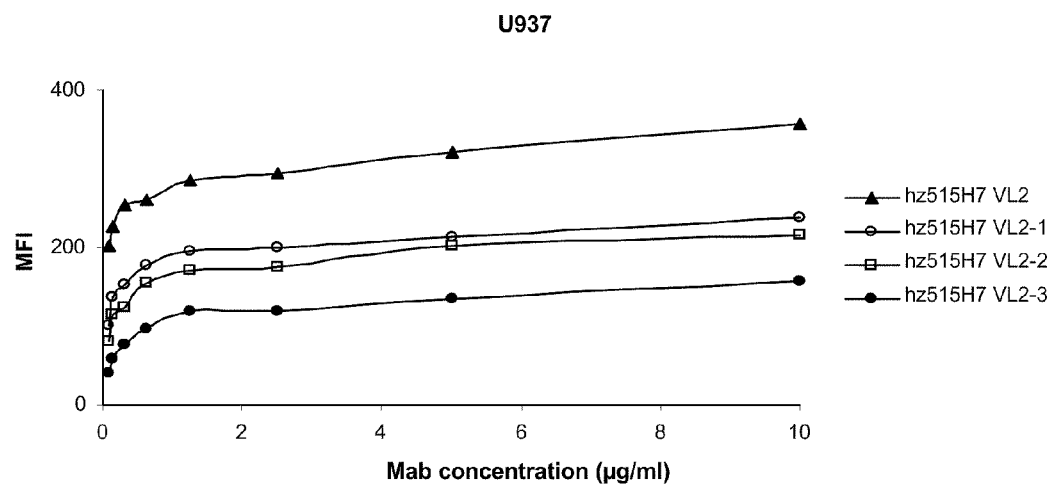
Figure 32C:
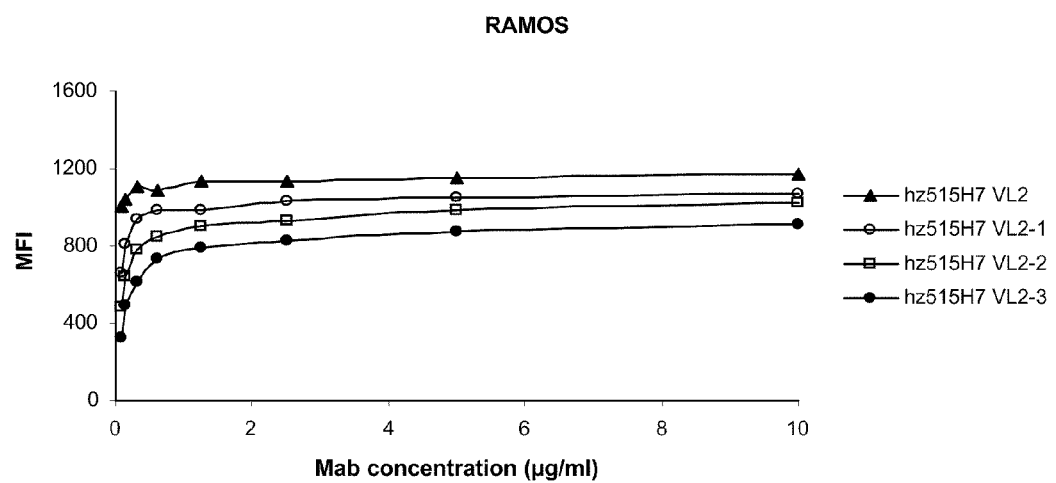

FIGS. 32A-32C show the 515H7 humanized Mabs (hz515H7 VH1 D76N VL2, hz515H7 VH1 D76N VL2.1, hz515H7 VH1 D76N VL2.2 and hz515H7 VH1 D76N VL2.3) specific binding to CXCR4 on NIH3T3-CXCR4 (FIG. 32A) U937 (FIG. 32B) and Ramos cells (FIG. 32C).

FIGS. 33A-33D and 34A-34B show the modulation of G protein activation by m515H7, c515H7 and humanized Mabs 515H7 (hz515H7 VH1 D76N VL2, hz515H7 VH1 D76N VL2.1, hz515H7 VH1 D76N VL2.2 and hz515H7 VH1 D76N VL2.3) by monitoring [$^{35}$S]GTPγS binding responses at wild-type CXCR4 receptor stably expressed in NIH-3T3 cells stimulated with SDF-1 (10 nM or 100 nM)).

Figure 35A:
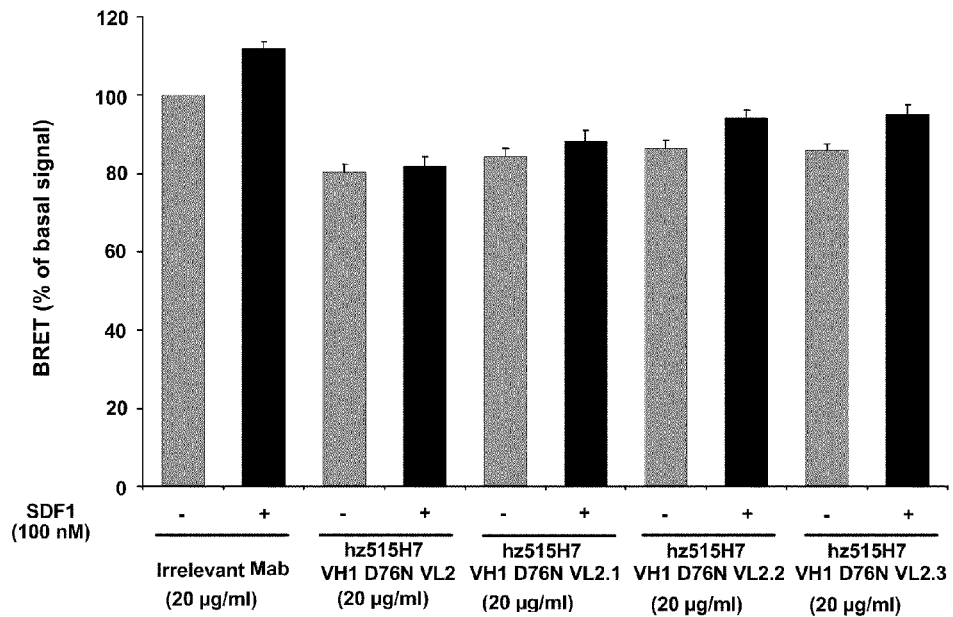
Figure 35B:
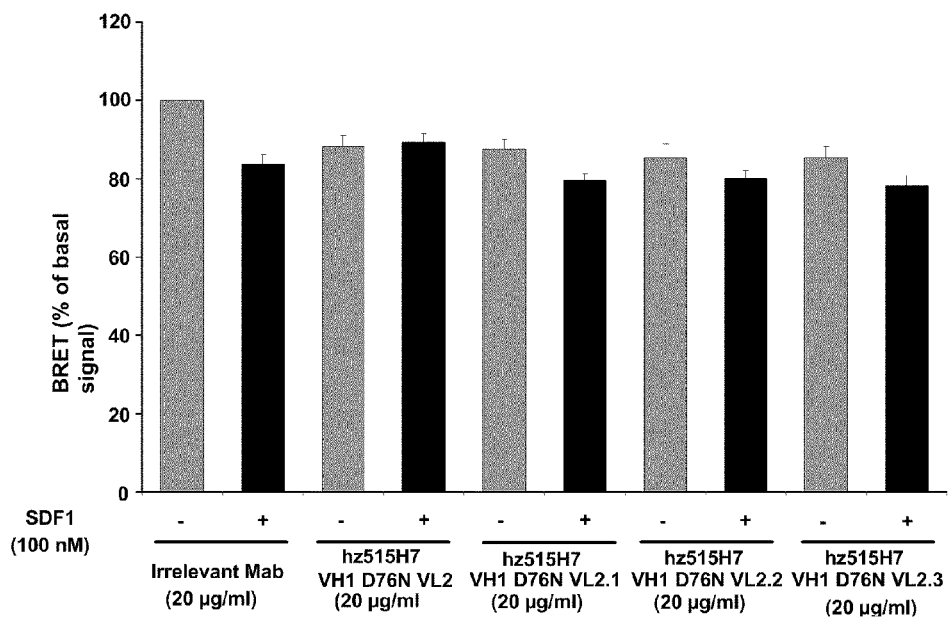
Figure 35C:
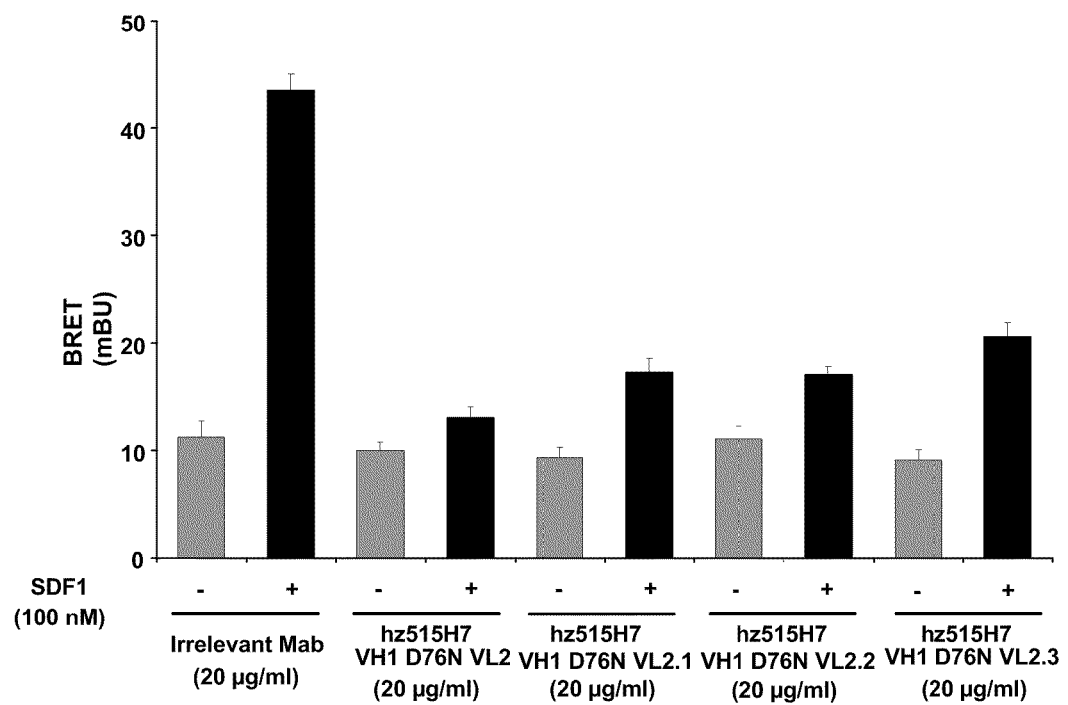

FIGS. 35A-35C show the modulation of CXCR4 receptor association with different interaction partners by SDF-1 and by humanized 515H7 Mabs (hz515H7 VH1 D76N VL2, hz515H7 VH1 D76N VL2.1, hz515H7 VH1 D76N VL2.2 and hz515H7 VH1 D76N VL2.3) via a bioluminescence resonance energy transfer (BRET) approach in HEK293 cells. (FIG. 35A: CXCR4:CXCR4 homo-dimerization; FIG. 35B: CXCR2:CXCR4 hetero-dimerization and FIG. 35C: CXCR4-mediated recruitment of β-arrestin).

FIGS. 36A-36D illustrate RAMOS and KARPAS299 xenograft tumors Glyofixx-fixed with a) and c) IHC staining using 515H7/b) and d) IHC staining using mIgG1.

FIGS. 37A-37D illustrate RAMOS and KARPAS299 xenograft tumors Formol-fixed with a) and c) IHC staining using 515H7/b) and d) IHC staining using mIgG1.

EXAMPLES

Example 1

Expression of CXCR4 and CXCR2 in Cancer Cells

Q-PCR Analysis

In order to quantify the relative expression of CXCR4 and CXCR2 in different cancer cell lines, a real time RT-PCR was used.

RNA samples were extracted from different cell lines using RNeasy Mini or Midi Protocols (Qiagen Corporation, France). The RNA samples were then controlled using the Experion automated electrophoresis system (BIO-RAD Corporation, France) and showed a good quality/integrity. One μg of each RNA sample was converted into cDNA template using the iScript cDNA Synthesis kit (BIO-RAD Corporation, France). cDNA levels were quantified using qPCR with either a TaqMan probe for CXCR2 or SYBERGreen for CXCR4. Comparing samples requires normalization, so was introduced the internal reference RPL0. TaqMan probes (used for CXCR2) carried a 5' FAM reporter label and a 3' TAMRA quencher group. The PCR enzyme was activated by heating for 2 min at 50° C. and 10 min at 95° C. A two step procedure was used, 15 sec at 95° C. and 1 min at 62° C. for 40 or 45 cycles in a PCR mix containing 5 μl of cDNA template (dilution 1/20), 1×qPCR Mastermix (TaqMan Universal PCR Master Mix, Applied Biosystems corporation, Branchburg N.J., USA), 50 to 900 nM of each primers and 50 to 100 nM probe in a total volume of 50 μl. All reactions were performed using iCycler instrument (BIO-RAD Corporation). Q-PCR allowed to determine Cycle threshold (Ct). The more the Ct value is small, the more the gene tested is expressed. Primers and probe for Human Ribosomal protein, large, P0 were:

forward primer,
(SEQ ID No. 32)
5'-GAAACTCTGCATTCTCGCTTCCTG-3';

reverse primer,
(SEQ ID No. 33)
5'-AGGACTCGTTTGTACCCGTTGA-3';

probe,
(SEQ ID No. 34)
5-(FAM)-TGCAGATTGGCTACCCAACTGTTGCA-(TAMRA)-3'.

Primers for Human CXCR4 (chemokine receptor 4) were:

forward primer,
(SEQ ID No. 35)
5'-CTCCTTCATCCTCCTGGAAATC-3';

reverse primer,
(SEQ ID No. 36)
5'-CCAAGGAAAGCATAGAGGATGG-3'.

Primers and probe for Human CXCR2 (chemokine receptor 2) were:

forward primer,
(SEQ ID No. 37)
5'-GTGGTCATTATCTATGCCCTGG-3';

reverse primer,
(SEQ ID No. 38)
5'-CGACCCTGCTGTATAAGATGAC-3';

probe,
(SEQ ID No. 39)
5-(FAM)-TATTCCTGCTGAGCCTGCTGGGAAA-(TAMRA)-3'.

In our comparative study, the expression of two genes [the gene tested (CXCR4 or CXCR2) and RPL0]) were quantified in two different samples: the cell line tested and a reference cell line. The reference cell line corresponded to the cell line containing the lowest expression of the gene quantified. Comparative gene expression calculation was made using the following formula:

Relative gene expression=
$(1+E_{gene})^{-\Delta Ct(1)}/(1+E_{RPL0})^{-\Delta Ct(2)}$ $E_{gene}$=PCR efficiency using primers/probe of the gene quantified
$E_{RPL0}$=PCR efficiency using the RPL0 primers/probe
Ct=threshold cycle
$\Delta Ct(1)=Ct_{gene}$ (cell line tested)–$Ct_{gene}$ (reference cell line)
$\Delta Ct(2)=Ct_{RPL0}$ (cell line tested)–$Ct_{RPL0}$ (reference cell line).

Figure 1A:
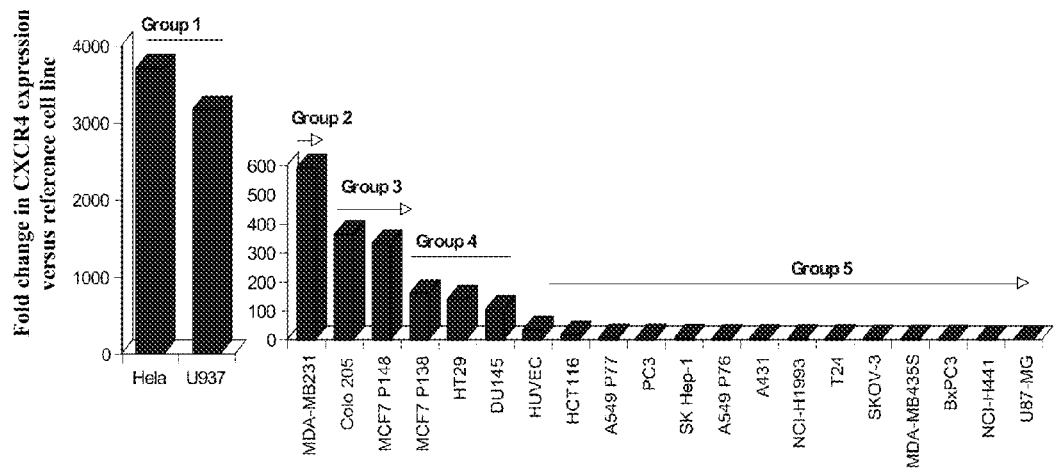
FIGS. 1A and 1B show CXCR4 and CXCR2 expression in cancer cells by qPCR analysis, respectively.
Figure 1B:
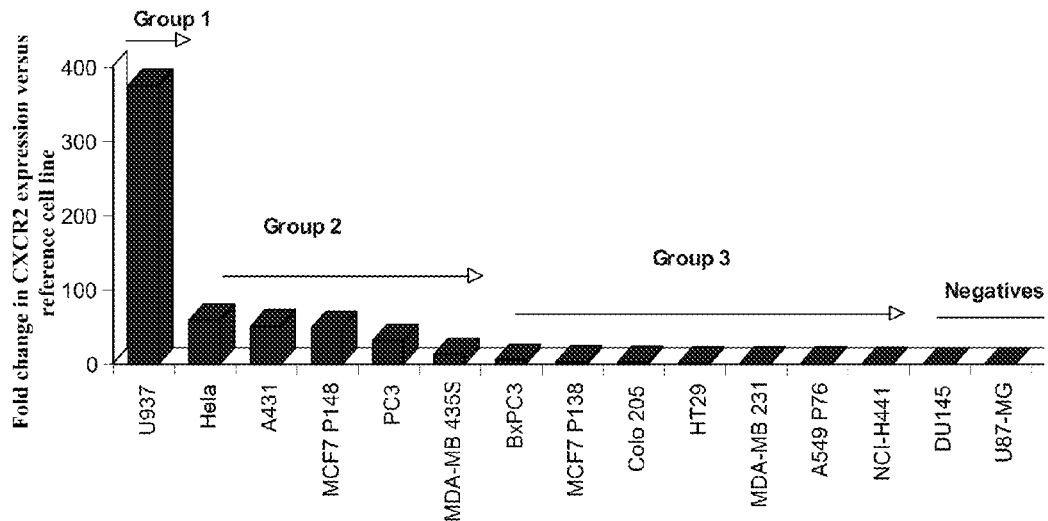

For each PCR series, a relative gene quantity value was calculated, and cancer cell lines were classified into groups considering their levels of expression from the highest to negative. All data are presented in FIGS. 1A and 1B. All the cancer cell lines tested expressed CXCR4 (FIG. 1A) and CXCR2 excepted DU145 and U-87MG for CXCR2 (FIG. 1B).

FACS Analysis

Figure 2:
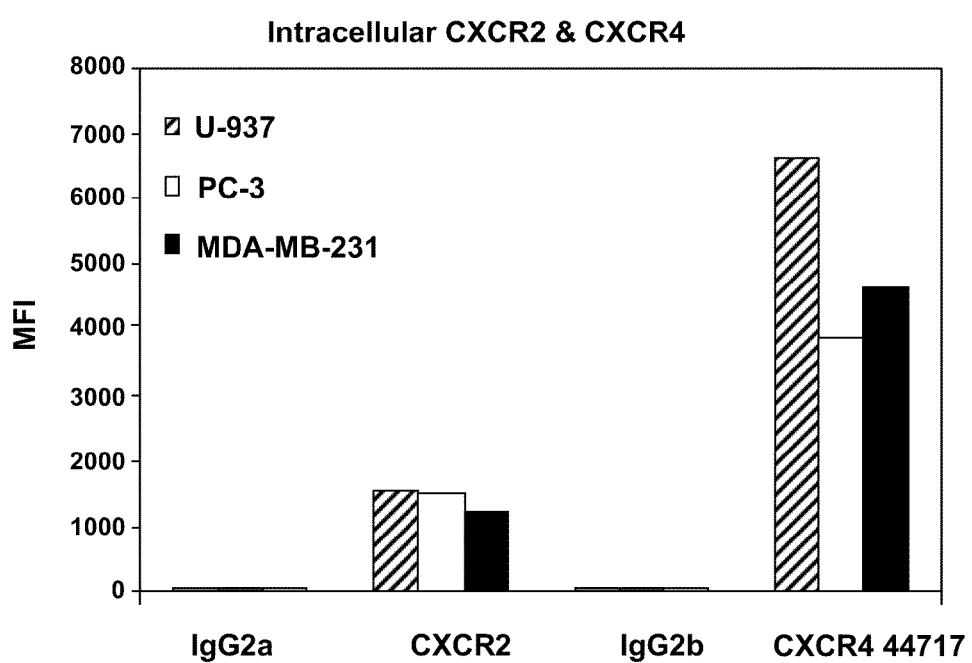
FIG. 2 shows CXCR4 and CXCR2 protein expression in cancer cells by FACS analysis.

MDA-MB-231, PC3 and U937 cancer cell lines were permebilized and then incubated with either 10 μg/mL of anti-CXCR4 monoclonal antibodies [44717 (R&D Systems) versus its isotype control IgG2b (SIGMA] or 10 μg/mL of anti-CXCR2 monoclonal antibodies (anti h-CXCR2, clone 48311, R&D Systems, Mab 331 versus its isotype control IgG2a). The cells were then washed with 1% BSA/PBS/0.01% NaN3. Next, Alexa-labeled secondary antibodies were added to the cells and were allowed to incubate at 4° C. for 20 min. Cells were then washed again two times. Following the second wash, FACS analysis was performed. Results of these binding studies are provided in FIG. 2. Thus, tumor cells such as MDA-MB-231, PC3 and U937 expressed both CXCR4 and CXCR2 proteins.

Example 2

Generation of Monoclonal Antibodies (Mabs) Against Human CXCR4

To generate monoclonal antibodies to CXCR4, Balb/c mice were immunized with recombinant NIH3T3-CXCR4 cells and/or peptides corresponding to CXCR4 extracellular N-term and loops. The mice 6-16 weeks of age upon the first immunization, were immunized once with the antigen in complete Freund's adjuvant subcutaneously (s.c.) followed by 2 to 6 immunizations with antigen in incomplete Freund's adjuvant s.c. The immune response was monitored by retro-orbital bleeds. The serum was screened by ELISA (as described bellow) and mice with the higher titers of anti-CXCR4 antibodies were used for fusions. Mice were boost intravenously with antigen two days before sacrifice and removal of the spleen.

ELISA

To select the mice producing anti-CXCR4 antibodies, sera from immunized mice was tested by ELISA. Briefly, microtiter plates were coated with purified [1-41] N-terminal peptide conjugated to BSA at 5 µg equivalent peptide/mL, 100⁴/well incubated at 4° C. overnight, then blocked with 250⁴/well of 0.5% gelatine in PBS. Dilutions of plasma from CXCR4-immunized mice were added to each well and incubated 2 hours at 37° C. The plates were washed with PBS and then incubated with a goat anti-mouse IgG antibody conjugated to HRP (Jackson Laboratories) for 1 hour at 37° C. After washing, plates were developed with TMB substrate, the reaction was stopped 5 min later by addition of 100 µL/well 1M $H_2SO_4$. Mice that developed the highest titers of anti-CXCR4 antibodies were used for antibody generation.

Generation of Hybridomas Producing Mabs to CXCR4

The mouse splenocytes, isolated from a Balb/c mice that developed the highest titers of anti-CXCR4 antibodies were fused with PEG to a mouse myeloma cell line Sp2/O. Cells were plated at approximately $1 \times 10^5$/well in microtiter plates followed by two weeks incubation in selective medium containing ultra culture medium+2 mM L-glutamine+1 mM sodium pyruvate+1×HAT. Wells were then screened by ELISA for anti-CXCR4 monoclonal IgG antibodies. The antibody secreting hybridomas were then subcloned at least twice by limiting dilution, cultured in vitro to generate antibody for further analysis.

Example 3

Characterization by FACS Analysis of Anti-CXCR4 Mabs 414H5 and 515H7 Binding Specificity and Cancer Cell Lines Recognition In this experiment, specific binding to human CXCR4 of anti-CXCR4 Mabs 414H5 and 515H7 was examined by FACS analysis.

NIH3T3, NIH3T3-hCXCR4 transfected cells, MDA-MB-231, Hela and U937 cancer cell lines were incubated with 10 µg/mL of monoclonal antibody 414H5 and 515H7. The cells were then washed with 1% BSA/PBS/0.01% NaN3. Next, Alexa-labeled secondary antibodies were added to the cells and were allowed to incubate at 4° C. for 20 min. The cells were then washed again two times. Following the second wash, FACS analysis was performed. Results of these binding studies are provided in the following Table 7 which shows [Mean Fluorescence Intensity (MFI) obtained by FACS] that anti-CXCR4 Mabs 414H5 and 515H7 bound specifically to human CXCR4-NIH3T3 transfected cell line whereas there was no recognition on the parent NIH3T3 cells. These Mab were also able to recognize human cancer cell lines, for examples MDA-MB-231 breast cancer cells, U937 promyelocytic cancer cells and Hela cervix cancer cells.

Anti-CXCR4 Mabs 414H5 and 515H7 recognized NIH3T3-hCXCR4 transfectant while there was no recognition of the parent NIH3T3 wild type cells. Mabs 414H5 and 515H7 were also able to recognize cancer cell lines.

TABLE 8

| Clone (10 µg/ml) | MFI on cell lines | | | | |
|---|---|---|---|---|---|
| | NIH3T3 | NIH3T3-CXCR4 | MDA-MB-231 | Hela | U937 |
| 414H5 | 21 | 2162 | 32 | 467 | 95 |
| 515H7 | 16 | 2752 | 239 | 1851 | 645 |

Example 4

Competition binding of anti-CXCR4 Mabs 414H5 and 515H7 for [$^{125}$I]SDF-1 at CHO-K1 membranes stably expressing human CXCR4 receptor This assay allows to evaluate the ability of 414H5 and 515H7 Mabs to compete for binding of radio labeled [$^{125}$I] SDF-1 to human CXCR4 receptor, at either orthosteric or allosteric binding sites.

CHO-K1 cells, stably and constitutively expressing human CXCR4 receptor were obtained upon transfection of naïve CHO-K1 cells (ATCC CCL-61) with a mammalian expression vector carrying the whole coding sequence of human CXCR4 receptor (RefSeq NM_003467). Cells were propagated in complete culture medium [DMEM-Ham's F12 supplemented with 5% fetal calf serum (FCS) and 500 µg/ml of geneticin]. Radioligand binding experiments were conducted on cell membranes obtained upon mechanical scrapping of CHO/CXCR4 cells in lysis buffer [Hepes 20 mM, pH 7.4, NaCl 150 mM] followed by centrifugation (10000 g, 15 min). [$^{125}$I]SDF-1 binding (specific activity: 1500 Ci/mmol) was performed using the SPA technology (scintillation proximity assay—GE Healthcare). Briefly, cell membranes (30 µg/well) were incubated in binding buffer [Hepes 20 mM, pH 7.4, $CaCl_2$ 1 mM, $MgCl_2$ 5 mM, NaCl 150 mM, BSA 1%] together with compound to evaluate (SDF-1 or mAb), radioligand (1 nM) and finally SPA-WGA-PVT beads (7.3 mg/well). Binding equilibrium was reach after 1H at 25° C. Upon centrifugation [1000 g for 10 min.] radioactive counts were measured in a scintillation counter (TopCount, Perkin Elmer). Non-specific binding was estimated in the presence of 10 µM of unlabelled SDF-1.

Figure 3A:
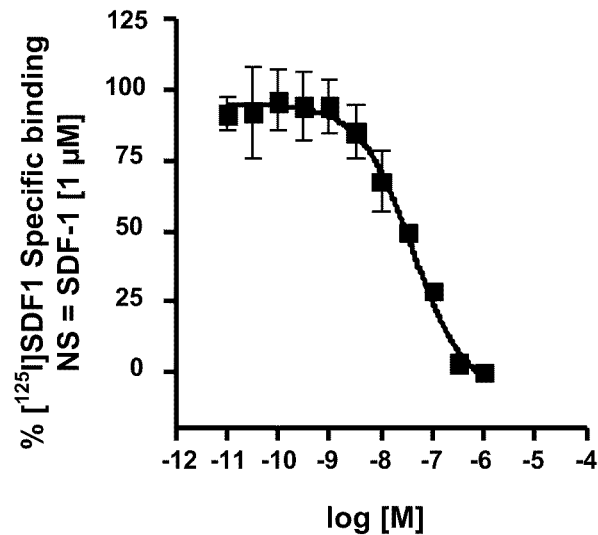
FIGS. 3A and 3B show the competition of specific [$^{125}$I] SDF1 binding by unlabeled SDF-1 (FIG. 3A) and 414H5 and 515H7 Mabs (FIG. 3B) on cellular membranes of CHO-K1 cells stably expressing wild-type human CXCR4 (T: total binding; NS: non-specific binding).
Figure 3B:
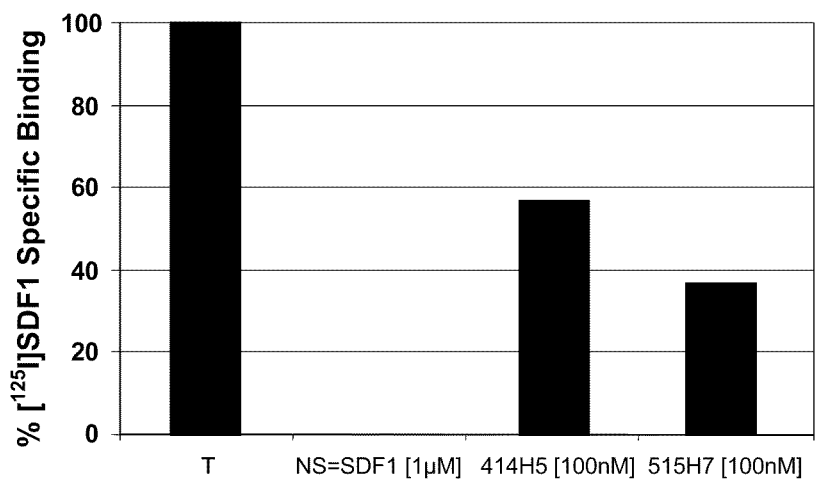

Unlabelled SDF-1 dose-dependently inhibited [$^{125}$I] SDF-1 binding with a pKi value ($IC_{50}$=ligand concentration yielding 50% inhibition of specific [$^{125}$I]SDF-1 binding) of 7.75±0.27 nM (n=4) (FIG. 3A). Under the same experimental conditions, our anti-CXCR4 Mabs (100 nM) efficiently competed for [$^{125}$I]SDF-1 binding with the following rank order of competition efficacy (% inhibition of [$^{125}$I]SDF-1): 515H7 (64±3%) 414H5 (43±4%) (FIG. 3B).

Example 5

Modulation of [$^{35}$S]GTPγS Binding at Cellular Membranes Expressing Wild Type CXCR4 Receptor by Anti-CXCR4 Mabs 414H5 and 515H7

This functional assay allows to monitor G protein activation via wild type human CXCR4 receptor and its modulation by CXCR4 ligands and 414H5 and 515H7 mAbs.

NIH-3T3 cells stably and constitutively expressing wild-type CXCR4 receptor were obtained as described in the example above for CHO-K1 cells. HeLa (human cervix carcinoma) cells were propagated in complete culture medium [EMEM supplemented with 10% FCS, 1% L-glutamine, 2μ sodium bicarbonate]. [$^{35}$S]GTPγS binding was performed on cellular membranes obtained upon mechanical scrapping in lysis buffer [Hepes 20 mM, pH 7.4, NaCl 150 mM] and further centrifugation (10000 g, 15 min). Incorporation and detection of [$^{35}$S]GTPγS (specific activity: 1000 Ci/mmol) was performed using the SPA technology (scintillation proximity assay—GE Healthcare). Briefly, cell membranes (10 μg/well) were incubated in binding buffer [Hepes 20 mM, GDP 3 μM, MgCl$_2$ 10 mM, NaCl 100 mM, EDTA 1 mM, pH=7.4] together with compound to evaluate (SDF-1 or Mab of interest), [$^{35}$S]GTPγS (0.2-0.4 nM) and finally SPA-WGA-PVT beads (7.3 mg/well). Binding reaction was performed during 1H at 25° C. Upon centrifugation [1000 g for 10 min.] radioactive counts were measured in a scintillation counter (TopCount, Perkin Elmer). Antagonist potency was calculated by applying the Cheng Prussof equation:

$K_B$=[conc antago]/{(EC$_{50}$/EC$_{50}$)−1} where EC$_{50}$ and EC$_{50}$, are respectively the potency of SDF-1 in the absence and presence of mAb.

Figure 4A:
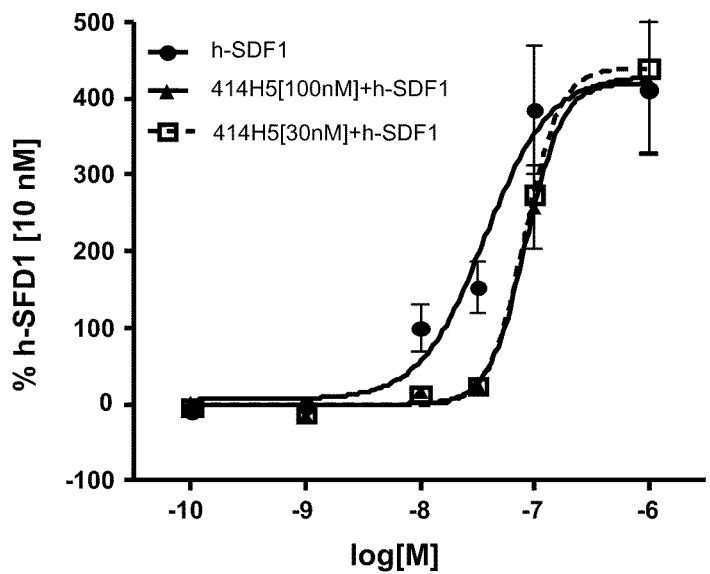
FIGS. 4A and 4B show the modulation of G protein activation by 414H5 Mab (FIG. 4A) and 515H7 Mab (FIG. 4B) by monitoring [$^{35}$S]GTPγS binding responses at wild-type CXCR4 receptor stably expressed in NIH-3T3 cells.
Figure 4B:
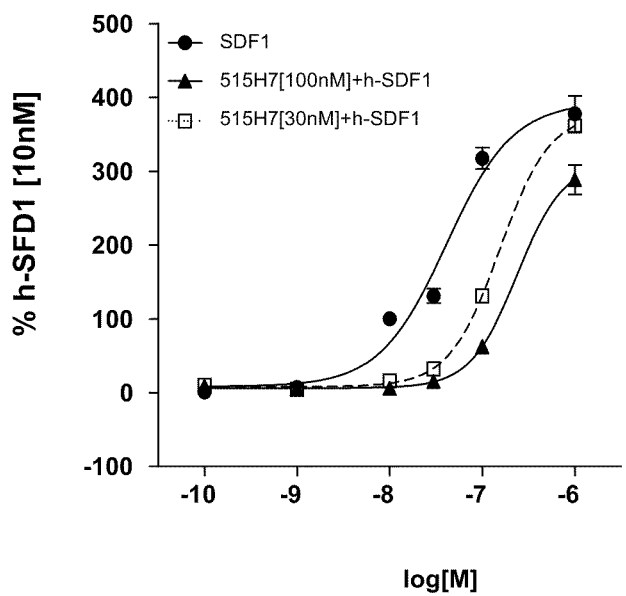
Figure 5:
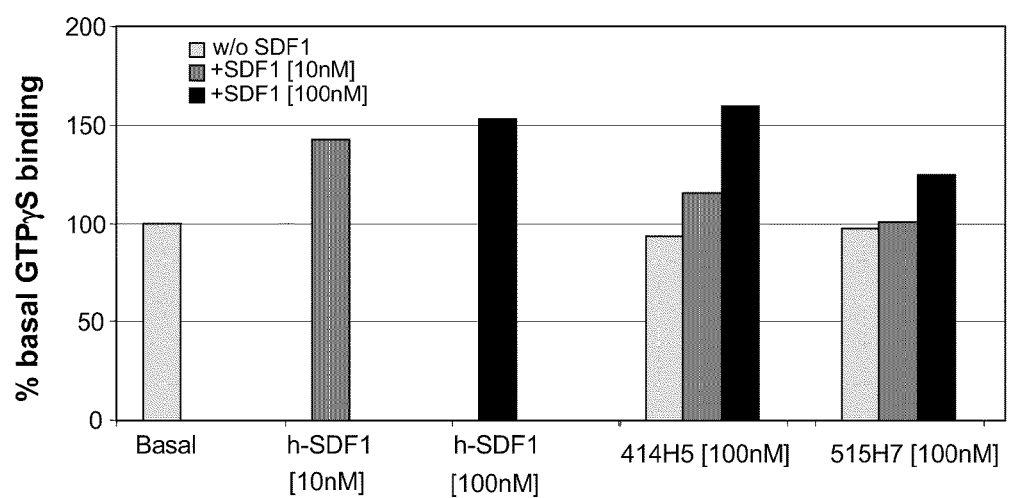
FIG. 5 shows the modulation of G protein activation by anti-CXCR4 Mabs 414H5 and 515H7 by monitoring [$^{35}$S] GTPγS binding responses at HeLa human tumor cells stimulated with SDF-1 (10 and 100 nM).

SDF-1 induced a dose-dependent increase of [$^{35}$S]GTPγS binding, as the result of G protein activation by CXCR4 receptor. Maximal stimulation of [$^{35}$S]GTPγS binding represents respectively 167% and 320% over basal [$^{35}$S]GTPγS binding for HeLa and NIH3T3/CXCR4 cell membranes. The potency of SDF-1 was similar for both cell lines and corresponded to 41.3±9.7 nM (FIGS. 4A-4B). Under these experimental conditions, the antagonist potency of 414H5 and 515H7 Mabs, as determined in NIH3T3/CXCR4 cells was 51 nM and 15 nM, respectively. Similar antagonist efficacy was observed for HeLa cells (FIG. 5).

Example 6

Association of CXCR4 with Different Interaction Partners: Homo and Heterodimerization, Recruitment of β-Arrestin Via a Bioluminescence Resonance Energy Transfer (BRET) Approach and Effect of 414H5 and 515H7 Mabs on These Dimmers This functional assay allows to evaluate the conformational changes induced upon SDF-1 and/or 414H5 and 515H7 Mabs binding to CXCR4 receptor at the level of CXCR4 homo-dimer and CXCR2/CXCR4 hetero-dimer formation as well as the recruitment of the β-arrestin-2 signaling protein.

Expression vectors for each of the investigated interaction partners were constructed as fusion proteins with the corresponding dye (*Renilla reniformis* luciferase, Rluc and Yellow fluorescent protein, YFP) by applying conventional molecular biology techniques. Two days prior performing BRET experiments, HEK293 cells were transiently transfected with expression vectors coding for the corresponding BRET partners: [CXCR4/Rluc+CXCR4/YFP] to study CXCR4 homo dimerization, [CXCR4/Rluc+CXCR2:YFP] to study CXCR4 and CXCR2 hetero-dimerization and [CXCR4/Rluc+β-arr2:YFP] to study CXCR4-mediated recruitment of β-arrestin-2. The day after, cells were distributed in poly-lysine pre-coated white 96 MW plates in complete culture medium [DMEM supplemented with 10% FBS]. Cells were first cultivated at 37° C. with CO$_2$ 5% in order to allow cell attachment to the plate. Cells were then starved with 200 μl DMEM/well overnight. Immediately prior to the BRET experiment, DMEM was removed and cells were quickly washed with PBS. Cells were then incubated in PBS in the presence or absence of antibody, 10 min at 37° C. prior to the addition of coelenterazine H 5 μM with or without SDF-1 300 nM in a final volume of 50 μl. After incubation for further 10 minutes at 37° C., light-emission acquisition at 485 nm and 530 nm was initiated using the Mithras LB940 multilabel reader (Berthold) (1 s/wavelength/well repeated 15 times at room temperature).

Calculation of BRET ratio was performed as previously described (Angers et al., 2000): [(emission$_{530\ nm}$)−(emission$_{485\ nm}$)×Cf]/(emission$_{485\ nm}$), where Cf=(emission$_{530\ nm}$)/(emission$_{485\ nm}$) for cells expressing the Rluc fusion protein alone under the same experimental conditions. Simplifying this equation shows that BRET ratio corresponds to the ratio 530/485 nm obtained when the two BRET partners are present, corrected by the ratio 530/485 nm obtained under the same experimental conditions, when only the partner fused to Rluc is present in the assay. For sake of readability, results are expressed in milliBRET units (mBU); mBU corresponds to the BRET ratio multiplied by 1000.

Figure 6A:
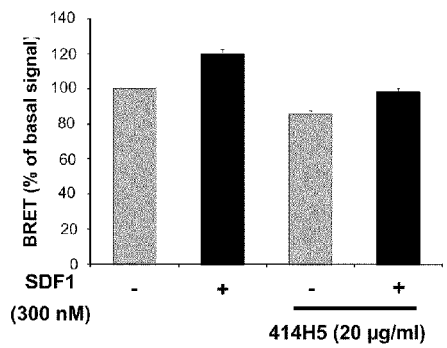
FIGS. 6A-6F show the modulation of CXCR4 receptor association with different interaction partners by SDF-1 and by 414H5 and 515H7 Mabs via a bioluminescence resonance energy transfer (BRET) approach in HEK293 cells.
Figure 6B:
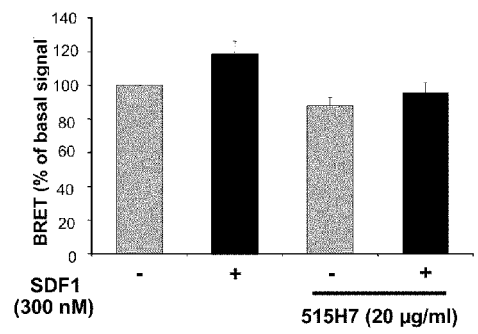
Figure 6C:
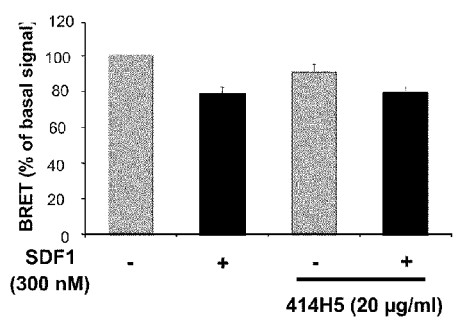
Figure 6D:
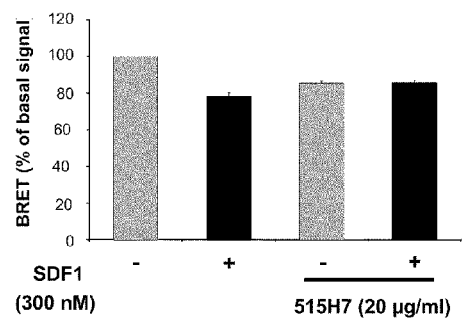

SDF1 (300 nM) increased by about 20% the BRET signal resulting from the spatial proximity of the adaptor and acceptor proteins fused to CXCR4 receptor, it is likely to indicate CXCR4/CXCR4 homo-dimers formation or conformational changes of pre-existing dimers (FIGS. 6A and 6B). Interestingly, SDF1 (300 nM) decreased by about 24% the BRET signal resulting from the spatial proximity of the adaptor and acceptor proteins fused to CXCR2 and CXCR4, likely indicating as well CXCR2/CXCR4 hetero-dimers formation or conformational changes of pre-existing dimers (FIGS. 6C and 6D). In this latter case, SDF-1-activated conformation of CXCR4/CXCR2 seems less favorable for BRET energy transfer. In both cases, 414H5 and 515H7 Mabs were able to modulate SDF-1-induced conformational changes for CXCR4 homo-dimers (63% inhibition of SDF-1-induced BRET increase for 414H5 and 69% inhibition of SDF-1-induced BRET increase for 515H7, FIGS. 6A and 6B, respectively) as well as for CXCR2/CXCR4 hetero-dimer formation (50% inhibition of SDF-1-induced BRET decrease for 414H5 and 90% inhibition of SDF-1-induced BRET decrease for 515H7, FIGS. 6C and 6D, respectively). 414H5 and 515H7 Mabs were also able to modulate by themselves CXCR4/CXCR4 and CXCR2/CXCR4 spatial proximity respectively, indicating an influence of 414H5 and 515H7 Mabs on both CXCR4/CXCR4 homo and CXCR2/CXCR4 hetero-dimer conformation (FIGS. 6A, 6B, 6C and 6D).

Figure 6E:
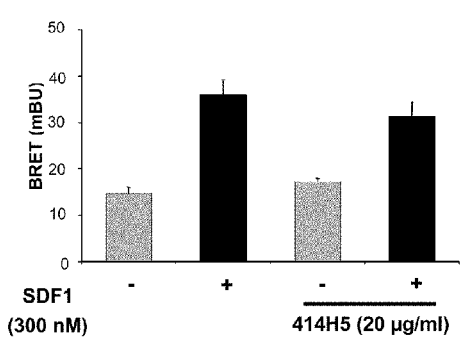
Figure 6F:
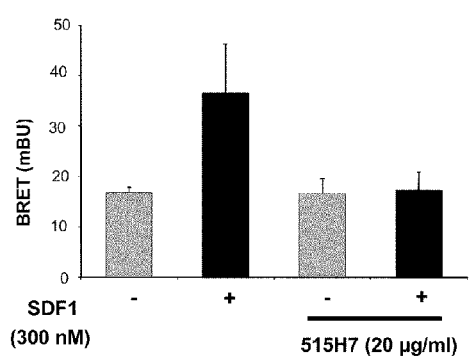

CXCR4 activation by SDF-1 (300 nM) yielded a strong recruitment of the intracellular signaling molecule β-arrestin, as shown by the 233% enhancement in BRET signal (FIGS. 6E and 6F). This recruitment was partially inhibited by 414H5 and 515H7 Mabs (about 20% inhibition for 414H5 and 95% for 515H7, FIGS. 6E and 6F, respectively) showing the effect of Mabs 414H5 and 515H7 on signaling.

Example 7

CXCR4-Mediated Inhibition of cAMP Production

This functional assay was designed to monitor CXCR4 receptor signaling at the level of adenylate cyclases via inhibitory Gi/o proteins.

The cAMP LANCE procedure (Perkin Elmer) was applied as detailed by the supplier. Briefly, NIH3T3 cells stably and constitutively expressing wild type CXCR4 receptor were obtained and propagated as described above. Cells were collected using the trypsin-free agent Versene and resuspended at a concentration of $10^6$ cells/ml in a solution containing the AlexaFluor-bound anti cAMP Mab ($1/100^{th}$ dilution) and compound (forskolin, SDF-1 and/or 414H5 and 515H7 Mabs). Upon incubation for 30 min. at room temperature, the detection mix containing the Europium-Streptavidin ($1/125^{th}$ dilution) and Biotin-cAMP ($1/125^{th}$ dilution) complexes was added. Upon incubation for 1 hour at room temperature, the resulting FRET signal was measured in a Mithras LB940 (Berthold) multilabel reader. Data are expressed either as arbitrary fluorescent values or as a relative stimulation versus SDF-1 response upon substraction of the FK effect.

Figure 7A:
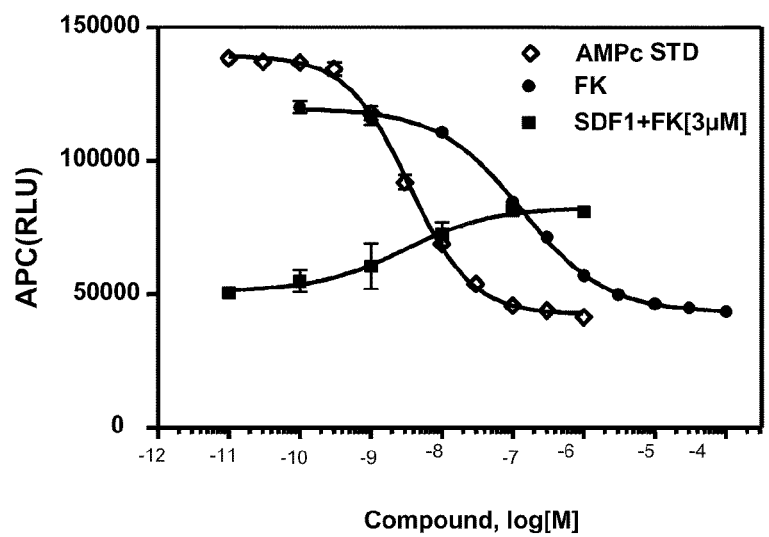
FIGS. 7A and 7B show the inhibition of forskolin-stimulated cAMP production by SDF-1 and 414H5 and 515H7 Mabs in NIH3T3 cells stably expressing CXCR4 receptor.
Figure 7B:
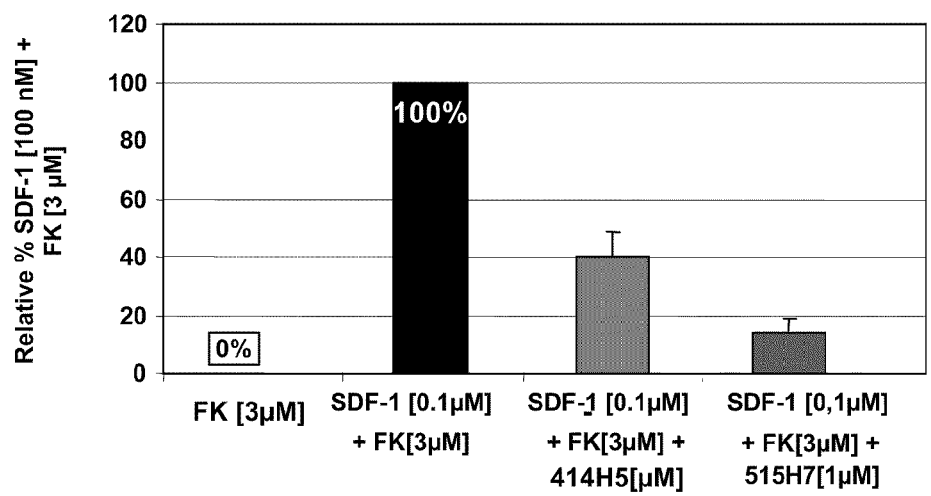

Forskolin (FK) dose-dependently stimulated cAMP production with a potency of about 0.3 µM in NIH3T3/CXCR4 cells (FIG. 7A). In the co-presence of SDF-1, intracellular cAMP levels decreased as a result of inhibitory Gi/o protein activation by CXCR4 receptor. The potency of SDF-1 was 5.0±3.1 nM (FIG. 7A). 414H5 and 515H7 Mabs efficiently inhibited the forskolin-stimulated effect of SDF-1 (100 nM) by more than 60% for 414H5 and by more than 80% for 515H7 (FIG. 7B).

Example 8

Modulation of [$^{35}$S]GTPγS Binding at Cellular Membranes Expressing Constitutively Active Mutant Asn$^{119}$Ser CXCR4 Receptor by Mabs 414H5 and 515H7

This functional assay allows to monitor G protein activation via a constitutively active mutant (CAM) Asn$^{119}$Ser CXCR4 receptor (see Zhang et al., 2002). This sensitive assay allows to discriminate CXCR4 ligands based on their intrinsic activity (partial agonist, silent antagonist or inverse agonist). As previously described by Zhang and colleagues, CXCR4 ligands such as AMD3100 or T140 behaved respectively as partial agonist and inverse agonist at CAM CXCR4 receptor. Identification of silent antagonist may be difficult since this class of molecule must display similar affinities for both active and inactive states of CXCR4 (Wurch et al., 1999).

Introduction of an Asn119Ser mutation in the coding sequence of CXCR4 receptor was performed by applying conventional molecular biology techniques (QuickChange site directed mutagenesis kit, Stratagene US). CHO-K1 cells stably and constitutively expressing CAM CXCR4 receptor were obtained as described in the example above. [$^{35}$S]GTPγS binding was performed on cellular membranes obtained upon mechanical scrapping in lysis buffer [Hepes 20 mM, pH 7.4, NaCl 150 mM] and further centrifugation (10000 g, 15 min). Incorporation of [$^{35}$S]GTPγS (specific activity: 1000 Ci/mmol) was performed using the SPA technology (scintillation proximity assay—GE Healthcare). Briefly, cell membranes (10 µg/well) were incubated in binding buffer [Hepes 20 mM, GDP 3 µM, MgCl$_2$ 10 mM, NaCl 100 mM, EDTA 1 mM, pH=7.4] together with compound to evaluate (SDF-1 or mAb), [$^{35}$S]GTPγS (0.2-0.4 nM) and finally SPA-WGA-PVT beads (7.3 mg/well). Binding reaction was performed during 1H at 25° C. Upon centrifugation [1000 g for 10 min.] radioactive counts were measured in a scintillation counter (Top-Count, Perkin Elmer).

Figure 8:
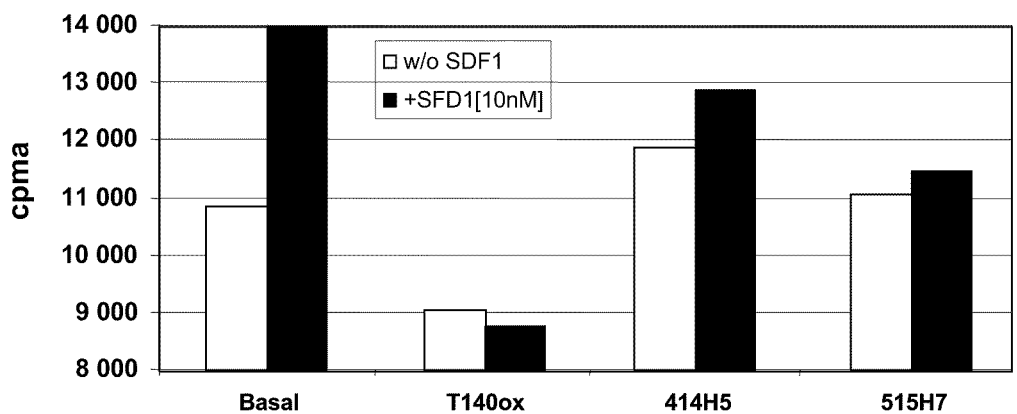
FIG. 8 shows the modulation of G protein activation by anti-CXCR4 Mabs 414H5 and 515H7 by monitoring [$^{35}$S] GTPγS binding responses at constitutively active mutant Asn$^{119}$Ser CXCR4 receptor stably expressed in CHO-K1 cells.

SDF-1 (100 nM) stimulated [$^{35}$S]GTPγS binding by 130%. The inverse agonist T140 inhibited both basal (−17%) and SDF-1-stimulated (−159%) [$^{35}$S]GTPγS binding. In contrast, 414H5 and 515H7 Mabs behaved as silent antagonists at CAM CXCR4, without altering basal [$^{35}$S]GTPγS binding (FIG. 8) but inhibiting SDF-1 induced [$^{35}$S]GTPγS binding (FIG. 8).

Example 9

Inhibition of SDF-1-Induced Hela Cell Proliferation by CXCR4 Mab 414H5 In Vitro

HeLa cells from ATCC were routinely cultured in EMEM medium (Lonza Corporation. Verviers. Belgium), 10% FCS (SIGMA Corporation. St Louis. USA), 1% L-Glutamine (Invitrogen Corporation. Scotland. UK), 2% Sodium bicarbonate 7.5% solution (Invitrogen Corporation. Scotland. UK). Cells were split 3 days before proliferation assays so that they were confluent.

SDF-1-Induced Hela Cell Proliferation

HeLa cells were plated in 96-well tissue culture plates at a density of $1 \times 10^4$ cells/well in 200 µl of serum free medium (EMEM medium plus 1% L-Glutamine. 2% sodium bicarbonate 7.5% solution). Twenty four hours after plating, appropriate dilutions of SDF-1 were added to HeLa cells. After a total of 76 hours of culture, cells were pulsed with 0.25 µCi of [$^3$H]thymidine (Amersham Biosciences AB. Uppsala. Sweden) for 16 hours. The magnitude of [$^3$H]thymidine incorporated in DNA was quantified by liquid scintillation counting.

Results were expressed as proliferation Index=[mean cpm of cells+SDF-1/mean cpm of cells−SDF-1].

HeLa cells were incubated with SDF-1 (0 to 1000 ng/ml). SDF-1 stimulated in vitro HeLa cells proliferation 1.5 to 2 folds. The concentration of SDF-1 to obtain the highest and reproducible proliferation index was 200 ng/ml (25 nM).

Inhibition of SDF-1-Induced Hela Cell Proliferation In Vitro by CXCR4 414H5 Mab

HeLa cells were plated in 96-well tissue culture plates at a density of $1 \times 10^4$ cells/well in 200 µl of serum free medium (EMEM medium plus 1% L-Glutamine. 2% sodium bicarbonate 7.5% solution). Twenty four hours after plating, appropriate dilutions of anti-CXCR4 Mab 414H5, diluting media were added in triplicate to HeLa cells either in presence or in absence of SDF-1 at a final concentration of 200 ng/ml (25 nM). After a total of 76 hours of culture, cells were pulsed with 0.25 µCi of [$^3$H]thymidine (Amersham Biosciences AB. Uppsala. Sweden) for 16 hours. The magnitude of [$^3$H]thymidine incorporated in DNA was quantified by liquid scintillation counting.

Results were expressed as affected fraction (Fa) calculated using the formula:

$$Fa = [1-[\text{mean cpm of cells incubated with Mab+SDF-1/mean cpm of cells incubated with diluting media+SDF-1}]] \times 100.$$

Figure 9:
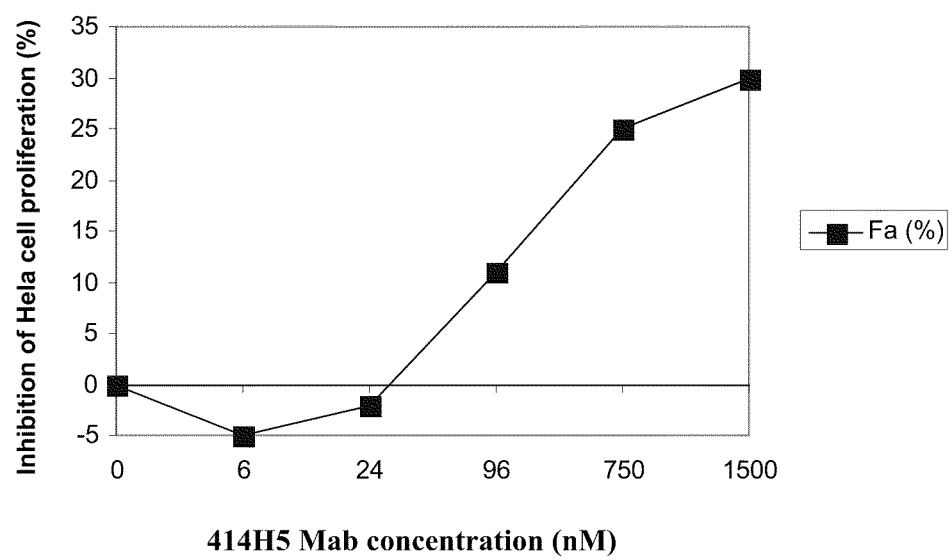
FIG. 9 illustrates the inhibition of SDF-1 induced Hela cell proliferation by the Mab 414H5 in vitro.

The in vitro effect of anti-CXCR4 Mab 414H5 on SDF-1-induced HeLa cell proliferation was characterized. HeLa cells were incubated with either 414H5 Mab or control with or without SDF-1 (200 ng/ml). SDF-1 stimulated the in vitro growth of HeLa cells (1.5 to 2 folds). Dose-response curve for 414H5 Mab was obtained by treating cells with serial two fold dilutions of Mab ranging from 0 to 1500 nM 24 h after cell plating. As cell proliferation was evaluated 76 hours after plating, each tested condition corresponds to a 48 h exposure time to Mab or control. Results were expressed as affected fraction using Fa formula described above. The results (represented in FIG. 9) showed that CXCR4 Mab 414H5 inhibited SDF-1-induced Hela cell proliferation in vitro.

Example 10

Figure 10A:
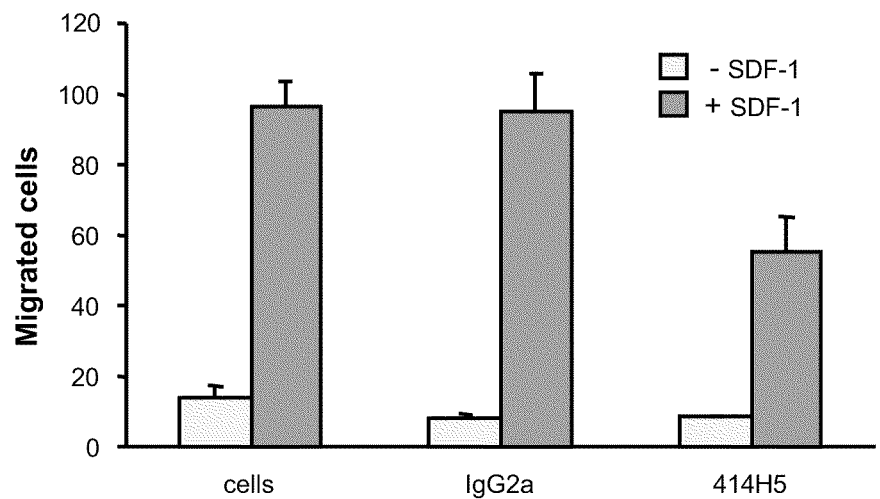
FIGS. 10A and 10B show the inhibition of SDF-1-induced U937 cells migration by CXCR4 Mab 414H5 (FIG. 10A) and Mab 515H7 (FIG. 10B) in vitro.
Figure 10B:
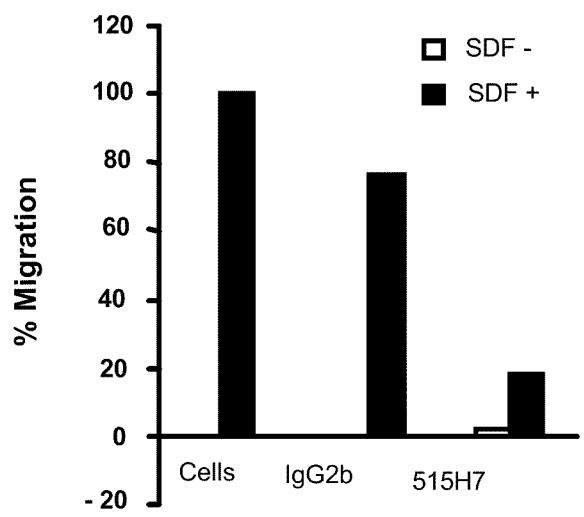

Effect of Anti-CXCR4 Mabs 414H5 and 515H7 on SDF-1-Induced U937 Cells Migration To evaluate the inhibiting effect of the anti-CXCR4 monoclonal antibodies 414H5 and 515H7 on the migration process, 100 000 U-937 cells in RPMI 1640 medium supplemented with 2% FCS, were plated in the upper chamber of migration chambers (24 wells plates with 8-μm pore size) either in presence or in absence of SDF-1 in the lower part of the wells and with or without Mabs 414H5 and 515H7 in the upper chamber. In this test murine IgG2a and IgG2B were introduced as an isotype controls. Two hours after plating, migrating cells were counted. The results presented in FIGS. 10A for 414H5 and 10B for 515H7 demonstrated that, as expected SDF-1 was able to induce a significant increase of U-937 cells migration. No effect was observed when cells were incubated with the IgG2 isotype control. In contrast, for cells incubated with the 414H5 and 515H7 Mabs, a significant and reproducible decrease in SDF-1-induced U937 cells migration was observed: 50% with 414H5 Mab and more than 80% with 515H7 Mab.

Example 11

Anti-CXCR4 Mab 414H5 Inhibition of MDA-MB-231 Xenograft Tumor Growth in Nod/Scid Mice The goal of these experiments was to evaluate the ability of anti-CXCR4 Mabs 414H5 and 515H7 to inhibit the growth of MDB-MB-231 xenograft in Nod/Scid mice.

MDA-MB-231 cells from ECACC were routinely cultured in DMEM medium (Invitrogen Corporation, Scotland, UK), 10% FCS (Sigma, St Louis Md., USA). Cells were split 48 hours before engraftment so that they were in exponential phase of growth. Ten million MDA-MB-231 cells were engrafted in PBS to 7 weeks old Nod/Scid mice (Charles River, France). Five days after implantation, tumors were measurable ($34\ mm^3 < V^3 < 40\ mm^3$) and animals were divided into groups of 6 mice with comparable tumor size. Mice were treated i.p. with a 2 mg/mouse loading dose of Mab 414H5 and Mab 515H7, respectively.

Then, mice were injected twice a week at 1 mg/dose/mouse of Mab 414H5 twice a week or 0.5 mg/dose/mouse of Mab 515H7 three time a week. A PBS group was introduced as a control group in this experiment. Tumor volume was measured twice a week and calculated by the formula: $\pi/6 \times length \times width \times height$. Statistical analysis were performed at each measure using a Mann-Whitney test.

Figure 11A:
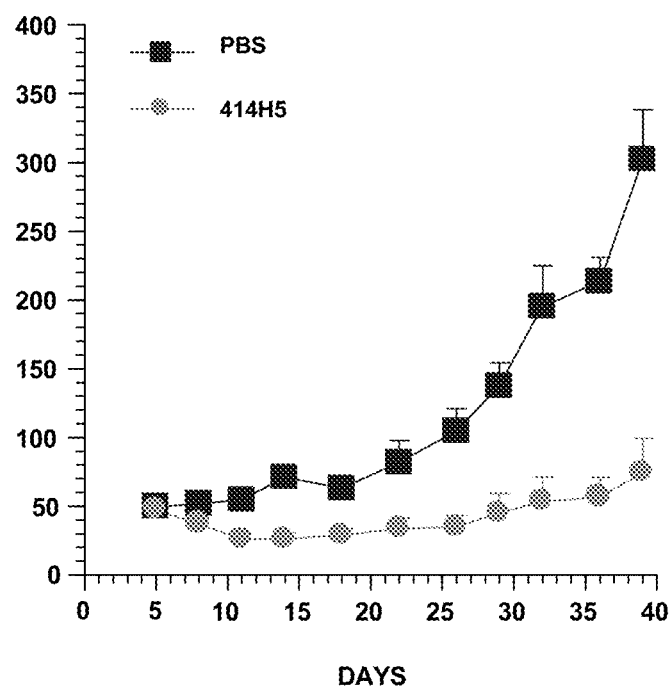
FIGS. 11A and 11B show inhibition of MDA-MB-231 xenograft tumor growth by anti-CXCR4 Mab 414H5 (FIG. 11A) and Mab 515H7 (FIG. 11B) in Nod/Scid mice.
Figure 11B:
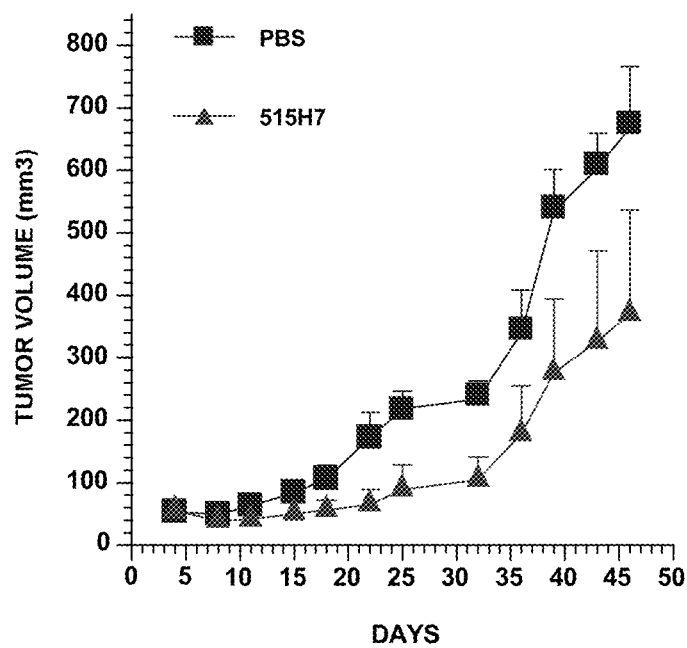

In these experiments, no mortality was observed during treatment. Compared to PBS group, there was a significant inhibition of tumor growth between D7 and D39 ($p \leq 0.002$) for 415H5 Mab 1 mg/dose or 515H7 0.5 mg/dose and the average tumor volume after 5 weeks of treatment was reduced by 82% and 50% versus PBS for Mab 415H5 and 515H7, respectively (FIGS. 11A and 11B).

Example 12

Anti-CXCR4 Mab 414H5 Activity in U937 Mice Survival Model

U937 cells from ATCC were cultured in RPMI 1640 medium, 10% FCS, 1% L-Glutamine. Cells were split two days before engraftment so that they were in exponential phase of growth. Ten million U937 cells injected i.p. to female NOD/SCID mice. Two days after implantation, mice were treated s.c. with a loading dose of 2 mg of 414H5 mAb/mouse and then twice a week with 1 mg of antibody/mouse. Control mice received PBS injections as it has been shown in previous studies that no difference in survival was observed between mice injected with PBS and mice administered with a mouse IgG isotype control. Mice survival was monitored every day.

Figure 12:
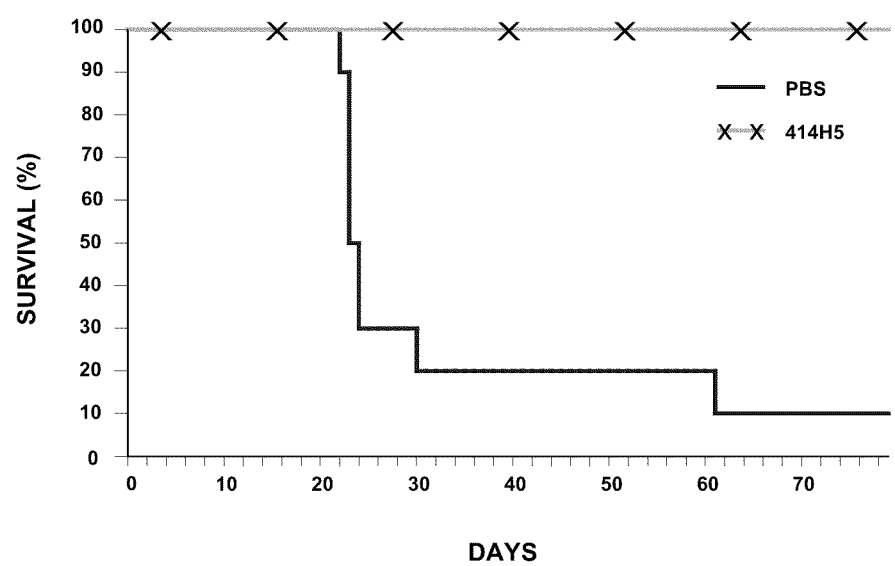
FIG. 12 shows the anti-CXCR4 Mab 414H5 activity in U937 Nod/Scid mice survival model.

Results described in FIG. 12 showed that mice treated with the 414H5 Mab had a dramatic and significant increase in life span with T/C % about 343.

Example 13

CXCR4 Receptor-Mediated Mobilization of Intracellular Calcium Stores

This functional assay was designed to monitor CXCR4 receptor signaling via stimulation of the phospholipase C pathway, inducing calcium liberation from intracellular stores from the endoplasmic reticulum.

CHO-K1 cells stably and constitutively expressing wild-type CXCR4 receptor were obtained as described in the example above. MDA-MB-231 (human breast adenocarcinoma) and U937 (human lymphoma) cells were propagated in complete culture medium, respectively [DMEM supplemented with 10% FCS] and [RPMI 1640 supplemented with 10% FCS, 20 mM HEPES, 1% non-essential amino acid solution, 1% sodium pyruvate, 1% L-glutamine, 4.5 g/l glucose]. All cell types were plated in black 96MW plates at a density of 100,000 cells/well in appropriate culture medium. Cells were starved overnight before conducting the experiments. Cells are loaded with the fluorescent calcium dye (Fluo-4 No Wash, Invitrogen US) in loading buffer [HBSS 1×, HEPES 20 mM, Probenicid acid 25 mM] for 30 min. at 37° C. followed by 30 min. at 25° C. Stimulation by SDF-1 was performed by direct injection into each well. For antagonism experiments, 10 μL1 of Mab solution are added directly into the loading buffer at least 10 min. before SDF-1. Kinetic fluorescence measurements are performed on a multi-mode fluorescence microplate reader Mithras LB940 (Berthold) using the following settings: excitation at 485 nm, emission at 535 nm, excitation energy at 10000 arbitrary units. Fluorescence in each well is recorded during 0.1 second every second and for a time period of 20 sec prior SDF-1 injection (basal signal). Then 20 μL1 of SDF-1 are injected and data recording follows for a time period of 2 min. Each experimental condition is performed in duplicate. Values for each well are first corrected by substracting the basal fluorescence and the fluorescence emitted by a control well without cells. Relative data are expressed as a percentage of the maximal stimulation obtained by SDF-1 (100 nM).

Figure 13A:
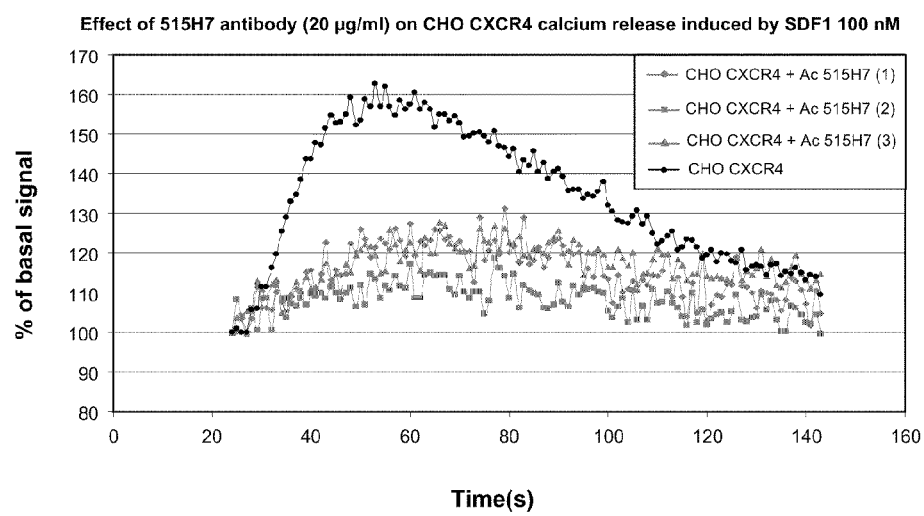
FIGS. 13A-13C show the SDF-1-induced calcium release inhibition by anti-CXCR4 Mab 515H7 in CHO-CXCR4 cells (FIG. 13A) and MDA-MB-231 (FIG. 13B), U937 (FIG. 13C) cancer cells.
Figure 13B:
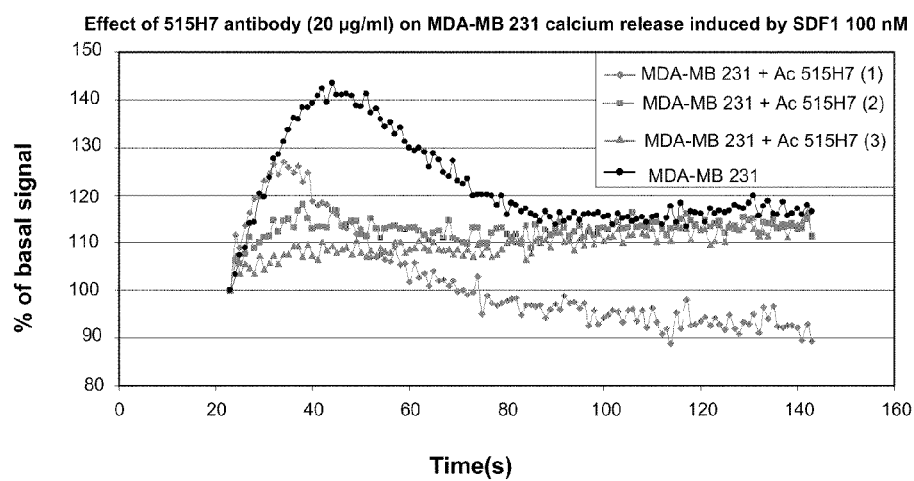
Figure 13C:
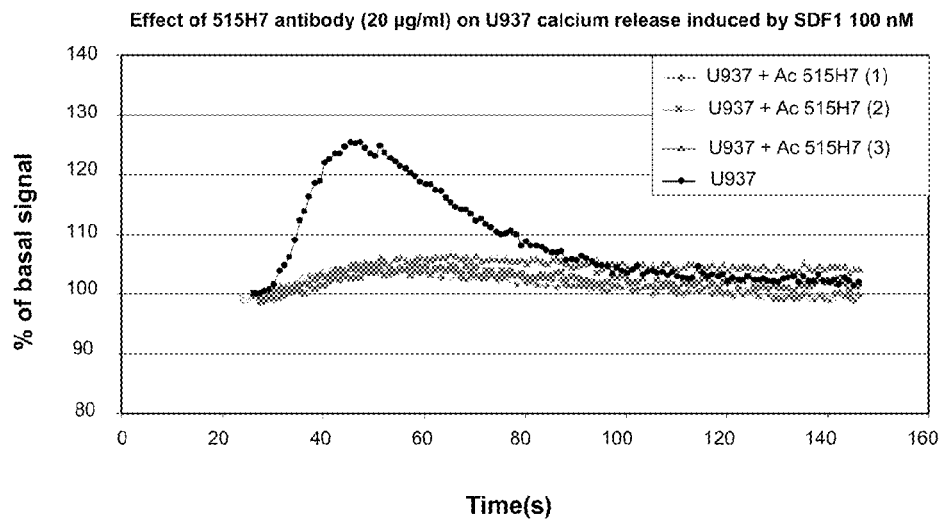

SDF1 (100 nM) induced a rapid and strong release of intracellular calcium in recombinant CHO/CXCR4, whereas no fluorescence signal was detected in naïve CHO-K1 cells. The maximal intensity reached>160% over basal fluorescence and was observed at about 30 sec. upon stimulation by SDF-1; similar kinetic curves were observed with both MDA-MB-231 and U-937 (FIGS. 13A, 13B, 13C), although the maximal fluorescence intensity by SDF-1 (100 nM) was lower (130-140% over basal). 515H7 antibody (133 nM) yielded a strong and almost complete inhibition of the SDF-1 (100 nM)-induced calcium signal in all three investigated cell lines.

Example 14

Anti-CXCR4 Mab 414H5 Inhibition of T-cell KARPAS 299 Xenograft Tumor Growth in Nod/Scid Mice The goal of this experiment was to evaluate the ability of anti-CXCR4 Mab 414H5 to inhibit the growth of KARPAS 299 xenograft in Nod/Scid mice.

KARPAS 299 cells from ECACC were routinely cultured in RPMI medium, 1% L-Glu and 10% FCS (Sigma, St Louis Md., USA). Cells were split 48 hours before engraftment so that they were in exponential phase of growth. Five million KARPAS 299 cells were engrafted in PBS to 7 weeks old Nod/Scid mice (Charles River, France). Five days after implantation, tumors were measurable (32 mm$^3$<V$^3$<49 mm$^3$) and animals were divided into groups of 6 mice with comparable tumor size. Mice were treated i.p. with a 2 mg/mouse loading dose of Mab 414H5.

Then, mice were injected twice a week at 1 mg/dose/mouse of Mab 414H5. A PBS group was introduced as a control group in this experiment. Tumor volume was measured twice a week and calculated by the formula: $\pi/6 \times \text{length} \times \text{width} \times \text{height}$. Statistical analysis were performed at each measure using a Mann-Whitney test.

Figure 14:
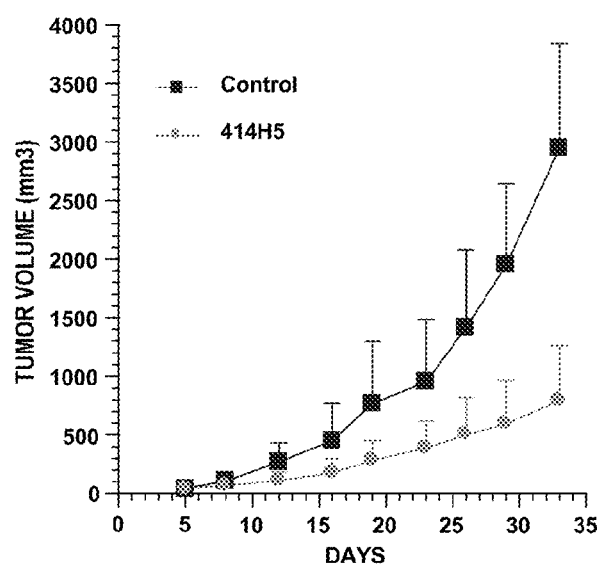
FIG. 14 shows the inhibition of T-cell KARPAS 299 xenograft tumor in Nod/Scid mice by 414H5.

In this experiment, no mortality was observed during treatment. Compared to PBS group, there was a significant inhibition of tumor growth between D7 and D33 ($p \leq 0.002$) for 414H5 Mab 1 mg/dose and the average tumor volume after 5 weeks of treatment was reduced by 73% for Mab 414H5 versus PBS (FIG. 14).

Example 15

Anti-CXCR4 Mab 515H7 Activity in U937 Mice Survival Model

U937 cells from ATCC were cultured in RPMI 1640 medium, 10% FCS, 1% L-Glutamine. Cells were split two days before engraftment so that they were in exponential phase of growth. Ten million U937 cells injected i.p. to female NOD/SCID mice. Two days after implantation, mice were treated s.c. with a loading dose of 2 mg of 515H7 Mab/mouse and then twice a week with 1 mg of antibody/mouse. Control mice received PBS injections as it has been shown in previous studies that no difference in survival was observed between mice injected with PBS and mice administered with a mouse IgG isotype control. Mice survival was monitored every day.

Figure 15:
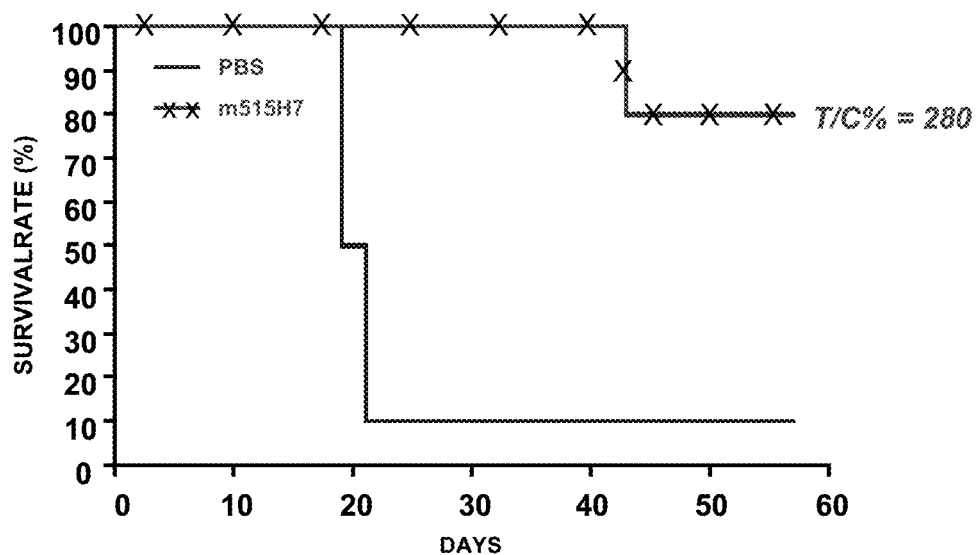
FIG. 15 shows the activity of murine anti-CXCR4 Mab m515H7 in U937 Nod/Scid mice survival model.

Results described in FIG. 15 showed that mice treated with 515H7 Mab had a dramatic and significant increase in life span with T/C % about 280 for 515H7 Mab (FIG. 15).

Example 16

Anti-CXCR4 Mab 515H7 Inhibition of T-cell KARPAS 299 Xenograft Tumor Growth in Nod/Scid Mice The goal of this experiment was to evaluate the ability of anti-CXCR4 Mab 515H7 to inhibit the growth of KARPAS 299 xenograft in Nod/Scid mice.

KARPAS 299 cells from ECACC were routinely cultured in RPMI medium, 1% L-Glu and 10% FCS (Sigma, St Louis Md., USA). Cells were split 48 hours before engraftment so that they were in exponential phase of growth. Five million KARPAS 299 cells were engrafted in PBS to 7 weeks old Nod/Scid mice (Charles River, France). Five days after implantation, tumors were measurable (32 mm$^3$<V$^3$<49 mm$^3$) and animals were divided into groups of 6 mice with comparable tumor size. Mice were treated i.p. with a 2 mg/mouse loading dose of Mab 515H7.

Then, mice were injected twice a week at 1 mg/dose/mouse of Mab 515H7. A PBS group was introduced as a control group in this experiment. Tumor volume was measured twice a week and calculated by the formula: $\pi/6 \times \text{length} \times \text{width} \times \text{height}$. Statistical analysis were performed at each measure using a Mann-Whitney test.

Figure 16:
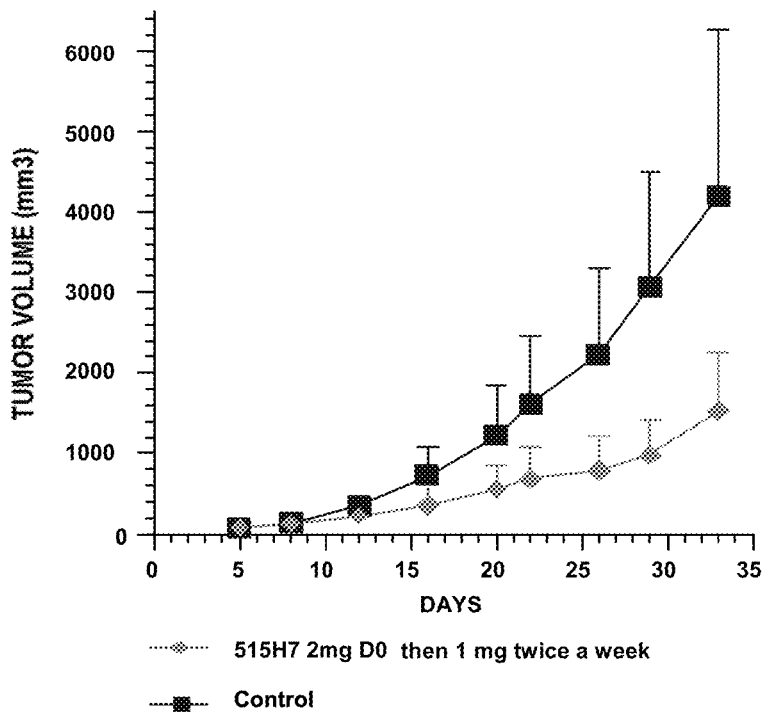
FIG. 16 shows the activity of murine anti-CXCR4 Mab m515H7 in inhibition of T-cell KARPAS 299 xenograft tumor growth in Nod/Scid mice.

In these experiments, no mortality was observed during treatment. Compared to PBS group, there was a significant inhibition of tumor growth between D7 and D33 ($p \leq 0.002$) for 515H7 Mab 1 mg/dose and the average tumor volume after 5 weeks of treatment was reduced by 63% for Mab 515H7 versus PBS (FIG. 16).

Example 17

Production of Anti-CXCR4 Chimeric Mabs c414H5 and c515H7

Chimeric formats of murine 414H5 and 515H7 Mabs were designed: they correspond to the light and heavy chain variable domains of the murine antibodies of interest, genetically fused to human Ckappa and IgG1 constant domains. All recombinant Mabs were produced upon transient transfection by using the HEK293/EBNA system with a pCEP4 expression vector (InVitrogen, US).

The entire nucleotide sequences corresponding to the variable domains of 414H5 and 515H7 Mabs light and heavy chains were synthesized by global gene synthesis (Genecust, Luxembourg). They were subcloned into a pCEP4 vector (InVitrogen, US) carrying the entire coding sequence of the constant domain of either the light [Ckappa] or the heavy [CH1-Hinge-CH2-CH3] chain of a human IgG1 immunoglobulin. All cloning steps were performed according to conventional molecular biology techniques as described in the Laboratory manual (Sambrook and Russel, 2001) or according to the supplier's instructions. Each genetic construct was fully validated by nucleotide sequencing using Big Dye terminator cycle sequencing kit (Applied Biosystems, US) and analyzed using a 3100 Genetic Analyzer (Applied Biosystems, US).

Suspension-adapted HEK293 EBNA cells (InVitrogen, US) were routinely grown in 250 ml flasks in 50 ml of serum-free medium Excell 293 (SAFC Biosciences) supplemented with 6 mM glutamine on an orbital shaker (110 rpm rotation speed). Transient transfection was performed with $2.10^6$ cells/ml using linear 25 kDa polyethyleneimine (PEI) (Polysciences) prepared in water at a final concentration of 1 mg/ml mixed and plasmid DNA (final concentration of 1.25 µg/ml for heavy to light chain plasmid ratio of 1:1). At 4 hours post-transfection, the culture was diluted with one volume of fresh culture medium to achieve a final cell density of $10^6$ cells/ml. Cultivation process was monitored on the basis of cell viability and Mab production. Typically, cultures were maintained for 4 to 5 days. Mabs were purified using a conventional chromatography approach on a Protein A resin (GE Healthcare, US). All different Mabs were produced at levels suitable with functional evaluations. Productivity levels are typically ranging between 6 and 15 mg/l of purified Mabs.

Example 18

Characterization by FACS Analysis of Anti-CXCR4 Chimeric Mabs c414H5 and c515H7 Binding Specificity and Cancer Cell Line Recognition In this experiment, specific binding to human CXCR4 of anti-CXCR4 chimeric Mabs c414H5 and c515H7 was examined by FACS analysis.

NIH3T3, NIH3T3-hCXCR4 transfected cells and MDA-MB-231 cancer cell line were incubated with 10 µg/mL of monoclonal antibody c414H5 and c515H7. The cells were then washed with 1% BSA/PBS/0.01% NaN3. Next, Alexa-labeled secondary antibodies were added to the cells and were allowed to incubate at 4° C. for 20 min. The cells were then washed again two times. Following the second wash, FACS analysis was performed. Results of these binding studies are provided in the following Table 8 which shows [Mean Fluorescence Intensity (MFI) obtained by FACS] that anti-CXCR4 chimeric Mabs c414H5 and c515H7 bound specifically to human CXCR4-NIH3T3 transfected cell line and also recognize human cancer cell lines, for example MDA-MB-231 breast cancer cells.

TABLE 9

| Clone | MFI on cell lines | |
| --- | --- | --- |
| (10 µg/ml) | NIH3T3-CXCR4 | MDA-MB-231 |
| c414H5 | 1039 | Not tested |
| c515H7 | 2294 | 118 |

Example 19

Competition Binding of Anti-CXCR4 Murine Mabs m414H5 and m515H7 and Chimeric Mabs c414H5 and c515H7 for [$^{125}$I]SDF-1 at CHO-K1 Membranes Stably Expressing Human CXCR4 Receptor This assay allows to evaluate the ability of murine Mabs m414H5, m515H7 and chimeric Mabs c414H5, c515H7 to compete for binding of radio labeled [$^{125}$I]SDF-1 to human CXCR4 receptor, at either orthosteric or allosteric binding sites.

CHO-K1 cells, stably and constitutively expressing human CXCR4 receptor were obtained upon transfection of naïve CHO-K$^1$ cells (ATCC CCL-61) with a mammalian expression vector carrying the whole coding sequence of human CXCR4 receptor (RefSeq NM_003467). Cells were propagated in complete culture medium [DMEM-Ham's F12 supplemented with 5% fetal calf serum (FCS) and 500 µg/ml of geneticin]. Radioligand binding experiments were conducted on cell membranes obtained upon mechanical scrapping of CHO/CXCR4 cells in lysis buffer [Hepes 20 mM, pH 7.4, NaCl 150 mM] followed by centrifugation (10000 g, 15 min). [$^{125}$I]SDF-1 binding (specific activity: 1500 Ci/mmol) was performed using the SPA technology (scintillation proximity assay—GE Healthcare). Briefly, cell membranes (30 µg/well) were incubated in binding buffer [Hepes 20 mM, pH 7.4, CaCl$_2$ 1 mM, MgCl$_2$ 5 mM, NaCl 150 mM, BSA 1%] together with compound to evaluate (SDF-1 or mAb), radioligand (1 nM) and finally SPA-WGA-PVT beads (7.3 mg/well). Binding equilibrium was reach after 1H at 25° C. Upon centrifugation [1000 g for 10 min.] radioactive counts were measured in a scintillation counter (TopCount, Perkin Elmer). Non-specific (NS) binding was estimated in the presence of 10 µM of unlabelled SDF-1.

Figure 17:
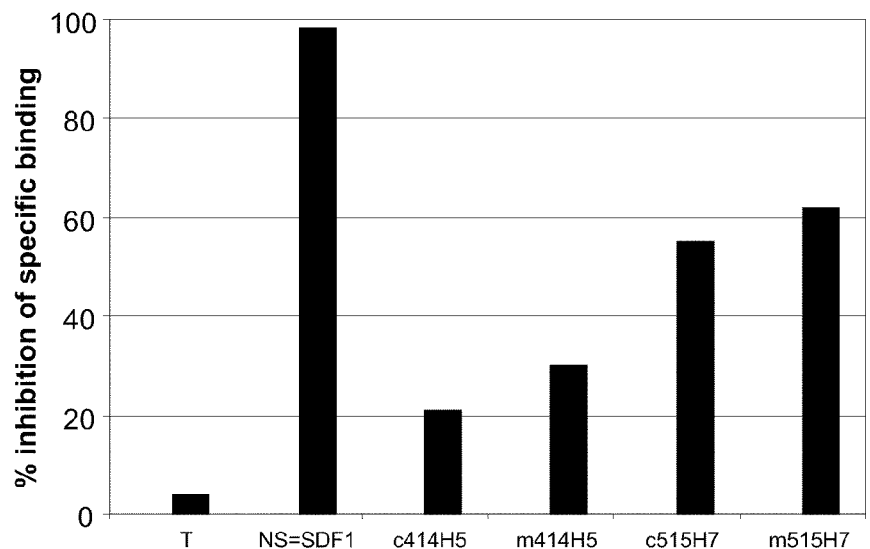
FIG. 17 shows the competition of specific [$^{125}$I]SDF1 binding by murine m414H5 and m515H7 Mabs and chimeric Mabs c414H5 and c515H7 on cellular membranes of CHO-K1 cells stably expressing wild-type human CXCR4 (T: total binding; NS: non-specific binding).

Anti-CXCR4 Mabs (100 nM) efficiently competed for [$^{125}$I]SDF-1 binding with the following rank order of competition efficacy (% inhibition of [$^{125}$I]SDF-1): m515H7 (62±10%), c515H7 (55±4%), m414H5 (30±5%) and c414H5 (21±10%) (FIG. 17).

Example 20

Modulation of [$^{35}$S]GTPγS Binding at Cellular Membranes Expressing Wild Type CXCR4 Receptor by Anti-CXCR4 Murine Mabs m414H5 and m515H7 and Chimeric Mabs c414H5 and c515H7

This functional assay allows to monitor G protein activation via wild type human CXCR4 receptor and its modulation by anti-CXCR4 murine Mabs m414H5, m515H7 and chimeric Mabs c414H5, c515H7.

NIH-3T3 cells stably and constitutively expressing wild-type CXCR4 receptor were obtained as described in the example above for CHO-K1 cells. HeLa (human cervix carcinoma) cells were propagated in complete culture medium [EMEM supplemented with 10% FCS, 1% L-glutamine, 2 µM sodium bicarbonate]. [$^{35}$S]GTPγS binding was performed on cellular membranes obtained upon mechanical scrapping in lysis buffer [Hepes 20 mM, pH 7.4, NaCl 150 mM] and further centrifugation (10000 g, 15 min). Incorporation and detection of [$^{35}$S]GTPγS (specific activity: 1000 Ci/mmol) was performed using the SPA technology (scintillation proximity assay—GE Healthcare). Briefly, cell membranes (10 µg/well) were incubated in binding buffer [Hepes 20 mM, GDP 3 µM, MgCl$_2$ 10 mM, NaCl 100 mM, EDTA 1 mM, pH=7.4] together with compound to evaluate (SDF-1 and Mab of interest), [$^{35}$S]GTPγS (0.2-0.4 nM) and finally SPA-WGA-PVT beads (7.3 mg/well). Binding reaction was performed during 1H at 25° C. Upon centrifugation [1000 g for 10 min.] radioactive counts were measured in a scintillation counter (TopCount, Perkin Elmer). IC$_{50}$ were calculated for each Mab.

Figure 18:
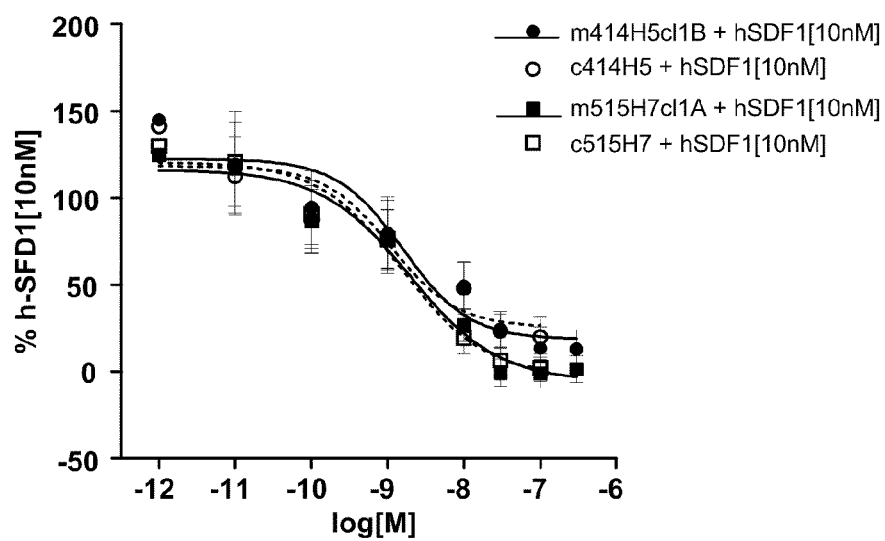
FIG. 18 shows the modulation of G protein activation by murine m414H5 and m515H7 Mabs and by chimeric Mabs c414H5 and c515H7 by monitoring [$^{35}$S]GTPγS binding responses at wild-type CXCR4 receptor stably expressed in NIH-3T3 cells stimulated with SDF-1 (10 nM).
Figure 19:
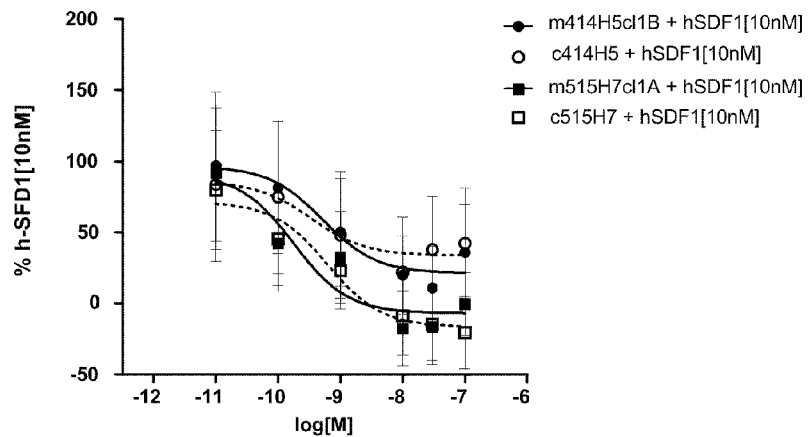
FIG. 19 shows the modulation of G protein activation by anti-CXCR4 murine m414H5 and m515H7 Mabs and chimeric Mabs c414H5 and c515H7 by monitoring [$^{35}$S]GTPγS binding responses at HeLa human tumor cells stimulated with SDF-1 (10 nM).

Under these experimental conditions, IC$_{50}$ of m414H5, c414H5, m515H7 and c515H7 Mabs, as determined in NIH3T3/CXCR4 cells were 1.6 nM, 1.1 nM, 1.9 nM and 1.5 nM, respectively (FIG. 18). The IC$_{50}$ of m414H5, c414H5, m515H7 and c515H7 Mabs determined using Hela cells in the same experimental conditions were 0.5 nM, 0.3 nM, 0.2 nM and 0.6 nM, respectively (FIG. 19).

Example 21

Association of CXCR4 with Different Interaction Partners: Homo and Heterodimerization, Recruitment of β-Arrestin Via a Bioluminescence Resonance Energy Transfer (BRET) Approach and Effect of Murine Mabs m414H5, m515H7 and Chimeric Mabs c414H5 and c515H7 on These Dimers This functional assay allows to evaluate the conformational changes induced upon SDF-1 and/or m414H5, m515H7 murine Mabs and c414H5, and c515H7 chimeric Mabs binding to CXCR4 receptor at the level of CXCR4 homo-dimer and CXCR2/CXCR4 hetero-dimer formation as well as the recruitment of the β-arrestin-2 signaling protein.

Expression vectors for each of the investigated interaction partners were constructed as fusion proteins with the corresponding dye (Renilla reniformis luciferase, Rluc and Yellow fluorescent protein, YFP) by applying conventional molecular biology techniques. Two days prior performing BRET experiments, HEK293 cells were transiently transfected with expression vectors coding for the corresponding BRET partners: [CXCR4/Rluc+CXCR4/YFP] to study CXCR4 homo dimerization, [CXCR4-Rluc+CXCR2-YFP] to study CXCR4 and CXCR2 hetero-dimerization and [CXCR4-Rluc+β-arr2-YFP] to study CXCR4-mediated recruitment of β-arrestin-2. The day after, cells were distributed in poly-lysine pre-coated white 96 MW plates in complete culture medium [DMEM supplemented with 10% FBS]. Cells were first cultivated at 37° C. with $CO_2$ 5% in order to allow cell attachment to the plate. Cells were then starved with 200 μL1 DMEM/well overnight. Immediately prior to the BRET experiment, DMEM was removed and cells were quickly washed with PBS. Cells were then incubated in PBS in the presence or absence of antibody, 15 min at 37° C. prior to the addition of coelenterazine H 5 μM with or without SDF-1 100 nM in a final volume of 50 μl. After incubation for 5 minutes at 37° C. and further incubation for 20 min at room temperature only for homo and hetero-dimers, light-emission acquisition at 485 nm and 530 nm was initiated using the Mithras LB940 multilabel reader (Berthold) (1 s/wavelength/well repeated 15 times at room temperature).

Calculation of BRET ratio was performed as previously described (Angers et al., 2000): $[(emission_{530\ nm})-(emission_{485\ nm}) \times Cf]/(emission_{485\ nm})$, where $Cf = (emission_{530\ nm})/(emission_{485\ nm})$ for cells expressing the Rluc fusion protein alone under the same experimental conditions. Simplifying this equation shows that BRET ratio corresponds to the ratio 530/485 nm obtained when the two BRET partners are present, corrected by the ratio 530/485 nm obtained under the same experimental conditions, when only the partner fused to Rluc is present in the assay. For sake of readability, results are expressed in milliBRET units (mBU); mBU corresponds to the BRET ratio multiplied by 1000.

Figure 20A:
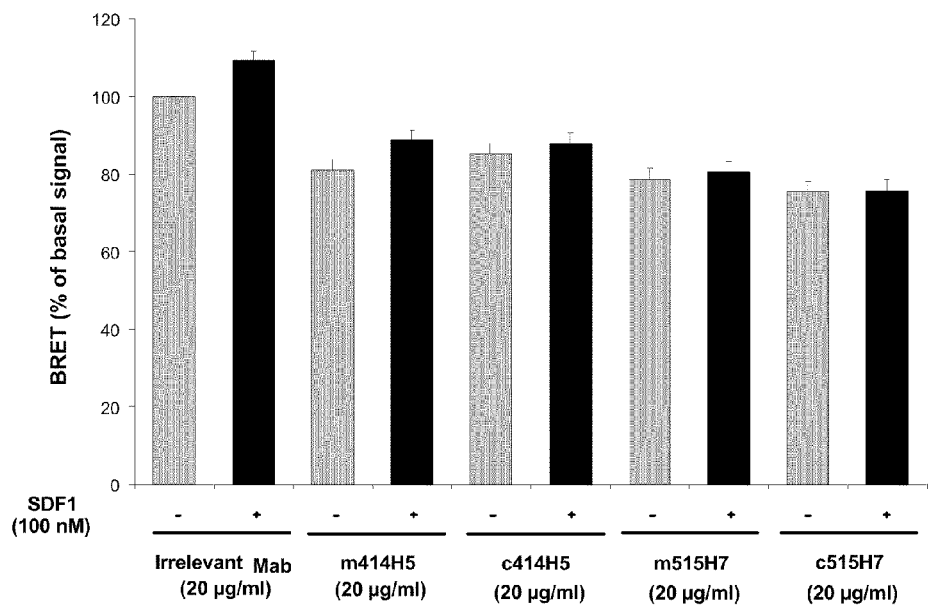
FIGS. 20A-20C show the modulation of CXCR4 receptor association with different interaction partners by SDF-1 and by m414H5, c414H5, m515H7 and c515H7 Mabs via a bioluminescence resonance energy transfer (BRET) approach in HEK293 cells.
Figure 20B:
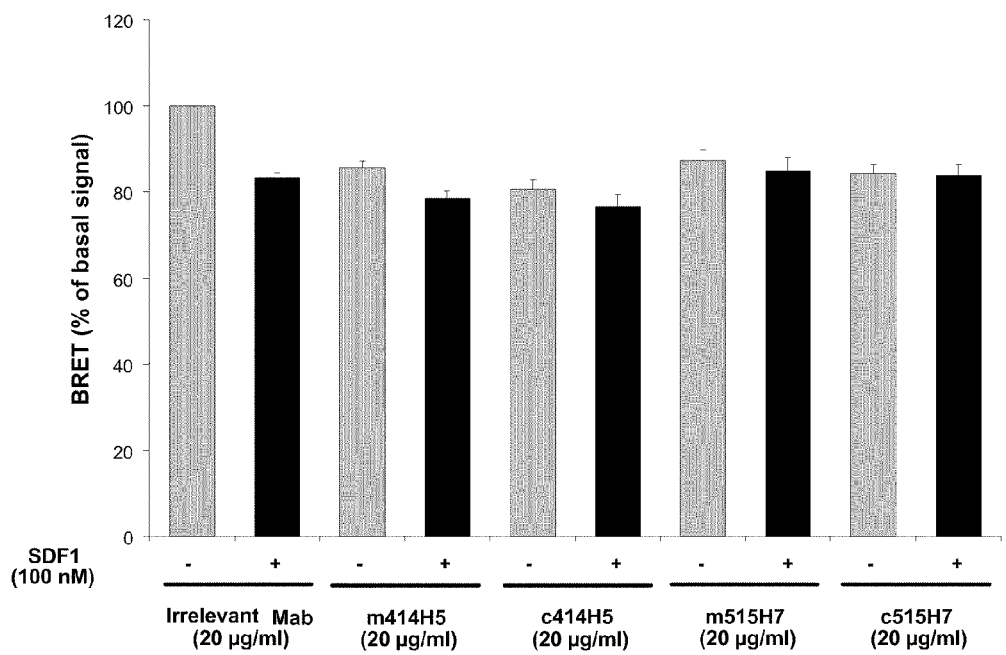

SDF1 (100 nM) increased by about 10% the BRET signal resulting from the spatial proximity of the donor and acceptor proteins fused to CXCR4 receptor, it is likely to indicate CXCR4/CXCR4 homo-dimers formation or conformational changes of pre-existing dimers (FIG. 20A). Interestingly, SDF1 (100 nM) decreased by about 17% the BRET signal resulting from the spatial proximity of the donor and acceptor proteins fused to CXCR4 and CXCR2, likely indicating as well CXCR2/CXCR4 hetero-dimers formation or conformational changes of pre-existing dimers (FIG. 20B). In this latter case, SDF-1-activated conformation of CXCR4/CXCR2 seems less favorable for BRET energy transfer. In both cases, m414H5, c414H5 and m515H7, c515H7 Mabs were able to modulate SDF-1-induced conformational changes for CXCR4 homo-dimers (75% inhibition of SDF-1-induced BRET increase for c414H5 and 96% inhibition of SDF-1-induced BRET increase for c515H7, FIG. 20A) as well as for CXCR2/CXCR4 hetero-dimer formation (77% inhibition of SDF-1-induced BRET decrease for c414H5 and 98% inhibition of SDF-1-induced BRET decrease for c515H7, FIG. 20B). m414H5, c414H5, m515H7 and c515H7 Mabs were also able to modulate by themselves CXCR4/CXCR4 and CXCR2/CXCR4 spatial proximity respectively, indicating an influence of these Mabs on both CXCR4/CXCR4 homo and CXCR2/CXCR4 hetero-dimer conformation (FIGS. 20A and 20B).

Figure 20C:
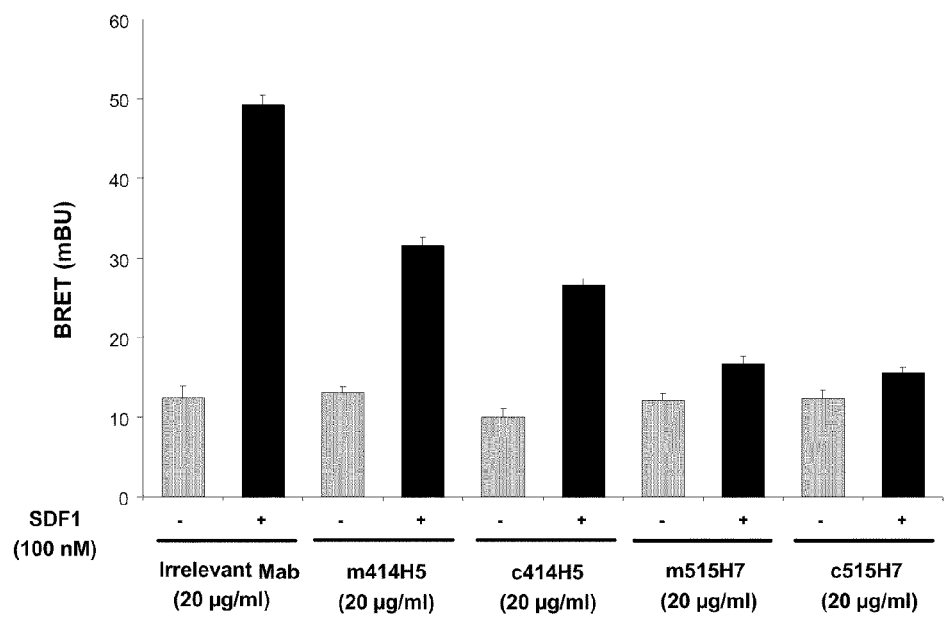

CXCR4 activation by SDF-1 (100 nM) yielded a strong recruitment of the intracellular signaling molecule β-arrestin, as shown by the 400% enhancement in BRET signal (FIG. 20C). This recruitment was partially inhibited by c414H5 and by c515H7 Mabs (about 63% inhibition for c414H5 and 93% for c515H7, FIG. 20C) showing the effect of these Mabs on signaling.

Example 22

CXCR4 Receptor-Mediated Mobilization of Intracellular Calcium Stores

This functional assay was designed to monitor CXCR4 receptor signaling via stimulation of the phospholipase C pathway, inducing calcium liberation from intracellular stores from the endoplasmic reticulum.

CHO-K1 cells stably and constitutively expressing wild-type CXCR4 receptor were obtained as described in the example above. U937 (human lymphoma) cells were propagated in complete culture medium, respectively [DMEM supplemented with 10% FCS] and [RPMI 1640 supplemented with 10% FCS, 20 mM HEPES, 1% non-essential amino acid solution, 1% sodium pyruvate, 1% L-glutamine, 4.5 g/l glucose]. All cell types were plated in black 96 MW plates at a density of 100,000 cells/well in appropriate culture medium. Cells were starved overnight before conducting the experiments. Cells are loaded with the fluorescent calcium dye (Fluo-4 No Wash, Invitrogen US) in loading buffer [HBSS 1×, HEPES 20 mM, Probenicid acid 25 mM] for 30 min. at 37° C. followed by 30 min. at 25° C. Stimulation by SDF-1 was performed by direct injection into each well. For antagonism experiments, 10 μl of Mab solution are added directly into the loading buffer at least 10 min. before SDF-1. Kinetic fluorescence measurements are performed on a multi-mode fluorescence microplate reader Mithras LB940 (Berthold) using the following settings: excitation at 485 nm, emission at 535 nm, excitation energy at 10000 arbitrary units. Fluorescence in each well is recorded during 0.1 second every second and for a time period of 20 sec prior SDF-1 injection (basal signal). Then 20 μA of SDF-1 are injected and data recording follows for a time period of 2 min. Each experimental condition is performed in duplicate. Values for each well are first corrected by substracting the basal fluorescence and the fluorescence emitted by a control well without cells. Relative data are expressed as a percentage of the maximal stimulation obtained by SDF-1 (100 nM).

Figure 21A:
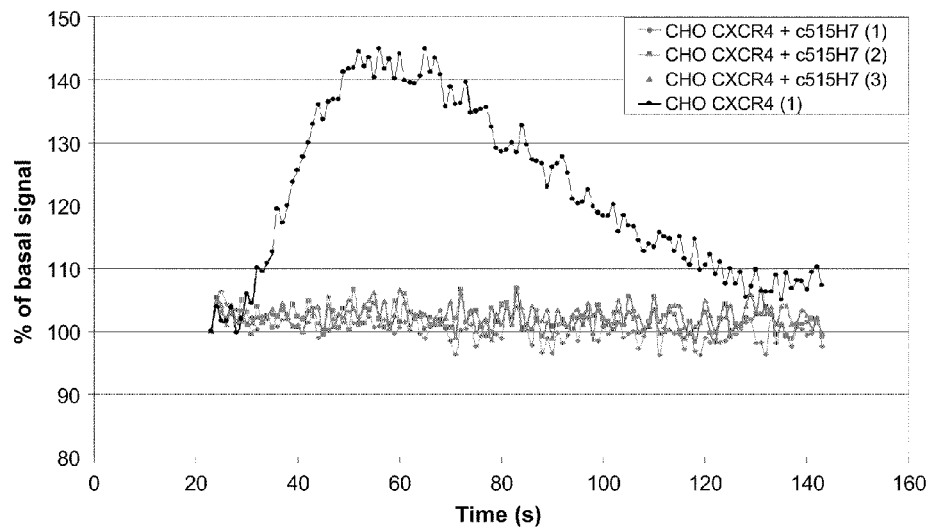
FIGS. 21A and 21B show the inhibition of SDF-1-induced calcium release in CHO-CXCR4 cells (FIG. 21A) and in U937 cells (FIG. 21B).
Figure 21B:
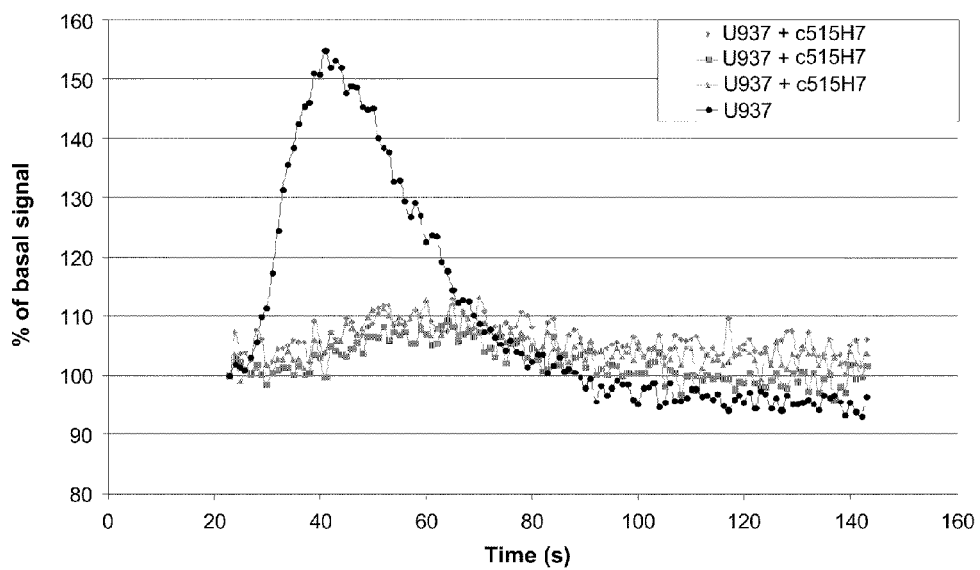

SDF1 (100 nM) induced a rapid and strong release of intracellular calcium in recombinant CHO/CXCR4, whereas no fluorescence signal was detected in naïve CHO-K1 cells. The maximal intensity reached>140% over basal fluorescence and was observed at about 40 sec. upon stimulation by SDF-1; similar kinetic curves were observed with U-937 cells (FIGS. 21A, 21B). Chimeric antibody c515H7 (133 nM) yielded a strong and almost complete inhibition of the SDF-1 (100 nM)-induced calcium signal in both investigated cell lines.

Example 23

Figure 22A:
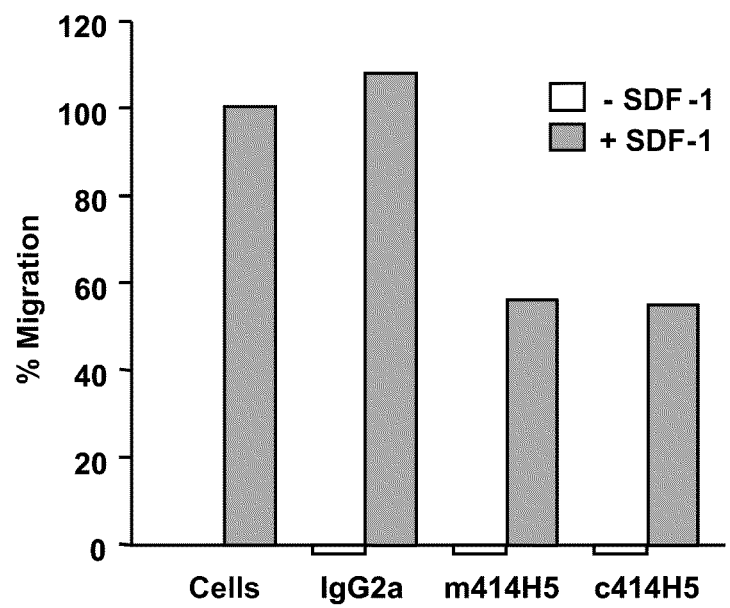
FIGS. 22A and 22B show the inhibition of SDF-1-induced U937 cells migration by CXCR4 Mabs m414H5 and c414H5 (FIG. 22A) and Mabs m515H7 and c515H7 (FIG. 22B) in vitro.
Figure 22B:
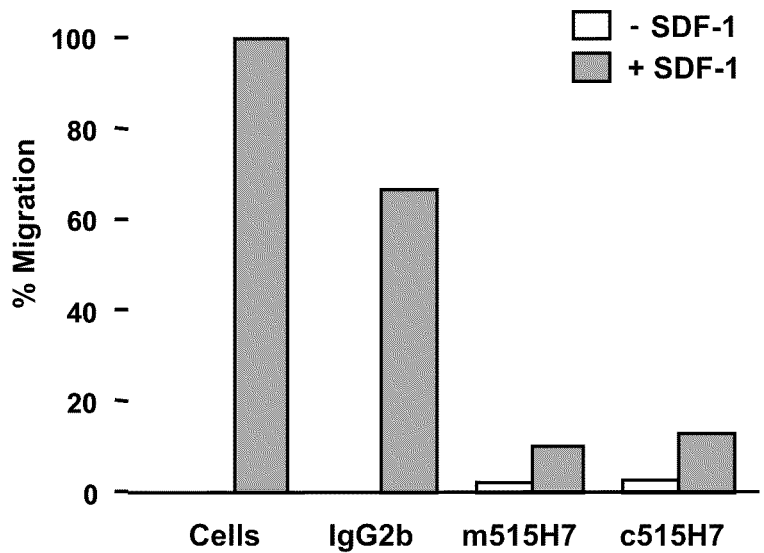

Effect of Anti-CXCR4 Murine Mabs m414H5, m515H7 and Chimeric Mabs c414H5, c515H7 on SDF-1-Induced U937 Cells Migration To evaluate the inhibiting effect of the anti-CXCR4 Mabs m414H5, m515H7, c414H5 and c515H7 on the migration process, 100 000 U-937 cells in RPMI 1640 medium supplemented with 2% FCS, were plated in the upper chamber of migration chambers (24 wells plates with 8-μm pore size) either in presence or in absence of SDF-1 in the lower part of the wells and with or without Mabs c414H5, m414H5, c515H7 and m515H7 in the upper chamber. In this test murine IgG2a and IgG2b were introduced as an isotype controls. Two hours after plating, migrating cells were counted. The results presented in FIG. 22A (for c414H5 versus m414H5) and 22B (for c515H7 versus m515H7) demonstrated that, as expected SDF-1 was able to induce a significant increase of U-937 cells migration. No effect was observed when cells were incubated with the IgG2 isotype control. In contrast, for cells incubated with the c414H5, m414H5, c515H7 and m515H7 Mabs, a significant and reproducible decrease in SDF-1-induced U937 cells migration was observed: about 50% with c414H5 and m414H5 Mabs and more than 80% with c515H7 and m515H7 Mabs.

Example 24

Anti-CXCR4 Chimeric Mabs c414H5 and c515H7 Activity in U937 Mice Survival Model

U937 cells from ATCC were cultured in RPMI 1640 medium, 10% FCS, 1% L-Glutamine. Cells were split two days before engraftment so that they were in exponential phase of growth. Ten million U937 cells injected i.p. to female NOD/SCID mice. Two days after implantation, mice were treated s.c. with a loading dose of 2 mg of c414H5 or c515H7 Mab/mouse and then twice a week with 1 mg of antibody/mouse. Control mice received PBS injections as it has been shown in previous studies that no difference in survival was observed between mice injected with PBS and mice administered with a mouse IgG isotype control. Mice survival was monitored every day.

Results described in FIG. 23 showed that mice treated with the c414H5 and c515H7 Mabs had a dramatic and significant increase in life span with T/C % about 210 and 180 for c414H5 and c515H7, respectively.

Example 25

Humanization of 515H7 anti-CXCR4 Murine Antibody

General Procedure

Humanization of 515H7 anti-CXCR4 antibody was performed by applying the global rules of CDR-grafting. Immunogenetic analysis and definition of CDR and framework (FR) regions were performed by applying the IMGT unique numbering scheme as well as the IMGT libraries and tools (Lefranc, 1997—www.imgt.org).

The efficiency of the humanization process was evaluated by testing the functional activity of the engineered antibodies for their ability to inhibit the SDF-1-mediated recruitment of β-arrestin by a Bioluminescence Resonance Energy Transfer (BRET) assay. In this assay CXCR4 was tagged with luciferase and β-arrestin with YFP. The SDF-1 mediated recruitment of β-arrestin to CXCR4 is an important step in the signal transduction of CXCR4. Binding of humanized variants of 515H7 was also determined on a NIH3T3 cell line stably transfected with human CXCR4. The binding activity was evaluated by a competition assay with the biotinylated mouse antibody. In a second attempt, humanized antibodies were evaluated for their ability to inhibit binding of biotinylated SDF-1 to RAMOS cells. RAMOS cells were chosen because of their high expression of CXCR4 and low expression of CXCR7 and SDF-1.

These assays were used to characterize the recombinant humanized versions of anti-CXCR4 antibodies. Variable domains were formatted with human IgG1/κ constant domains and cloned into the mammalian expression vector pCEP. Recombinant $IgG_1$/κ-derived antibodies were transiently expressed in HEK293 cells. Expression culture supernatants were filtered and antibodies were purified using protein A sepharose. Purified antibodies were re-buffered in PBS and antibodies concentrations determined by ELISA.

Humanization of 515H7 Variable Domains

In order to select an appropriate human germline for the CDR grafting, the human germline gene with the highest homology to the 515H7 VH murine sequence was identified. With the help of IMGT databases and tools, the human IGHV3-49*04 germline gene and human IGHJ4*01 J germline gene were selected as human acceptor sequences for the murine 515H7 VH CDRs. The human V-gene IGHV3-49*04 has a homology of 80.27% to the V-gene of the variable domain of the mouse 515H7 heavy chain. The homology for the human J-gene IGHJ4*01 J is 87.50%. Nineteen residues are different between the chosen human germline genes and the VH domain of the mouse antibody 515H7. The alignment between the VH domain of the parental antibody and the germline sequences is depicted in FIG. 24.

Concerning the variable domain of the light chain, the human germline genes IGKV4-1*01 and IGKJ1*01 were selected (FIG. 25). The homology with human V-gene IGKV4-1*01 is 79.12%. The 515H7 J-gene of the light chain has a homology of 84.85% to the human J-gene IGKJ1*01.

The amino acid sequence of the translated human germline genes IGHV3-49*04 and IGKV4-1*01 was used to identify homologous antibodies that have been crystallized. For the heavy chain the antibody with the accession number 1MAM at the RCSB Protein Data Bank was chosen as a model, while for the light chain the antibody 1SBS was chosen. The two domains were assembled using the computer program DS visual and used as a model for the humanized antibody 515H7.

Based on the position of each residue that is different between the parental antibody and the corresponding human germline sequence, a priority rank order was given for each residue differing between the human and mouse sequences (FIGS. 24 and 25). These priorities were used to create three different variants of each humanized variable domain named VH1, VH2 and VH3, respectively.

In a first series of experiments, we constructed and analysed the anti-CXCR4 binding activities of the three first humanized variants. The VH variant 1 (VH1) was combined with the murine VL and these constructs were evaluated in their capacity to inhibit the binding of a biotinylated murine 515H7 parental antibody. All constructs showed similar capacity to compete with the murine antibody (FIGS. 26A-26C). This indicates that the most human VH variant has the same binding capacity as the lesser human variants. Therefore, VH1 was combined with the three different variants of VL (FIGS. 26D-26F). Only the combination of VH1 and VL3 showed a reduced capacity to compete with the biotinylated murine antibody, while the most human variant VH1 VL1 that carries no back mutations in the frameworks showed the same cross blocking activity as the chimeric antibody.

Figures 28A, 28B, 28C, 28D:
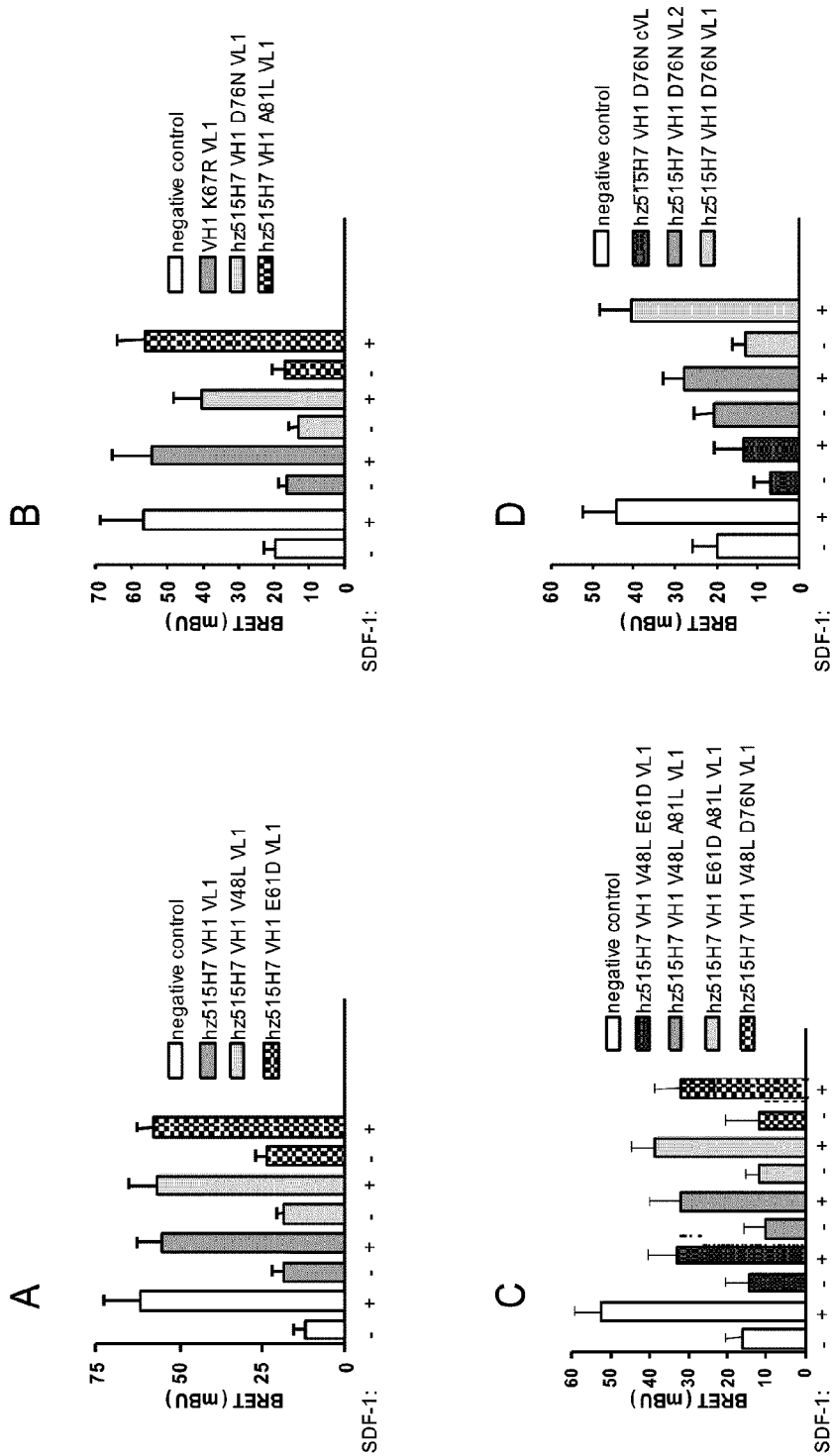

This variant VH1 VL1 was further tested for its capacity to inhibit SDF-1 mediated recruitment of β-arrestin in BRET assays (FIG. 27). Despite desirable binding activity to the receptor as determined by cross blocking of the parental antibody, the construct VH1 VL1 showed only a weak inhibition of the recruitment of β-arrestin. This lack of strong inhibitory activity makes substitution of human framework residues with murine residues necessary. Single back mutations were constructed for the VH1. The following residues were substituted: V48L, E61D, D76N and A81L (numbering according to the primary amino acid sequence). These single back mutants of the variant VH1 were combined with the variant VL1. Of these only the back mutation D76N led to an increased inhibition of the signal transduction as evaluated by BRET assay (FIG. 28B).

To increase the activity of this construct and further evaluate the importance of other residues different double back mutants were constructed for the VH 1. The inhibitory activity of these constructs was slightly improved (average inhibition of about 45-50%), but not satisfactory (FIG. 28C). The single back mutant D76N was then combined with the three different VL variants (FIG. 28D). The construct hz515H7 VH D76N VL2 showed an activity of 88.2% on average which is in the same range as the chimeric antibody.

Single and double back mutations were constructed in the variant VL1 domain and compared to the activity of the construct hz515H7 VH1 D76N VL2 (FIG. 29). None of the tested combinations had a similar or better activity as this construct.

The percentage of human residues in the framework was calculated for hz515H7 VH1 D76N VL2: it contains 14 non-human residues out of 180 residues, which equals a <<germinality index>> of 92.2%. By way of comparison, the humanized and marketed antibodies bevacizumab and trastuzumab contain respectively 30 and 14 non-human residues in their variable domains.

The four best humanized forms, showing the strongest efficacy to inhibit SDF-1-mediated β-arrestin recruitment were also tested for their capacity to inhibit the binding of biotinylated SDF-1 (FIG. 30A). A close correlation of inhibition of SDF-1 binding and β-arrestin recruitment was determined. This correlation indicates that the inhibition of SDF-1 binding is most likely the main mechanism of the inhibition of the signal transduction.

In order to further humanize the hz515H7 VL2 variant, three additional variants were designed, by using the information gained with the double and triple mutants evaluated in FIG. 29. Four and five additional residues were humanized in respectively variant VL2.1, VL2.2 and VL2.3. They correspond to the residues D9, P49, D66, S69, S83, L84; V89. An alignment of these three variants in comparison with VL2 is shown FIG. 31.

The capacity of these VL2 variants to inhibit the SDF-1 mediated recruitment of β-arrestin was evaluated. The humanized hz515H7 VH D76N VL2, VL2.1, VL2.2 and VL2.3 variants showed an activity similar to the chimeric antibody c515H7 (FIG. 29).

Example 26

Characterization by FACS Analysis of Anti-CXCR4 Humanized Mabs 515H7 Binding Specificity and Cancer Cell Line Recognition In this experiment, specific binding to human CXCR4 of anti-CXCR4 humanized Mabs 515H7 was examined by FACS analysis.

NIH3T3, NIH3T3-hCXCR4 transfected cells and Ramos, U934 cancer cell lines were incubated with 0 to 10 μg/mL of humanized Mabs 515H7 (hz515H7 VH1 D76N VL2, hz515H7 VH1 D76N VL2.1, hz515H7 VH1 D76N VL2.2 and hz515H7 VH1 D76N VL2.3) for 20 min at 4° C. in the dark in 100 μl Facs buffer. After 3 washing in Facs buffer, cells were incubated with the secondary antibody, a goat anti-human Alexa 488 (dilution 1/500), for 20 minutes at 4° C. in the dark. After 3 washing in Facs buffer, propidium iodide was added in each well and only viable cells were analyzed by Facs. At least 5000 viable cells were assessed to evaluate the mean value of fluorescence intensity for each condition.

Results of these binding studies are provided in FIGS. 32A-32C which show [Mean Fluorescence Intensity (MFI) obtained by FACS] that anti-CXCR4 humanized Mabs hz515H7 bound specifically to human CXCR4-NIH3T3 transfected cell line (FIG. 32A) (MFI=2.2 with NIH3T3 parent cells) and also recognize human cancer cell lines, for example U937 (FIG. 32B) and Ramos (FIG. 32C).

Example 27

Modulation of [$^{35}$S]GTPγS Binding at Cellular Membranes Expressing Wild Type CXCR4 Receptor by Anti-CXCR4 Humanized Mabs 515H7

This functional assay allows to monitor G protein activation via wild type human CXCR4 receptor and its modulation by anti-CXCR4 humanized Mabs 515H7.

NIH-3T3 cells stably and constitutively expressing wild-type CXCR4 receptor were obtained as described in the example above for CHO-K1 cells. [$^{35}$S]GTPγS binding was performed on cellular membranes obtained upon mechanical scrapping in lysis buffer [Hepes 20 mM, pH 7.4, NaCl 150 mM] and further centrifugation (10000 g, 15 min). Incorporation and detection of [$^{35}$S]GTPγS (specific activity: 1000 Ci/mmol) was performed using the SPA technology (scintillation proximity assay—GE Healthcare). Briefly, cell membranes (10 μg/well) were incubated in binding buffer [Hepes 20 mM, GDP 3 μM, MgCl$_2$ 10 mM, NaCl 100 mM, EDTA 1 mM, pH=7.4] together with compound to evaluate (SDF-1 and Mabs of interest), [$^{35}$S]GTPγS (0.2-0.4 nM) and finally SPA-WGA-PVT beads (7.3 mg/well). Binding reaction was performed during 1H at 25° C. Upon centrifugation [1000 g for 10 min.] radioactive counts were measured in a scintillation counter (TopCount, Perkin Elmer). IC$_{50}$ were calculated for each Mab.

Figure 33A:
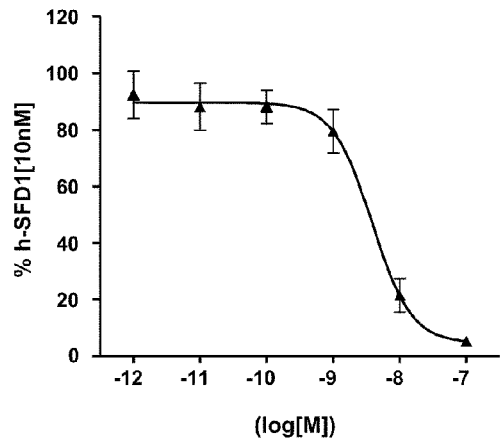
Figure 33B:
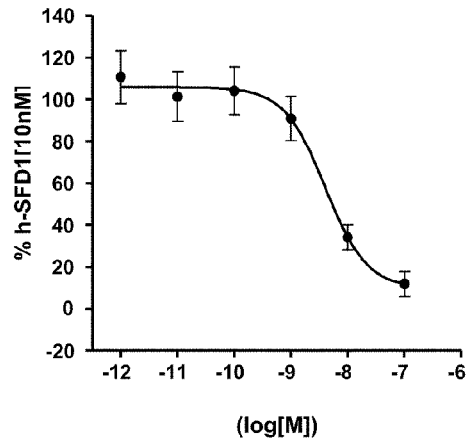
Figure 33C:
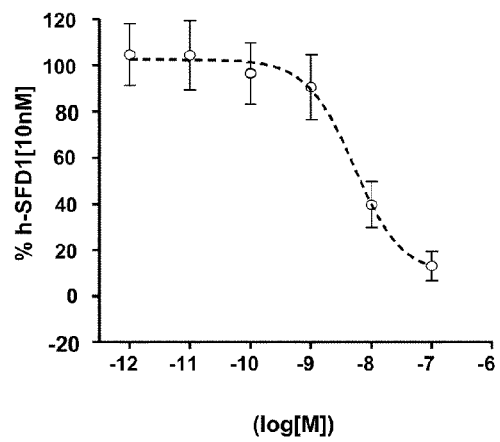
Figure 33D:
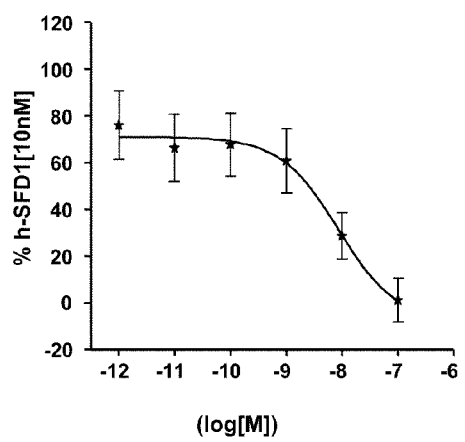
Figure 34A:
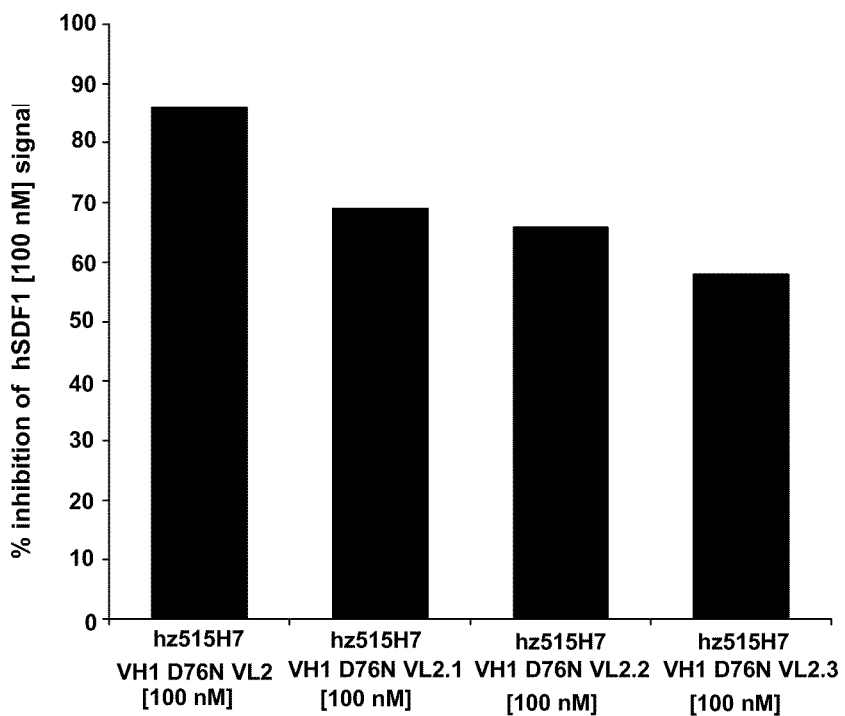
Figure 34B:
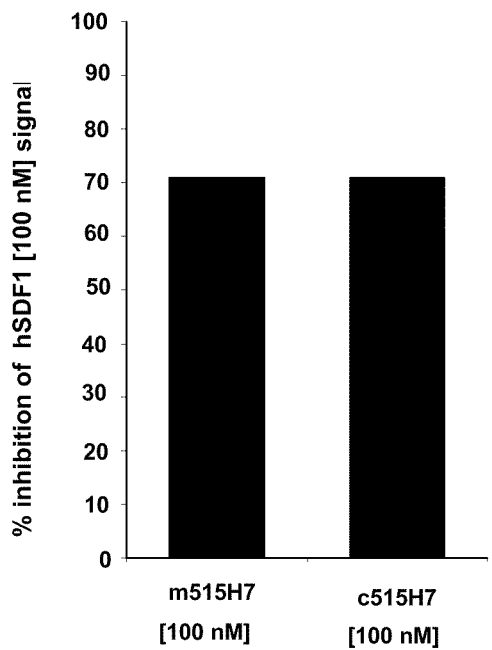

Under these experimental conditions, IC$_{50}$ 515H7 of humanized (hz) Mabs, as determined in NIH3T3/CXCR4 cells were 3.86 nM for hz515H7 VH1D76N-VL2 Mab (FIG. 33A), 4.05 nM for hz515H7 VH1D76N-VL2-1 Mab (FIG. 33B), 5.19 nM for hz515H7 VH1D76N-VL2-2 Mab (FIG. 33C) and 8.5 nM for hz515H7 VH1D76N-VL2-3 Mab (FIG. 33D).

m515H7, c515H7 and hz515H7 Mabs were also able to inhibit [$^{35}$S]GTPγS binding stimulated by SDF-1 (100 nM) with a % of inhibition of 86% for hz515H7 VH1D76N-VL2 Mab, 69% for hz515H7 VH1D76N-VL2-1 Mab, 66% for hz515H7 VH1D76N-VL2-2 Mab 58% for hz515H7 VH1D76N-VL2-3 Mab (FIG. 34A) and 71% for both m515H7, c515H7 (FIG. 34B).

Example 28

Association of CXCR4 with Different Interaction Partners: Homo and Heterodimerization, Recruitment of β-Arrestin Via a Bioluminescence Resonance Energy Transfer (BRET) Approach and Effect of Humanized Mabs 515H7 on These Dimers This functional assay allows to evaluate the conformational changes induced upon SDF-1 and/or 515H7 humanized Mabs binding to CXCR4 receptor at the level of CXCR4 homo-dimer and CXCR2/CXCR4 hetero-dimer formation as well as the recruitment of the β-arrestin-2 signaling protein.

Expression vectors for each of the investigated interaction partners were constructed as fusion proteins with the corresponding dye (*Renilla reniformis* luciferase, Rluc and Yellow fluorescent protein, YFP) by applying conventional molecular biology techniques. Two days prior performing BRET experiments, HEK293 cells were transiently transfected with expression vectors coding for the corresponding BRET partners: [CXCR4/Rluc+CXCR4/YFP] to study CXCR4 homo dimerization, [CXCR4-Rluc+CXCR2-YFP] to study CXCR4 and CXCR2 hetero-dimerization and [CXCR4-Rluc+β-arr2-YFP] to study CXCR4-mediated recruitment of β-arrestin-2. The day after, cells were distributed in poly-lysine pre-coated white 96 MW plates in complete culture medium [DMEM supplemented with 10% FBS]. Cells were first cultivated at 37° C. with $CO_2$ 5% in order to allow cell attachment to the plate. Cells were then starved with 200 μl DMEM/well overnight. Immediately prior to the BRET experiment, DMEM was removed and cells were quickly washed with PBS. Cells were then incubated in PBS in the presence or absence of antibody, 15 min at 37° C. prior to the addition of coelenterazine H 5 μM with or without SDF-1 100 nM in a final volume of 50 μl. After incubation for 5 minutes at 37° C. and further incubation for 20 min at room temperature only for homo- and hetero-dimers, light-emission acquisition at 485 nm and 530 nm was initiated using the Mithras LB940 multilabel reader (Berthold) (1 s/wavelength/well repeated 15 times at room temperature).

Calculation of BRET ratio was performed as previously described (Angers et al., 2000): [(emission$_{530\ nm}$)−(emission$_{485\ nm}$)×Cf]/(emission$_{485\ nm}$), where Cf= (emission$_{530\ nm}$)/(emission$_{485\ nm}$) for cells expressing the Rluc fusion protein alone under the same experimental conditions. Simplifying this equation shows that BRET ratio corresponds to the ratio 530/485 nm obtained when the two BRET partners are present, corrected by the ratio 530/485 nm obtained under the same experimental conditions, when only the partner fused to Rluc is present in the assay. For sake of readability, results are expressed in milliBRET units (mBU); mBU corresponds to the BRET ratio multiplied by 1000.

SDF1 (100 nM) increased by about 12% the BRET signal resulting from the spatial proximity of the donor and acceptor proteins fused to CXCR4 receptor, it is likely to indicate CXCR4/CXCR4 homo-dimers formation or conformational changes of pre-existing dimers (FIG. 35A). Interestingly, SDF1 (100 nM) decreased by about 16% the BRET signal resulting from the spatial proximity of the donor and acceptor proteins fused to CXCR4 and CXCR2, likely indicating as well CXCR2/CXCR4 hetero-dimers formation or conformational changes of pre-existing dimers (FIG. 35B). In this latter case, SDF-1-activated conformation of CXCR4/CXCR2 seems less favorable for BRET energy transfer. In both cases, 515H7 humanized Mabs were able to modulate SDF-1-induced conformational changes for CXCR4 homo-dimers with a percentage of inhibition of SDF-1-induced BRET increase of about 88% for hz515H7 VH1D76N-VL2 Mab, 65% for hz515H7 VH1D76N-VL2.1 Mab, 33% for hz515H7 VH1D76N-VL2.2 Mab and 21% for hz515H7 VH1D76N-VL2.3 Mab (FIG. 35A) as well as for CXCR2/CXCR4 hetero-dimer with a percentage of inhibition of SDF-1-induced BRET decrease about 100% for hz515H7 VH1D76N-VL2 Mab and 50% for hz515H7 VH1D76N-VL2.1, hz515H7 VH1D76N-VL2.2 and hz515H7 VH1D76N-VL2.3 Mabs (FIG. 35B). 515H7 humanized Mabs were also able to modulate by themselves CXCR4/CXCR4 and CXCR2/CXCR4 spatial proximity respectively, indicating an influence of these Mabs on both CXCR4/CXCR4 homo and CXCR2/CXCR4 hetero-dimer conformation (FIGS. 35A and 35B).

CXCR4 activation by SDF-1 (100 nM) yielded a strong recruitment of the intracellular signaling molecule β-arrestin, as shown by the 390% enhancement in BRET signal (FIG. 35C). This recruitment was partially inhibited by 515H7 humanized Mabs about 94% inhibition for hz515H7 VH1D76N-VL2 Mab, 81% for hz515H7 VH1D76N-VL2.1 Mab, 82% for hz515H7 VH1D76N-VL2.2 Mab and 71% for hz515H7 VH1D76N-VL2.3 Mab (FIG. 35C) showing the effect of these Mabs on signaling.

Example 29

Immunohistochemical Studies (IHC)

Sections were deparaffinized, rehydrated, and placed for 7 minutes in pre-warm at 98° C. EDTA pH8 for heat-induced epitope retrieval. After 3 washes in Tris Buffer Saline-0.05% tween 20 (TBS-T) (Dako S3006) the endogenous peroxidase activity was blocked using Peroxidase Blocking Reagent (Dako K4007) for five minutes. Sections were washed with TBS-T and incubated in blocking reagent (UltraV block-TA-125UB-LabVision) for 5 minutes before incubation with the anti-CXCR-4 mouse monoclonal antibody (50 μg/ml, clone 515H7, Pierre Fabre) or mouse IgG1/kappa (50 μg/ml, X0931, Dako) as a control overnight at ° C. Sections were washed with TBS-T and incubated with Envision Dual Link for 1 hour at room temperature. Diaminobenzidine was used for development of a brown reaction product (Dako K3468). The slides were immersed in hematoxylin for 4 minutes to counterstain (Dako S3309) and washed in PBS before being mounted in Faramount mounting medium plus coverslipe. In this immunohistochemistry procedure, the brown reaction product correlates to positive staining of the cell membrane and lack of brown reaction product correlates to negative staining and no visualization of the cell membrane.

The anti-CXCR-4 mouse monoclonal antibody, clone 515H7, differentially stained the cell membrane of various tumor types. FIGS. 36 and 37 illustrated staining performed in 2 xenograft models in which an anti-tumoral activity has been described for 515H7: RAMOS and KARPAS299. As shown in FIGS. 36 and 37, the staining obtained is fixative-dependant. Indeed, membranous staining was weaker when tissues were formalin fixed (FIGS. 37A and 37C), whereas, when Glyo-fixx (a substitute for formalin) was used, membranous staining was significantly increased (FIGS. 36A and 36C).

The invention claimed is:

1. An isolated anti-CXCR4 antibody capable of inhibiting activation of CXCR4, wherein the antibody comprises:
   a light chain comprising the CDR-L1 of the sequence SEQ ID No. 40, the CDR-L2 of the sequence SEQ ID No. 2, and the CDR-L3 of the sequence SEQ ID No. 41; and
   a heavy chain comprising the CDR-H1 of the sequence SEQ ID No. 44, the CDR-H2 of the sequence SEQ ID No. 5, and the CDR-H3 of the sequence SEQ ID No. 45.

2. The isolated antibody according to claim 1, wherein the antibody comprises a light chain sequence comprising the amino acid sequence SEQ ID No. 50, and a heavy chain sequence comprising the amino acid sequence SEQ ID No. 51.

3. A murine hybridoma deposited at the Collection Nationale de Cultures de Microorganismes (CNCM), 28 rue du Docteur Roux, 75724 Paris Cedex 15 (France), on Jun. 25, 2008, under number I-4019.

4. An antibody secreted by the hybridoma according to claim 3.

5. The antibody according to claim 1, wherein the antibody is a chimeric antibody.

6. The chimeric antibody according to claim 5, wherein the antibody comprises a light chain sequence comprising the amino acid sequence SEQ ID No. 66, and a heavy chain sequence comprising the amino acid sequence SEQ ID No. 67.

7. The antibody according to claim 1, wherein the antibody is a humanized antibody.

8. The humanized antibody according to claim 7, wherein the antibody comprises a heavy chain variable region sequence selected from SEQ ID Nos. 72, 73, 74, and 75.

9. The humanized antibody according to claim 7, comprising a heavy chain, wherein the complete sequence of the heavy chain, without a signal peptide sequence, is selected from SEQ ID Nos. 83, 84, 85, and 86.

10. The humanized antibody according to claim 7, wherein the antibody comprises a light chain variable region sequence selected from SEQ ID Nos. 76, 77, 78, 79, 80, 81, and 82.

11. The humanized antibody according to claim 7, comprising a light chain, wherein the complete sequence of the light chain, without a signal peptide sequence, is selected from SEQ ID Nos. 87, 88, 89, 90, 91, 92, and 93.

12. The humanized antibody according to claim 7, wherein the humanized antibody comprises a heavy chain variable region sequence selected from SEQ ID Nos. 72, 73, 74 and 75, and a light chain variable region sequence selected from SEQ ID Nos. 76, 77, 78, 79, 80, 81, and 82.

13. The humanized antibody according to claim 7, wherein the humanized antibody comprises:
   a heavy chain, wherein the complete sequence of the heavy chain, without a signal peptide sequence, is selected from SEQ ID Nos. 83, 84, 85, and 86; and
   a light chain, wherein the complete sequence of the light chain, without a signal peptide sequence, is selected from SEQ ID Nos. 87, 88, 89, 90, 91, 92, and 93.

14. The humanized antibody according to claim 7, wherein the humanized antibody comprises a heavy chain variable region of sequence SEQ ID No. 73, and a light chain variable region of sequence SEQ ID No. 78.

15. The humanized antibody according to claim 14, wherein the humanized antibody comprises a heavy chain of sequence SEQ ID No. 84, and a light chain of sequence SEQ ID No. 89.

16. The humanized antibody, according to claim 7, wherein the humanized antibody comprises a heavy chain variable region of sequence SEQ ID No. 73, and a light chain variable region of sequence SEQ ID No. 79.

17. The humanized antibody according to claim 16, wherein the humanized antibody comprises a heavy chain of sequence SEQ ID No. 84, and a light chain of sequence SEQ ID No. 90.

18. The humanized antibody according to claim 7, wherein the humanized antibody comprises a heavy chain variable region of sequence SEQ ID No. 73, and a light chain variable region of sequence SEQ ID No. 80.

19. The humanized antibody according to claim 18, wherein the humanized antibody comprises a heavy chain of sequence SEQ ID No. 84, and a light chain of sequence SEQ ID No. 91.

20. The humanized antibody according to claim 7, wherein the humanized antibody comprises a heavy chain variable region of sequence SEQ ID No. 73, and a light chain variable region of sequence SEQ ID No. 81.

21. The humanized antibody according to claim 20, wherein the humanized antibody comprises a heavy chain of sequence SEQ ID No. 84, and a light chain of sequence SEQ ID No. 92.

22. The humanized antibody according to claim 7, wherein the humanized antibody comprises a heavy chain variable region of sequence SEQ ID No. 74, and a light chain variable region of sequence SEQ ID No. 76.

23. The humanized antibody according to claim 22, wherein the antibody comprises a heavy chain of sequence SEQ ID No. 85, and a light chain of sequence SEQ ID No. 87.

24. The humanized antibody according to claim 7, wherein the humanized antibody comprises a heavy chain variable region of SEQ ID No. 74, and a light chain variable region of sequence SEQ ID No. 77.

25. The humanized antibody according to claim 24, wherein the humanized antibody comprises a heavy chain of sequence SEQ ID No. 85, and a light chain of sequence SEQ ID No. 88.

26. The humanized antibody, according to claim 7, wherein the humanized antibody comprises a heavy chain variable region of sequence SEQ ID No. 72, and a light chain variable region of sequence SEQ ID No. 76.

27. The humanized antibody according to claim 26, wherein the humanized antibody comprises a heavy chain of sequence SEQ ID No. 83, and a light chain of sequence SEQ ID No. 87.

28. A pharmaceutical composition comprising an isolated or a humanized antibody according to one of claims 1 and 7 and a pharmaceutically acceptable carrier and/or an excipient.

29. A composition comprising an antibody according to one of claims 1 and 7 and a pharmaceutically acceptable carrier.

30. A composition comprising a humanized antibody according to claim 7 and a pharmaceutically acceptable carrier.

31. The composition according to claim 29, wherein the composition further comprises, in addition, as a combination product for use in a simultaneous, separated, or extended fashion, an anti-tumor antibody other than an antibody directed against CXCR4.

32. The composition according to claim 29, wherein the composition further comprises, in addition, as a combination or conjugation product for use in a simultaneous, separated, or extended fashion, a cytotoxic/cytostatic agent, a cellular toxin, and/or a radioisotope.

33. A composition comprising the antibody of claim 2 and a pharmaceutically acceptable carrier.

34. An isolated anti-CXCR4 antibody wherein the isolated antibody:
(a) binds to a CXCR4/CXCR2 heterodimer comprising:
(1) a human CXCR4 whose amino acid sequence is that of SEQ ID No. 29 and a human CXCR2 whose amino acid sequence is that of SEQ ID No. 31; or
(2) a human CXCR4 whose amino acid sequence is that of SEQ ID No. 30 and a human CXCR2 whose amino acid sequence is that of SEQ ID No. 31;
(b) inhibits activation of CXCR4; and
(c) induces a conformational change in the heterodimer; and wherein the antibody comprises:
a light chain comprising the CDR-L1 of the sequence SEQ ID No. 40, the CDR-L2 of the sequence SEQ ID No. 2, and the CDR-L3 of the sequence SEQ ID No. 41; and
a heavy chain comprising the CDR-H1 of the sequence SEQ ID No. 44, the CDR-H2 of the sequence SEQ ID No. 5, and the CDR-H3 of the sequence SEQ ID No. 45.

35. The isolated antibody according to claim 34, wherein the isolated antibody is a silent antagonist that inhibits CXCR4 activation only in the presence of Stromal-cell-Derived Factor-1 (SDF-1).

36. A kit for diagnosis or prognosis of a CXCR4 expressing tumor, the kit comprising at least one anti-CXCR4 antibody, wherein the anti-CXCR4 antibody comprises, according to IMGT, i) a light chain comprising CDR regions CDR-L1, CDR-L2, and CDR-L3 comprising sequences SEQ ID Nos. 40, 2, and 41, respectively and ii) a heavy chain comprising CDR regions CDR-H1, CDR-H2, and CDR-H3 comprising sequences SEQ ID Nos. 44, 5, and 45, respectively.

37. A recombinant anti-CXCR4 antibody capable of inhibiting activation of CXCR4, wherein the antibody comprises:
a light chain comprising the CDR-L1 of the sequence SEQ ID No. 40, the CDR-L2 of the sequence SEQ ID No. 2, and the CDR-L3 of the sequence SEQ ID No. 41; and
a heavy chain comprising the CDR-H1 of the sequence SEQ ID No. 44, the CDR-H2 of the sequence SEQ ID No. 5, and the CDR-H3 of the sequence SEQ ID No. 45.

38. The recombinant antibody according to claim 37, wherein the antibody comprises a light chain sequence comprising the amino acid sequence SEQ ID No. 50, and a heavy chain sequence comprising the amino acid sequence SEQ ID No. 51.

39. The recombinant antibody according to claim 37, wherein the antibody is a chimeric antibody.

40. The chimeric antibody according to claim 39, wherein the antibody comprises a light chain sequence comprising the amino acid sequence SEQ ID No. 66, and a heavy chain sequence comprising the amino acid sequence SEQ ID No. 67.

41. A recombinant anti-CXCR4 antibody wherein the recombinant antibody:
(d) binds to a CXCR4/CXCR2 heterodimer comprising:
(3) a human CXCR4 whose amino acid sequence is that of SEQ ID No. 29 and a human CXCR2 whose amino acid sequence is that of SEQ ID No. 31; or
(4) a human CXCR4 whose amino acid sequence is that of SEQ ID No. 30 and a human CXCR2 whose amino acid sequence is that of SEQ ID No. 31;
(e) inhibits activation of CXCR4; and
(f) induces a conformational change in the heterodimer; and wherein the recombinant antibody comprises:
a light chain comprising the CDR-L1 of the sequence SEQ ID No. 40, the CDR-L2 of the sequence SEQ ID No. 2, and the CDR-L3 of the sequence SEQ ID No. 41; and
a heavy chain comprising the CDR-H1 of the sequence SEQ ID No. 44, the CDR-H2 of the sequence SEQ ID No. 5, and the CDR-H3 of the sequence SEQ ID No. 45.

42. A composition comprising the isolated antibody of any of claims 13-27 and a pharmaceutically acceptable carrier.

43. A composition comprising the recombinant antibody of any of claims 37-41 and a pharmaceutically acceptable carrier.

* * * * *